United States Patent
Simmons

(10) Patent No.: US 7,575,893 B2
(45) Date of Patent: Aug. 18, 2009

(54) METHODS FOR PRODUCING HUMANIZED ANTIBODIES AND IMPROVING YIELD OF ANTIBODIES OR ANTIGEN BINDING FRAGMENTS IN CELL CULTURE

(75) Inventor: Laura Simmons, Burlingame, CA (US)

(73) Assignee: Genentech, Inc., South San Francisco, CA (US)

(*) Notice: Subject to any disclaimer, the term of this patent is extended or adjusted under 35 U.S.C. 154(b) by 150 days.

(21) Appl. No.: 10/764,428

(22) Filed: Jan. 23, 2004

(65) Prior Publication Data

US 2004/0229310 A1    Nov. 18, 2004

Related U.S. Application Data

(60) Provisional application No. 60/442,484, filed on Jan. 23, 2003.

(51) Int. Cl.
  C12N 1/21    (2006.01)
  C12N 15/06   (2006.01)
  C12N 15/03   (2006.01)
  C12N 15/13   (2006.01)
  C07K 16/22   (2006.01)

(52) U.S. Cl. .............. 435/69.1; 435/252.3; 435/252.33; 435/320.1; 435/326; 435/335; 530/387.1; 530/387.3; 530/388.1; 530/388.23; 536/23.53

(58) Field of Classification Search .............. 435/69.1, 435/252.3, 252.8; 536/23.5
See application file for complete search history.

(56) References Cited

U.S. PATENT DOCUMENTS

| | | | |
|---|---|---|---|
| 3,645,090 A | 2/1972 | Mochizuki et al. | |
| 3,773,919 A | 11/1973 | Boswell et al. | |
| 3,940,475 A | 2/1976 | Gross | |
| RE30,985 E | 6/1982 | Cartaya | |
| 4,560,655 A | 12/1985 | Baker | |
| 4,657,866 A | 4/1987 | Kumar | |
| 4,737,456 A | 4/1988 | Weng et al. | |
| 4,767,704 A | 8/1988 | Cleveland et al. | |
| 4,816,567 A | 3/1989 | Cabilly et al. | |
| 4,927,762 A | 5/1990 | Darfler | |
| 4,943,529 A | 7/1990 | Van de Berg et al. | |
| 5,122,469 A | 6/1992 | Mather et al. | |
| 5,225,539 A | 7/1993 | Winter | |
| 5,264,365 A | 11/1993 | Georgiou et al. | |
| 5,508,192 A | 4/1996 | Georgiou et al. | |
| 5,534,615 A | 7/1996 | Baker et al. | |
| 5,545,807 A | 8/1996 | Surani et al. | |
| 5,558,564 A * | 9/1996 | Ascalon | 451/66 |
| 5,589,369 A | 12/1996 | Seidman et al. | |
| 5,591,669 A | 1/1997 | Krimpenfort et al. | |
| 5,639,635 A | 6/1997 | Joly et al. | |
| 5,648,237 A | 7/1997 | Carter | |
| 5,693,761 A | 12/1997 | Queen et al. | |
| 5,693,762 A * | 12/1997 | Queen et al. | 530/387.3 |
| 5,747,662 A | 5/1998 | Simmons et al. | |
| 5,821,337 A | 10/1998 | Carter et al. | |
| 5,840,523 A | 11/1998 | Simmons et al. | |
| 5,859,205 A | 1/1999 | Adair et al. | |
| 5,869,619 A | 2/1999 | Studnicka | |
| 6,027,888 A | 2/2000 | Georgiou et al. | |
| 6,075,181 A | 6/2000 | Kucherlapati et al. | |
| 6,083,715 A | 7/2000 | Georgiou et al. | |
| 6,172,213 B1 | 1/2001 | Lowman et al. | |
| 6,331,415 B1 | 12/2001 | Cabilly et al. | |
| 6,455,279 B1 | 9/2002 | Ambrosius et al. | |
| 6,479,284 B1 | 11/2002 | Marasco et al. | |
| 6,602,688 B1 | 8/2003 | Opper et al. | |
| 6,632,926 B1 | 10/2003 | Chen et al. | |
| 6,632,927 B2 | 10/2003 | Adair et al. | |
| 6,767,996 B1 | 7/2004 | Gorman et al. | |
| 6,800,738 B1 | 10/2004 | Carter et al. | |
| 6,881,557 B2 | 4/2005 | Foote | |
| 6,884,879 B1 * | 4/2005 | Baca et al. | 536/23.53 |
| 7,098,006 B1 | 8/2006 | Gorman et al. | |
| 2002/0032315 A1 | 3/2002 | Baca et al. | |
| 2002/0151682 A1 | 10/2002 | Athwal et al. | |
| 2002/0177170 A1 | 11/2002 | Luo et al. | |

(Continued)

FOREIGN PATENT DOCUMENTS

EP    0 139 383 A1    5/1985

(Continued)

OTHER PUBLICATIONS

Abaza et al, J of Protein Chemistry 11(5): 433-444, 1992.*
Rudikoff e tal, Proc Natl Acad Sci USA 79: 1979, 1983.*
Foote et al, J Mol Biol 224: 487-499, 1992.*
Kolbinger et al, Protein Engineering 6(8): 971-980, 1993.*
Wu et al, J Mol. Biol 294: 151-162, 1999.*
Anthony, "Metabolism in the methylotrophic yeasts", *The Biochemistry of Methylotrophs*, Chap. 10, pp. 269-292 (1982).
Bachmann, "Derivations and Genotypes of Some Mutant Derivatives of *Escherichia coli* K-12", *Escherichia coli and Salmonella typhimurium: Cellular and Molecular Biology, American Society for Microbiology*, 2:1190-1219 (ATCC Deposit No. 27,325) (1987).

(Continued)

*Primary Examiner*—Phuong Huynh
(74) *Attorney, Agent, or Firm*—Morrison & Foerster LLP

(57) ABSTRACT

The present invention provides methods for producing humanized antibodies and increasing the yield of antibodies and/or antigen binding fragments when produced in cell culture. In one aspect of the invention, at least one framework region amino acid residue of the variable domain is substituted by a corresponding amino acid from a variable domain consensus sequence subgroup that has the most sequence identity with the HVR1 and/or HVR2 amino acid sequence of the variable domain. In another aspect, an amino acid is placed at a position proximal to a cys residue that participates in an intrachain variable domain disulfide bond that corresponds to an amino acid found at that position in a variable domain consensus sequence subgroup that has the most sequence identity with the HVR1 and/or HVR2 amino acid sequenc of the variable domain.

70 Claims, 50 Drawing Sheets

FOREIGN PATENT DOCUMENTS

| | | |
|---|---|---|
| EP | 0 402 226 A1 | 12/1990 |
| EP | 0 183 070 B1 | 10/1991 |
| EP | 0 394 538 B1 | 10/1996 |
| EP | 0 549 581 B1 | 1/1997 |
| EP | 0 244 234 B2 | 11/2001 |
| WO | WO 87/00195 | 1/1987 |
| WO | WO 88/09344 | 12/1988 |
| WO | WO 90/03430 | 4/1990 |
| WO | WO 90/07861 | 7/1990 |
| WO | WO 91/00357 | 1/1991 |
| WO | WO 92/05274 | 4/1992 |
| WO | WO 93/17715 | 9/1993 |
| WO | WO 98/45331 | 10/1998 |
| WO | WO 98/45332 | 10/1998 |
| WO | WO 99/64460 | 12/1999 |
| WO | WO 00/29584 | 5/2000 |
| WO | WO 00/37502 | 6/2000 |
| WO | WO 01/32712 A2 | 5/2001 |
| WO | WO 01/70984 A2 | 9/2001 |
| WO | WO 01/83806 A1 | 11/2001 |
| WO | WO 02/056910 A1 | 7/2002 |
| WO | WO 02/061090 | 8/2002 |
| WO | WO 03/018771 A2 | 3/2003 |
| WO | WO 03/018771 A3 | 3/2003 |
| WO | WO 2004/006955 | 1/2004 |

OTHER PUBLICATIONS

Ballance et al., "Transformation of *Aspergillus nidulans* by the Orotidine-5'-Phosphate Decarboxylase Gene of *Neurospora crassa*", *Biochem. Biophys. Res. Commun.*, 112(1):284-289 (1983).
Barnes et al., "Methods for Growth of Cultured Cells in Serum-Free Medium", *Anal. Biochem.*, 102:255-270 (1980).
Bass et al., "Hormone Phage: An Enrichment Method for Variant Proteins with Altered Binding Properties", *Proteins*, 8:309-314 (1990).
Beach et al., "High-frequency transformation of the fission yeast *Schizosaccharomyces pombe*", *Nature*, 290:140-142 (1981).
Case et al., "Efficient Transformation of *Neurospora crassa* by Utilizing Hybrid Plasmid DNA", *Proc. Natl. Acad. Sci. USA*, 76:5259-5263 (1979).
Chen et al., "Selection and Analysis of an Optimized Anti-VEGF Antibody: Crystal Structure of an Affinity-matured Fab in Complex with Antigen", *J. Mol. Biol.*, 293:865-881 (1999).
Co et al., "Humanized antibodies for therapy", *Nature*, 351:501-502 (1991).
David et al., "Protein Iodination with Solid State Lactoperoxidase", *Biochemistry*, 13:1014-1021 (1974).
Fleer et al., "Stable Multicopy Vectors for High-Level Secretion of Recombinant Human Serum Albumin by *Kluyveromyces* Yeasts", *Bio/Technology*, 9:968-975 (1991).
Ham et al., "Media and Growth Requirements", *Meth. Enz.*, 58:44-93 (1979).
Hara et al., "Overproduction of Penicillin-Binding Protein 7 Suppresses Thermosensitive Growth Defect at Low Osmolarity due to an *spr* Mutation of *Escherichia coli*", *Microbiol. Drug Resistance*, 2:63-72 (1996).
Harris, "Therapeutic Monoclonals", *Biochem. Soc. Transactions*, 23:1035-1038 (1995).
Hunter et al., "Preparation of Iodine-131 Labelled Human Growth Hormone of High Specific Activity", *Nature*, 194:495-496 (1962).
Hurle et al., "Protein engineering techniques for antibody humanization", *Curr. Op. Biotech*, 5:428-433 (1994).
Jäger et al., "Folding and Assembly of an Antibody Fv Fragment, a Heterodimer Stabilized by Antigen", *J. Mol. Biol.*, 285:2005-2019 (1999).
Joly et al., "Overexpression of *Escherichia coli* oxidoreductases increases recombinant insulin-like growth factor-I accumulation", *Proc. Natl. Acad. Sci. USA*, 95:2773-2777 (1998).
Kabat et al., "Sequence of Proteins of Immunological Interest", *National Institute of Health* (4th Ed.) pp. 41-42, 167-178 (1991).

Kabat et al., "Sequence of Proteins of Immunological Interest", *National Institute of Health, Public Health Service* (5th Ed.), pp. 647-669 (1991).
Kelly et al., "Transformation of *Aspergillus niger* by the *amdS* gene of *Aspergillus nidulans*", *EMBO J.*, 4:475-479 (1985).
Kikuchi et al., "The nucleotide sequence of the promoter and the amino-terminal region of alkaline phosphatase structural gene (phoA) of *Escherichia coli*", *Nucleic Acids Res.*, 9(21):5671-5678 (1981).
Knappik et al., "Engineered turns of a recombinant antibody improve its in vivo folding", *Protein Engineering*, 8(1):81-89 (1995).
Kostelny et al., "Formation of a Bispecific Antibody by the Use of Leucine Zippers", *J. Immunol.*, 148:1547-1553 (1992).
Li et al., "Influences of amino acid sequences in FRI region on binding activity of the scFv and Fab of an antibody to human gastric cancer cells", *Immunology Letters*, 71:157-165 (2000).
Lindmark et al., "Binding of Immunoglobulins to Protein A and Immunoglobulin Levels in Mammalian Sera", *J. Immunol. Meth.*, 62:1-13 (1983).
Louvencourt et al., "Transformation of *Kluyveromyces lactis* by Killer Plasmid DNA", *J. Bacteriol.*, 154(2):737-742 (1983).
Mather, "Establishment and Characterization of Two Distinct Mouse Testicular Epithelial Cell Lines", *Biol Reprod.*, 23:243-252 (1980).
Milstein et al., "Hybrid hybridomas and their use in immunohistochemistry", *Nature*, 305:537-540 (1983).
Muller et al., "VEGF and the Fab fragment of a humanized neutralizing antibody: crystal structure of the complex at 2.4 Å resolution and mutational analysis of the interface", *Structure*, 6:1153-1167 (1998).
Nygren, "Conjugation of Horseradish Peroxidase to Fab Fragments with Different Homobifunctional and Heterobifunctional Cross-Linking Reagents", *Histochem. and Cytochem.*, 30:407-412 (1982).
O'Sullivan et al., "Methods for the Preparation of Enzyme—Antibody Conjugates for USe in Enzyme Immunoassay", *Methods in Enzumology*, 73:147-166 (1981).
Pain et al., "Preparation of Protein A-Peroxidase Monoconjugate Using a Heterobifunctional Reagent, and its Use in Enzyme Immunoassays", *J. Immunol. Methods*, 40:219-230 (1981).
Picken et al., "Nucleotide Sequence of the Gene for Heat-Stable Enterotoxin II of *Escherichia coli*", *Infect. Immun.*, 42(1):269-275 (1983).
Roguska et al., "A comparison of two murine monoclonal antibodies humanized by CDR-grafting and variable domain resurfacing", *Protein Engineering*, 9(10):895-904 (1996).
Scholtissek et al., "A cloning cartridge of λ $t_o$ terminator", *Nucleic Acids Res.*, 15(7):3185 (1987).
Simmons et al., "Expression of full-length immunoglobulins in *Escherichia coli*: rapid and efficient production of aglycosylated antibodies", *J. Immunol. Methods*, 263:133-147 (2002).
Sreekrishna et al., "High level expression of heterologous proteins in methylotrophic yeast *Pichia pastoris*", *J. Basic Microbiol.*, 28(4):265-278 (1988).
Sutcliffe, "Complete Nucleotide Sequence of the *Escherichia coli* Plasmid pBR322", *DNA: Replication and Recombination, Cold Spring Harbor Symp. Quant. Biol.*, 43:77-90 (1979).
Tilburn et al., "Transformation by integration in *Aspergillus nidulans*", *Gene*, 26:205-221 (1983).
Urlaub et al., "Isolation of Chinese Hamster Cell Mutants Deficient in Dihydrofolate Reductase Activity", *Proc. Natl. Acad. Sci. USA*, 77(7):4216-4220 (1980).
Van den Berg et al., "*Kluyveromyces* as a Host Heterologous Gene Expression : Expression and Secretion of Prochymosin", *Bio/Technology*, 8:135-139 (1990).
Vaswani et al., "Humanized antibodies as potential therapeutic drugs", *Ann. Allergy, Asthma & Immunol.*, 81:105-119 (1998).
Wöm et al., "Mutual Stabilization of $V_L$ and $V_H$ in Single-Chain Antibody Fragments, Investigated with Mutants Engineered for Stability", *Biochemistry*, 37:13120-13127 (1998).
Yanofsky et la., "The complete nucleotide sequence of the tryptophan operan of *Escherichia coli*", *Nucleic Acids Res.*, 9:6647-6668 (1981).
Yelton et al., "Transformation of *Aspergillus nidulans* by using a *trpC* plasmid", *Proc. Natl. Acad. Sci. USA*, 81:1470-1474 (1984).

Arie et al., "Chaperone function of FkpA, a heat shock prolyl isomerase, in the periplasm of *Escherichia coli*", *Molecular Microbiology*, 39(1):199-210 (2001).

Arndt et al., "Factors Influencing the Dimer to Monomer Transition of an Antibody Single-Chain Fv Fragment", *Biochemistry*, 37:12918-12926 (1998).

Barbas et al., "In vitro evolution of a neutralizing human antibody to human immunodeficiency virus type 1 to enhance affinity and broaden strain cross-reactivity", *Proc. Nat. Acad. Sci. USA*, 91:3809-3813 (1994).

Benhar et al., "Identification of Residues that Stabilize the Single-Chain Fv of Monoclonal Antibodies B3", *The Journal of Biological Chemistry*, 270(40):23373-23380 (1995).

Bothmann et al., The Periplasmic *Escherichia coli* Peptidylprolyl cis,trans-Isomerase FkpA, *Journal of Biological Chemistry*, 275(22):17100-17105 (2000).

Carter et al., "Humanization of an anti-p185$^{HER2}$ antibody for human cancer therapy", *Proc. Natl. Acad. Sci. USA*, 89:4285-4289 (1992).

Chen et al., "Chaperone Activity of DsbC", *Journal of Biological Chemistry*, 274(28):19601-19605 (1999).

Chothia et al., "Domain Association in Immunoglobulin Molecules", *J. Mol. Biol.*, 186:651-663 (1985).

Chothia et al., "Canonical Structures for the Hypervariable Regions", *J. Mol. Biol.*, 196:901-917 (1987).

Dall'Acqua, W. et al., "Antibody Engineering", *Current Opinion in Structural Biology*, 8:443-450 (1998).

de Haard et al., "Absolute conservation of residue 6 of immunoglobulin heavy chain variable regions of class IIA is required for correct folding", *Prot. Eng.*, 11(12):1267-1276 (1998).

Dumoulin, M. et al., "Single-domain antibody fragments with high conformational stability", *Nat. Struct. Biol.*, 11:500-515 (2002).

Forsberg, G. et al., "Identification of Framework Residues in a Secreted Recombinatnt Antibody Fragment that Control Production Level and Localization in *Escherichia coli*", *J. Biol. Chem.*, 272:12430-12436 (1997).

Hawkins et al., "Selection of Phage Antibodies by Binding Affinity: Mimicking Affinity Maturation", *J. Mol. Biol.*, 226:889-896 (1992).

Honneger et al., "The influence of the Buried Glutamine or Glutamate Residue in Position 6 on the Structure of Immunoglobulin Variable Domains", *J. Mol. Biol.*, 309:687-699 (2001).

Jackson et al., "In Vitro Antibody Maturation: Improvement of a High Affinity, Neutralizing Antibody Against IL-1β", *J. Immunol.*, 154(7):3310-3319 (1995).

Jones et al., "Replacing the complementarity-determining regions in a human antibody with those from a mouse", *Nature*, 321:522-525 (1986).

Jung, S. et al., "Selection for Improved Protein Stability by Phage Display", *J. Mol. Biol.*, 294:163-180 (1999).

Jung et al., "The Importance of Framework Residues H6, H7 and H10 in Antibody Heavy Chains: Experimental Evidence for a New Structural Subclassification of Antibody $V_H$ Domains", *J. Mol. Biol.*, 309:701-716 (2001).

Knappik, A. et al., "Fully Synthetic Human Combinatorial Antibody Libraries (HuCAL) Based on Modular Consensus Frameworks and CDRs Randomized with Trinucleotides", *J. Mol. Biol.*, 296:57-86 (2000).

Ladner, R. et al., "Novel frameworks as a source of high-affinity ligands", *Curr. Opin. Biotechnol.*, 12:406-410 (2001).

Langedijk et al., "The Nature of Antibody Heavy Chain Residue H6 Strongly Influences the Stability of a $V_H$ Domain Lacking the Disulfide Bridge", *J. Mol. Biol.*, 283:95-110 (1998).

Marks et al., "By-Passing Immunization: Building High Affinity Human Antibodies by Chain Shuffling", *Bio/Technology*, 10:779-783 (1992).

Miller, "Protein-Protein Recognition and the Association of Immunoglobulin Constant Domains", *J. Mol. Biol.*, 216:965-973 (1990).

Morrison et al., "Chimeric human antibody molecules: Mouse antigen-binding domains with human constant region dimmers", *Proc. Natl. Acad. Sci USA*, 81(21):6851-6855 (1984).

Muller et al., :VEGF and the Fab fragment of a humanized neutralizing antibody: cyrstal structure of the complex at 2.4 Å resolution and mutational analysis of the interface, *Structure*, 6:1153-1167 (1998).

Nieba et al., "Disrupting the hydrophobic patches at the antibody variable/constant domain interface: improved in vivo folding and physical characterization of an engineered scFv fragment", *Protein Engineerig*, 10(4):435-444 (1997).

Novotny et al., "Structural invariants of antigen binding: Comparison of immunoglobulin $V_L$-$V_H$ and $V_L$-$V_L$ domain dimmers", *Proc. Natl. Acad. Sci USA.*, 82:4592-4596 (1985).

Padlan et al., "Antibody Fab Assembly: The Interface Residues Between CH1 and CL", *Mol. Immunol.*, 23(9): 951-960 (1986).

Plückthun, A., "Antibodies from *Escherichia coli*", *The Pharmacology of Monoclonal Antibodies*, vol. 113, Rosenburg and Moored eds. Springer-Verlag, New York, pp. 269-315 (1994).

Presta, "Antibody Engineering", *Curr. Op. Struct. Biol.*, 2:593-596 (1992).

Presta et al., "Humanization of an Anti-Vascular Endothelial Growth Factor Monoclonal Antibody for the Therapy of Solid Tumors and Other Disorders", *Cancer Res.*, 57:4593-4599 (1997).

Proba et al,, "Functional antibody single-chain fragments from the cytoplasm of *Escherichia coli*: influence of thioredoxin reductase (TrxB)", *Gene*, 159:203-207 (1995).

Ramm et al., "The Periplasmic *Escherichia coli* Peptidylprolyl cis,trans-Isomerase FkpA", *J. Mol. Biol.*, 275(22):17106-17113 (2000).

Ramm et al., "Removal of the Conserved Disulfide Bridges from the scFv Fragment of an Antibody: Effects on Folding Kinetics and Aggregation", *J. Mol. Biol.*, 290:535-546 (1999).

Riechmann et al., "Reshaping human antibodies for therapy", *Nature*, 332:323-327 (1988).

Schier et al., "Identification of functional and structural amino-acid residues by parsimonious mutagenesis", *Gene*, 169:147-155 (1995).

Shields et al., "Inhibition of Allergic Reactions with Antibodies to IgE", *Int. Arch. Allergy Immunol.*, 107:308-312 (1995).

Simmons et al., "Translational level is a critical factor for the secretion of heterologous proteins in *Escherichia coli*", *Nature Biotechnology*, 14:629-634 (1996).

Sims et al., "A Humanized CD18 Antibody Can Block Function without Cell Destruction", *J. Immunol.*, 151:2296-2308 (1993).

Verhoeyen et al., "Reshaping Human Antibodies: Grafting an Antilysozyme Activity", *Science*, 239:1534-1536 (1988).

Wall et al., "The hierarchy of mutations influencing the folding of antibody domains in *Escherichia coli*", *Protein Engineering*, 12(7):605-611 (1999).

Worn et al., "Stability Engineering of Antibody Single-chain Fv Fragments", *J. Mol. Biol.*, 305:989-1010 (2001).

Yelton et al., "Affinity Maturation of the BR96 Anti-Carcinoma Antibody by Codon-Based Mutagenesis", *J. Immunol.*, 155:1994-2004 (1995).

Zapata, G. et al., "Engineering linear F(ab')$_2$ fragments for efficient production in *Escherichia coli* and enhanced antiproliferative activity", *Protein Eng.*, 8(10):1057-1062 (1995).

Zhu et al., "Remodeling domain inerfaces to enhance heterodimer formation", *Protein Science*, 6:781-788 (1997).

Tan et al., "Superhumanized Antibodies: Reduction of Immunogenic Potential by Complementarity-Determining Region Grafting with Human Germline Sequences: Application to an Anti-CD28", *The Journal of Immunology*, 169:1119-1125 (2002).

Jin, N. et al., "Gene Therapy of Murine Solid Tumors with T Cells Transduced with a Retroviral Vascular Endothelial Growth Factor-Immunotoxin Target Gene," *Human Gene Therapy*, vol. 13, pp. 497-508 (Mar. 1, 2002).

Lustgarten, J. et al., "Prolonged Inhibition of IgE Production in Mice Following Treatment with an IgE-Specific Immunotoxin", *Molecular Immunology*, vol. 33, No. 3, pp. 245-251 (1996).

CDR Residues, *J. Mol. Biol.*, 294:151-162 (1999).

Ye et al., "Gene Synthesis and Expression in *E. coli* for PUMP, a Human Matrix Metalloproteinase", *Biochem. Biophys. Res. Comm.*, 186(1):143-149 (1992).

Carter et al., "High Level *Escherichia coli* Expression and Production of a Bivalent Humanized Antibody Fragment", *Bio/Technology*, 10:163-167 (1992).

Chomeczynski et al., "Single-Step Method of RNA Isolation by Acid Guanidinium Thiocyanate-Phenol-Chloroform Extraction", *Anal. Biochem.*, 162:156-159 (1987).

Chothia et al, "Structural Repertoire of the Human VH Segments", *J. Mol. Biol.*, 227:799-817 (1992).

Foote et al., "Antibody Residues Affecting Conformation of the Hypervariable Loops", *J. Mol. Biol.*, 224:487-499 (1992).

Hampe et al., "A novel monoclonal antibody specific for the N-terminal end of GAD65", *Journal of Neuroimmunology*, 113:63-71 (2001).

Hansen et al., "Monoclonal Antibodies Identifying a Novel T Cell Antigen and Ia Antigens of Human Lymphocytes", *Immunogenetics*, 10:247-260 (1980).

Henikoff et al., "Amino acid substitution matrices from protein blocks", *Proc. Natl. Acad. Sci. USA*, 89:10915-10919 (1992).

Jin et al., "High Resolution Functional Analysis of Antibody-Antigen Interactions", *J. Mol. Biol.*, 226:851-865 (1992).

Jonsson et al., "Real-Time Biospecific Interaction Analysis Using Surface Plasmon Resonance and a Sensor Chip Technology", *BioTechniques*, 11:620-627 (1991).

Licea et al., "FAB Fragments of the Monoclonal Antibody BCF2 are Capable of Neutralizing the Whole Soluble Venom from the Scorpion *Centruroides Noxius* Hoffmann", *Toxicon*, 34(8):843-847 (1996).

MacCallum et al. "Antibody-antigen Interactions: Contact Analysis and Binding Site Topography", *J. Mol. Biol.*, 262:732-745 (1996).

Martin et al., "Structural Families in Loops of Homologous Proteins: Automatic Classification, Modelling and Application to Antibodies", *J. Mol. Biol.*, 263:800-815 (263), 1996.

Mhashilkar et al., "Inhibition of Human Immunodeficiency Virus Type I Replication in Vitro in Acutely and Persistently Infected Human CDR4[4] Mononuclear Cells Expressing Murine and Humanized Anti-Human Immunodeficiency Virus Type I Tat Single-Chain Variable Fragment Intrabodies", *Human Gene Therapy*, 10:1453-1467 (1999).

Morea et al., "Antibody Modeling: Implications for Engineering and Design", *Methods*, 20:267-279 (2000).

Padlan, E.A., "A Possible Procedure for Reducing the Immunogenicity of Antibody Variable Domains while Preserving their Ligand-Binding Properties", *Mol. Immunol.*, 28(4):489-498 (1991).

Padlan et al., "Identification of specificity-determining residues in antibodies", *FASEB J.*, 9:133-139 (1995).

Rosok et al., "A Combinatorial Library Strategy for the Rapid Humanization of Anticarcinoma BR96 Fab", *The Journal of Biological Chemistry*, 271(37):22611-22618 (1996).

Rudikoff et al., "Single amino acid substitution altering antigen-binding specificity", *Proc. Natl. Acad. Sci. USA*, 79:1979-1983 (1982).

Rutgeerts et al., "Efficacy and Safety of Retreatment With Anti-Tumor Necrosis Factor Antibody (Infliximab) to Maintain Remission in Crohn's Disease", *Gastroenterology*, 117:761-769 (1999).

Selisko et al., "Antibody BCF2 Against Scorpion Toxin Cn2 From *Centruroides noxius* Hoffmann: Primary Structure and Three-Dimensional Model as Free Fv Fragment and Complexed With Its Antigen", *Proteins: Structure, Function and Genetics*, 37:130-143 (1999).

Tamara et al., "Structural Correlates of an Anticarcinoma Antibody: Identification of Specificity-Determining Residues (SDRs) and Development of a Minimally Immunogenic Antibody Variant by Retention of SDRs Only", *The Journal of Immunology*, 164:1432-1441 (2000).

Tan et al., "Superhumanized Antibodies:Reduction of Immunogenic Potential by Complementarity-Determining Region Grafting with Human Germline Sequences :Application to Anti-CD28", *The Journal of Immunology*, 169:1119-1125 (2002).

Tomlinson et al., "The Structural Repertoire of the Human Vk Domain", *EMBO J.*, 14(18):4628-4638 (1995).

Tramontano et al., *J. Mol. Biol.*, 215:175-182 (1990).

Wu et al., "An Analysis of the Sequences of the Variable Regions of Bence Jones Proteins and Myeloma Light Chains and Their Implications for Antibody Complementarity", *J. Exp. Med.*, 132:211-250 (1970).

Wu et al., Humanization of a Murine Monoclonal Antibody by Simultaneous Optimization of Framework and.

Non-Final Office Action for U.S. Appl. No. 11/928,201, mailed on Jun. 12, 2009, 14 pages.

Wiens et al., J Immunol (2001) 167:2179-2186.

Xiang et al., J Mol Biol (1995) 253:385-390.

* cited by examiner

FIG. 3A
FIG. 3B
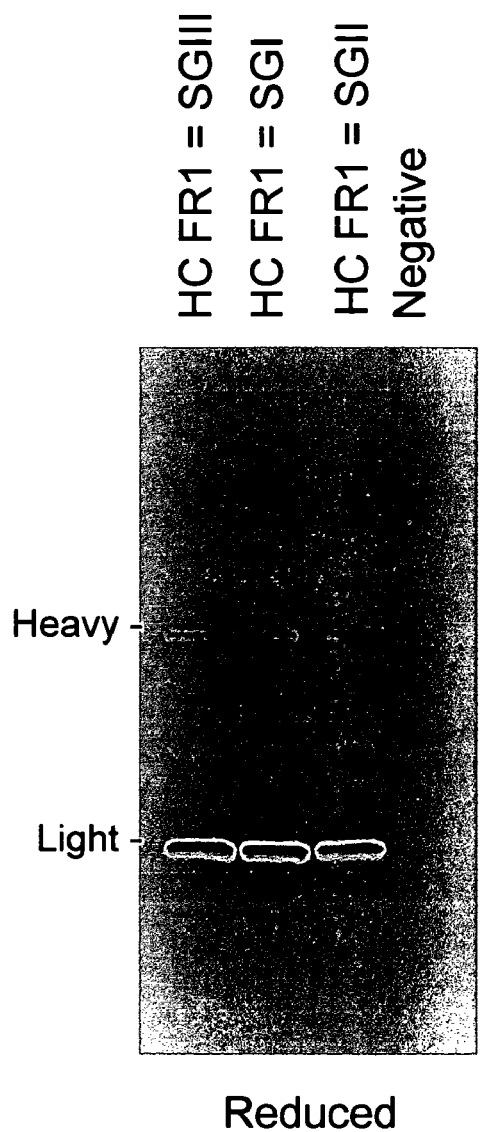
Reduced
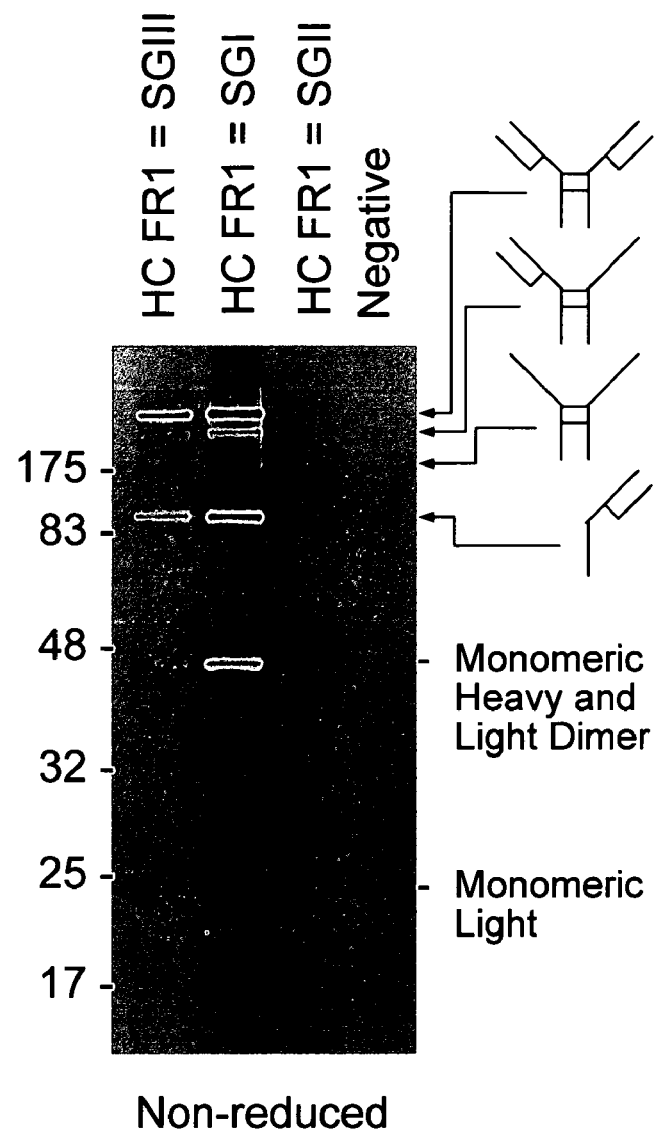
Non-reduced

αVEGF (YO317) Reduced

αVEGF (YO317) Non-reduced

*Includes an A24V change as part of humanization.

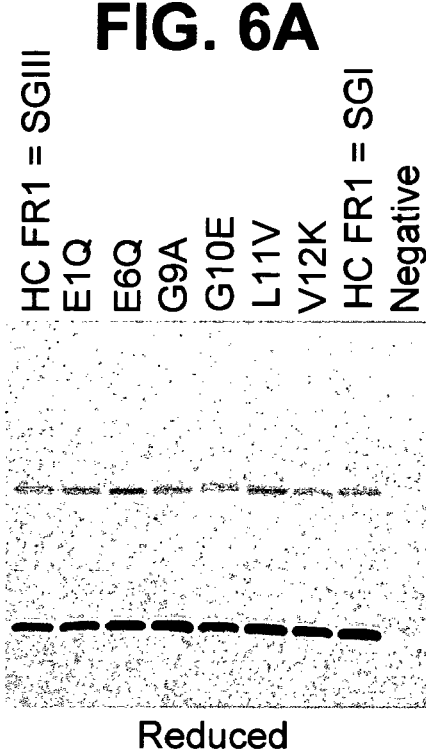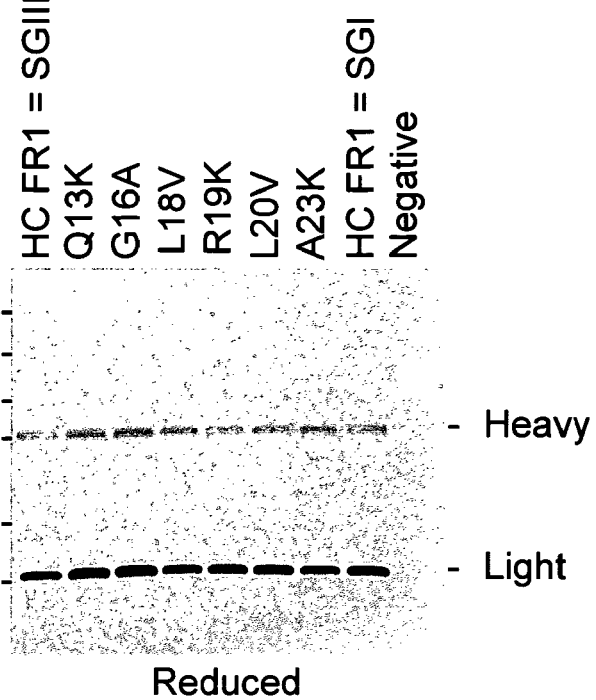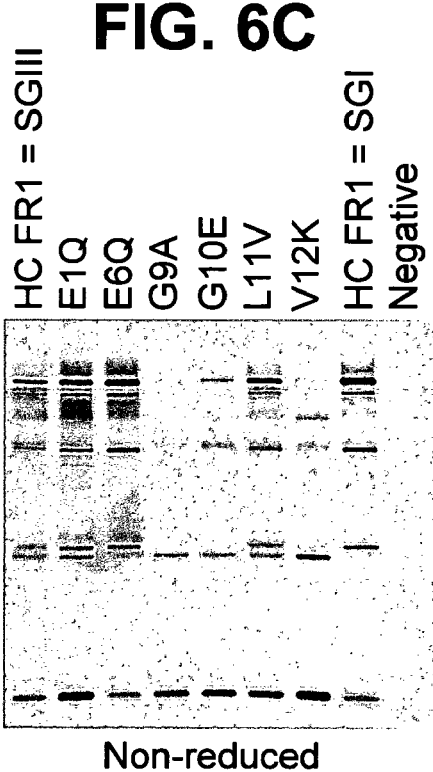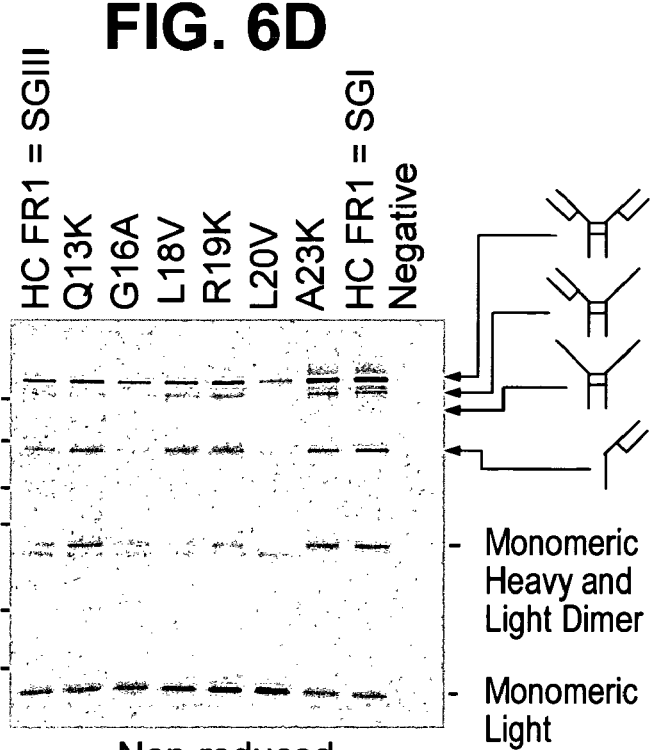

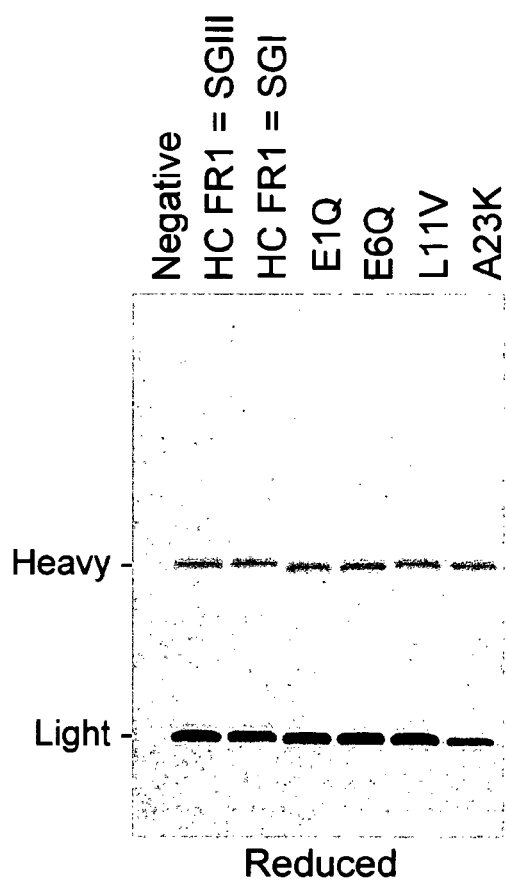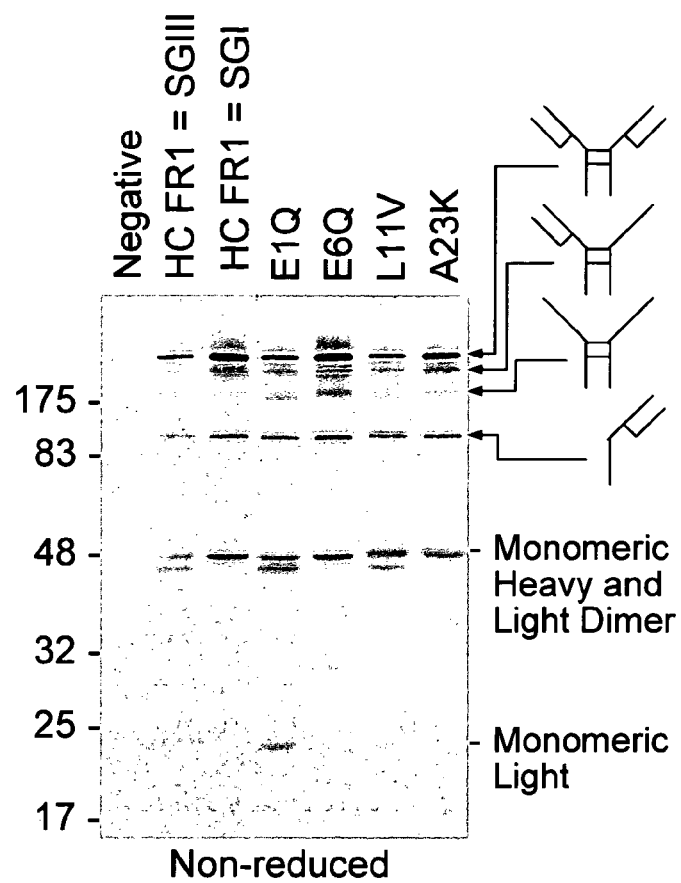

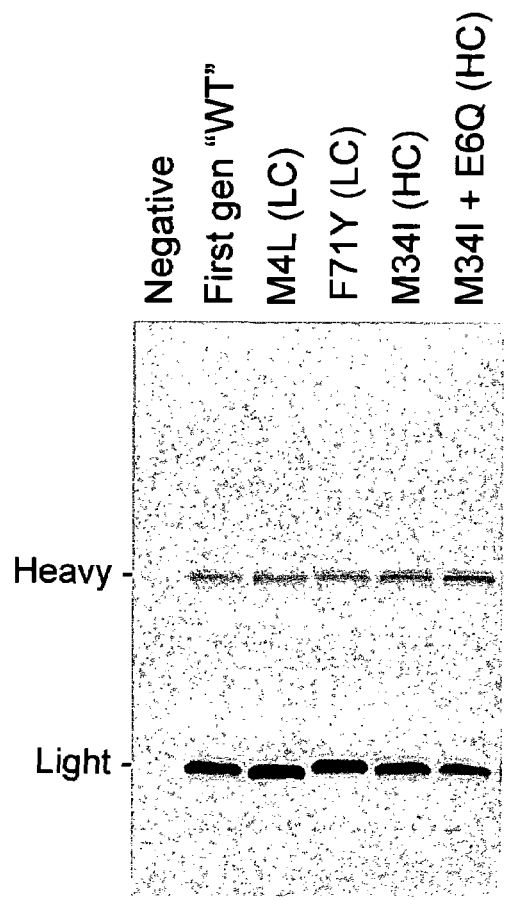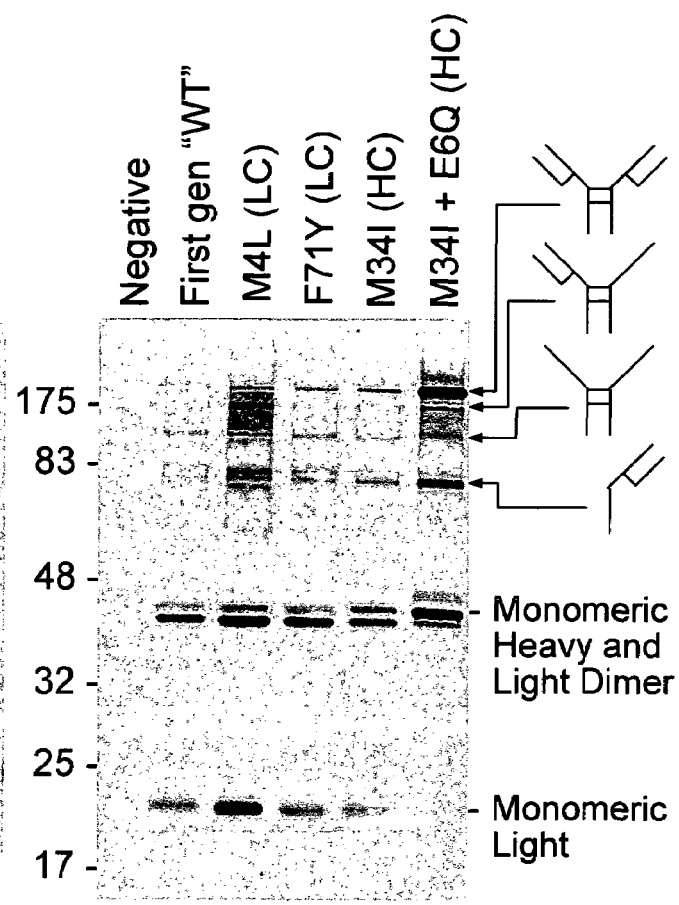

Reduced

Non-reduced

Reduced

Non-reduced

Coomassie Stain
Soluble Fraction

αFc Blot
Soluble Fraction

\* Except for residues changed during humanization.

Coomassie Stain
Soluble Fraction xFab Blot
Whole Cell
Lysates

FIG. 15A

```
GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

GAACTGTGTG CGCAGGTAGA AGCTTTGGAG ATTATCGTCA CTGCAATGCT TCGCAAATAG GCCAAAATG ACCAACAGCG GTTGATTGAT CAGGTAGAGG
CTTGACACAC GCGTCCATCT TCGAAACCTC TAATAGCAGT GACGTTACGA AGCGTTTATC CGGTTTTAC TGGTTGTCGC CAACTAACTA GTCCATCTCC

GGGCGCTGTA CGAGGTAAAG CCCGATGCCA CGACGATACG GAGCTGCTGC GCGATTACGT AAAGAAGTTA TTTCTTCAAT AACTTCGTAG GAGCAGTCAT
CCCGCGACAT GCTCCATTTC GGGCTACGGT GCTGCTATGC CTCGACGACG CGCTAATGCA TTTCTTCAAT AAAGAAGTTA TTGAAGCATC CTCGTCAGTA

AAAAGTTAAT CTTTTCAACA GCTGTCATAA AGTTGTCACG GCCGAGACTT ATAGTCGCTT TGTTTTTATT TTTTAATGTA TTTGTAACTA GTACGCAAGT
TTTTCAATTA GAAAAGTTGT CGACAGTATT TCAACAGTGC CGGCTCTGAA TATCAGCGAA ACAAAAATAA AAAATTACAT AAACATTGAT CATGCGTTCA

TCACGTAAAA AGGGTATCTA GAATTATGAA GCATTCTTTC GCGATAGGGT GCCTCTGTGG CTCCCCTGAG GTTCGTTTTT TCTATTGCTA CAAACGCGTA CGCTGATATC
AGTGCATTTT TCCCATAGAT CTTAATACTT CGTAAGAAG CGCTATCCCA CGGAGACAGG GAGGGGACTC CAAGCAAAA AGATAACGAT GTTTGCGCAT GCGACTATAG
              M  K  K  N  I    A  F  L  L    A  S  M    F  V  F    S  I  A  T    N  A  Y    A  D  I
             ^STII Signal TIR -1                                                                  ^anti-VEGF Light Chain^

CAGTTGACCC AGTCCCCGAG CTCCCTGTGG GCCTCTGTGG GCGATAGGGT CACCATCACC TCTCTCCACT CTTCACCTCC TTCTCGCTTC GTTCTGGGAC TTAAACTGGT
GTCAACTGGG TCAGGGGCTC GAGGGACACC CGGAGACAGG CGCTATCCCA GTGGTAGTGG AGAGAGGTGA GAAGTGGAGG AAGAGCGAAG AGACTAGCC CAAGACCCTG AATTTGACCA
Q  L  T  Q    S  P  S    S  L  S    A  S  V  G    D  R  V    T  I  T    C  S  A  S    Q  D  I  S    N  Y    L  N  W  Y
                                                                         ^variable light (VL) cys ATCAACAGAA ACCAGGAAAA GCTCCGAAAG TACTGATTTA GCCAGAAGAC TTCGCAACTT ATTACTGTCA ACAGTATAGC ATTACTGATAGG CCGTAGAGCT CCT
TAGTTGTCTT TGGTCCTTTT CGAGGGCTTTC ATGACTAAAT CGGTCTTCTG AAGCGTTGAA TAATGACAGT TGTCATATCG TAATGACTA AGACCTAGCC ACAGGGTACC
Q  Q  K    P  G  K    A  P  K  V    L  I  Y    F  T  S    S  L  H  S    G  V  P    S  R  F    S  G  S  G    S  G  T GGATTTCACT CTGACCATCA GCAGTCTGCA GCCAGAAGAC CGGTCTTCTG AAGCGTTGAA ACAGTATAGC ATTACTGATA TGTCATATCG TAATGACT AGACCTAGCC ACAGGGTACC
CCTAAAGTGA GACTGGTAGT CGTCAGACGT CGGTCTTCTG GCCAGAAGAC TTCGCAACTT TGTCATATCG TAATGACTAT ACAGTATAGC ATTACTGATA TCTGGATCCG GGTCCCCATGG
D  F  T    L  T  I  S    S  L  Q    P  E  D    F  A  T  Y    Y  C  Q    Q  Y  S    T  V  P  W    T  F  G    Q  G  T AAGGTGGAGA TCAAACGAAC TGTGGCTGCA CCATCTGTCT TCATCTTCCC GCCATCTGAT GAGCAGTTGA AATCTGGAAC TGCTTCTGTT GTGTGCCTGC
TTCCACCTCT AGTTTGCTTG ACACCGACGT AGTAGAACAGA AGTAGAAGGG CGGTAGACTA CTCGTCAACT TTAGACCTTG ACGAAGACAA CACACGGACG
K  V  E  I    K  R  T    V  A  A    P  S  V  F    I  F  P    P  S  D    E  Q  L  K    S  G  T    A  S  V    V  C  L  L
                                                                         ^Constant Light cys^
```

FIG. 15B

```
TGAATAACTT CTATCCCAGA GAGGCCAAAG TACAGTGGAA GGTGATAAC GCCCTCCAAT CGGGTAACTC CCAGGAGAGT GTCACAGAGC AGGACAGCAA
ACTTATTGAA GATAGGGTCT CTCCGGTTTC ATGTCACCTT CCACTATTG CGGGAGGTTA GCCCATTGAG GGTCCTCTCA CAGTGTCTCG TCCTGTCGTT
 N  N  F  Y  P  R  E  A  K  V  Q  W  K  V  D  N  A  L  Q  S  G  N  S  Q  E  S  V  T  E  Q  D  S  K

GGACAGCACC TACAGCCTCA GCAGCACCCT GACGCTGAGC CGCAGACTCG AAAGCAGACT ACGAGAAACA CAAAGTCTAC GCCTGCGAAG GGCCTGAGC
CCTGTCGTGG ATGTCGGAGT CGTCGTGGGA CTGCGACTCG GCGTCTGAGC TTTCGTCTGA TGCTCTTTGT GTTTCAGATG CGGACGCTTC CCGGACTCG
 D  S  T  Y  S  L  S  S  T  L  T  L  S  K  A  D  Y  E  K  H  K  V  Y  A  C  E  V  T  H  Q  G  L  S
                                                                           ^Constant Light cys TCGCCCGTCA CAAAGAGCTT CAACAGGGGA GAGTGTTAAT TAAATCCTCT ACGGCCGACG CATCGTGGCG AGCTCGGTAC CCGGGGATCT AGGCCTAACG
AGCGGGCAGT GTTTCTCGAA GTTGTCCCCT CTCACAATTA ATTTAGGAGA TGCCGGCTGC GTAGCACCGC TCGAGCCATG GGCCCCTAGA TCCGGATTGC
 S  P  V  T  K  S  F  N  R  G  E  C  O
                        ^cys to bind heavy        start lambda t0 terminator CTCGGTTGCC GCCCGGCGTT TTTTATTGTT GCCGACGCGC ATCTCGAATG AACTGTGTGC GCAGGTAGAA GCTTTGGAGA TTATGTCAC TGCAATGCTT
GAGCCAACGG CGGGCCGCAA AAAATAACAA CGGTGCGCG TAGAGCTTAC TTGACACACG CGTCCATCTT CGAAACCTCT AATAGCAGTG ACGTTACGAA
^end lambda t0 terminator CGCAATATGG CGCAAAATGA CCAACAGCGG TTGATTGATC AGGTAGAGGG GGGCTGTAC GAGGTAAAGC CTCCATTTCG CCGATGCCAG CATTCCTGAC GACGATACGG
GCGTTATACC GCGTTTTACT GGTTGTCGCC AACTAACTAG TCCAATCCCC CCCGACATG CTCCATTTCG GGCTACGGTC GTAAGGACTG CTGCTATGCC AGCTGCTGCG CGATTACGTA AAGAAGTTAT TGAAGCATCC TCGTCAGTAA AAAGTTAATC TTTTCAACAG CTGTCATAAA GTTGTCACGG CCGAGACTTA
TCGACGACGC GCTAATGCAT TTCTTCAATA ACTTCGTAGG AGCAGTCATT AAAGTTGTC GACAGTATTT CAACAGTGCC GGCTCTGAAT TAGTCGCTTT GTTTTTATTT TTTAAATGTAT TTGTAACTAG TACGCAAGTT CACGTAAAAA GGGTATCTAG AATTATGAAG AAGATATCG CATTTCTTCT
ATCAGCGAAA CAAAATAAA AAATTACATA AACATTGATC ATGCATTCAA GTGCATTTTT CCCATAGATC TTAATACTTC TTCTTATAGC GTAAAGAAGA
                                                                           M  K  K  N  I  A  F  L  L
                                                                           ^STII Signal TIR-1

TGCATCCTATG TTCGTTTTTT CTATTGCTAC AAACGCGGTAC GCTGAGGTTC AGCTGGTGGA GTCTGGCGGT GGCCTGGTGC AGCCAGGGGG CTCACTCCGT
ACGTAGATAC AAGCAAAAAA GATAACGATG TTTGCCGATG CGACTCCAAG TCGACCACCT CAGACCGCCA CCGGACCACG TCGGTCCCCC GAGTGAGGCA
 A  S  M  F  V  F  S  I  A  T  N  A  Y  A  E  V  Q  L  V  E  S  G  G  G  L  V  Q  P  G  G  S  L  R
                         ^anti-VEGF heavy chain (VNERK version)

TTGTCCTGTG CAGCTTCTGG CTATACCTTC ACCAACTATG GTATAAACTG GTTCCGTCAG GCCCCGGGTA AGGGCCTGGA ATGGGTTGGA TGGATTAACA
AACAGGACAC GTCGAAGACC GATATGGAAG TGGTTGATAC CATATTTGAC CAAGGCAGTC CGGGGCCAT TCCCGGACCT TACCCAACCT ACCTAATTGT
 L  S  C  A  A  S  G  Y  T  F  T  N  Y  G  I  N  W  V  R  Q  A  P  G  K  G  L  E  W  V  G  W  I  N  T
 ^Variable Heavy (VH) Cys CCTATACCGG TGAACCGACC TATGCCGACC ATTTCAAACG TCGTTTCACT TTTTCTTTAG ACACCTCCAA AAGCACAGCA TACCTGCAGA TGAACAGCCT
GGATATGGCC ACTTGGCTGG ATACGACGCC TAAAGTTTGC AGCAAAGTGA AAAAGAAATC TGTGGAGGTT TTCGTGTCGT ATGGACGTCT ACTTGTCGGA
 Y  T  G  E  P  T  Y  A  A  D  F  K  R  R  F  T  F  S  L  D  T  S  K  S  T  A  Y  L  Q  M  N  S  L
```

FIG. 15C

```
GCGGCGCTGAG GACACTGCCG TCTATTACTG TGCAAAGTAC CCGCACTATT ATGTGAACGA GCGGAGAGAG CACTGGTATT TCGACGTCTG GGGTCAAGGA
CGGCGGACTC CTGTGACGGC AGATAATGAC ACGTTTCATG GGCTGATAA TACACTTGCT CGCCTTCTCG GTGACCATAA AGCTGCAGAC CCCAGTTCCT
 R  A  E     D  T  A  V     Y  Y  C     A  K  Y     P  H  Y  Y     V  N  E     R  K  S     H  W  Y  F     D  V  W     G  Q  Q
                            ^VH cys ACCCTGGTCA CCGTCTCCTC GGCCTCCACC AAGGGCCCAT CGGTCTTCCC CCTGGCACCC TCCTCCAAGA GCACCTCTGG GGGCACAGCG GCCCTGGGCT
TGGGACCAGT GGCAGAGGAG CCGGAGGTGG TTCCCGGGTA GCCAGAAGGG GGACCGTGGG AGGAGGTTCT CGTGGAGACC CCCGTGTCGC CGGGACCCGA
 T  L  V  T     V  S  S     A  S  T     K  G  P  S     V  F  P     L  A  P     S  S  K  S     T  S  G     G  T  A     A  L  G  C
                                                                                                               Constant Heavy 1 (CH1) cys^

GCCTGTGTCAA GGACTACTTC CCCGAACCGG TGACGGTGTC GTGGAACTCA GGCGCCCTGA CCAGCGGCGT GCACACCTTC CCGGCTGTCC TACAGTCCTC
CGGACACAGTT CCTGATGAAG GGGCTTGGCC ACTGCCACAG CACCTTGAGT CCGCGGGACT GGTCGCCGCA CGTGTGGAAG GGCCGACAGG ATGTCAGGAG
 L  V  K     D  Y  F     P  E  P  V     T  V  S     W  N  S     G  A  L  T     S  G  V     H  T  F     P  A  V  L     Q  S  S

AGGACTCTAC TCCCTCAGCA GCGTGGTGAC TGTGCCCTCT AGCAGCTTGG GCACCCAGAC CTACATCTGC AACGTGAATC ACAAGCCCAG CAACACCAAG
TCCTGAGATG AGGGAGTCGT CGCACCACTG ACACGGGAGA TCGTCGAACC CGTGGGTCTG GATGTAGACG TTGCACTTAG TGTTCGGGTC GTTGTGGTTC
 G  L  Y     S  L  S  S     V  V  T     V  P  S     S  S  L  G     T  Q  T     Y  I  C     N  V  N  H     K  P  S     N  T  K
                                                                                        ^CH1 cys GTGGACAAGA AAGTTGAGCC CAAATCTTGT GACAAAACTC ACACATGTCC ACCGTGCCCA GCACCTGAAC TCCTGGGGGG ACCGTCAGTC TTCCTCTTCC
CACCTGTTCT TTCAACTCGG GTTTAGAACA CTGTTTTGAG TGTGTACAGG TGGCACGGGT CGTGGACTTG AGGACCCCCC TGGCAGTCAG AAGGAGAAGG
 V  D  K  K     V  E  P     K  S  C     D  K  T  H     T  C  P     P  C  P     A  P  E  L     L  G  G     P  S  V     F  L  F  P
                            ^cys to bind light chain   ^hinge cys
                                                       ^hinge cys CCCCAAAAACC CAAGGACACC CTCATGATCT CCCGGACCCC TGAGGTCACA TGCGTGGTGG TGGACGTGAG CCACGAAGAC CCTGAGGTCA AGTTCAACTG
GGGGTTTTTGG GTTCCTGTGG GAGTACTAGA GGGCCTGGGG ACTCCAGTGT ACGCACCACC ACCTGCACTC GGTGCTTCTG GGACTCCAGT TCAAGTTGAC
 P  K  P     K  D  T     L  M  I  S     R  T  P     E  V  T     C  V  V  V     D  V  S     H  E  D     P  E  V  K     F  N  W
                                                                 ^Constant Heavy 2 (CH2) cys GTACGTGGAC GGCGTGGAGG TGCATAATGC CAAGACAAAG CCGCGGGAGG AGCAGTACAA CAGCACGTAC CGTGTGGTCA GCACCGTCCT CGTCCTGCAC CGTCCTGCAC
CATGCACCTG CCGCACCTCC ACGTATTACG GTTCTGTTTC GGCGCCCTCC TCGTCATGTT GTCGTGCATG GCACACCAGT GCAGGAGGTG GCAGGACGTG
 Y  V  D     G  V  E  V     H  N  A     K  T  K     P  R  E  E     Q  Y  N     S  T  Y     R  V  V  S     V  L  T     V  L  H CAGGACTGGC TGAATGGCAA GGAGTACAAG TGCAAGGTCT CCAACAAAGC CCTCCCAGCC CCCATCGAGA AAACCATCTC CAAAGCCAAA GGGCAGCCCC
GTCCTGACCG ACTTACCGTT CCTCATGTTC ACGTTCCAGA GGTTGTTTCG GGAGGGTCGG GGGTAGCTCT TTTGGTAGAG GTTTCGGTTT CCCGTCGGGG
 Q  D  W  L     N  G  K     E  Y  K     C  K  V  S     N  K  A     L  P  A     P  I  E  K     T  I  S     K  A  K     G  Q  P  R
                            ^CH2 cys GAGAACCACA GGTGTACACC CTGCCCCCAT CCCGGGAAGA GATGACCAAG AACCAGGTCA GCCTGACCTG CCTGGTCAAA GGCTTCTATC CCAGCGACAT
CTCTTGGTGT CCACATGTGG GACGGGGGTA GGGCCCTTCT CTACTGGTTC TTGGTCCAGT CGGACTGGAC GGACCAGTTT CCGAAGATAG GGTCGCTGTA
 E  P  Q     V  Y  T     L  P  P  S     R  E  E     M  T  K     N  Q  V  S     L  T  C     L  V  K     G  F  Y  P     S  D  I
                                                                              ^Constant Heavy 3 (CH3) cys
```

FIG. 15D

```
CGCCGTGGAG TGGGAGAGCA ATGGGCAGCC GGAGAACAAC TACAAGACCA CGCCTCCCGT GCTGGACTCC GACGGCTCCT TCTTCCTCTA CAGCAAGCTC
GCGGCACCTC ACCCTCTCGT TACCCGTCGG CCTCTTGTTG ATGTTCTGGT GCGGAGGGCA CGACCTGAGG CTGCCGAGGA AGAAGGAGAT GTCGTTCGAG
 A  V  E   W  E  S   N  G  Q   P  E  N  N   Y  K  T  T   P  P  V   L  D  S   D  G  S  F   F  L  Y   S  K  L

ACCGTGGACA AGAGCAGGTG GCAGCAGGGG AACGTCTTCT CATGCTCCGT GATGCATGAG GCTCTGCACA ACCACTACAC GCAGAAGAGC CTCTCCCTGT
TGGCACCTGT TCTCGTCCAC CGTCGTCCCC TTGCAGAAGA GTACGAGGCA CTACGTACTC CGAGACGTGT TGGTGATGTG CGTCTTCTCG GAGAGGACA
 T  V  D  K   S  R  W   Q  Q  Q   G  N  V  F  S   C  S  V   M  H  E   A  L  H  N   H  Y  T   Q  K  S   L  S  L  S
                                               ^CH3 cys CTCCGGGTAA ATAAGCATGC GAGTCCCTAA GACGGCCCTA CGCTCGGTTG CCGCCGGTCG TTTTTTATTG TTAACTCATG TTTGACAGCT TATCATCGAT
GAGGCCCATT TATTCGTACG CTGCCGGGAT CTGCCGGGAT GCGAGCCAAC GGCGGCCCGC AAAAAATAAC AATTGAGTAC AAACTGTCGA ATAGTAGCTA
 P  G  K   O                                                     ^end lambda t0 terminator
                       ^start lambda t0 terminator                                       ^start of tet resistance promoter
                                                                                          ^-35 of promoter AAGCTTTAAT GCGGTAGTTT ATCACAGTTA AATTGCTAAC GCAGTCAGGC ACCGTGTATG AAATCTAACA ATGCGGCTCAT CGTCATCCTC GGCACCGTCA
TTCGAAATTA CGCCATCAAA TAGTGTCAAT TTAACGATTG CGTCAGTCCG TGGCACATAC TTTAGATTGT TACGCCGAGTA GCAGTAGGAG CCGTGGCAGT
 ^-10 region of tet resistance promoter                           ^start of tet resistance translation CCCTGGATGC TGTAGGCATA GGCTTGGTTA TGCCCGTACT GCCGGGCCTC TTGCGGGATA TCGTCCATTC CGACAGCATC GCCAGTCACT ATGGCGTGCT
GGGACCTACG ACATCCGTAT CCGAACCAAT ACGGGCATGA CGGCCCGGAG AACGCCCTAT AGCAGGTAAG GCTGTCGTAG CGGTCAGTGA TACCGCACGA
```

FIG. 16A

```
GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

GAACTGTGTG CGCAGGTAGA AGCTTTGGAG ATTATCGTCA CTGCAATGCT TCGCAATATG GCGCAAAATG ACCAACAGCG GTTGATTGAT CAGGTAGAGG
CTTGACACAC GCGTCCATCT TCGAAACCTC TAATAGCAGT GACGTTACGA AGCGTTATAC CGCGTTTTAC TGGTTGTCGC CAACTAACTA GTCCATCTCC

GGGCGCTGTA CGAGGTAAAG CCCGATGCCA GCATTCCTGA CGACGATACG GAGCTGCTGC GCGATTACGT AAAGAAGTTA TTGAAGCATC CTCGTCAGTA
CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT

AAAAGTTAAT CTTTTCAACA GCTGTCATAA AGTTGTCACG GCCGAGACTT ATAGTCGCTT TGTTTTTATT TTTTAATGTA TTTGTAACTA GTACGCAAGT
TTTTCAATTA GAAAAGTTGT CGACAGTGT TCAACAGTGC CGGCTCTGAA TATCAGCGAA ACAAAAATAA AAAATTACAT AAACATTGAT CATGCGTTCA

TCACGTAAAA AGGGTATCTA GAATTATGAA GCATTTCTTC GTTCGTTTTT TCTATTGCTA CAAACGCGTA CGCTGATATC
AGTGCATTTT TCCCATAGAT CTTAATACTT CGTAAAGAAG CAAGCAAAAA AGATAACGAT GTTTGCGCAT GCGACTATAG
                M  K  N  I  A  F  L  L  A  S  M  F  V  F  S  I  A  T  N  A  Y  A  D  I
             ^STII Signal TIR -1              Anti-VEGF Light chain (version Y0317)^

CAGTTGACCC AGTCCCCGAG CTCCCTGTCC GCCTCTGTGG GCGATAGGGT CACCATCACC TGCAGCGCAA GTCAGGATAT TAGCAACTAT TTAAACTGGT
GTCAACTGGG TCAGGGCTC GAGGGACAGG CGGAGACACC CGCTATCCCA GTGGTAGTGG ACGTCGCGTT CAGTCCTATA ATCGTTGATA AATTTGACCA
  Q  L  T  Q  S  P  S  S  L  S  A  S  V  G  D  R  V  T  I  T  C  S  A  S  Q  D  I  S  N  Y  L  N  W  Y

ATCAACAGAA ACCAGGGAAA GCTCCGAAAG TACTGATTTA CTTCACCTCC TCTCTCCACT CTGGAGTCCC TTCTCGCTTC TCTGGATCCG GTTCTGGGAC
TAGTTGTCTT TGGTCCCTTT CGAGGCTTTC ATGACTAAAT GAAGTGGAGG AGAGAGGTGA GACCTCAGGG AAGAGCGAAG AGACCTAGGC CAAGACCCTG
  Q  Q  K  P  G  K  A  P  K  V  L  I  Y  F  T  S  S  L  H  S  G  V  P  S  R  F  S  G  S  G  S  G  T

GGATTCACT CTGACCATCA GCAGTCTGCA GCCTGAAGAC TTCGCAACTT ATTACTGTCA ACAGTATAGC ACCGTGCCGT GGACGTTTGG ACAGGGTACC
CCTAAGTGA GACTGGTAGT CGTCAGACGT CGGACTTCTG AAGCGTTGAA TAATGACAGT TGTCATATCG TGGCACGGCA CCTGCAAACC TGTCCATGG
  D  F  T  L  T  I  S  S  L  Q  P  E  D  F  A  T  Y  Y  C  Q  Q  Y  S  T  V  P  W  T  F  G  Q  G  T

AAGGTGGAGA TCAAACGAAC TGTGGCTGCA CCATCTGTCT TCATCTTCCC GCCATCTGAT GAGCAGTTGA AATCTGGAAC TGCTTCTGTT GTGTGCCTGC
TTCCACCTCT AGTTTGCTTG ACACCGACGT AGTAGACAGA AGTAGAAGGG CGGTAGACTA CTCGTCAACT TTAGACCTTG ACGAAGACAA CACACGGACG
  K  V  E  I  K  R  T  V  A  A  P  S  V  F  I  F  P  P  S  D  E  Q  L  K  S  G  T  A  S  V  V  C  L  L

TGAATAACTT CTATCCCAGA GAGGCCAAAG TACAGTGGAA GGTGGATAAC GCCCTCCAAT CGGGTAACTC CCAGGAGAGT GTCACAGAGC AGGACAGCAA
ACTTATTGAA GATAGGGTCT CTCCGGTTTC ATGTCACCTT CCACCTATTG CGGGAGGTTA GCCCATTGAG GGTCCTCTCA CAGTGTCTCG TCCTGTCGTT
  N  N  F  Y  P  R  E  A  K  V  Q  W  K  V  D  N  A  L  Q  S  G  N  S  Q  E  S  V  T  E  Q  D  S  K
```

FIG. 16B

```
GGACAGCACC TACAGCCTCA GCAGCACCCT GACGCTGAGC AAAGCAGACT ACGAGAAACA CAAAGTCTAC GCCTGCGAAG TCACCCATCA GGGCCTGAGC
CCTGTCGTGG ATGTCGGAGT CGTCGTGGGA CTGCGACTCG TTTCGTCTGA TGCTCTTTGT GTTTCAGATG CGGACGCTTC AGTGGGTAGT CCCGACTCG
 D   S   T   Y   S   L   S   S   T   L   T   L   S   K   A   D   Y   E   K   H   K   V   Y   A   C   E   V   T   H   Q   G   L   S

TCGCCCGTCA CAAAGAGCTT CAACAGGGGA GAGTGTTAAT ATCTCGAATG ACGCCGGACG CATCGTGGCG AGCTCGGTAC CCGGGGATCT AGGCCTAACG
AGCGGGCAGT GTTTCTCGAA GTTGTCCCCT CTCACAATTA TAGAGCTTAC TGCGGCCTGC GTAGCACCGC TCGAGCCATG GGCCCCTAGA TCCGATTGC
 S   P   V   T   K   S   F   N   R   G   E   C   Q

CTCGGTTGCC GCCGGGCGTT TTTTATTGTT GCCGACGCGC ATCTCGAATG AACTGTGTGC GCAGGTAGAA GCTTTGGAGA TTATCGTCAC TGCAATGCTT
GAGCCAACGG CGGCCCGCAA AAAATAACAA CGGCTGCGCG TAGAGCTTAC TTGACACACG CGTCCATCTT CGAAACCTCT AATAGCAGTG ACGTTACGAA

CGCAAATATG CCAACAGCGG TTGATTGATC AGGTAGAGGG GCCGACGCGC GAGGTAAAGC CCGATGCCAA CATTCCTGAC GACGATACGG
GCGTTATACC GGTTGTCGCC AACTAACTAG TCCATCTCCC CGGCGCACATG CTCCATTTCG GGCTACGGTC GTAAGGACTG CTGCTATGCC

AGCTGTCGCG CGATTACGTA AAGAAGTTAT TGAAGCATCC TCGTCAGTAA AAAGTTAATC TTTTCAACAG CTGTCATAAA GTTGTCACGG CCGAGACTTA
TCGACGACGC GCTAATGCAT TTCTTACAATA ACTTCGTAGG AGCAGTCATT TTTCAATTAG AAAAGTTGTC GACAGTATTT CAACAGTGCC GGCTCTGAAT

TAGTCGCTTT GTTTTTATTT TTTAATGTAT TTGTAACTAG TACGCAAGTT CACGTATCTAG AATTATGAAG AAGAATATCG CATTTCTTCT
ATCAGCGAAA CAAAATAAA AATTACATA AACATTGATC ATGCGTTCAA GTGCATTTT CCCATAGATC TTAATACTTC TTCTTATAGC GTAAAGAAGA
                                                                                              M   K   K   N   I   A   F   L   L
                                                                                              ^STII signal TIR-1

TGCATCTATG TTCGTTTTTT CTATTGCTAC AAACGCGTAC GCTGAGGTTC AGCTGGTGGA GTCTGGCGGT GGCCTGGTGC AGCCAGGGGG CTCACTCCGT
ACGTAGATAC AAGCAAAAAA GATAACGATG TTTGCGCATG CGACTCCAAG TCGACCACCT CAGACCGCCA CCGGACCACG TCGGTCCCCC GAGTGAGGCA
 A   S   M   F   V   F   S   I   A   T   N   A   Y   A   E   V   Q   L   V   E   S   G   G   G   L   V   Q   P   G   G   S   L   R
                                                    ^Anti-VEGF Heavy Chain (version Y0317)

TTGTCCTGTG CAGCTTCTGG CTACGACTTC ACGCACTACG GGTCCGTCAG GCCCGGGTCA GGGCCTCGAG ATGGGCCTGA ATGGGTTGGA TGGATTAACA
AACAGGACAC GTCGAAGACC GATGCTGAAG TGCGTGATGC CCAGGCAGTC CGGGCCCAGT TCCCGGACCT CGGAGGCTC TACCCAACCT ACCTAATTGT
 L   S   C   A   A   S   G   Y   D   F   T   H   Y   G   M   N   W   V   R   Q   A   P   G   K   G   L   E   W   V   G   W   I   N   T

CCTATACCGG TGAACCGACC TATGCTGCCG ATTTCAAACG TCGTTTCACT TTTTCTTTAG ACACCTCCAA AAGCACAGCA TTTCGACGTC TGAACAGCCT
GGATATGGCC ACTTGGCTGG ATACGACGGC TAAAGTTTGC AGCAAAGTGA AAAAGAAATC TGTGGAGGTT TTCGTGTCGT ATGGAGGCT ACTTGTCGGA
 Y   T   G   E   P   T   Y   A   A   D   F   K   R   R   F   T   F   S   L   D   T   S   K   S   T   A   Y   L   Q   M   N   S   L

GCGCGCTGAG GACACTGCCG TCTATTACTG TGCAAAGTAC ACGTTTCATG GCATGATAAA CCACTGGTAT TTCGACGTCT GGGGTCAAGG AACCCTGGTC
CGCGCGACTC CTGTGACGGC AGATAATGAC ACGTTTCATG CGTACTATTT GGTGACCATA AAGCTGCAGA CCCCAGTTCC TTGGACCAG
 R   A   E   D   T   A   V   Y   Y   C   A   K   Y   P   Y   Y   Y   G   T   S   H   W   Y   F   D   V   W   G   Q   G   T   L   V

ACCGTCTCCT CGGCCTCCAC CAAGGGCCCA TCGGTCTTCC CCCTGGCACC AGCACCTCTG GGGGCACAGC GGCCCTGGGC TGCCTGGTCA ACGGACCAGT
TGGCAGAGGA GCCGGAGGTG GTTCCCGGGT AGCCAGAAGG GGGACCGTGG TCGTGGAGAC CCCCGTGTCG CCGGGACCCG ACGGACCAGT TGCCTGGTCA
 T   V   S   S   A   S   T   K   G   P   S   V   F   P   L   A   P   S   S   K   S   T   S   G   G   T   A   A   L   G   C   L   V   K
```

FIG. 16C

```
AGGACTACTT CCCGAACCG GTGACGGTGT CGTGAACTC AGGGCCCTG ACCAGGCGGG TGCACACCTT CCGGCTGTC CTACAGTCCT
TCCTGATGAA GGGGCTTGGC CACTGCCACA GCACCTTGAG TCCGGGGAC TGTCGCCGC ACGTGTGGAA GGGCCACAG GATGTCAGGA GTCCTGAGAT
 D  Y  F   P  E  P    V  T  V  S    W  N  S    G  A  L    T  S  G  V    H  T  P    P  A  V    L  Q  S  S   G  L  Y

CTCCCTCAGC AGCTGGTGA CTGTGCCCTC TAGCAGCTTG ATCGTCGAAC CCGTGGGTCT GGCACACCAG CAACGTGAAT CACAAGCCCA GCAACACCAA GGTGGACAAG
GAGGGAGTCG TCGACCACT GACACGGGAG ATCGTCGAAC CCGTGGGTCT GGATGTAGAC GTTGCACTTA GTGTTCGGGT CGTTGTGGTT CCACCTGTTC
 S  L  S   S  V  V  T    V  P  S    S  S  L    G  T  Q  T    Y  I  C    N  V  N    H  K  P  S   N  T  K   V  D  K

AAAGTTGAGC CCAAATCTTG TGACAAAACT CACACATGCC CACCGTGCCC AGCACCTGAA CTCCTGGGGG GACCGTCAGT CTTCCTCTTC CCCCCAAAAC
TTTCAACTCG GGTTTAGAAC ACTGTTTTGA GTGTGTACGG GTGGCACGGG TCGTGGACTT GAGGACCCCC CTGGCAGTCA GAAGGAGAAG GGGGGTTTTG
 K  V  E  P   K  S  C    D  K  T    H  T  C  P    P  C  P    A  P  E    L  L  G  G    P  S  V   F  L  F   P  P  K  P

CCAAGGACAC CCTCATGATC TCCCGGACCC CTGAGGTCAC ATGCGTGGTG GTGGACGTGA GCCACGAAGA CCCTGAGGTC AAGTTCAACT GGTACGTGGA
GGTTCCTGTG GGAGTACTAG AGGGCCTGGG GACTCCAGTG TACGCACCAC CACCTGCACT CGGTGCTTCT GGGACTCCAG TTCAAGTTGA CCATGCACCT
 K  D  T   L  M  I    S  R  T  P    E  V  T    C  V  V    V  D  V  S    H  E  D    P  E  V    K  F  N  W   Y  V  D

CGGCGTGGAG GTGCATAATG CCAAGACAAA GCCGCGGGAG GAGCAGTACA ACAGCACGTA CCGTGTGGTC AGCGTCCTCA CCGTCCTGCA CCAGGACTGG
GCCGCACCTC CACGTATTAC GGTTCTGTTT CGGCGCCCTC CTCGTCATGT TGTCGTGCAT GGCACACCAG TCGCAGGAGT GGCAGGACGT GGTCCTGACC
 G  V  E   V  H  N  A    K  T  K    P  R  E    E  Q  Y  N    S  T  Y    R  V  V    S  V  L  T   V  L  H   Q  D  W

CTGAATGGCA AGGAGTACAA GTGCAAGGTC TCCAACAAAG CCCTCCCAGC CCCCATCGAG AAAACCATCT CCAAAGCCAA AGGGCAGCCC CGAGAACCAC
GACTTACCGT TCCTCATGTT CACGTTCCAG AGGTTGTTTC GGGAGGGTCG GGGGTAGCTC TTTTGGTAGA GGTTTCGGTT TCCCGTCGGG GCTCTTGGTG
 L  N  G  K   E  Y  K    C  K  V    S  N  K  A    L  P  A    P  I  E    K  T  I  S    K  A  K   G  Q  P   R  E  P  Q

AGGTGTACAC CCTGCCCCCA TCCCGGGAAG AGATGACCAA GAACCAGGTC AGCCTGACCT GCCTGGTCAA AGGCTTCTAT CCCAGCGACA TCGCCGTGGA
TCCACATGTG GGACGGGGGT AGGGCCCTTC TCTACTGGTT CTTGGTCCAG TCGGACTGGA CGGACCAGTT TCCGAAGATA GGGTCGCTGT AGCGGCACCT
 V  Y  T   L  P  P    S  R  E  E    M  T  K    N  Q  V    S  L  T  C    L  V  K    G  F  Y    P  S  D  I   A  V  E

GTGGGAGAGC AATGGGCAGC CGGAGAACAA CTACAAGACC ACGCCTCCCG TGCTGGACTC CGACGGCTCC TTCTTCCTCT ACAGCAAGCT CACCGTGGAC
CACCCTCTCG TTACCCGTCG GCCTCTTGTT GATGTTCTGG TGCGGAGGGC ACGACCTGAG GCTGCCGAGG AAGAAGGAGA TGTCGTTCGA GTGGCACCTG
 W  E  S   N  G  Q  P    E  N  N    Y  K  T    T  P  P  V    L  D  S    D  G  S    F  F  L  Y   S  K  L   T  V  D

AAGAGCAGGT GGCAGCAGGG GAACGTCTTC TCATGCTCCG TGATGCATGA GGCTCTGCAC AACCACTACA CGCAGAAGAG CCTCTCCCTG TCTCCGGGTA
TTCTCGTCCA CCGTCGTCCC CTTGCAGAAG AGTACGAGGC ACTACGTACT CCGAGACGTG TTGGTGATGT GCGTCTTCTC GGAGAGGGAC AGAGGCCCAT
 K  S  R  W   Q  Q  G    N  V  F    S  C  S  V    M  H  E    A  L  H    N  H  Y  T    Q  K  S   L  S  L   S  P  G  K

AATAAGCATG CGACGGCCCT AGAGTCCCTA ACGCTCGGTT GCCGCCGGGC GTTTTTATT GTTAACTCAT GTTTGACACA TTATCATCGA TAAGCTTTAA
TTATTCGTAC GCTGCCGGGA TCTCAGGGAT TGCGAGCCAA CGGCGGCCCG CAAAAAATAA CAATTGAGTA CAAACTGTCG AATAGTAGCT ATTCGAAATT
 O

TGCGTAGTT TATCACAGTT AAATTGCTAA CGCAGTCAGG CACCGTGTAT GAAATCTAAC AATGCGCTCA TCGTCATCCT CGGCACCGTC ACCCTGGATG
ACGCCATCAA ATAGTGTCAA TTTAACGATT GCGTCAGTCC GTGGCACATA CTTTAGATTG TTACGCGAGT AGCAGTAGGA GCCGTGGCAG TGGGACCTAC
                                              ^Start Tet Resistance Coding Sequence
```

CTGTAGGCAT AGGCTTGGTT ATGCCGGTAC TGCCGGGCCT CTTGCGGGAT ATCGTCCATT CCGACAGCAT CGCCAGTCAC TATGGCGTGC TGCTAGCGCT
GACATCCGTA TCCGAACCAA TACGGCCATG ACGGCCCGGA GAACGCCCTA TAGCAGGTAA GGCTGTCGTA GCGGTCAGTG ATACCGCACG ACGATCGCGA

GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

GAACTGTGTG CGCAGGTAGA AGCTTTGGAG ATTATCGTCA CTGCAATGCT TCGCAATATG GCGCAAAATG ACCAACAGCG GTTGATTGAT CAGGTAGAGG
CTTGACACAC GCGTCCATCT TCGAAACCTC TAATAGCAGT GACGTTACGA AGCGTTATAC CGCGTTTTAC TGGTTGTCGC CAACTAACTA GTCCATCTCC

GGGCGCTGTA CGAGGTAAAG CCCGATGCCA GCATTCCTGA CGACGATACG GAGCTGCTGC GCGATTACGT AAAGAAGTTA TTGAAGCATC CTCGTCAGTA
CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT

AAAAGTTAAT CTTTTCAACA GCTGTCATAA AGTTGTCACG GCCGAGACTT ATAGTCGCTT TGTTTTTATT TTTTAATGTA TTTGTAACTA GTACGCAAGT
TTTTCAATTA GAAAAGTTGT CGACAGTATT TCAACAGTGC CGGCTCTGAA TATCAGCGAA ACAAAAATAA AAAATTACAT AAACATTGAT CATGCGTTCA

TCACGTAAAA AGGGTATCTA GAATTATGAA GAAGAATATC GCATTTCTTC TTGCATCTAT GTTCGTTTTT TCTATTGCTA CAAACGCGTA CGCTGATATC
AGTGCATTTT TCCCATAGAT CTTAATACTT CTTCTTATAG CGTAAAGAAG AACGTAGATA CAAGCAAAAA AGATAACGAT GTTTGCGCAT GCGACTATAG
M K K N I A F L L A S M F V F S I A T N A Y A D I
^STII Signal TIR -1 .anti-VEGF Light Chain^

CAGTTGACCC AGTCCCCGAG CTCCCTGTCC GCCTCTGTGG GCGATAGGGT CACCATCACC TGCAGCGCAA GTCAGGATAT TAGCAACTAT TTAAACTGGT
GTCAACTGGG TCAGGGGCTC GAGGGACAGG CGGAGACACC CGCTATCCCA GTGGTAGTGG ACGTCGCGTT CAGTCCTATA ATCGTTGATA AATTTGACCA
Q L T Q S P S S L S A S V G D R V T I T C S A S Q D I S N Y L N W Y
^variable light (VL) cys ATCAACAGAA ACCAGGAAAA GCTCCGAAAG TACTGATTTA CTTCACCTCC TCTCTCCACT CTGGAGTCCC TTCTCGCTTC TCTGGATCCG GTTCTGGGAC
TAGTTGTCTT TGGTCCTTTT CGAGGCTTTC ATGACTAAAT GAAGTGGAGG AGAGAGGTGA GACCTCAGGG AAGAGCGAAG AGACCTAGGC CAAGACCCTG
Q Q K P G K A P K V L I Y F T S S L H S G V P S R F S G S G S G T GGATTTCACT CTGACCATCA GCAGTCTGCA GCCAGAAGAC TTCGCAACTT ATTACTGTCA ACAGTATAGC ACCGTGCCGT GGACGTTTGG ACAGGGTACC
CCTAAAGTGA GACTGGTAGT CGTCAGACGT CGGTCTTCTG AAGCGTTGAA TAATGACAGT TGTCATATCG TGGCACGGCA CCTGCAAACC TGTCCCATGG
D F T L T I S S L Q P E D F A T Y Y C Q Q Y S T V P W T F G Q G T
^Variable light cys AAGGTGGAGA TCAAACGAAC TGTGGCTGCA CCATCTGTCT TCATCTTCCC GCCATCTGAT GAGCAGTTGA AATCTGGAAC TGCTTCTGTT GTGTGCCTGC
TTCCACCTCT AGTTTGCTTG ACACCGACGT GGTAGACAGA AGTAGAAGGG CGGTAGACTA CTCGTCAACT TTAGACCTTG ACGAAGACAA CACACGGACG
K V E I K R T V A A P S V F I F P P S D E Q L K S G T A S V V C L L
Constant Light cys^

FIG. 17B

```
TGAATAACTT CTATCCCAGA GAGGCCAAAG TACAGTGAA GGTGATAAC GCCCTCCAAT CGGGTAACTC CAGGAGAGT GTCACAGAGC AGGACAGCAA
ACTTATTGAA GATAGGGTCT CTCCGGTTTC ATGTCACCTT CCACTATTG CGGGAGGTTA GCCCATTGAG GTCCCTCTCA CAGTGTCTCG TCCTGTCGTT
         N  N  F  Y  P  R  E  A  K  V  Q  W  K  V  D  N  A  L  Q  S  G  N  S  Q  E  S  V  T  E  Q  D  S  K

GGACAGCACC TACAGCCTCA GCAGCACCCT GACGCTGAGC GACGGCGAGT AAAGCAGACT ACGAGAAACA CAAAGTCTAC GCCTGCGAAG TCACCCATCA GGGCCTGAGC
CCTGTCGTGG ATGTCGGAGT CGTCGTGGGA CTGCGACTCG TTTCGTCTGA TGCTCTTTGT GTTTCAGATG CGGACGCTTC AGTGGGTAGT CCCGGACTCG
         D  S  T  Y  S  L  S  S  T  L  T  L  S  K  A  D  Y  E  K  H  K  V  Y  A  C  E  V  T  H  Q  G  L  S
                                                                                       ^Constant Light cys TCGCCCGTCA CAAAGAGCTT CAACAGGGGA GAGTGTAAT TAAATCCTCT ACGCCGGACG CATCGTGGCG AGCTCGGTAC CCGGGGATCT AGGCCTAACG
AGCGGGCAGT GTTTCTCGAA GTTGTCCCCT CTCACAATTA ATTTAGGAGA TGCGGCCTGC GTAGCACCGC TCGAGCCATG GGCCCCTAGA TCCGGATTGC
         S  P  V  T  K  S  F  N  R  G  E  C  O                                               start lambda t0 terminator^
                                           ^cys to bind heavy CTCGGTTGCC GCCGGCGTT TTTTATTGTT GCCGACGCGC ATCTCGAATG AACTGTGTGC GCAGGTAGAA GCTTTGGAGA GTTTGTCAC TTATCGTCTT TGCAATGCTT
GAGCCAACGG CGGCCCGCAA AAAATAACAA CGGCTGCGCG TAGAGCTTAC TTGACACACG CGTCCATCTT CGAAACCTCT CAAATAGCAGTG ACGTTACGAA
                      ^end lambda t0 terminator CGCAATATGG CGCAAAATGA CCAACAGCGG TTGATTGATC AGGTAGAGGG GGCGCTGTAC GAGGTAAAGC CCGATGCCAG CATTCCTGAC GACGATACGG
GCGTTATACC GCGTTTTACT GGTTGTCGCC AACTAACTAG TCCATCTCCC CCGCGACATG CTCCATTTCG GGCTACGGTC GTAAGGACTG CTGCTATGCC AGCTGCTGCG CGATTACGTA AAGAAGTTAT TGAAGCATCC TCGTCAGTAA AAAGTTAATC TTTCAATTAG AAAAGTTGTC CTGTCATAAA GTTGTCACGG CCGAGACTTA
TCGACGACGC GCTAATGCAT TTCTTCAATA ACTTCGTAGG AGCAGTCATT TTTCAATTAG AAAGTTAATC AGCAGTCATT GACAGTATTT CAACAGTGCC GGCTCTGAAT TAGTCGCTTT GTTTTATTTT TTTAATGTAT TTGTAACTAG TACGCAAGTT CAGTAAAAA GGGTATCTAG AATTATGAAG TTAATACTTC TTCTTATAGC CATTTCTCTCT
ATCAGGCGAAA CAAAATAAAA AAATTACATA AACATTGATC ATGCGTTCAA GTCATTTT CCCATAGATC TTAATACTTC TTCTTATAGC GTAAAGAGA
                                                                                   M  K  K  N  I  A  F  L  L
                                                                                    ^STII Signal TIR-1

TGCATCTATG TTCGTTTTT CTATTGCTAC AAACGCGTAC GCTCAGGTTC AGCTGGTGCA GTCTGGGCA GAGGTGAAAA AGCCAGGGGC TTCAGTTAAA
ACGTAGATAC AAGCAAAAA GATAACGATG TTTGCGCATG CGAGTCCAAG TCGACCAGT CAGACCCGGT CTCCACTTT TCGGTCCCCG AAGTCAATTT
         A  S  M  F  V  F  S  I  A  T  N  A  Y  A  Q  V  Q  L  V  Q  S  G  A  E  V  K  K  P  G  A  S  V  K
                                               ^anti-VEGF Heavy Chain (VNERK version)
                                                 ^Heavy Chain FR1 changed to Subgroup1 consensus sequence GTATCCTGTA AAGCTTCTGG CTATACCTTC ACCAACTATG GTATAAACTG GGTCCGTCAG GCCCCGGGTA AGGGCCTGGA ATGGGTTGGA ATGGGTTAACA
CATAGGACAT TTCGAAGACC GATATGGAAG TGGTTGATAC CATATTGAC CCAGGCAGTC CGGGGCCCAT TCCCGGACCT TACCCAACCT ACCTAATTGT
         V  S  C  K  A  S  G  Y  T  F  T  N  Y  G  I  N  W  V  R  Q  A  P  G  K  G  L  E  W  V  G  W  I  N  T
         ^Variable Heavy (VH) cys CCTATACCGG TGAACCGACC TATGCTGCGG ATTTCAAACG TCGTTTCACT TTTTCTTTAG ACACCTCCAA AAGCACAGCA TACCTGCAGA TGAACAGCCT
GGATATGGCC ACTTGGCTGG ATACGACGCC ATACGACGCC TAAAGTTTGC AGCAAGTGA AAAAGAAATC TGTGGAGGTT TTCGTGTCGT ATGGACGTCT ACTTGTCGGA
         Y  T  G  E  P  T  Y  A  A  D  F  K  R  R  F  T  F  S  L  D  T  S  K  S  T  A  Y  L  Q  M  N  S  L
```

FIG. 17C

```
GCGGCGCTGAG GACACTGCCG TCTATTACTG TGCAAAGTAC CCGCACTATT ATGTGAACGA GCGGAAGAGC CACTGGTATT TCGACGTCTG GGGTCAAGGA
CGGCGGACTC CTGTGACGGC AGATAATGAC ACGTTTCATG GGCGTGATAA TACACTTGCT CGCCTTCTCG GTGACCATAA AGCTGCAGAC CCCAGTTCCT
 R   A   E   D   T   A   V   Y   Y   C   A   K   Y   P   H   Y   Y   V   N   E   R   K   S   H   W   Y   F   D   V   W   G   Q   G
                                ^VH cys ACCCTGGTCA CCGTCTCCTC GGCCTCCACC AAGGGCCCAT CGGTCTTCCC CCTGGCACCC TCCTCCAAGA GCACCTCTGG GGGCACAGCG GCCCTGGGCT
TGGGACCAGT GGCAGAGGAG CCGGAGGTGG TTCCCGGGTA GCCAGAAGGG GGACCGTGGG AGGAGGTTCT CGTGGAGACC CCCGTGTCGC CGGGACCCGA
 T   L   V   T   V   S   S   A   S   T   K   G   P   S   V   F   P   L   A   P   S   S   K   S   T   S   G   T   A   A   L   G   C
                                                                                          Constant Heavy 1 (CH1) cys^

GCCTGGTCAA GGACTACTTC CCCGAACCGG TGACGGTGTC GTGGAACTCA GGCGCCCTGA CCAGCGGCGT GCACACCTTC CCGGCTGTCC TACAGTCCTC
CGGACCAGTT CCTGATGAAG GGGCTTGGCC ACTGCCACAG CACCTTGAGT CCGCGGGACT GGTCGCCGCA CGTGTGGAAG GGCCGACAGG ATGTCAGGAG
 L   V   K   D   Y   F   P   E   P   V   T   V   S   W   N   S   G   A   L   T   S   G   V   H   T   F   P   A   V   L   Q   S   S

AGGACTCTAC TCCCTCAGCA GCGTGGTGAC CGTGCCCTCC AGCAGCTTGG GCACCCAGAC CTACATCTGC AACGTGAATC ACAAGCCCAG CAACACCAAG
TCCTGAGATG AGGGAGTCGT CGCACCACTG GCACGGGAGG TCGTCGAACC CGTGGGTCTG GATGTAGACG TTGCACTTAG TGTTCGGGTC GTTGTGGTTC
 G   L   Y   S   L   S   S   V   V   T   V   P   S   S   S   L   G   T   Q   T   Y   I   C   N   V   N   H   K   P   S   N   T   K
                                                                              ^CH1 cys GTGGACAAGA AAGTTGAGCC CAAATCTTGT GACAAAACTC ACACATGCCC ACCGTGCCCA GCACCTGAAC TCCTGGGGGG ACCGTCAGTC TTCCTCTTCC
CACCTGTTCT TTCAACTCGG GTTTAGAACA CTGTTTTGAG TGTGTACGGG TGGCACGGGT CGTGGACTTG AGGACCCCCC TGGCAGTCAG AAGGAGAAGG
 V   D   K   K   V   E   P   K   S   C   D   K   T   H   T   C   P   P   C   P   A   P   E   L   L   G   G   P   S   V   F   L   F   P
                  ^cys to bind light chain    ^hinge     ^hinge cys
                                                cys CCCCAAAACC CAAGGACACC CTCATGATCT CCCGGACCCC TGAGGTCACA TGCGTGGTGG TGGACGTGAG CCACGAAGAC CCTGAGGTCA AGTTCAACTG
GGGGTTTTGG GTTCCTGTGG GAGTACTAGA GGGCCTGGGG ACTCCAGTGT ACGCACCACC ACCTGCACTC GGTGCTTCTG GGACTCCAGT TCAAGTTGAC
 P   K   P   K   D   T   L   M   I   S   R   T   P   E   V   T   C   V   V   V   D   V   S   H   E   D   P   E   V   K   F   N   W
                                                        ^Constant Heavy 2 (CH2) cys GTACGTGGAC GGCGTGGAGG TGCATAATGC CAAGACAAAG CCGCGGGAGG AGCAGTACAA CAGCACGTAC CGTGTGGTCA GCGTCCTCAC CGTCCTGCAC
CATGCACCTG CCGCACCTCC ACGTATTACG GTTCTGTTTC GGCGCCCCTC TCGTCATGTT GTCGTGCATG GCACACCAGT CGCAGGAGTG GCAGGACGTG
 Y   V   D   G   V   E   V   H   N   A   K   T   K   P   R   E   E   Q   Y   N   S   T   Y   R   V   V   S   V   L   T   V   L   H CAGGACTGGC TGAATGGCAA GGAGTACAAG TGCAAGGTCT CCAACAAAGC CCTCCCAGCC CCCATCGAGA AAACCATCTC CAAAGCCAAA GGGCAGCCCC
GTCCTGACCG ACTTACCGTT CCTCATGTTC ACGTTCCAGA GGTTGTTTCG GGAGGGTCGG GGGTAGCTCT TTTGGTAGAG GTTTCGGTTT CCCGTCGGGG
 Q   D   W   L   N   G   K   E   Y   K   C   K   V   S   N   K   A   L   P   A   P   I   E   K   T   I   S   K   A   K   G   Q   P   R
                          ^CH2 cys GAGAACCACA GGTGTACACC CTGCCCCCAT CCCGGGAAGA GATGACCAAG AACCAGGTCA GCCTGACCTG CCTGGTCAAA GGCTTCTATC CCAGCGACAT
CTCTTGGTGT CCACATGTGG GACGGGGGTA GGGCCCTTCT CTACTGGTTC TTGGTCCAGT CGGACTGGAC GGACCAGTTT CCGAAGATAG GGTCGCTGTA
 E   P   Q   V   Y   T   L   P   P   S   R   E   E   M   T   K   N   Q   V   S   L   T   C   L   V   K   G   F   Y   P   S   D   I
                                                                                          ^Constant Heavy 3 (CH3) cys
```

FIG. 17D

```
CGCCGTGGAG TGGGAGAGCA ATGGGCAGCC GGAGAACAAC TACAAGACCA CGCCTCCCGT GCTGGACTCC TCTTCCTCTA CAGCAAGCTC
GCGGCACCTC ACCCTCGTCG TACCCGTCGG CCTCTTGTTG ATGTTCTGGT GCGGAGGGCA CGACCTGAGG CTGCCGAGGA GTCGTTCGAG
 A  V  E   W  E  S   N  G  Q   P  E  N   N  Y  K   T  T   P  P  V   L  D  S   D  G  S   F  L  Y   S  K  L

ACCGTGGACA AGAGCAGGTG GCAGCAGGGG AACGTCTTCT CATGCTCCGT GATGCATGAG GCTCTGCACA ACCACTACAC GCAGAAGAGC CTCTCCCTGT
TGGCACCTGT TCTCGTCCAC CGTCGTCCCC TTGCAGAAGA GTACGAGGCA CTACGTACTC CGAGACGTGT TGGTGATGTG CGTCTTCTCG GAGAGGGACA
 T  V  D  K   S  R  W   Q  Q  G   N  V  F  S   C  S  V   M  H  E   A  L  H  N   H  Y  T   Q  K  S   L  S  L  S
                                                 ^CH3 cys CTCCGGGTAA ATAAGCATGC GACGGCCCTA CGCTCGGTTG CCGCCCGGGCG TTTTTTATTG TTAACTCATG TTTGACAGCT TATCATCGAT
GAGGCCCATT TATTCGTACG CTGCCGGGAT CGCGAGCCAAC GGCGGCCCGC AAAAAATAAC AATTGAGTAC AAACTGTCGA ATAGTAGCTA
 P  G  K   O                                                              ^end lambda t0 terminator
           ^start lambda t0 terminator                                                    ^start of tet resistance promoter
                                                                                           ^-35 of promoter AAGCTTTAAT GCGGTAGTTT ATCACAGTTA AATTGCTAAC GCAGTCAGGC ACCGTGTATG AAATCTAACA ATGCGCTCAT CGTCATCCTC GGCACCGTCA
TTCGAAATTA CGCCATCAAA TAGTGTCAAT TTAACGATTG CGTCAGTCCG TGGCACATAC TTTAGATTGT TACGCGAGTA GCAGTAGGAG CCGTGGCAGT
 ^-10 region of tet resistance promoter           ^start of tet resistance translation CCCTGGATGC TGTAGGCATA GGCTTGGTTA TGCCCGGTACT GCCGGGGCCTC TTGCCGGGATA TCGTCCATTC CGACAGCATC GCCAGTCACT ATGGCGTGCT
GGGACCTACG ACATCCGTAT CCGAACCAAT ACGGCCCATGA CGGCCCGGAG AACGGCCCTAT AGCAGGTAAG GCTGTCGTAG CGGTCAGTGA TACCGCACGA
```

FIG. 18A

```
GAATTCAACT TCTCCATACT TTTGGATAAGG AAATACAGAC ATGAAAAATC TCATTGCTGA GTTGTTATTT AAGCTTGCCC AAAAAGAAGA AGAGTCGAAT
CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

GAACTGTGTG CGCAGGTAGA AGCTTTGGAG ATTATCGTCA CTGCAATGCT TCGCAATATG GCGCAAAATG ACCACACAGC GTTGATTGAT CAGGTAGAGG
CTTGACACAC GCGTCCATCT TCGAAACCTC TAATAGCAGT GACGTTACGA AGCGTTATAC CGCGTTTTAC TGGTGTCGC CAACTAACTA GTCCATCTCC
                                              M  K  K  N  I  A  F  L  L  A  S  M
                                              ^STII Signal TIR -1

GGGCGCTGTA CGAGGTAAAG CCCGATGCCA GACGATACG GAGCTGCTGC GCGATTACGT AAAGAAGTTA TTGAAGCATC CTCGTCAGTA
CCCGCGACAT GCTCCATTTC GGGCTACGGT CTGCTATGC CTCGACGACG CGCTAGCG CGCTAATGCA TTTCTTCAAT AACTTCGTAG GAGCAGTCAT
           F  V  F  S  I  A  T  N  A  Y  A  D  I
                                             ^anti-VEGF Light Chain AAAGTTAAT CTTTTCAACA GCTGTCACG GCCGAGACTT ATAGTCGCTT TGTTTTTATT TTTTAATGTA TTTGTAACTA GTACGCAAGT
TTTCAATTA GAAAAGTTGT CGACAGTATT TCGGCTCTGAA TATCAGCGAA ACAAAAATAA AAAATTACAT AAACATTGAT CATGCGTTCA TCACGTAAAA AGGGTATCTA GAATTATGAA GCATTCTCTTC GCATTCTCT TGTCGTTTTT TCTATTGCTA CAAACGCGTA CGCTGATATC
AGTGCATTTT TCCCATAGAT CTTAATACTT CGTAAAGAAG CGTAAGAAG AAACGCAAAAA AGATAACGAT GTTTGCGCAT GCGACTATAG
                                               F  V  F  S  I  A  T  N  A  Y  A  D  I
                                                                                    ^anti-VEGF Light Chain CAGTTGACCC AGTCCCCGAG CTCCCTGTCT GCCTCTGTGG GCGATAGGGT CACCATCACC TGCTCAGCGCA GTCAGGATAT TAGCAACTAT TTAAACTGGT
GTCAACTGGG TCAGGGCTC GAGGGACAG CGGAGAGGACACC CGGATACCCA GTGGTAGTGG ACGTCGCGTT CAGTCCTATA ATCGTTGATA AATTTGACCA
 Q  L  T  Q  S  P  S  S  L  S  A  S  V  G  D  R  V  T  I  T  C  S  A  S  Q  D  I  S  N  Y  L  N  W  Y
                                                                         ^variable light (VL) cys ATCAACAGAA ACCAGGAAAA GCTCCGAAAG CTCCTGAAGG CTGGATTA CTTCACCTCC TCTCTCCACT GAAGTGGAGG AGAGCGAAG GTTCTCGCTTC TCTGGATCCG GTTCTGGGAC
TAGTTGTCTT TGGTCCTTT CGAGGCTTTC GAGGACTTCC ATGACTAAAT GAAGTGGAGG AGAGAGGGTGA CTTCACCTCC TCTCGCTTC AAGAGCGAAG AGACCTAGGC CAAGACCCTG
 Q  Q  K  P  G  K  A  P  K  V  L  I  Y  F  T  S  S  L  H  S  G  V  P  S  R  F  S  G  S  G  S  G  T GGATTTCACT CTGACCATCA GCAGTCTGCA GCCAGAAGAC TTCGCAACTT ATTACTGTCA ACAGTATAGC ACAGTATCGT TGTCATATGG GGACGTTTGG GGACCTCAAACC ACAGGGTACC
CCTAAAGTGA GACTGGTAGT CGTCAGACGT CGGTCTTCTG AAGCGTTGAA TAATGACAGT TGTCATATCG TGTCATAGCA ACAGTATACC CCTGCAAACC TGTCCATGG
 D  F  T  L  T  I  S  S  L  Q  P  E  D  F  A  T  Y  Y  C  Q  Q  Y  S  T  V  P  W  T  F  G  Q  G  T
                                                            ^variable light cys AAGGTGGAGA TCAAACGAAC TGTGGCTGCA CCATCTGTCT TCATCTTCCC GCCATCTGAT GAGCAGTTGA AATCTGGAAC TGCTTCTGTT GTGTGCCTGC
TTCCACCTCT AGTTTGCTTG ACACCGACGT GGTAGACAGA AGTAGAAGGG CGGTAGACTA CTCGTCAACT TTAGACCTTG ACGAAGACAA CACACGGACG
 K  V  E  I  K  R  T  V  A  A  P  S  V  F  I  F  P  P  S  D  E  Q  L  K  S  G  T  A  S  V  V  C  L  L
                                                                                      ^Constant Light cys
```

FIG. 18B

```
TGAATAACTT CTATCCCAGA GAGGCCAAAG TACAGTGGAA GGTGATAAC GCCCTCCAAT CGGGTAACTC CCAGAGAGT GTCACAGAGC AGGACAGCAA
ACTTATTGAA GATAGGGTCT CTCCGGTTTC ATGTCACCTT CCACCTATTG CGGGAGGTTA GCCCATTGAG GGTCCTCTCA CAGTGTCTCG TCCTGTCGTT
 N  N  F     Y  P  R    E  A  K  V    Q  W  K    V  D  N    A  L  Q  S    G  N  S    Q  E  S    V  T  E  Q  D  S  K

GGACAGCACC TACAGCCTCA GCAGCACCCT GACGCTGAGC GAGCTGACAA AAAGCAGACT ACGAGAAACA CAAAGTCTAC GCCTGCGAAG TCACCCATCA GGGCCTGAGC
CCTGTCGTGG ATGTCGGAGT CGTCGTGGGA CTGCGACTCG GCTCGACTGA TTTCGTCTGA TGCTCTTTGT GTTTCAGATG CGGACGCTTC AGTGGGTAGT CCCGGACTCG
 D  S  T    Y  S  L  S    S  T  L    T  L  S    K  A  D  Y    E  K  H    K  V  Y    A  C  E  V    T  H  Q    G  L  S
                                                                                              ^Constant Light cys TCGCCCGTCA CAAAGAGCTT CAACAGGGGA GAGTGTTAAT TAAATCCTCT ACGCCGGACG CATCGTGGCC CCGGGGATCT AGCCTAACG
AGCGGGCAGT GTTTCTCGAA GTTGTCCCCT CTCACAATTA ATTTAGGAGA TGCGGCCTGC GTAGCACCGG TCGAGCCATG GGCCCCTAGA TCCGGATTGC
 S  P  V  T    K  S  F    N  R  G    E  C  O
                                 ^cys to bind heavy                                         start lambda t0 terminator^

CTCGGTTGCC GCCGGGCGTT TTTTATTGTT GCCGACGCGC ATCTCGAATG AACTGTGTGC GGCGCTGTAC GAGGTAGAA GCTTTGGAGA TTATCGTCAC TGCAATGCTT
GAGCCAACGG CGGCCCGCAA AAAATAACAA CGGCTGCGCG TAGAGCTTAC TTGACACACG CCGCGACATG CTCCATTCG CGAAACCTCT AATAGCAGTG ACGTTACGAA
                                                  ^end lambda t0 terminator CGCAATATGG CGCAAAATGA CCAACAGCCG TTGATTGATC AGTAGAGGG GGCGCTAAAGC CCGATGCCAG GAGGTAAAGC CATTCCTGAC GACGATACGG
GCGTTATACC GCGTTTTACT GGTTGTCGGC AACTAACTAG TCCATCTCCC CCGCGACATG CGGCCATTCG CGGACCATG GGCCATTCG CTGATAGGACTG CTGCTATGCC AGCTGCTGCC CGATTACGTA AAGAAGTTAT TGAACCATCC TCGTCAGTAA AAAGTTAATC TTTTCAACAG CTGTCATAAA GTTGTCACGG CCGAGACTTA
TCGACGACGC GCTAATGCAT TTCTTCAATA ACTTGGTAGG AGCAGTCATT ATGGCTTCAA CATATTTGAC GAGAAGTTC GACAGTATTT CAACAGTGCC GGCTCTGAAT TAGTCGCTTT GTTTTTATTT TTTAAATGTAT TGTAACTAG TACGCAAGTT CACGTAAAAA GGGTATCTAG AATTATGAAG AAGAATATCG CATTTCTCT
ATCAGCGAAA CAAAATAAA AAATTACATA AACATTGATC AACATTGATC AACATTGATC ATGCCGTTCAA GTGCATTTT CCCATAGATC TTAATACTTC TTCTTATAGC GTAAAGAAGA
                                                                                                  M  K  K  N  I  A    F  L  L
                                                                                                 ^STII Signal TIR-1

TGCATCTATG TTCGTTTTTT CTATTGCTAC AAACGCGTAC GCTCAGGTTC AGCTGCAAGA GCTGCACCG GCTTGGCCCG GGCGACCACT TTGGTAGAGT CTGAGAGAGG
ACGTAGATAC AAGCAAAAAA GATAACGATG TTTGCGCATG CGAGTCCAAG TCGACGTTCT CAGATCGGGC CCGACCACT TTGGTAGAGT CTGAGAGAGG
                                                       ^anti-VEGF heavy chain (VNERK version)
 A  S  M    F  V  F  S    I  A  T    N  A  Y    A  Q  V  Q  L  Q  E    S  G  P    G  L  V  K    P  S  Q    T  L  S
                                                       ^Heavy chain FR1 changed to Subgroup II consensus sequence TTGACTTGTA CTGTTTCTGG CTATACCTTC ACCAACTATG GTATAAACTG GTCCGTCAG AGGGCCTCAG AGGGGCTGGA ATGGGTTGGA TGGATTAACA
AACTGAACAT GACAAAGACC GATATGGAAG TGGTTGATAC CATATTTGAC CAGGCAGTC CGGGCCCAT TCCCGGACCT TACCCAACCT ACCTAATTGT
 L  T  C    T  V  S  G    Y  T  F    T  N  Y    G  I  N  W    V  R  Q    A  P  G    K  G  L  E    W  V  G    W  I  N  T
       ^Variable Heavy (VH) cys CCTATACCGG TGAACCGACC TATGCTGCCG ATTTCAAACG TCGTTTCACT TTTTCTTTAG ACACCTCCAA AAGCACAGCA TACCTGCAGA TGAACAGCCT
GGATATGGCC ACTTGGCTGG ATACGACGCC TAAAGTTTGC AGCAAAGTGA AAAAGAAATC TGTGGAGGTT TTCGTGTCGT ATGGACGTCT ACTTGTCGGA
 Y  T  G    E  P  T    Y  A  A  D    F  K  R    R  F  T    F  S  L  D    T  S  K    S  T  A    Y  L  Q  M    N  S  L
```

FIG. 18C

```
GCGGCTGAG GACACTGCCG TCTATTACTG TGCAAAGTAC CCGGCACTATT ATGTGAACGA GCGGAAGAGC CACTGGTATT TCGACGTCTG GGGTCAAGGA
CGGCGGACTC CTGTGACGGC AGATAATGAC ACGTTTCATG GGCGTGATAA TACACTTGCT CGCCTTCTCG GTGACCATAA AGCTGCAGAC CCCAGTTCCT
 R  A  E   D  T  A  V   Y  Y  C     A  K  Y    P  H  Y  Y    V  N  E    R  K  S    H  W  Y  F    D  V  W     G  Q  G
                       ^VH cys ACCCTGGTCA CCGTCTCCTC GGCCTCCACC AAGGGCCCAT CGGTCTTCCCC CCTGGCACCC TCCTCCAAGA GCACCTCTGG GGGCACAGCG GCCCTGGGCT
TGGGACCAGT GGCAGAGGAG CCGGAGGTGG TTCCCGGGTA GCCAGAAGGG GGACCGTGGG AGGAGGTTCT CGTGGAGACC CCCGTGTCGC CGGGACCCGA
 T  L  V   T  V  S  S    A  S  T    K  G  P    S  V  F  P    P  L  A  P    S  S  K  S    T  S  G    G  T  A     A  L  G  C^
                                                                                    Constant Heavy 1 (CH1) Cys^

GCCTGGTCAA GGACTACTTC CCCGAACCGG TGACGGTGTC GTGGAACTCA GGCGCCCTGA CCAGCGGCGT GCACACCTTC CCGGCTGTCC TACAGTCCTC
CGGACCAGTT CCTGATGAAG GGGCTTGGCC ACTGCCACAG CACCTTGAGT CCGCGGGACT GGTCGCCGCA CGTGTGGAAG GGCCGACAG ATGTCAGGAG
 L  V  K    D  Y  F    P  E  P  V    T  V  S    W  N  S    G  A  L  T    S  G  V    H  T  F    P  A  V  L     Q  S  S

AGGACTCTAC TCCCTCAGCA GCGTGGTGAC TGTGCCCTCT AGCAGCTTGG GCACCCAGAC CTACATCTGC AACGTGAATC ACAAGCCCAG CAACACCAAG
TCCTGAGATG AGGGAGTCGT CGCACCACTG ACACGGGAGA TCGTCGAACC CGTGGGTCTG GATGTAGACG TTGCACTTAG TGTTCGGGTC GTTGTGGTTC
 G  L  Y   S  L  S  S    V  V  T    V  P  S    S  S  L  G    T  Q  T    Y  I  C    N  V  N  H    K  P  S     N  T  K
                                                                          ^CH1 Cys

GTGGACAAGA AAGTTGAGCC CAAATCTTGT GACAAAACTC ACACATGCCC ACCGTGCCCA GCACCTGAAC TCCTGGGGGG ACCGTCAGTC TTCCTCTTCC
CACCTGTTCT TTCAACTCGG GTTTAGAACA CTGTTTTGAG TGTGTACGGG TGGCACGGGT CGTGGACTTG AGGACCCCCC TGGCAGTCAG AAGGAGAAGG
 V  D  K  K   V  E  P    K  S  C    D  K  T  H    T  C  P    P  C  P    A  P  E  L    L  G  G    P  S  V     F  L  F  P
                        ^cys to bind light chain     ^hinge cys
                                                      ^hinge cys CCCCAAAACC CAAGGACACC CTCATGATCT CCCGGACCCC TGAGGTCACA TGCGTGGTGG TGGACGTGAG CCACGAAGAC CCTGAGGTCA AGTTCAACTG
GGGGTTTTGG GTTCCTGTGG GAGTACTAGA GGGCCTGGGG ACTCCAGTGT ACGCACCACC ACCTGCACTC GGTGCTTCTG GGACTCCAGT TCAAGTTGAC
 P  K  P   K  D  T    L  M  I  S    R  T  P    E  V  T    C  V  V  V    D  V  S    H  E  D    P  E  V  K     F  N  W
                                                          ^Constant Heavy 2 (CH2) cys GTACGTGGAC GGCGTGGAGG TGCATAATGC CAAGACAAAG CCGCGGGAGG AGCAGTACAA CAGCACGTAC CGTGTGGTCA GGTCCTCCAC CGTCCTGCAC
CATGCACCTG CCGCACCTCC ACGTATTACG GTTCTGTTTC GGCGCCCTCC TCGTCATGTT GTCGTGCATG GCACACCAGT CCAGGAGGTG GCAGGACGTG
 Y  V  D    G  V  E  V    H  N  A    K  T  K    P  R  E  E    Q  Y  N    S  T  Y    R  V  V  S    V  L  T     V  L  H CAGGACTGGC TGAATGGCAA GGAGTACAAG TGCAAGGTCT CCAACAAAGC CCTCCCAGCC CCCATCGAGA AAACCATCTC CAAAGCCAAA GGGCAGCCCC
GTCCTGACCG ACTTACCGTT CCTCATGTTC ACGTTCCAGA GGTTGTTTCG GGAGGGTCGG GGGTAGCTCT TTTGGTAGAG GTTTCGGTTT CCCGTCGGGG
 Q  D  W   L  N  G  K    E  Y  K    C  K  V  S    N  K  A    L  P  A    P  I  E  K    T  I  S    K  A  K     G  Q  P  R
                         ^CH2 cys GAGAACCACA GGTGTACACC CTGCCCCCAT CCCGGGAAGA GATGACCAAG AACCAGGTCA GCCTGACCTG CCTGGTCAAA GGCTTCTATC CCAGCGACAT
CTCTTGGTGT CCACATGTGG GACGGGGGTA GGGCCCTTCT CTACTGGTTC TTGGTCCAGT CGGACTGGAC GGACCAGTTT CCGAAGATAG GGTCGCTGTA
 E  P  Q   V  Y  T    L  P  P  S    R  E  E    M  T  K    N  Q  V  S    L  T  C    L  V  K    G  F  Y  P     S  D  I
                                                                                             ^Constant Heavy 3 (CH3) cys
```

FIG. 18D

```
CGCCGTGGAG TGGGAGAGCA ATGGGCAGCC GGAGAACAAC TACAAGACCA CGCCTCCCGT GCTGGACTCC TCTTCCTCTA CAGCAAGCTC
GCGGCACCTC ACCCTCTCGT TACCCGTCGG CCTCTTGTTG ATGTTCTGGT GCGGAGGGCA CGACCTGAGG CTGCCGAGGA AGAAGGAGAT GTCGTTCGAG
 A  V  E   W  E  S  N   G  Q  P   E  N  N   Y  K  T  T   P  P  V   L  D  S   D  G  S  F   F  L  Y   S  K  L

ACCGTGGACA AGAGCAGGTG GCAGCAGGGG AACGTCTTCT CATGCTCCGT GATGCATGAG GCTCTGCACA ACCACTACAC GCAGAAGAGC CTCTCCCTGT
TGGCACCTGT TCTCGTCCAC CGTCGTCCCC TTGCAGAAGA GTACGAGGCA CTACGTACTC CGAGACGTGT TGGTGATGTG CGTCTTCTCG GAGAGGACA
 T  V  D  K   S  R  W   Q  Q  G   N  V  F  S   M  H  E   A  L  H   N  H  Y  T   Q  K  S   L  S  L  S
                                        ^CH3 cys CTCCGGGTAA ATAAGCATGC GACGGCCCTA GAGTCCCTAA CGCTCGGTTG CCGCCGGTCG TTTTTTATTG TTAACTCATG TATCATCGAT
GAGGCCCATT TATTCGTACG CTGCCGGGAT CTCAGGGATT GCGAGCCAAC GGCGGCCCGC AAAAAATAAC AATTGAGTAC AAACTGTCGA ATAGTAGCTA
 P  G  K   O                            ^start lambda t0 terminator    ^end lambda t0 terminator
                                                                                ^start of tet resistance promoter
                                                                                          ^-35 of promoter AAGCTTTAAT GCGGTAGTTT ATCACAGTTA AATTGCTAAC GCAGTCAGGC ACCGTGTATG AAATCTAACA ATGCGCTCAT CGTCATCCTC GGCACCGTCA
TTCGAAATTA CGCCATCAAA TAGTGTCAAT TTAACGATTG CGTCAGTCCG TGGCACATAC TTTAGATTGT TACGCGAGTA GCAGTAGGAG CCGTGGCAGT
 ^-10 region of tet resistance promoter                         ^start of tet resistance translation CCCTGGATGC TGTAGGCATA GGCTTGGTTA TGCCCGGTACT GCCGGGCCTC TTGCGGGATA TCGTCCATTC CGACAGCATC GCCAGTCACT ATGGCGTGCT
GGGACCTACG ACATCCGTAT CCGAACCAAT ACGGCCCATGA CGGCCCCGAG AACGCCCTAT AGCAGGTAAG GCTGTCGTAG CGGTCAGTGA TACCGCACGA
```

FIG. 19A

```
GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

GAACTGTGTG CGCAGGTAGA AGCTTTGGAG ATTATCGTCA CTGCAATGCT TCGCAATATG GCGCAAAATG ACCAACAGCG GTTGATTGAT CAGGTAGAGG
CTTGACACAC GCGTCCATCT TCGAAACCTC TAATAGCAGT GACGTTACGA AGCGTTATAC CGCGTTTTAC TGGTTGTCGC CAACTAACTA GTCCATCTCC

GGGGCCTGTA CGAGGTAAAG CCCGATGCCA GCATTCCTGA CGACGATACG GAGCTGCTGC GCGATTACGT AAAGAAGTTA TTGAAGCATC CTCGTCAGTA
CCCGGACAT GCTCCATTTC GGGCTACGGT CGTAAGGACT GCTGCTATGC CTCGACGACG CGCTAATGCA TTTCTTCAAT AACTTCGTAG GAGCAGTCAT

AAAAGTTAAT CTTTTCAACA GCTGTCATAA AGTTGTCACG GCCCGAGACTT ATAGTCGCTT TGTTTTTATT TTTTAAATGTA TTTGTAACTA GTACGCAAGT
TTTTCAATTA GAAAAGTTGT CGACAGTATT TCAACAGTGC CGGCTCTGAA TATCAGCGAA ACAAAAATAA AAAATTACAT CATGCGTTCA

TCACGTAAAA AGGGTATCTA GAATTATGAA GAAGAATATC GCATTTCTTC GTTCGTTTTT TCTATTGCTA CAAACGCGTA CGCTGATATC
AGTGCATTTT TCCCATAGAT CTTAATACTT CTTCTTATAG CGTAAAGAAG AACGTAGATA CAAGCAAAAA AGATAACGAT GTTTGCGCAT GCGACTATAG
                    M K N I   A F L L   A S M   F V F   S I A T   N A Y   A D I
            ^STII Signal TIR -1                                 Anti-VEGF Light chain (version Y0317)^

CAGTTGACCC AGTCCCCGAG CTCCCTGTCT GCCGATAGGGT CACCATCACC TGCAGCGCAA GTCAGGATAT TAGCAACTAT TTAAACTGTGT
GTCAACTGGG TCAGGGGCTC GAGGACAGG CGGAGACACC CGCTATCCCA GTGGTAGTGG ACGTCGCGTT CAGTCCTATA ATCGTTGATA AATTTGACCA
 Q L T Q   S P S   S L S   A S V G   D R V   T I T   C S A S   Q D I   S N Y   L N W Y

ATCAACAGAA ACCAGAGAAA GCTCCGAAAG TACTGATTTA CTTCACCTCC TCTCTCCACT CTGGAGTCCC TTCTCGCTTC TCTGGATCCG GTTCTGGGAC
TAGTTGTCTT TGGTCTCTTT CGAGGCTTTC ATGACTAAAT GAAGTGGAGG AGAGAGGTGA GACCTCAGGG AAGAGCGAAG AGACCTAGGC CAAGACCCTG
 Q Q K   P G K   A P K V   L I Y   F T S   S L H S   G V P   S R F   S G S G   S G T

GGATTTCACT CTGACCATCA GCAGTCTGCA GCCGAAGAAC TTCGCAACTT ATTACTGTCA ACAGTACAGT TGTCATATCG ACCGTGCCGT GGACGGTACC
CCTAAGTGA GACTGGTAGT CGTCAGACGT CGGCTTCTTG AAGCGTTGAA TAATGACAGT TGTCATGTCA ACAGTATAGC TGGCACGGCA CCTGCCATGG
 D F T   L T I S   S L Q   P E D   F A T Y   Y C Q   Q Y S   T V P W   T F G   Q G T

AAGGTGGAGA TCAAACGAAC TGTGGCTGCA CCATCTGTCT TCATCTTCCC GCCATCTGAT GAGCAGTTGA AATCTGGAAC TGCTTCTGTT GTGTGCCTGC
TTCCACCTCT AGTTTGCTTG ACACCGACGT GGTAGACAGA AGTAGAAGGG CGGTAGACTA CTCGTCAACT TTAGACCTTG ACGAAGACAA CACACGGACG
 K V E I   K R T   V A A   P S V F   I F P   P S D   E Q L K   S G T   A S V   V C L L

TGAATAACTT CTATCCCAGA GAGGCCAAAG TACAGTGGAA GGTGGATAAC GCCCTCCAAT CGGGTAACTC CCAGGAGAGT GTCACAGAGC AGGACAGCAA
ACTTATTGAA GATAGGGTCT CTCCGGTTTC ATGTCACCTT CCACCTATTG CGGGAGGTTA GCCCATTGAG GGTCCTCTCA CAGTGTCTCG TCCTGTCGTT
 N N F   Y P R   E A K V   Q W K   V D N   A L Q S   G N S   Q E S   V T E Q   D S K
```

FIG. 19B

```
GGACAGCACC TACAGCCTCA GCAGACACCT GACGCTGAGC AAAGCAGACT ACGAGAAACA CAAAGTCTAC GCCTGCGAAG TCACCCATCA GGGCCTGAGC
CCTGTCGTGG ATGTCGGAGT CGTCGTGGGA CTGCGACTCG TTTCGTCTGA TGCTCTTTGT GTTTCAGATG CGGACGCTTC AGTGGGTAGT CCCGGACTCG
 D  S  T  Y  S  L  S   S  T  L   T  L  S    K  A  D  Y    E  K  H    K  V  Y    A  C  E  V    T  H  Q    G  L  S

TCGCCCGTCA CAAAGAGCTT CAACAGGGGA GAGTGTTAAT TAAATCCTCT ACGCCCGACG CATCGTGGCG AGCTCGGTAC CCGGGGATCT AGGCCTAACG
AGCGGGCAGT GTTTCTCGAA GTTGTCCCCT CTCACAATTA ATTTAGGAGA TGCGGGCTGC GTAGCACCGC TCGAGCCATG GGCCCCTAGA TCCGGATTGC
 S  P  V  T    K  S  F    N  R  G    E  C  O

CTCGGTTGCC GCCGGGCGTT TTTTATTGTT GCCGACGCGC ATCTCGAATG AACTGTGTGC GCAGGTAGAA GCTTTGGAGA TTATCGTCAC TGCAATGCTT
GAGCCAACGG CGGCCCGCAA AAAATAACAA CGGCTGCGCG TAGAGCTTAC TTGACACACG CGTCCATCTT CGAAACCTCT AATAGCAGTG ACGTTACGAA

CGCAATATGG CGCAAAATGA CCAACAGCGG TTGATTGATC AGGTAGAGGG GGCGCTGTAC GAGGTAAAGC CCGATGCCAG CATTCCTGAC GACGATACGG
GCGTTATACC GCGTTTTACT GGTTGTCGCC AACTAACTAG TCCATCTCCC CCGCGACATG CTCCATTTCG GCTACGGTC GTAAGGACTG CTGCTATGCC

AGTCTGCTGCG CGATTACGTA AAGAAGTTAT TGAAGCATCC TCGTCAGTAA AAAGTTAATC TTTTCAACAG CTGTCATAAA GTTGTCACGG CCGAGACTTA
TCAGACGACGC GCTAATGCAT TTCTTCAATA ACTTCGTAGG AGCAGTCATT TTTCAATTAG AAAAGTTGTC GACAGTATTT CAACAGTGCC GGCTCTGAAT

TAGTCGCTTT GTTTTTATTT TTTAATGTAT TTGTAACTAG TACGCAAGTT CACGTAAAAA GGGTATCTAG AATTATGAAG AAGAATATCG CATTTCTTCT
ATCAGCGAAA CAAAAATAAA AAATTACATA AACATTGATC ATGCGTTCAA GTGCATTTTT CCCATAGATC TTAATACTTC TTCTTATAGC GTAAAGAAGA
                                                                                              M  K  K  N  I  A    F  L  L
                                                                                             ^STII Signal TIR-1

TGCATCTATG TTCGTTTTTT CTATTGCTAC AAACCGGTAC GCTCAGGTTC AGCTGGTACA GTCTGGTGCA GAGGTGAAAA AGCCAGGGGC TTCAGTTAAA
ACGTAGATAC AAGCAAAAAA GATAACGATG TTTGCCATG CGAGTCCAAG TCGACCACGT CAGAGCCACGT CTCCACTTTT TCGGTCCCCG AAGTCAATTT
 A  S  M    F  V  F  S    I  A  T    N  A  Y    A  Q  V  Q    L  V  Q   S  G  A   E  V  K  K    P  G  A   S  V  K
                                                            ^Anti-VEGF (version Y0317) Heavy Chain
                                                              ^Heavy Chain FR1 changed to Subgroup1 consensus sequence GTATCCTGTA AAGCTTCTGG CTACGACTTC ACGCACTACG GTCGTGATGC GTATGAACTG GGTCCGTCAG AGGGCCGGGTA ATGGGTTGGA TGGATTAACA
CATAGGACAT TTCGAAGACC GATGCTGAAG TGCGTGATGC CATACTTGAC CAGCACTACG CCAGGCAGTC TCCCGGACCT TACCCAACCT ACCTAATTGT
 V  S  C  K   A  S  G   Y  D  F   T  H  Y  G     M  N  W   V  R  Q    A  P  G  K    G  L  E    W  V  G    W  I  N  T CCTATACCGG TGAACCGACC TATGCCGCGG ATTTCAAACG TCGTTTCACT TTTTCTTTAG ACACCTCCAA AAGCACAGCA TACCTGCAGA TGAACAGCCT
GGATATGGCC ACTTGGCTGG ATACGACGCC TAAAGTTTGC AGCAAAGTGA AAAAGAAATC TGTGGAGGTT TTCGTGTCGT ATGGACGTCT ACTTGTCGGA
 Y  T  G    E  P  T    Y  A  A  D    F  K  R    R  F  T    F  S  L  D    T  S  K    S  T  A    Y  L  Q  M    N  S  L GCGGCTGAG GACACTGCCG TCTATTACTG TGCAAAGTAC CCGTACTATT ATGGGACGAG CCACTGGTAT TTCGACGTCT GGGGTCAAGG CCCCAGTTCC TTGGACCAG
CGCCGACTC CTGTGACGGC AGATAATGAC ACGTTTCATG GCATGATATA ACCCTGCTC GGTGACCATA AAGCTGCAGA CCCCAGTTCC GGGGTCAAGG AACCTGGTC
 R  A  E    D  T  A  V    Y  Y  C    A  K  Y    P  Y  Y  Y    Y  G  T  S    H  W  Y    F  D  V  W    G  Q  G    T  L  V ACCGTCTCCT CGGCCTCCAC CAAGGGCCCA TCGGTCTTCC CCCTGGCACC CTCCTCCAAG AGCACCTCTG GGGGCACAGC GGCCCTGGGC TGCCTGGTCA
TGGCAGAGGA GCCGGAGGTG GTTCCCGGGT AGCCAGAGG GGGACCGTGG GAGGAGGTTC TCGTGGAGAC CCCCGTGTCG CCGGGACCCG ACGGACCAGT
 T  V  S  S    A  S  T    K  G  P    P  S  V  F    P  L  A  P    S  S  K    S  T  S  G    G  T  A    A  L  G    C  L  V  K
```

FIG. 19C

```
AGGACTACTT CCCCGAACCG GTGACGGTGT CGTGGAACTC AGGGCCCCTG ACCAGCGGGC TGCACACCTT CCCGGCTGTC CTACAGTCCT CAGGACTCTA
TCCTGATGAA GGGGCTTGGC CACTGCCACA GCACCTTGAG TCCCGGGGAC TGGTCGCCGC ACGTGTGGAA GGGCCGACAG GATGTCAGGA GTCCTGAGAT
 D  Y  F  P  E  P  V  T  V  S  W  N  S  G  A  L  T  S  G  V  H  T  F  P  A  V  L  Q  S  S  G  L  Y

CTCCCTCAGC AGCGTGGTGA CTGTGCCCTC TAGCAGCTTG GGCACCCAGA CCTACATCTG CAACGTGAAT CACAAGCCCA GCAACACCAA GGTGGACAAG
GAGGGAGTCG TCGCACCACT GACACGGGAG ATCGTCGAAC CCGTGGGTCT GGATGTAGAC GTTGCACTTA GTGTTCGGGT CGTTGTGGTT CCACCTGTTC
 S  L  S  S  V  V  T  V  P  S  S  S  L  G  T  Q  T  Y  I  C  N  V  N  H  K  P  S  N  T  K  V  D  K

AAAGTTGAGC CCAAATCTTG TGACAAAACT CACACATGCC CACCGTGCCC AGCACCTGAA CTCCTGGGGG GACCGTCAGT CTTCCTCTTC CCCCCAAAAC
TTTCAACTCG GGTTTAGAAC ACTGTTTTGA GTGTGTACGG GTGGCACGGG TCGTGGACTT GAGGACCCCC CTGGCAGTCA GAAGGAGAAG GGGGGTTTTG
 K  V  E  P  K  S  C  D  K  T  H  T  C  P  P  C  P  A  P  E  L  L  G  G  P  S  V  F  L  F  P  P  K  P

CCAAGGACAC CCTCATGATC TCCCGGACCC CTGAGGTCAC ATGCGTGGTG GTGGACGTGA GCCACGAAGA CCCTGAGGTC AAGTTCAACT GGTACGTGGA
GGTTCCTGTG GGAGTACTAG AGGGCCTGGG GACTCCAGTG TACGCACCAC CACCTGCACT CGGTGCTTCT GGGACTCCAG TTCAAGTTGA CCATGCACCT
 K  D  T  L  M  I  S  R  T  P  E  V  T  C  V  V  V  D  V  S  H  E  D  P  E  V  K  F  N  W  Y  V  D

CGGCGTGGAG GTGCATAATG CCAAGACAAA GCCGCGGGAG GAGCAGTACA ACAGCACGTA CCGTGTGGTC AGCGTCCTCA CCGTCCTGCA CCAGGACTGG
GCCGCACCTC CACGTATTAC GGTTCTGTTT CGGCGCCCTC CTCGTCATGT TGTCGTGCAT GGCACACCAG TCGCAGGAGT GGCAGGACGT GGTCCTGACC
 G  V  E  V  H  N  A  K  T  K  P  R  E  E  Q  Y  N  S  T  Y  R  V  V  S  V  L  T  V  L  H  Q  D  W

CTGAATGGCA AGGAGTACAA GTGCAAGGTC TCCAACAAAG CCCTCCCAGC CCCCATCGAG AAAACCATCT CCAAAGCCAA AGGGCAGCCC CGAGAACCAC
GACTTACCGT TCCTCATGTT CACGTTCCAG AGGTTGTTTC GGGAGGGTCG GGGGTAGCTC TTTTGGTAGA GGTTTCGGTT TCCCGTCGGG GCTCTTGGTG
 L  N  G  K  E  Y  K  C  K  V  S  N  K  A  L  P  A  P  I  E  K  T  I  S  K  A  K  G  Q  P  R  E  P  Q

AGGTGTACAC CCTGCCCCCA TCCCGGGAAG AGATGACCAA GAACCAGGTC AGCCTGACCT GCCTGGTCAA AGGCTTCTAT CCCAGCGACA TCGCCGTGGA
TCCACATGTG GGACGGGGGT AGGGCCCTTC TCTACTGGTT CTTGGTCCAG TCGGACTGGA CGGACCAGTT TCCGAAGATA GGGTCGCTGT AGCGGCACCT
 V  Y  T  L  P  P  S  R  E  E  M  T  K  N  Q  V  S  L  T  C  L  V  K  G  F  Y  P  S  D  I  A  V  E

GTGGGAGAGC AATGGGCAGC CGGAGAACAA CTACAAGACC ACGCCTCCCG TGCTGGACTC CGACGGCTCC TTCTTCCTCT ACAGCAAGCT CACCGTGGAC
CACCCTCTCG TTACCCGTCG GCCTCTTGTT GATGTTCTGG TGCGGAGGGC ACGACCTGAG GCTGCCGAGG AAGAAGGAGA TGTCGTTCGA GTGGCACCTG
 W  E  S  N  G  Q  P  E  N  N  Y  K  T  T  P  P  V  L  D  S  D  G  S  F  F  L  Y  S  K  L  T  V  D

AAGAGCAGGT GGCAGCAGGG GAACGTCTTC TCATGCTCCG TGATGCATGA GGCTCTGCAC AACCACTACA CGCAGAAGAG CCTCTCCCTG TCTCCGGGTA
TTCTCGTCCA CCGTCGTCCC CTTGCAGAAG AGTACGAGGC ACTACGTACT CCGAGACGTG TTGGTGATGT GCGTCTTCTC GGAGAGGGAC AGAGGCCCAT
 K  S  R  W  Q  Q  G  N  V  F  S  C  S  V  M  H  E  A  L  H  N  H  Y  T  Q  K  S  L  S  L  S  P  G  K

AATAAGCATG CGACGCCCCT AGAGTCCTA ACGCTCGGTT GCCGCCGGGC GTTTTTTATT GTTAACTCAT GTTTGACGAC TTAATCATGA TAAGCTTTAA
TTATTCGTAC GCTGCGGGGA TCTCAGGAT TGCGAGCCAA CGGCGGCCCG CAAAAAATAA CAATTGAGTA CAAACTGCTG AATTAGTACT ATTCGAAATT
                                                                                                  ○

TGCGGTAGTT TATCACAGTT AAATTGCTAA CGCAGTCAGG CACCGTGTAT GAAATCTAAC AATGCGCTCA TCGTCATCCT CGGCACCGTC ACCCTGGATG
ACGCCATCAA ATAGTGTCAA TTTAACGATT GCGTCAGTCC GTGGCACATA CTTTAGATTG TTACGCGAGT AGCAGTAGGA GCCGTGGCAG TGGGACCTAC
                                      ^Start Tet Resistance Coding Sequence
```

FIG. 19D

```
CTGTAGGCAT AGGCTTGGTT ATGCCGGTAC TGCCGGGCCT CTTGCGGGAT ATCGTCCATT CCGACAGCAT CGCCAGTCAC TATGGCGTGC TGCTAGCGCT
GACATCCGTA TCCGAACCAA TACGGCCATG ACGGCCCGGA GAACGCCCTA TAGCAGGTAA GGCTGTCGTA GCGGTCAGTG ATACCGCACG ACGATCGCGA
```

```
GCAGGACAGC AAGGACAGCA CCTACAGCCT CAGCAGCAGA CTGACGCTGA GCAAGCAGA CTACGAGAAA CACAAAGTCT ACGCTGCGA AGTCACCAT
CGTCCTGTCG TTCCTGTCGT GGATGTCGGA GTCGTCGTCT GACTGCGACT GCGTTTCGTCT GATGCTCTTT GTGTTTCAGA TGCGGACGCT TCAGTGGGTA
 Q  D  S   K  D  S  T   Y  S  L   S  S  T   L  T  L  S   K  A  D   Y  E  K   H  K  V  Y   A  C  E   V  T  H
                                                              ECO

CAGGGCCTGA GCTCGCCCGT CACAAAGAGC TTCAACAGGG GAGAGTGTTA ATTAAATCCT CTACGCCGGA CCGATCGTGG CGAGCTCGT ACCCGGGGAT
GTCCCGGACT CGAGCGGGCA GTGTTTCTCG AAGTTGTCCC CTCTCACAAT TAATTTAGGA GATGCGGCCT GCGTAGCACC GCTCGAGCCA TGGGCCCCTA
 Q  G  L  S  S  P  V   T  K  S   F  N  R  G   E  C  O

CTAGGCCTAA CGCTCGGTTG CCGCCGGGCG TTTTTTATTG TTGCCGACGC GCATCTCGAA TGAACTGTGT GCGCAGGTAG AAGCTTTGA GATTATCGTC
GATCCGGATT GCGAGCCAAC GGCGGCCCGC AAAAAATAAC AACGGCTGCG CGTAGAGCTT ACTTGACACA CGCGTCCATC TTCGAAACCT CTAATAGCAG

ACTGCAATGC TTCGCAATAT GGCGCAAAAT GACCAACAGC GGTTGATTGA TCAGGTAGAG GGGCGCGTGT ACGAGGTAAA GCCCGATGCC AGCATTCCTG
TGACGTTACG AAGCGTTATA CCGCGTTTTA CTGGTTGTCG CCAACTAACT AGTCCATCTC CCCCGCGACA TGCTCCATTT CGGGCTACGG TCGTAAGGAC

ACGACGATAC GGAGCTGCTG CGCGATTACG TAAAGAAGTT ATTGAAGCAT TCTTTTTCAAC AGTCTGTCATA AAGTTGTCAC
TGCTGCTATG CCTCGACGAC GCGCTAATGC ATTTCTTCAA TAACTTCGTA AGAAAAAGTTG TCAGACAGTAT TTCAACAGTG

GGCCGAGACT TATAGTCGCT TTGTTTTTAT TTTTTAATGT ATTTGTAACT AGTACGCAAG TTCACGTAAA AAGGGTATCT AGAATTATGA AGAAGAATAT
CCGGCTCTGA ATATCAGCGA AACAAAAATA AAAAATTACA TAAACATTGA TCATGCGTTC AAGTGCATTT TTCCCATAGA TCTTAATACT TCTTCTTATA
                                                                                             M  K  N  I
                                                                                           ^STII Signal TIR-1

CGCATTTCTT CTTGCATCTA TGTTCGTTTT TTCTATTGCT ACAAACGCGT ACGCTGAGGT TCAGCTGGTG GAGTCTGGCG GTGGCCTGGT GCAGCCAGGG
GCGTAAAGAA GAACTGTAGAT ACAAGCAAA AAGATAACGA TGTTTGCGCA TGCGACTCCA AGTCGACCAC CTCAGACCGC CACCGGACCA CGTCGGTCCC
 A  F  L   L  A  S  M   F  V  F   S  I  A   T  N  A  Y   A  E  V   Q  L  V   E  S  G  G   G  L  V   Q  P  G
                                                    ^anti-IgE heavy chain GGCTCACTCC GTTTGTCCTG TGCAGTTTCT GGCTACTCCA TCACCTCCGG ATATAGCTGG AACTGGATCC GTCAGGCCCC GGGTAAGGGC CTGGAATGGG
CCGAGTGAGG CAAACAGGAC ACGTCAAAGA CCGATGAGGT AGTGGAGGCC TATATCGACC TTGACCTAGG CAGTCCGGGG CCCATTCCCG GACCTTACCC
 G  S  L  R  L  S  C   A  V  S   G  Y  S  I   T  S  G   Y  S  W   N  W  I  R   Q  A  P   G  K  G   L  E  W  V TTGCATCGAT TACGTATGAC GGATCGACTA ACTATAACCC TAGCGTCAAG GGCCGTCAGT TCCGCATAGT CTATAAGTCG CGACGACTCC AAAAACACAT TCTACCTGCA
AACGTAGCTA ATGCATACTG CCTAGTCGAT TGATATTGGG ATCGCAGTTC CCGGCAGTCA AGGCGTATCA GATATTCAGC GCTGCTGAGG TTTTTGTGTA AGATGGACGT
 A  S  I   T  Y  D   G  S  T  N   Y  N  P   S  V  K   G  R  I  T   I  S  R   D  D  S   K  N  T  F   Y  L  Q GATGAACAGC CTGCGTGCTG AGGACACTGC CGTCTATTAT TGTGCTCGAG GCAGCCACTA TTTTCGGTCAC TGGCACTTCG CCGTGTGGGG TCAAGGAACC
CTACTTGTCG GACGCACGAC TCCTGTGACG GCAGATAATA ACACGAGCTC CGTCGGTGAT AAAGCCAGTG ACCGTGAAGC GGCACACCCC AGTTCCTTGG
 M  N  S   L  R  A  E   D  T  A   V  Y  Y   C  A  R  G   S  H  Y   F  G  H   W  H  F  A   V  W  G   Q  G  T CTGGTCACCG TCTCCTCGGC CTCCACCAAG GGCCCATCGG TCTTCCCCCT GGCACCCTCC TCCAAGAGCA CCTCTGGGGG CACAGCGGCC CTGGGCTGCC
GACCAGTGGC AGAGGAGCCG GAGGTGGTTC CCGGGTAGCC AGAAGGGGGA CCGTGGGAGG AGGTTCTCGT GGAGACCCCC GTGTCGCCGG GACCCGACGG
 L  V  T  V  S  S  A   S  T  K   G  P  S  V   F  P  L   A  P  S   S  K  S  T   S  G  G   T  A  A   L  G  C  L
```

FIG. 20C

```
TGGTCAAGGA CTACTTCCCC GAACCGGTGA CGGTGTCGTG GAACTCAGGC GCCCTGACCA GCGGGTGTCA CACCTTCCCG GCTGTCCTAC AGTCCTCAGG
ACCAGTTCCT GATGAAGGGG CTTGGCCACT GCCACAGCAC CTTGAGTCCG CGGGACTGGT GTGGAAGGGC CGACAGATG TCAGGAGTCC
    V  K  D  Y  F  P  P  E  P  V  T  V  S  W  N  S  G  A  L  T  S  G  V  H  T  F  P  A  V  L  Q  S  S  G

ACTCTACTCC CTCAGCAGCG TGGTGACTGT GCCCTCTAGC AGCTTGGGCA CCCAGACCTA CATCTGCAAC GTGAATCACA AGCCCAGCAA CACCAAGGTG
TGAGATGAGG GAGTCGTCGC ACCACTGACA CGGGAGATCG TCGAACCCGT GGGTCTGGAT GTAGACGTTG CACTTAGTGT TCGGGTCGTT GTGGTTCCAC
    L  Y  S  L  S  S  V  V  T  V  P  S  S  S  L  G  T  Q  T  Y  I  C  N  V  N  H  K  P  S  N  T  K  V

GACAAGAAAG TTGAGCCCAA ATCTTGTGAC AAAACTCACA CATGCCCACC GTGCCCAGCA CCTGAACTCC TGGGGGGACC GTCAGTCTTC CTCTTCCCCG
CTGTTCTTTC AACTCGGGTT TAGAACACTG TTTTGAGTGT GTACGGGTGG GGACTTGAGG ACCCCCCTGG CAGTCAGAAG GAGAGGGGC
    D  K  K  V  E  P  K  S  C  D  K  T  H  T  C  P  P  C  P  A  P  E  L  L  G  G  P  S  V  F  L  F  P  P

CAAAACCCAA GGACACCCTC ATGATCTCCC GGACCCCTGA GGTCACATGC GTGGTGGTGG ACGTGAGCCA CGAAGACCCT GAGGTCAAGT TCAACTGGTA
GTTTTGGGTT CCTGTGGGAG TACTAGAGGG CCTGGGGACT CCAGTGTACG CACCACCACC TGCACTCGGT GCTTCTGGGA CTCCAGTTCA AGTTGACCAT
    K  P  K  D  T  L  M  I  S  R  T  P  E  V  T  C  V  V  V  D  V  S  H  E  D  P  E  V  K  F  N  W  Y

CGTGGACGGC GTGGAGGTGC ATAATGCCAA GACAAAGCCG CGGGAGGAGC AGTACAACAG CACGTACCGT GTGGTCAGCG TCCTCACCGT CCTGCACCAG
GCACCTGCCG CACCTCCACG TATTACGGTT CTGTTTCGGC GCCCTCCTCG TCATGTTGTC GTGCATGGCA CACCAGTCGC AGGAGTGGCA GGACGTGGTC
    V  D  G  V  E  V  H  N  A  K  T  K  P  R  E  E  Q  Y  N  S  T  Y  R  V  V  S  V  L  T  V  L  H  Q

GACTGGCTGA ATGGCAAGGA GTACAAGTGC AAGGTCTCCA ACAAAGCCCT CCCAGCCCCC ATCGAGAAAA CCATCTCCAA AGCCAAAGGG CAGCCCCGAG
CTGACCGACT TACCGTTCCT CATGTTCACG TTCCAGAGGT TGTTTCGGGA GGGTCGGGGG TAGCTCTTTT GGTAGAGGTT TCGGTTTCCC GTCGGGGCTC
    D  W  L  N  G  K  E  Y  K  C  K  V  S  N  K  A  L  P  A  P  I  E  K  T  I  S  K  A  K  G  Q  P  R  E

AACCACAGGT GTACACCCTG CCCCCATCCC GGGAAGAGAT GACCAAGAAC CAGGTCAGCC TGACCTGCCT GGTCAAAGGC TTCTATCCCA GCGACATCGC
TTGGTGTCCA CATGTGGGAC GGGGGTAGGG CCCTTCTCTA CTGGTTCTTG GTCCAGTCGG ACTGGACGGA CCAGTTTCCG AAGATAGGGT CGCTGTAGCG
    P  Q  V  Y  T  L  P  P  S  R  E  E  M  T  K  N  Q  V  S  L  T  C  L  V  K  G  F  Y  P  S  D  I  A

CGTGGAGTGG GAGAGCAATG GGCAGCCGGA GAACAACTAC AAGACCACGC CTCCCGTGCT GGACTCCGAC GGCTCCTTCT TCCTCTACAG CAAGCTCACC
GCACCTCACC CTCTCGTTAC CCGTCGGCCT CTTGTTGATG TTCTGGTGCG GAGGGCACGA CCTGAGGCTG CCGAGGAAGA AGGAGATGTC GTTCGAGTGG
    V  E  W  E  S  N  G  Q  P  E  N  N  Y  K  T  T  P  P  V  L  D  S  D  G  S  F  F  L  Y  S  K  L  T

GTGGACAAGA GCAGGTGGCA GCAGGGGAAC GTCTTCTCAT GCTCCGTGAT GCATGAGGCT CTGCACAACC ACTACACGCA GAAGAGCCTC TCCCTGTCTC
CACCTGTTCT CGTCCACCGT CGTCCCCTTG CAGAAGAGTA CGAGGACACTA CGTACTCCGA GACGTGTTGG TGATGTGCGT CTTCTCGGAG AGGGACAGAG
    V  D  K  S  R  W  Q  Q  G  N  V  F  S  C  S  V  M  H  E  A  L  H  N  H  Y  T  Q  K  S  L  S  L  S  P

CGGGTAAATA AGCATGCGAC GGCCCTAGAG TCCCTAACGC TCGGTTGCCG CCGGGCGTTT TTTATTGTTA ACTCATGTTT GACAGCTTAT CATCGATAAG
GCCCATTTAT TCGTACGCTG CCGGGATCTC AGGGATTGCG AGCCAACGGC GGCCCGCAAA AAATAACAAT TGAGTACAAA CTGTCGAATA GTAGCTATTC
    G  K  O

CTTTAATGCG GTAGTTTATC ACAGTTAAAT TGCTAACGCA GTCAGGCACC GTGTATGAAA TCTAACAATG CGCTCATCGT CATCCTCGGC ACCGTCACCC
GAAATTACGC CATCAAATAG TGTCAATTTA ACGATTGCGT CAGTCCGTGG CACATACTTT AGATTGTTAC GCGAGTAGCA GTAGGAGCCG TGGCAGTGGG
```

FIG. 20D

TGGATGCTGT AGGCATAGGC TTGGTTATGC CGGTACTGCC GGGCCTCTTG CGGGATATCG TCCATTCCGA CAGCATCGCC AGTCACTATG GCGTGCTGCT
ACCTACGACA TCCGTATCCG AACCAATACG GCCATGACGG CCCGGAGAAC GCCCTATAGC AGGTAAGGCT GTCGTAGCGG TCAGTGATAC CGCACGACGA

```
GCAGGACAGC AAGGACAGCA CCTACAGCCT CAGCAGCACC CTGACGCTGA GCAAAGCAGA CTACGAGAAA CACAAAGTCT ACGCCTGCGA AGTCACCCAT
CGTCCTGTCG TTCCTGTCGT AGGATGTCGGA GTCGTCGTGG GACTGCGACT CGTTTCGTCT GATGCTCTTT GTGTTTCAGA TGCGGACGCT TCAGTGGGTA
 Q  D  S    K  D  S  T    Y  S  L    S  S  T    L  T  L  S    K  A  D    Y  E  K    H  K  V  Y    A  C  E    V  T  H

CAGGGCCTGA GCTCGCCCGT CACAAAGAGC TTCAACAGGG GAGAGTGTTA ATTAAATCTC CTACGCCGGA CGCATCGTGG CGAGCTCGGT ACCCGGGGAT
GTCCCGGACT CGAGCGGGCA AGTGTTTCTCG AAGTTGTCCC CTCTCACAAT TAATTTAGGA GATGCGGCCT GCGTAGCACC GCTCGAGCCA TGGGCCCCTA
 Q  G  L  S    S  P  V    T  K  S    F  N  R  G    E  C  O

CTAGGCCTAA CGCTCGGTTG CCGCCGGGCG TTTTTTATTG TTGCCGACGC GCATCTCGAA TGAACTGTGT GCGCAGGTAG AAGCTTTGGA GATTATCGTC
GATCCGGATT GCGAGCCAAC GGCGGCCCGC AAAAAATAAC AACGGCTGCG CGTAGAGCTT ACTTGACACA CGCGTCCATC TTCGAAACCT CTAATAGCAG

ACTGCAATGC TTCGCAATAT GGGCGCAAAT GACCAACAGC GGTTGATTGA TCAGGTAGAG GGGGGCCTGT ACGAGGTAAA GCCCGATGCC AGCATTCCTG
TGACGTTACG AAGCGTTATA CCCGCGTTTA CTGGTTGTCG CCAACTAACT AGTCCATCTC CCCCGGACA TGCTCCATTT CGGGCTACGG TCGTAAGGAC

ACGACGATAC GGAGCTGCTG CGCGATTACG TAAAGAAGTT ATTGAAGCAT CCTCGTCAGT AAAAAGTTAA TCTTTTCAAC AGCTGTCATA AAGTTGTCAC
TGCTGCTATG CCTCGACGAC GCGCTAATGC ATTTCTTCAA TAACTTCGTA GGAGCAGTCA TTTTTCAATT AGAAAAGTTG TCGACAGTAT TTCAACAGTG

GGCCGAGACT TATAGTCGCT TTGTTTTTAT TTTGTTTTTAA ATTTGTAACT AGTACGCAAG TTCAGTGAAA AAGGTATCT AGAATTATGA AGAAGAATAT
CCGGCTCTGA ATATCAGCGA ACACAAATA AAACAAAATTA TAAACATTGA TCATGCGTTC AAGTGCATTT TTCCCATAGA TCTTAATACT TCTTCTATA
                                                                                                M  K  N  I
                                                                                                ^STII Signal TIR-1

CGCATTTCTT CTTGCATCTA TGTTCGTTTT TTCTATTGCT ACAAACGCGT ACGCTCAGGT TCAGCTGCAA GAGTCTGGCC CGGGCCTGGT GAAACCATCT
GCGTAAAGAA GAACGTAGAT ACAAGCAAAA AAGATAACGA TGTTTGCGCA TGCGAGTCCA AGTCGACGTT CTCAGACCGG GCCCGGACCA CTTTGGTAGA
 A  F  L    L  A  S  M    F  V  F    S  I  A    T  N  A  Y    A  Q  V    Q  L  Q    E  S  G  P    G  L  V    K  P  S
                                              ^anti-IgE Heavy Chain
                                              ^Heavy Chain FR1=SubgroupII consensus sequence CAGACTCTCT CCTTGACTTG TACTGTTTCT GGCTACTCCA TCACCTCCGG ATATAGCTGG AACTGGATCC GTCAGGCCCC GGGTAAGGGC CTGGAATGGG
GTCTGAGAGA GGAACTGAAC ATGACAAAGA CCGATGAGGT AGTGGAGGCC TATATCGACC TTGACCTAGG CAGTCCGGGG CCCATTCCCG GACCTTACCC
 Q  T  L  S    L  T  C    T  V  S    G  Y  S  I    T  S  G    Y  S  W    N  W  I  R    Q  A  P    G  K  G    L  E  W  V TTGCATCGAT TACGTATGAC GGATCGACTA ACTATAACCC TAGCGTCAAG GGCCGTATCA CTATAAGTCG GGACGACTCC AAAAACACAT TCTACCTGCA
AACGTAGCTA ATGCATACTG CCTAGCTGAT TGATATTGGG ATCGCAGTTC CCGGCATAGT GATATTCAGC CCTGCTGAGG TTTTTGTGTA AGATGGACGT
 A  S  I    T  Y  D    G  S  T  N    Y  N  P    S  V  K    G  R  I  T    I  S  R    D  D  S    K  N  T  F    Y  L  Q GATGAACAGC CTGCGTGCTG AGGACACTGC CGTCTATTAT TGTGCTCGAG CGAGCCACTA TTTCGGTCAC TGGCACTTCG CCGTGTGGGG TCAAGGAACC
CTACTTGTCG GACGCACGAC TCCTGTGACG GCAGATAATA ACACGAGCTC GCTCGGTGAT AAAGCCAGTG ACCGTGAAGC GGCACACCCC AGTTCCTTGG
 M  N  S    L  R  A  E    D  T  A    V  Y  Y    C  A  R  G    S  H  Y    F  G  H    W  H  F  A    V  W  G    Q  G  T CTGGTCACCG TCTCCTCGGC CTCCACCAAG GGCCCATCGG TCTTCCCCCT GGCACCCTCC TCCAAGAGCA CCTCTGGGGG CACAGCGGCC CTGGGCTGCC
GACCAGTGGC AGAGGAGCCG GAGGTGGTTC CCGGGTAGCC AGAAGGGGGA AGGTTCTCGT GGAGACCCCC GTGTCGCCGG GACCCGACGG
 L  V  T  V    S  S  A    S  T  K    G  P  S  V    F  P  L    A  P  S    S  K  S  T    S  G  G    T  A  A    L  G  C  L
```

FIG. 21C

```
TGGTCAAGGA CTACTTCCCC GAACCGGTGA CGGTGTCGTG GAACTCAGGC GCCCTGACCA GCGGCGTGCA CACCTTCCCG GCTGTCCTAC AGTCCTCAGG
ACCAGTTCCT GATGAAGGGG CTTGGCCACT GCCACAGCAC CTTGAGTCCG CGGGACTGGT CGCCGCACGT GTGGAAGGGC CGACAGGATG TCAGGAGTCC
 V  K  D  Y  F  P  E  P  V  T  V  S  W  N  S  G  A  L  T  S  G  V  H  T  F  P  A  V  L  Q  S  S  G

ACTTACTCC CTCAGCAGCG TGGTGACTGT GCCCTCTAGC AGCTTGGGCA CCCAGACCTA CATCTGCAAC GTGAATCACA AGCCCAGCAA CACCAAGGTG
TGACATGAGG GAGTCGTCGC ACCACTGACA CGGGAGATCG TCGAACCCGT GGGTCTGGAT GTAGACGTTG CACTTAGTGT TCGGGTCGTT GTGGTTCCAC
 L  S  S  V  V  T  V  P  S  S  S  L  G  T  Q  T  Y  I  C  N  V  N  H  K  P  S  N  T  K  V

GACAAGAAAG TTGAGCCCAA ATCTTGTGAC AAAACTCACA CATGCCCACC GTGCCCAGCA CCTGAACTCC TGGGGGGACC GTCAGTCTTC CTCTTCCCCC
CTGTTCTTTC AACTCGGGTT TAGAACACTG TTTTGAGTGT GTACGGGTGG GGACGGGTCGT GGACTTGAGG ACCCCCCTGG CAGTCAGAAG GAGAAGGGG
 D  K  K  V  E  P  K  S  C  D  K  T  H  T  C  P  P  C  P  A  P  E  L  L  G  G  P  S  V  F  L  F  P  P

CAAAACCCAA GGACACCCTC ATGATCTCCC GGACCCCTGA GGTCACATGC GTGGTGGTGG ACGTGAGCCA CGAAGACCCT GAGGTCAAGT TCAACTGGTA
GTTTTGGGTT CCTGTGGGAG TACTAGAGGG CCTGGGGACT CCAGTAGTAG CACCACCACC TGCACTCGGT GCTTCTGGGA CTCCAGTTCA AGTTGACCAT
 K  P  K  D  T  L  M  I  S  R  T  P  E  V  T  C  V  V  V  D  V  S  H  E  D  P  E  V  K  F  N  W  Y

CGTGGACGGC GTGGAGGTGC ATAATGCCAA GACAAAGCCG CGGGAGGAGC AGTACAACAG CACGTACCGT GTGGTCAGCG TCCTCACCGT CCTGCACCAG
GCACCTGCCG CACCTCCACG TATTACGGTT CTGTTTCGGC GCCCTCCTCG TCATGTTGTC GTGCATGGCA CACCAGTCGC AGGAGTGGCA GGACGTGGTC
 V  D  G  V  E  V  H  N  A  K  T  K  P  R  E  E  Q  Y  N  S  T  Y  R  V  V  S  V  L  T  V  L  H  Q

GACTGGCTGA ATGGCAAGGA GTACAAGTGC AAGGTCTCCA ACAAAGCCCT CCCAGCCCCC ATCGAGAAAA CCATCTCCAA AGCCAAAGGG CAGCCCCGAG
CTGACCGACT TACCGTTCCT CATGTTCACG TTCCAGAGGT TGTTTCGGGA GGGTCGGGGG TAGCTCTTTT GGTAGAGGTT TCGGTTTCCC GTCGGGGCTC
 D  W  L  N  G  K  E  Y  K  C  K  V  S  N  K  A  L  P  A  P  I  E  K  T  I  S  K  A  K  G  Q  P  R  E

AACCACAGGT GTACACCCTG CCCCCATCCC GGGAAGAGAT GACCAAGAAC CAGGTCAGCC TGACCTGCCT GGTCAAAGGC TTCTATCCCA GCGACATCGC
TTGGTGTCCA CATGTGGGAC GGGGGTAGGG CCCTTCTCTA CTGGTTCTTG GTCCAGTCGG ACTGGACGGA CCAGTTTCCG AAGATAGGGT CGCTGTAGCG
 P  Q  V  Y  T  L  P  P  S  R  E  E  M  T  K  N  Q  V  S  L  T  C  L  V  K  G  F  Y  P  S  D  I  A

CGTGGAGTGG GAGAGCAATG GGCAGCCGGA GAACAACTAC AAGACCACGC CTCCCGTGCT GGACTCCGAC GGCTCCTTCT TCCTCTACAG CAAGCTCACC
GCACCTCACC CTCTCGTTAC CCGTCGGCCT CTTGTTGATG TTCTGGTGCG GAGGGCACGA CCTGAGGCTG CCGAGGAAGA AGGAGATGTC GTTCGAGTGG
 V  E  W  E  S  N  G  Q  P  E  N  N  Y  K  T  T  P  P  V  L  D  S  D  G  S  F  F  L  Y  S  K  L  T

GTGGACAAGA GCAGGTGGCA GCAGGGGAAC GTCTTCTCAT GCTCCGTGAT GCATGAGGCT CTGCACAACC ACTACACGCA GAAGAGCCTC TCCCTGTCTC
CACCTGTTCT CGTCCACCGT CGTCCCCTTG CAGAAGAGTA CGAGGCACTA CGTACTCCGA GACGTGTTGG TGATGTGCGT CTTCTCGGAG AGGGACAGAG
 V  D  K  S  R  W  Q  Q  G  N  V  F  S  C  S  V  M  H  E  A  L  H  N  H  Y  T  Q  K  S  L  S  L  S  P

CGGGTAAATA AGCATGCGAC GGCCTAACGC TCCCTAACGG TCGGTGTGCC CCGGGGGTTT TTTATTGTTA ACTCATGTTT GACAGTTAT CATCGATAAG
GCCCATTTAT TCGTACGCTG CCGGATTGCG AGGGATTGCC AGCCACACGG GGCCCCGCAAA AAATAACAAT TGAGTACAAA CTGTCGAATA GTAGCTATTC
 G  K  O

CTTTAATGCC GTAGTTTATC ACAGTTAAAT TGCTAACGCA GTCAGGCACC GTGTATGAAA TCTAACAATG CGCTCATCGT CATCCTCGGC ACCGTCACCC
GAAATTACGG CATCAAATAG TGTCAATTTA ACGATTGCGT CAGTCCGTGG CACATACTTT AGATTGTTAC GCGAGTAGCA GTAGGAGCCG TGGCAGTGGG
```

FIG. 21D

```
TGGATGCTGT AGGCATAGGC TTGGTTATGC CGGTACTGCC GGGCCTCTTG CGGGATATCG TCCATTCCGA CAGCATCGCC AGTCACTATG GCGTGCTGCT
ACCTACGACA TCCGTATCCG AACCAATACG GCCATGACGG CCCGGAGAAC GCCCTATAGC AGGTAAGGCT GTCGTAGCGG TCAGTGATAC CGCACGACGA
```

FIG. 22A

```
GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA

GAACTGTGTG CGCAGGTAGA AGCTTTGGAG ATTATCGTCA CTGCAATGCT TCGCAATATG GCGCAAAATG ACCAACAGCG GTTGATTGAT CAGGTAGAGG
CTTGACACAC GCGTCCATCT TCGAAACCTC TAATAGCAGT GACGTTACGA AGCGTTATAC CGCGTTTTAC TGGTTGTCGC CAACTAACTA GTCCATCTCC

GGGCGCTGTA CGAGGTAAAG CCCGATGCCA GCATTCCTGA CGACGATACG GAGCTGCTGC GCGATTACGT AAAGAAGTTA TTGAAGCATC CTCGTCAGTA
CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT

AAAAGTTAAT CTTTTCAACA GCTGTCACGG AGTTGTCACG GCCGAGACTT ATAGTCGCTT TGTTTTTATT TTTTAATGTA GTACGCAAGT
TTTTCAATTA GAAAAGTTGT CGACAGTGCC TCAACAGTGC CGGCTCTGAA TATCAGCGAA ACAAAAATAA AAAATTACAT AAACATTGAT CATGCGTTCA

TCACGTAAAA AGGGTATCTA GAATTATGAA GAAGAATATC GCATTTCTTC GTTCGTTTTT TCTATTGCTA CAAACGCGTA CGCTGATATC
AGTGCATTTT TCCCATAGAT CTTAATTACTT CTTCTTATAG CGTAAAGAAG AACGTAGATA AGATAACGAT GTTTGCGCAT GCGACTATAG
                    M  K  K  N  I  A  F  L  L  A  S  M  F  V  F  S  I  A  T   N  A  Y  A  D  I
           ^STII Signal TIR -1                                      anti-VEGF Light Chain (1st generation)^

CAGATGACCC AGTCCCCGAG CTCCCTGTCC GCGATAGGGT CACCATCACC TGCAGCGCAA GTCAGGATAT TAGCAACTAT TTAAACTGGT
GTCTACTGGG TCAGGGCTC GAGGGACACC CGGAGACACC CGGTATCCCA GTGGTAGTGG ACGTCGCGTT CAGTCCTATA ATCGTTGATA AATTTGACCA
 Q  M  T  Q  S  P  S  S  L  S  A  S  V  G  D  R  V  T  I  T  C  S  A  S  Q  D  I  S  N  Y  L  N  W  Y

ATCAACAGAA ACCAGGAAAA GCTCCGAAAG TACTGATTTA CTTCACCTCC TCTCTCCACT GAGAGGTGA ACAGTATATC ATTACTGTCA
TAGTTGTCTT TGGTCCTTTT CGAGGCTTTC ATGACTAAAT GAAGTGGAGG AGAGAGGTGA TGTCATATAG TAATGACAGT
 Q  Q  K  P  G  K  A  P  K  V  L  I  Y  F  T  S  S  L  H  S  G  V  P  S  R  F  S  G  S  G  S  G  T

GGATTCACT CTGACCATCA GCAGTCTGCA GCCAGAAGAC TTCGCAACTT ATTACTGTCA ACAGTATATC GAGCAGTTGA CCGGTGCCGT GGACGTTTGG ACAGGGTACC
CCTAAGTGA GACTGGTAGT CGTCAGACGT CGGTCTTCTG AAGCGTTGAA TAATGACAGT TGTCATATAG CTCGTCAACT TGGCCACGGC CCTGCAAACC TGTCCCATGG
 D  F  T  L  T  I  S  S  L  Q  P  E  D  F  A  T  Y  Y  C  Q  Q  Y  S  T  V  P  W  T  F  G  Q  G  T

AAGGTGGAGA TCAAACGAAC TGTGGCTGCA CCATCTGTCT TCATCTTCCC GCCATCTGAT GAGCAGTTGA AATCTGGAAC TGCTTCTGTT GTGTGCCTGC
TTCCACCTCT AGTTTGCTTG ACACCGACGT GGTAGACAGA AGTAGAAGGG CGGTAGACTA CTCGTCAACT TTAGACCTTG ACGAAGACAA CACACGGACG
 K  V  E  I  K  R  T  V  A  A  P  S  V  F  I  F  P  P  S  D  E  Q  L  K  S  G  T  A  S  V  V  C  L  L

TGAATAACTT CTATCCCAGA GAGGCCAAAG TACAGTGGAA GGTGGATAAC GCCCTCCAAT CGGGTAACTC CCAGGAGAGT GTCACAGAGC AGGACAGCAA
ACTTATTGAA GATAGGGTCT CTCCGGTTTC ATGTCACCTT CCACCTATTG CGGGAGGTTA GCCCATTGAG GGTCCTCTCA CAGTGTCTCG TCCTGTCGTT
 N  N  F  Y  P  R  E  A  K  V  Q  W  K  V  D  N  A  L  Q  S  G  N  S  Q  E  S  V  T  E  Q  D  S  K
```

FIG. 22B

```
GGACAGCACC TACAGCCTCA GCAGCACCCT GACGCTGAGC AAAGCAGACT ACGAGAAACA CAAAGTCTAC GCCTGCGAAG TCACCCATCA GGGCCTGAGC
CCTGTCGTGG ATGTCGGAGT CGTCGTGGGA CTGCGACTCG TTTCGTCTGA TGCTCTTTGT GTTTCAGATG CGGACGCTTC AGTGGGTAGT CCCGGACTCG
 D  S  T  Y  S  L  S  S  T  L  T  L  S  K  A  D  Y  E  K  H  K  V  Y  A  C  E  V  T  H  Q  G  L  S

TCGCCCGTCA CAAAGAGCTT CAACAGGGGA GAGTGTTAAT TAAATCCTCT ACGCCGGACG CATCGTGGCG AGCTCGTGAC CCGGGGATCT AGGCCTAACG
AGCCGGCAGT GTTTCTCGAA GTTGTCCCCT CTCACAATTA ATTTAGGAGA TGCGGCCTGC GTAGCACCGC TCGAGCCACTG GGCCCCTAGA TCCGGATTGC
 S  P  V  T  K  S  F  N  R  G  E  C  O

CTCGGTTGCC GCCGGGCGTT TTTTATTGTT GCCGACGCGC ATCTCGAATG AACTGTGTGC GCAGTAGAA GCTTTGGAGA TTATCGTCAC TGCAATGCTT
GAGCCAACGG CGGCCCGCAA AAAATAACAA CGGCTGCGCG TAGAGCTTAC TTGACACACG CGTCCATCTT CGAAACCTCT AATAGCAGTG ACGTTACGAA

CGCAATATGG CGCAACAGCG TTGATTGATC AGGTAGAGGG GGGCGTGTAC GAGGTGAAAGC CCGATGCCAG CATTCCTGAC GACGATACGG
GCGTTATACC GCGTTGTCGC AACTAACTAG TCCATCTCCC CCCGCACATG CTCCATTTCG GGCTACGGTC GTAAGGACTG CTGCTATGCC

AGCTGCTGCG CGATTACGTA AAGAAGTTAT TGAAGCATCC TCGTCAGTAA AAAGTTAATC TTTTCAACAG CTGTCATAAA GTTGTCACGG CCGAGACTTA
TCGACGACGC GCTAATGCAT TTCTTCAATA ACTTCGTAGG AGCAGTCATT TTTCAATTAG AAAAGTTGTC GACAGTATTT CAACAGTGCC GGCTCTGAAT

TAGTCGCTTT GTTTTATTT TTTAAATGAT TTGTAACTAG TACGCAAGTT CACGTAACTA AATTATGAAG AAGAATATCG CATTTCTTCT
ATCAGCGAAA CAAAATAAAA AAATTACATA AACATTGATC ATGCCGTTCAA GTGCATTTTT CCCATAGATC TTAATACTTC TTCTTATAGC GTAAGAAGA
                                                                          M  K  K  N  I  A  F  L  L
                                                                          ^STII Signal TIR-1

TGCATCTATG TTCGTTTTTT CTATTGCTAC AAACGCGTAC GCTGAGCTTC AGCTGGTGGA GTCTGGCGGT GGCCTGGTGC AGCCAGGGGG CTCACTCCGT
ACGTAGATAC AAGCAAAAAA GATAACGATG TTTGCGCATG CGACTCGAAG TCGACCACCT CAGACCGCCA CCGGACCACG TCGGTCCCCC GAGTGAGGCA
 A  S  M  F  V  F  S  I  A  T  N  A  Y  A  E  V  Q  L  V  E  S  G  G  G  L  V  Q  P  G  G  S  L  R
                                           ^anti-VEGF (1st generation) heavy chain TTGTCCTGTG CAGCTTCTGG CTATACCTTC ACCAACTACG GTATGAACTG GGTCCGTCAG GCCCCGGGTA AGGGCCTGGA ATGGGTTGGA TGGATTAACA
ACAGGACACG GTCGAAGACC GATATGGAAG TGGTTGATGC CATACTTGAC CCAGGCAGTC CGGGGCCCAT TCCCGGACCT TACCCAACCT ACCTAATTGT
 L  S  C  A  A  S  G  Y  T  F  T  N  Y  G  M  N  W  V  R  Q  A  P  G  K  G  L  E  W  V  G  W  I  N  T CCTATACCGG TGAACCGACC TATGGCTCGG ATTTCAAACG TCGTTTCACT TTCAGCTTAG ACACCTCCAA GTCGACAGCA TACCTGCAGA TGAACAGCCT
GGATATGGCC ACTTGGCTGG ATACGAGCC TAAAGTTTGC AGCAAAGTGA AAGTCGAATT TGTGGAGTT CAGCTGTCGT ATGGACGTCT ACTTGTCGGA
 Y  T  G  E  P  T  Y  G  S  D  F  K  R  R  F  T  F  S  L  D  T  S  K  S  T  A  Y  L  Q  M  N  S  L GCGTGCTGAG GACACTGCCG TCTATTACTG TGCAAAGTAC ATGGGAGCAG CCCCACTATT ATGGGAGCAG CCCCACTATT GGGGTCAAGG AACCCTGGTC
CGCACGACTC CTGTGACGGC AGATAATGAC ACGTTTCATG TACCCTCGTC GGGTGATAA TACCCTCGTC GGGTGATAA CCCCAGTTCC TTGGGACCAG
 R  A  E  D  T  A  V  Y  Y  C  A  K  Y  P  H  Y  Y  G  S  S  H  W  Y  F  D  V  W  G  Q  G  T  L  V ACCGTCTCCT CGGGCCTCCAC CAAGGGCCCA TCGGTCTTCC CCCTGGCACC CTCCTCCAAG AGCACCTCTG GGGGCACAGC GGCCCTGGGC TGCCTGGTCA
TGGCAGAGGA GCCCGGAGGTG GTTCCCGGGT AGCCAGAAGG GGGACCGTGG GAGGAGGTTC TCGTGGAGAC CCCCGTGTCG CCGGGACCCG ACGGACCAGT
 T  V  S  S  A  S  T  K  G  P  S  V  F  P  L  A  P  S  S  K  S  T  S  G  G  T  A  A  L  G  C  L  V  K
```

FIG. 22C

```
AGGACTACTT CCCCGAACCG GTGACGGTGT CGTGGAACTC AGGCGCCCTG ACCAGCGGCG TGCACACCTT CCCGGCTGTC CTACAGTCCT CAGGACTCTA
TCCTGATGAA GGGGCTTGGC CACTGCCACA GCACCTTGAG TCCGCGGGAC TGGTCGCCGC ACGTGTGGAA GGGCGACAC GGCCGACAG GTCCTGAGAT
 D   Y   F   P   E   P   V   T   V   S   W   N   S   G   A   L   T   S   G   V   H   T   F   P   A   V   L   Q   S   S   G   L   Y
CTCCCTCAGC AGCGTGGTGA CTGTGCCCTC TAGCAGCTTG GGCACCCAGA CCTACATCTG CAACGTGAAT CACAAGCCCA GCAACACCAA GGTGGACAAG
GAGGGAGTCG TCGCACCACT GACACGGGAG ATCGTCGAAC CCGTGGGTCT GGATGTAGAC GTTGCACTTA GTGTTCGGGT CGTTGTGGTT CCACCTGTTC
 S   L   S   S   V   V   T   V   P   S   S   S   L   G   T   Q   T   Y   I   C   N   V   N   H   K   P   S   N   T   K   V   D   K
AAAGTTGAGC CCAAATCTG TGACAAAACT CACACATGCC CAGCACCTGAA CTCCTGGGG GACCGTCAGT CTTCCTCTTC CCCCAAAAC
TTTCAACTCG GGTTTAGAAC ACTGTTTTGA GTGTGTACGG GTGGCACGGG TCGTGGACTT GAGGACCCCC CTGGCAGTCA GAAGGAGAAG GGGGGTTTTG
 K   V   E   P   K   S   C   D   K   T   H   T   C   P   P   C   P   A   P   E   L   L   G   G   P   S   V   F   L   F   P   P   K   P
CCAAGGACAC CCTCATGATC TCCCGACCC CTGAGGTCAC ATGCGTGGTG GTGGACGTGA GCCACGAAGA CCCTGAGGTC AAGTTCAACT GGTACGTGGA
GGTTCCTGTG GGAGTACTAG AGGGCCTGGG GACTCCAGTG TACGCACCAC CACCTGCACT CGGTGCTTCT GGGACTCCAG TTCAAGTTGA CCATGCACCT
 K   D   T   L   M   I   S   R   T   P   E   V   T   C   V   V   V   D   V   S   H   E   D   P   E   V   K   F   N   W   Y   V   D
CGGCGTGGAG GTGCATAATG CCAAGACAAA GCCGCGGGAG GAGCAGTACA ACAGCACGTA CCGTGTGGTC AGCGTCCTCA CCGTCCTGCA CCAGGACTGG
GCCGCACCTC CACGTATTAC GGTTCTGTTT CGGCGCCCTC CTCGTCATGT TGTCGTGCAT GGCACACCAG TCGCAGGAGT GGCAGGACGT GGTCCTGACC
 G   V   E   V   H   N   A   K   T   K   P   R   E   E   Q   Y   N   S   T   Y   R   V   V   S   V   L   T   V   L   H   Q   D   W
CTGAATGGCA AGGAGTACAA GTGCAAGGTC TCCAACAAAG CCCTCCCAGC CCCCATCGAG AAAACCATCT CCAAAGCCAA AGGGCAGCCC CGAGAACCAC
GACTTACCGT TCCTCATGTT CACGTTCCAG AGGTTGTTTC GGGAGGGTCG GGGGTAGCTC TTTTGGTAGA GGTTTCGGTT TCCCGTCGGG GCTCTTGGTG
 L   N   G   K   E   Y   K   C   K   V   S   N   K   A   L   P   A   P   I   E   K   T   I   S   K   A   K   G   Q   P   R   E   P   Q
AGGTGTACAC CCTGCCCCCA TCCCGGGAAG AGATGACCAA GAACCAGGTC AGCCTGACCT GCCTGGTCAA AGGCTTCTAT CCCAGCGACA TCGCCGTGGA
TCCACATGTG GGACGGGGGT AGGGCCCTTC TCTACTGGTT CTTGGTCCAG TCGGACTGGA CGGACCAGTT TCCGAAGATA GGGTCGCTGT AGCGGCACCT
 V   Y   T   L   P   P   S   R   E   E   M   T   K   N   Q   V   S   L   T   C   L   V   K   G   F   Y   P   S   D   I   A   V   E
GTGGGAGAGC AATGGGCAGC CGGAGAACAA CTACAAGACC ACGCCTCCCG TGCTGGACTC CGACGGCTCC TTCTTCCTCT ACAGCAAGCT CACCGTGGAC
CACCCTCTCG TTACCCGTCG GCCTCTTGTT GATGTTCTGG TGCGGAGGGC ACGACCTGAG GCTGCCGAGG AAGAAGGAGA TGTCGTTCGA GTGGCACCTG
 W   E   S   N   G   Q   P   E   N   N   Y   K   T   T   P   P   V   L   D   S   D   G   S   F   F   L   Y   S   K   L   T   V   D
AAGAGCAGGT GGCAGCAGGG GAACGTCTTC TCATGCTCCG TGATGCATGA GGCTCTGCAC AACCACTACA CGCAGAAGAG CCTCTCCCTG TCTCCGGGTA
TTCTCGTCCA CCGTCGTCCC CTTGCAGAAG AGTACGAGGC ACTACGTACT CCGAGACGTG TTGGTGATGT GCGTCTTCTC GGAGAGGGAC AGAGGCCCAT
 K   S   R   W   Q   Q   G   N   V   F   S   C   S   V   M   H   E   A   L   H   N   H   Y   T   Q   K   S   L   S   L   S   P   G   K
AATAAGCATG CGACGGCCCT AGAGTCCCTA ACGCTCGGTT GCCGAGCCA TGGGAGCCCG GCCGCCGGGC GTTTTTTATT GTTAACTCAT TTATCATGA TAAGCTTTAA
TTATTCGTAC GCTGCCGGGA TCTCAGGGAT TGCGAGCCAA CGGCTCGGT ACCCTCGGGC CGGCGGCCCG CAAAAAATAA CAATTGAGTA CAAACTGTCG AATAGTAGCT ATTCGAAATT
 *
TGCGGTAGTT TATCACAGTT AAATTGCTAA CGCAGTCAGG CACCGTGTAT GAAATCTAAC AATGCGCTCA TCGTCATCCT CGGCACCGTC ACCCTGGATG
ACGCCATCAA ATAGTGTCAA TTTAACGATT GCGTCAGTCC GTGGCACATA CTTTAGATTG TTACGCGAGT AGCAGTAGGA GCCGTGGCAG TGGGACCTAC
CTGTAGGCAT AGGCTTGGTT ATGCCGGTAC TGCCGGGCCT CTTGCCGGGA ATCGTCCATT CCGACAGCAT CGGCAGTCGT TATGGCGTGC TGCTAGCCT
GACATCCGTA TCCGAACCAA TACGGCCATG ACGGCCCGGA GAACGGCCCT TAGCAGGTAA GGCTGTCGTA GCCGTCAGTG ATACCGCACG ACGATCGGA
```

FIG. 23A

>Anti-VEGF (VNERK version) IgG1 Expression Cassette with heavy chain FR1,2,3,4=consensus subgroupI

```
     ecoRI         pflMI                              bsrDI                  hindIII           earI/ksp632I
GAATTCAACT TCTCCATACT TTGGATAAGG AAATACAGAC ATGAAAAATC TCATTGCTGA GTTGTTATTT AAGCTTGCCC AAAAAGAAGA AGAGTCGAAT
CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA
     bspMI
     aviII/fspI hindIII                          bsrDI                                                  bclI
GAACTGTGTG CCAGGTAGA AGCTTTGGAG ATTATCGTCA CTGCCAATGCT TCGCAATATG GCGCAAAATG ACCAACAGCG GTTGATTGAT CAGGTAGAGG
CTTGACACAC GGTCCATCT TCGAAACCTC TAATAGCAGT GACGTTACGA AGCGTTATAC CGCGTTTTAC TGGTTGTCGC CAACTAACTA GTCCATCTCC snaBI
GGGCGCTGTA CGAGGTAAAG CCCGATGCCA GCATTCCTGA CGAGGATACG GAGCTGCTGC GCGATTACGT AAAGAAGTTA TTGAAGCATC CTCGTCAGTA
CCCGCGACAT GCTCCATTTC GGGCTACGGT CGTAAGGACT GCTCCTATGC CTCGACGACG CGCTAATGCA TTTCTTCAAT AACTTCGTAG GAGCAGTCAT
           pvuII          ahdI/eam1105I
           eagI/xmaIII/eclXI                                                                        speI
AAAGTTAAT CTTTTCAACA GCTGTCATAA AGTTGCACG GCCGAGACTT ATAGTCGCTT TGTTTTTATT TTTTAATGTA TTTGTAACTA GTACGCAAGT
TTTCAATTA GAAAAGTTGT CGACAGTATT TCAACAGTGC CGGCTCTGAA TATCAGCGAA ACAAAAATAA AAAATTACAT AAACATTGAT CATGCGTTCA
                                                                                           bsiWI/splI
                                                                                           mluI    ecoRV
TCACGTAAAA AGGGTATCTA GAATTATGAA GAAGAATATC GCATTCTTC TTGCATCTGC GTTCGTTTTT TCTATTGCTA CAAACGCGTA CGCTGATATC
AGTGCATTTT TCCCATAGAT CTTAATACTT CTTCTTATAG CGTAAAGAAG AACGTAGATA CAAGCAAAAA AGATAACGAT GTTTGCGCAT GCGACTATAG
                 M  K  K  N  I  A  F  L  L  A  S  M  F  V  F  S  I  A  T  N  A  Y  A  D  I
                    ^STII Signal TIR ~1                                                    ^Light chain sstI
    tth111I/aspI sacI                                                                           ahaIII/draI
    pflFI     ecl136II  eciI                          bstEII         pstI
                                                                     bspMI
CAGTTGACCC AGTCCCCGAG CTCCCTGTCC GCCTCTGTGG GCGATAGGGT CACCATCACC TGCAGCGCAA GTCAGGATAT TAGCAACTAT TTAAACTGGT
GTCAACTGGG TCAGGGGCTC GAGGGACAGG CGGAGACACC CGCTATCCCA GTGGTAGTGG ACGTCGCGTT CAGTCCTATA ATCGTTGATA AATTTGACCA
 Q  L  T  Q  S  P  S  S  L  S  A  S  V  G  D  R  V  T  I  T  C  S  A  S  Q  D  I  S  N  Y  L  N  W  Y bpmI/gsuI
                               scaI              bseRI                                        bamHI
ATCAACAGAA ACCAGGAAAA GCTCCGAAAG TACTGATTTA CTTCACCTCC TCTCTCCACT GAAGTGGAGG AGAGGTGA GACCTCAGGG TTCTCGCTTC TCTGGATCCG GTTCTGGGAC
TAGTTGTCTT TGGTCCTTTT CGAGGCTTTC ATGACTAAAT GAAGTGGAGG AGAGAGGTGA CTTCACCTCC TCTCCACT CTGGAGTCCC AAGAGCGAAG AGACCTAGGC CAAGACCCTG
 Q  Q  K  P  G  K  A  P  K  V  L  I  Y  F  T  S  S  L  H  S  G  V  P  S  R  F  S  G  S  G  S  G  T
```

FIG. 23B

```
                                                                                          kpnI
                                                                                          asp718
                                                                                          acc65I
GGATTTCACT CTGACCATCA GCAGTCTGCA GCCAGAAGAC TTCGAACTT ATTACTGTCA ACAGTATAGC ACCGTGCCGT GGACGTTTGG ACAGGGTACC
CCTAAAGTGA GACTGGTAGT CGTCAGACGT CGGTCTTCTG AAGCGTTGAA TAATGACAGT TGTCATATCG TGGCACGGCA CCTGCAAACC TGTCCCATGG
 D  F  T  L  T  I  S  S  L  Q   P  E  D   F  A  T  Y   Y  C  Q   Q  Y  S   T  V  P  W  T  F  G   Q  G  T
              pstI                                                                 xmnI
                     bpuAI                                                         asp700
                     bbsI
                                    bpuAI
                                    bbsI
AAGGTGGAGA TCAAACGAAC TGTGGCTGCA CCATCTGTCT TCATCTTCCC GCCATCTGAT GAGCAGTTGA AATCTGGAAC TGCTTCTGTT GTGTGCCTGC
TTCCACCTCT AGTTTGCTTG ACACCGACGT GGTAGACAGA AGTAGAAGGG CGGTAGACTA CTCGTCAACT TTAGACCTTG ACGAAGACAA CACACGGACG
 K  V  E  I   K  R  T   V  A  A   P  S  V  F   I  F  P   P  S  D   E  Q  L  K   S  G  T   A  S  V   V  C  L  L
     xmnI
     asp700
TGAATAACTT CTATCCCAGA GAGGCCAAAG TACAGTGGAA GGTGGATAAC GCCCTCCAAT CGGGTAACTC CCAGGAGAGT GTCACAGAGC AGGACAGCAA
ACTTATTGAA GATAGGGTCT CTCCGGTTTC ATGTCACCTT CCACCTATTG CGGGAGGTTA GCCCATTGAG GGTCCTCTCA CAGTGTCTCG TCCTGTCGTT
 N  N  F   Y  P  R   E  A  K  V   Q  W  K  V   D  N   A  L  Q  S   G  N  S   Q  E  S   V  T  E  Q   D  S  K
                                                                                                   sstI
                                                                                                   sacI
                     celII/espI                                                                    ecl136II
                     blpI/bpu1102I                                                        alwNI
                                                                                          alw26I/bsmAI
GGACAGCACC TACAGCCTCA GCAGCACCCT GACGCTGAGC AAAGCAGACT ACGAGAAACA CAAAGTCTAC GCCTGCGAAG TCACCCATCA GGGCCTGAGC
CCTGTCGTGG ATGTCGGAGT CGTCGTGGGA CTGCGACTCG TTTCGTCTGA TGCTCTTTGT GTTTCAGATG CGGACGCTTC AGTGGGTAGT CCCGGACTCG
 D  S  T   Y  S  L  S   S  T  L   T  L  S   K  A  D  Y   E  K  H   K  V  Y   A  C  E  V   T  H  Q   G  L  S
                                                                                          xmaI/pspAI
                                                                                kpnI
                                                                                asp718
                                                                           sstI acc65I
                                                                           sacI
                     pacI                                                  ecl136II  smaI       stuI
TCGCCCGTCA CAAAGAGCTT CAACAGGGGA GAGTGTTAAT TAAATCCTCT ACGCCCGGACG CATCGTGTGC AGCTCGGTAC CCGGGGATCT AGGCCTAACG
AGCGGGCAGT GTTTCTCGAA GTTGTCCCCT CTCACAATTA ATTTAGGAGA TGCGGGCCTGC GTAGCACACG TCGAGCCATG GGCCCCTAGA TCCGGATTGC
 S  P  V  T   K  S  F   N  R  G   E  C  O
                                                                                          start lambda t0 terminator^
              bspMI
                     aviIII/fspI hindIII                                                           bsrDI
CTCGGTTGCC GCCGGGCGTT TTTTATTGTT GCCGACGCGC ATCTCGAATG AACTGTGTGC GCAGGTAGAA GCTTTGGAGA TTATCGTCAC TGCAATGCTT
GAGCCAACGG CGGCCCGCAA AAAATAACAA CGGCTGCGCG TAGAGCTTAC TTGACACACG CGTCCATCTT CGAAACCTCT AATAGCAGTG ACGTTACGAA
                                                                                 ^end lambda t0 terminator
```

```
                          xmaI/pspAI
            bsp1407I/bsrGI    smaI earI/ksp632I      sexAI            bspMI
GAGACCACA GGTGTACACC CTGCCCCCAT CCCGGGAAGA GATGACCAAG AACCAGGTCA GCCTGACCTG CCTGGTCAAA GGCTTCTATC CCAGGACAT
CTCTGGTGT CCACATGTGG GACGGGGTA GGGCCCTTCT CTACTGGTTC TTGGTCCAGT CGGACTGGAC GGACCAGTTT CCGAAGATAG GGTCGTCTA
 E  P  Q  V  Y  T  L  P  P  S  R  E  E  M  T  K  N  Q  V  S  L  T  C  L  V  K  G  F  Y  P  S  D  I
                 bsrDI
CGGCTGGAG TGGGAGAGCA ATGGGCAGCC GGAGAACAAC TACAAGACCA CGCCTCCCGT GCTGGACTCC GACGGCTCCT TCTTCCTCTA CAGCAAGCTC
GCCGACCTC ACCCTCTCGT TACCCGTCGG CCTCTTGTTG ATGTTCTGGT GCGGAGGGCA CGACCTGAGG CTGCCGAGGA AGAAGGAGAT GTCGTTCGAG
 A  V  E  W  E  S  N  G  Q  P  E  N  N  Y  K  T  T  P  P  V  L  D  S  D  G  S  F  F  L  Y  S  K  L
                               bpuAI                            ppuIOI                    sapI
              bspMI          xmnI bbsI                         nsiI/avaIII bsgI         earI/ksp632I
ACCGTGGACA AGAGCAGGTG GCAGCAGGGG AAGGTCTTCT CATGCTCCGT GATGCATGAG GCTCTGCACA ACCACTACAC GCAGAAGAGC CTCTCCCTGT
TGGCACCTGT TCTCGTCCAC CGTCGTCCCC TTCCAGAAGA GTACGAGGCA CTACGTACTC CGAGACGTGT TGGTGATGTG CGTCTTCTCG GAGAGGGACA
 T  V  D  K  S  R  W  Q  Q  G  N  V  F  S  C  S  V  M  H  E  A  L  H  N  H  Y  T  Q  K  S  L  S  L
                                                                                           claI/bsp106
         sphI                                                         hpaI                     bspDI
CTCCGGGTAA ATAAGCATGC GACGGGCCTA GAGTCCCGAA CGGCTGGGTG CCGGCCGGGCG TTTTTTATG TTAACTCAAG TTTGACAGCT TATCATCGAT
GAGGCCCATT TATTCGTACG CTGCCCGGAT CTCAGGGCTT GCGAGCCCAC GGCCGGCCCGC AAAAAATAAC AATTGAGTAC AAACTGTCGA ATAGTAGCTA
 P  G  K  O
                                     "lambda to terminator"
 hindIII                                                         ecoRV
AAGCTTTAAT GCCGTAGTTT ATCACAGTTA AATTGCTAAC GCAGTCAGGC ACCGTGTATG AAATCTAACA ATGGGCTCAT CGTCATCCTC GGCACCGTCA
TTCGAAATTA CGGCATCAAA TAGTGTCAAT TTAACGATTG CGTCAGTCCG TGGCACATAC TTTAGATTGT TACCCGAGTA GCAGTAGGAG CCGTGGCAGT CCCTGGAGC TGTAGGCATA GGCTTGGTTA TGCCGGTACT GCCGGGCCTC TTGCGGGATA TCGTCCATTC CGACAGCATC GCCAGTACT ATGGCGTGCT
GGGACCTACG ACATCCGTAT CCGAACCAAT ACGGCCATGA ACGGCCCGAG AACGCCCTAT AGCAGGTAAG GCTGTCGTAG CGGTCAGTGA TACCGCACGA
```

> length: 3300

```
aatII(GACGTC):        1983
acc65I(GGTACC):       795  1176
ageI(ACCGGT):         1806 2126
ahaIII(TTTAAA):       590
ahdI(GACNNNNNGTC):    346  1495 2380
alw26I(GTCTC):        1089 1770 2359
alw44I(GTGCAC):       1930 2169
```

FIG. 23E

METHODS FOR PRODUCING HUMANIZED ANTIBODIES AND IMPROVING YIELD OF ANTIBODIES OR ANTIGEN BINDING FRAGMENTS IN CELL CULTURE

CROSS REFERENCE TO RELATED APPLICATIONS

This application claims priority to U.S. Ser. No. 60/442,484, filed Jan. 23, 2003, under 35 U.S.C. 119(e), which application is hereby incorporated by reference.

FIELD OF THE INVENTION

The present invention generally concerns the production of antibodies or antigen binding fragments in cell culture. More specifically, the invention provides methods for improving the yield of recombinant antibodies or antigen binding fragments in cell culture.

BACKGROUND

Antibodies, particularly humanized antibodies, have become very useful for diagnostic and therapeutic purposes. Humanized antibodies are antibodies in which CDRs or hypervariable regions (HVRs) from a non-human antibody are combined with human framework regions to form an antigen binding molecule. This exchange is sometimes known as a "CDR swap". There are different ways of selecting human framework sequences for humanized antibodies. One method involves selecting a human variable domain sequence that has a very similar framework sequence to that of the non-human antibody that is the source of the CDRs. Another method involves using a human variable domain consensus sequence as the source of the human framework regions. Often, a straight CDR swap does not result in high affinity antigen binding molecules so that additional changes or modifications are required to improve binding affinity of the humanized antibody. The necessity of making additional modifications can make humanization of antibodies a very time consuming process. In addition, humanization may not result in an antibody that can be produced in high yield in cell culture.

Some of the uses of antibodies require large quantities of full-length completely assembled antibodies. Many techniques are now available for producing antibodies recombinantly using a variety of host cell systems including *E. coli*, yeast, plant cells, insect cells, and mammalian cells. Eukaryotic and prokaryotic systems have been used in large-scale production of antibodies. In particular, *E. coli* provides a useful organism for the expression of antibodies, including engineered antibodies, such as humanized antibodies. There are several advantages to *E. coli* expression systems, including a well-studied and convenient gene technology which permits constructs to be made easily and directly expressed, and the relatively convenient and economical large-scale production of product made possible by the fast growth of *E. coli* and its comparatively simple fermentation.

Full-length antibodies comprise two heavy chains linked together by disulfide bonds and two light chains, each light chain being linked to one of the heavy chains by a disulfide bond. Each chain has an N-terminal variable domain ($V_H$ or $V_L$) and one or more constant domains at the C-terminus; the constant domain of the light chain is aligned with and disulfide bonded to the first constant domain of the heavy chain, and the light chain variable domain is aligned with the variable domain of the heavy chain. Each of the variable domains of the heavy and light chain includes framework regions (FRs) and hypervariable regions (HVRs) and an intrachain disulfide bond. (See e.g. Chothia et al., *J. Mol. Biol.* 186:651-663 (1985); Novotny and Haber, *Proc. Natl. Acad. Sci. USA* 82:45924596 (1985); Padlar et al., *Mol. Immunol.*, 23(9): 951-960 (1986); and S. Miller, *J. Mol. Biol.*, 216:965-973 (1990). Antibody fragments are also often produced and include combinations of heavy and light chain variable domains so as to form an antigen binding site. Antibody fragments include, for example, Fab, Fab', F(ab')$_2$, Fv, scFv, Fd, and Fd' fragments.

Generally, antibody production in prokaryotes involves synthesis of the light and heavy chains in the cytoplasm followed by secretion into the periplasm where processing of the chains takes place. Alternatively, the heavy and light chains can be directed to accumulate in the cytoplasm where they typically form inclusion bodies. Folding of the light and heavy chains occurs in conjunction with assembly of the folded light and heavy chains to form an antibody molecule. Multiple covalent and non-covalent interactions occur between and within the heavy and light chains during these folding and assembly processes. Antibody yield can be greatly affected by the efficiency and fidelity of these processes. Following synthesis of the heavy and light chains, protein aggregation or proteolysis can occur thereby reducing the yield of the antibody.

Production and stability of antibody fragments have been studied more extensively than that of full length antibodies. Often the stability and/or production yields of scFv or Fab fragments of natural antibodies produced in host cells have been found to be insufficient. Honneger et al., *J. Mol. Biol.*, 309:687-699 (2001). Stability of the antibody or antibody fragment when incubated under physiological conditions is important for therapeutic efficacy in vivo. Production yields and folding efficiency are important to increase the yield of antibodies or antibody fragments for therapeutic use. The stability of scFv fragments is not always correlated with expression yield in the bacterial periplasm. Worn et al., *J. Mol. Biol.*, 305:989-1010 (2001). Some stable scFv fragments show only poor expression yields in bacterial periplasm and some mutations can affect in vivo folding efficiency but not stability. Worn et al., supra. The many factors that affect the periplasmic expression yield and/or stability of scFv are not yet fully understood.

Some structural features thought to be involved in stability and/or in vivo folding of antibody fragments have been previously described. For example, the FR1 of antibody fragments has been found to influence in vivo folding of antibody fragments in bacteria. de Haard et al., *Prot. Eng.*, 11: 1267-1276 (1998). In particular, the data of de Haard et al. suggested that mutations at residue 6 in the heavy chain interfered with the correct folding of a scFv. de Haard et al. supra. Jung et al. have described four different conformations of the FR1 based on the amino acids found at positions H6, H7 and H10 (H9). Jung et al. *J. Mol. Biol.*, 309:701 (2001). Mutations at these residues, especially at residue 6, that disrupt the FR1 conformation can have adverse effects on folding yields and stability of scFv. Jung et al. supra. Residue 6 in the heavy chain is also thought to contribute to the stability of Fab, Fv, and ScFv fragments lacking disulfide bonds. Langdyk et al., *J. Mol. Biol.*, 283:95 (1998). Disulfide bonds also contribute to the stability of antibody domains. When disulfide bonds are removed, the H6 residue helped to stabilize the scFv but not when the disulfide bond was restored. A number of other point mutations at residues have been described as stabilizing or destabilizing in specific scFv fragments. Worn et al., supra. However, the effect of a mutation at a specific residue in an antibody or antibody framework may be unpredictable and may or may not affect the in vivo folding efficiency. A mutation at a residue in one antibody or antibody fragment that is beneficial for folding efficiency and yield may not be beneficial in another.

Methods for producing high affinity humanized antibodies can be time consuming and result in an antibody that is not optimal for production in cell culture. Multiple factors affect the yield and/or stability of antibodies and/or antibody fragments when produced in cell culture. Many of these factors are not yet well understood and may be unpredictable. Thus, there remains a need for improving the process of producing humanized antibodies and for improving the yield of antibodies or antibody fragments in cell culture, especially bacterial cell culture.

SUMMARY OF THE INVENTION

The present invention concerns methods for improving the process of humanizing an antibody or antigen binding fragment and for improving the yield of antibodies or antigen binding fragments in cell culture, especially bacterial cell culture. The invention is based on the discovery that the primary sequence of antibody variable domains can be designed or modified to contribute to correct folding, assembly, and yield of antibodies or antigen binding fragments. The invention involves identifying not only which residues should be substituted but also identifying which substitutions to make at those residues in a more predictable manner to result in improved yield of the antibodies.

One method for humanizing antibodies involves combining HVRs from a non-human antibody with human consensus framework regions that were derived from the most commonly occurring heavy and light chain subgoups in the sequence compilation of Kabat et al, Sequences of Proteins of Immunological Interest, NIH 1991. It has been discovered that selecting the most commonly occurring heavy and light chain consensus sequences may not provide an antibody that can be produced in high yield in cell culture. In one embodiment, the invention provides a method for selecting a human subgroup consensus sequence for at least one of the framework region or regions based on identifying the subgroup consensus sequence that has the most sequence identity with the HVR1 and/or HVR2 sequence of the non-human antibody. The method may decrease the time to prepare a humanized antibody or antigen binding fragment that can be produced in high yield in cell culture.

In some embodiments, the method of producing a recombinant or humanized antibody or antigen binding fragment comprises expressing a variable domain comprising at least one FR sequence from a selected human subgroup variable domain consensus sequence, and a HVR1 and/or HVR2 sequence of a non-human antibody in a host cell, wherein the selected human subgroup consensus sequence is the human subgroup consensus sequence that has a HVR1 and/or HVR2 sequence that has the most sequence identity to the HVR1 and/or HVR2 of the non-human antibody; and recovering the antibody variable domain or an antibody or antigen binding fragment comprising the variable domain from the host cell.

In other embodiments, a method comprises comparing the HVR1 and/or HVR2 amino acid sequence of the non-human antibody with the corresponding HVR1 and/or HVR2 of the human consensus subgroups for the heavy or light chain, identifying the human variable domain subgroup consensus sequence with the most identity to that HVR1 and/or HVR2 amino acid sequence of the non-human antibody, and selecting at least one of the FRs of that subgroup consensus sequence as the FR sequence for the recombinant antibody or antigen binding fragment. A single selected FR or more than one FR selected from the group consisting of FR1, FR2, FR3, FR4 and mixtures thereof can be used to prepare the recombinant antibody. In one embodiment, a humanized antibody or antigen binding fragment includes the selected FR1 of the human heavy chain subgroup consensus sequence that has the most seqeunce identity with HVR1 and/or HVR2 of the non-human antibody. This method for improving the process of humanization may provide for a humanized antibody or antigen binding fragment that can be produced in high yield in cell culture in less time.

In one aspect of the invention, a method is provided for producing an antibody or antigen binding fragment in high yield in cell culture. A method comprises expressing a variable domain of the antibody or antigen binding fragment comprising at least one modified FR in a host cell, wherein the modified FR has a substitution of at least one amino acid position with a different amino acid, wherein the different amino acid is the amino acid found at the corresponding FR position of a human subgroup variable domain consensus sequence that has a HVR1 and/or HVR2 amino acid sequence with the most sequence identity with a corresponding HVR1 and/or HVR2 sequence of the variable domain, wherein the antibody or antigen binding fragment variable domain comprising the modified FR has improved yield in cell culture compared to an unmodified antibody or antigen binding fragment; and recovering the antibody or antigen binding fragment variable domain comprising the modified framework from the host cell.

In one aspect of the invention, a method is provided for preparing an antibody with improved yield when produced in cell culture. The method comprises expressing a variable domain of the antibody or antigen binding fragment comprising at least one modified FR in a host cell, wherein the modified FR is obtained by substituting at least one amino acid in a FR of a parent variable domain of the antibody or antigen binding fragment with a different amino acid; wherein the different amino acid is an amino acid found at the corresponding FR position of a human subgroup variable domain consensus sequence that has a HVR1 and/or HVR2 amino acid sequence with the most sequence identity to a corresponding HVR1 and/or HVR2 amino acid sequence of the parent variable domain to form a modified FR. The antibody or antigen binding fragment having the modified FR has improved yield in a cell culture compared to an antibody or antigen binding fragment comprising the parent variable domain and is recovered from the host cell.

In one embodiment, the method comprises comparing a) a HVR1 and/or HVR2 amino acid sequence of a variable domain of a parent antibody or antigen binding fragment to a corresponding HVR1 and/or HVR2 amino acid sequence of each of human subgroup variable domain consensus sequences and selecting the consensus sequence that has the most sequence identity with the HVR1 and/or HVR2 sequence of the variable domain; b) identifying at least one amino acid in a FR of the variable domain that is different from an amino acid at a corresponding position of the selected human subgroup variable domain consensus sequence; and c) substituting the at least one amino acid identified in step (b) with the amino acid in the corresponding position of the selected subgroup variable domain consensus sequence to form a variable domain with a modified FR.

At least one FR of a heavy or light chain variable domain or both can be modified or selected for use in accord with the methods of the invention. Modifications can be made in 1 FR or more than one FR selected from the group consisting of FR1, FR2, FR3, FR4 and mixtures thereof. Within a FR, at least one, and preferably more than one, amino acid substitution is made in the FR. In one embodiment, all of the framework region residues of the parent antibody that are different than the selected subgroup consensus sequence are substituted with the amino acids found at those positions in the selected subgroup consensus sequence.

In another embodiment, the method comprises expressing a heavy chain variable domain of the antibody or antigen binding fragment comprising at least one modified FR in a host cell, wherein the modified FR has a substitution of at least one amino acid position with a different amino acid, wherein the different amino acid is the amino acid found at the corresponding FR position of a human heavy chain subgroup variable domain consensus sequence that has a HVR1 and/or HVR2 amino acid sequence with the most sequence identity with a corresponding HVR1 and/or HVR2 sequence of the heavy chain variable domain, wherein the antibody or antigen binding fragment with the modified FR of the heavy chain has improved yield in cell culture compared to an unmodified parent antibody or antigen binding fragment; and recovering the antibody or antigen binding fragment variable domain comprising the modified framework from the host cell.

Another aspect of the invention provides another method for improving the yield of antibody or antigen binding fragment in culture. The method comprises modifying at least one FR sequence of a variable domain of the antibody or antigen binding fragment such that it is at least 50% identical in sequence to the corresponding FR sequence of a selected subgroup consensus sequence to form a modified FR, wherein the modified FR has a substitution of at least one amino acid position with a different amino acid, wherein the different amino acid is the amino acid found at the corresponding FR position of a selected human subgroup variable domain consensus sequence, wherein the selected human consensus subgroup sequence has a HVR1 and/or HVR2 amino acid sequence with the most sequence identity with a corresponding HVR1 and/or HVR2 sequence of the variable domain, wherein the antibody or antigen binding fragment with the modified FR has improved yield in cell culture compared to an unmodified parent antibody or antigen binding fragment; and recovering the variable domain with the modified FR.

Another aspect of the invention provides another method for producing an antibody or antigen binding fragment in high yield in cell culture. The method comprises expressing a modified variable domain of the antibody or antigen binding fragment in a host cell, wherein the modified variable domain has a substitution of at least one amino acid position proximal to a cys residue that participates in an intrachain variable domain disulfide bond with a different amino acid, wherein the different amino acid is the amino acid found at corresponding position of a human subgroup variable domain consensus sequence that has a HVR1 and/or HVR2 amino acid sequence with the most sequence identity with a corresponding HVR1 and/or HVR2 amino acid sequence of the variable domain, wherein the antibody or antigen binding fragment comprising the modified variable domain has improved yield in cell culture compared to the antibody or antigen binding fragment; and recovering the antibody or antigen binding fragment comprising the modified variable domain from the host cell.

Another aspect of the invention provides another method for improving the yield of antibody or antigen binding fragment in culture. The method comprises: a) identifying at least one amino acid position in a first variable domain of a parent antibody or antigen binding fragment that is proximal to a cys residue that forms an intrachain variable domain disulfide bond in the first variable domain; b) selecting a variable domain consensus sequence having the most sequence identity with a HVR1 and/or HVR2 amino acid sequence of the first variable domain; and c) placing at that position a different amino acid, wherein the different amino acid is an amino acid found at the corresponding position in the selected human subgroup consensus sequence to form a modified variable domain of the parent antibody or antigen binding fragment. In one embodiment, an antibody or antigen binding fragment whose sequence is known or readily ascertainable has at least one amino acid proximal to a cys residue substituted with the amino acid found at the corresponding position in the selected human subgroup consensus sequence. In one embodiment, at least one amino acid proximal to a cys residue can be modified and then incorporated into a humanized antibody or antigen binding fragment.

Another aspect of the invention involves expressing a polynucleotide molecule in a host cell. The method comprises expressing a polynucleotide encoding a variable domain of the antibody or antigen binding fragment comprising at least one modified FR in a host cell, wherein the modified FR has a substitution in at least one amino acid position in at least one FR with a different amino acid, wherein the different amino acid is the amino acid found at the corresponding FR position of a human subgroup variable domain consensus sequence with the most sequence identity with a corresponding HVR1 and/or HVR2 amino acid sequence of the variable domain, wherein the antibody or antigen binding fragment comprising the modified FR region has improved yield in cell culture when compared to a parent unmodified antibody or antigen binding fragment; and recovering the antibody or antigen binding fragment comprising the modified FR from the host cell.

In one embodiment, the method comprises expressing a polynucleotide molecule encoding a modified variable domain of the antibody or antigen binding fragment in a host cell, wherein the modified variable domain has a substitution of at least one amino acid position proximal to a cys residue that participates in an intrachain variable domain disulfide bond with a different amino acid, wherein the different amino acid is the amino acid found at the corresponding position of a human subgroup variable domain consensus sequence that has a HVR1 and/or HVR2 amino acid sequence with the most sequence identity with a corresponding HVR1 and/or HVR2 amino acid sequence of the variable domain, wherein the antibody or antigen binding fragment comprising the modified variable domain has improved yield as compared to an unmodified antibody or antigen binding fragment when produced in cell culture; and recovering the antibody or antigen binding fragment comprising the modified variable region from the host cell.

The invention also provides for antibody variable domains, antibodies, or antigen binding fragments that have modifications to the amino acid sequence to provide for increased yield when produced in cell culture.

BRIEF DESCRIPTION OF THE FIGURES

FIG. 3 shows that substitution of heavy chain (HC) FR1 subgroup III amino acid residues with FR1 subgroup I amino acid residues in anti-VEGF VNERK antibody improves assembled antibody yield in E. coli. The yield of heavy and light chains is shown in panel A and the yield of assembled antibody products is shown in panel B. Whole cell lysates were prepared under reducing (A) and non-reducing (B) conditions and were analyzed by SDS PAGE immunoblot. Lane 1 is anti-VEGF VNERK with HC FR1 subgroup III sequence (HCFR1=SGIII); lane 2 is anti-VEGF VNERK with HC FR1 subgroup I sequence (HCFR1=SGI); lane 3 is anti-VEGF VNERK with HC FR1 subgroup II sequence (HCFR1=SGII); and lane 4 is the negative control. In FIG. 3A, the samples were prepared under reducing conditions, and positions of the heavy and light chains are identified. In FIG. 3B, the samples were prepared under non-reducing conditions and the figures to the right of the gel show positions of completely assembled (at the top) and partially assembled antibody products.

FIG. 6 shows the assembled antibody yields of anti-VEGF antibodies with single amino acid substitutions in HC FR1 replacing subgroup III residues with the subgroup I residue at each position. The yield of heavy and light chains is shown in panels A and B and the yield of assembled antibody products is shown in panels C and D. Whole cell lysates were prepared under reducing (A, B) and non-reducing (C, D) conditions and were analyzed by SDS PAGE immunoblot. In panels A and C, lane 1 is the wt anti-VEGF with HC FR1 subgroup III sequence; lane 2 is an antibody with a substitution E1Q; lane 3 is an antibody with an E6Q substitution; lane 4 is an antibody with a G9A substitution; lane 5 is an antibody with G10E substitution; lane 6 is an antibody with a L11V substitution; lane 7 is an antibody with V12K substitution; and lane 8 is an antibody with the HC FR1 subgroup I; lane 9 is the negative control. In panels B and D, lane 1 is the wild type with HC FR1 subgroup III; lane 2 is an antibody with Q13K; lane 3 is an antibody with G16A substitution; lane 4 is an antibody with L18V substitution; lane 5 is an antibody with R19K substitution; lane 6 is an antibody with L20V substitution; lane 7 is an antibody with A23K substitution; lane 8 is an antibody with HC FR1 subgroup I; and lane 9 is a negative control.

FIG. 7 shows the assembled antibody yields of anti-VEGF antibodies with single amino acid substitutions in the heavy chain FR1 replacing subgroup III residues with the subgroup I residue at those positions. The yield of heavy and light chains is shown in panel A and the yield of assembled antibody products is shown in panel B. Whole cell lysates were prepared under reducing (A) and non-reducing (B) conditions and were analyzed by SDS PAGE immunoblot. Lane 1 is negative control; lane 2 is the anti-VEGF VNERK wt with HC FR1 subgroup III sequence (HCFR1=SGIII); lane 3 is the anti-VEGF antibody with HC FR1 subgroup I sequence (HCFR1=SGI); lane 4 is an antibody with E1Q substitution; lane 5 is an antibody with E6Q substitution; lane 6 is an antibody with L11V substitution; and lane 7 is an antibody with A23K substitution.

FIG. 8 shows the yield of assembled antibody products (B) and the heavy and light chains (A) of anti-VEGF first generation wild-type antibodies. The antibodies have single or double amino acid substitutions at positions proximal to cys residues that form an intrachain disulfide bond. Whole cell lysates were prepared under reducing (A) and non-reducing (B) conditions and were analyzed by SDS PAGE immunoblot. Lane 1 is a negative control; lane 2 is the first generation wild type anti-VEGF antibody; lane 3 is an antibody with a M4L substitution in the light chain; lane 4 is an antibody with a F71Y substitution in the light chain; lane 5 is an antibody with a M34I substitution in the heavy chain; and lane 6 is an antibody with E6Q and M34I substitutions in the heavy chain.

FIG. 15A-D shows the polynucleotide sequence (SEQ ID NO: 4) encoding an amino acid sequence (SEQ ID NO: 5) of heavy and light chains of anti-VEGF antibody VNERK in plasmid pxVG11VNERK. The positions of cys residues that form an intravariable domain disulfide bond are shown in the heavy and light chain variable domains.

FIG. 16A-D shows the polynucleotide sequence (SEQ ID NO: 6) encoding an amino acid sequence (SEQ ID NO: 7) of the heavy and light chains of anti-VEGF antibody YO317 in plasmid pxVG2AP11.

FIG. 17A-D shows the polynucleotide sequence (SEQ ID NO: 8) encoding an amino acid sequence of (SEQ ID NO: 9) of heavy and light chains of anti-VEGF VNERK with heavy chain FR1 subgroup I consensus sequence in plasmid pVKFR1-2. The positions of cys residues that form an intravariable domain disulfide bond are also shown.

FIG. 18A-D shows the polynucleotide sequence (SEQ ID NO: 10) encoding an amino acid sequence (SEQ ID NO: 11) of the heavy and light chains of anti-VEGF antibody VNERK with heavy chain FR1 subgroup II consensus in plasmid pVKSGII. The position of cys residues that form an intravariable disulfide bond are also shown for the heavy and light domains.

FIG. 19A-D shows the polynucleotide sequence (SEQ ID NO: 12) encoding an amino acid sequence (SEQ ID NO: 13) of the heavy and light chains of anti-VEGF antibody YO317 with heavy chain FR1 subgroup I consensus sequence in plasmid pYOFR1-2.

FIG. 20A-D shows the polynucleotide sequence (SEQ ID NO: 20) encoding an amino acid sequence (SEQ ID NO: 21) of heavy and light chains of anti-IgE antibody E25 in pE25-11.

FIG. 21A-D shows the polynucleotide sequence (SEQ ID NO: 22) encoding an amino acid sequence (SEQ ID NO: 23) of heavy and light chains of anti-IgE antibody E25 with heavy chain FR1 subgroup II consensus sequence in plasmid pE25-SGII.

FIG. 22A-C shows the polynucleotide sequence (SEQ ID NO: 24) encoding an amino acid sequence (SEQ ID NO: 25) of heavy and light chains of anti-VEGF first generation wild type in plasmid pVG50.

FIG. 23A-E shows the polynucleotide sequence (SEQ ID NO: 26) encoding an amino acid sequence (SEQ ID NO: 27) of the heavy and light chains of anti-VEGF VNERK antibodies in plasmid pVKSGI with FR 1, 2, 3, and 4 with a subgroup I consensus sequence.

Table of Sequences

Figure 1:
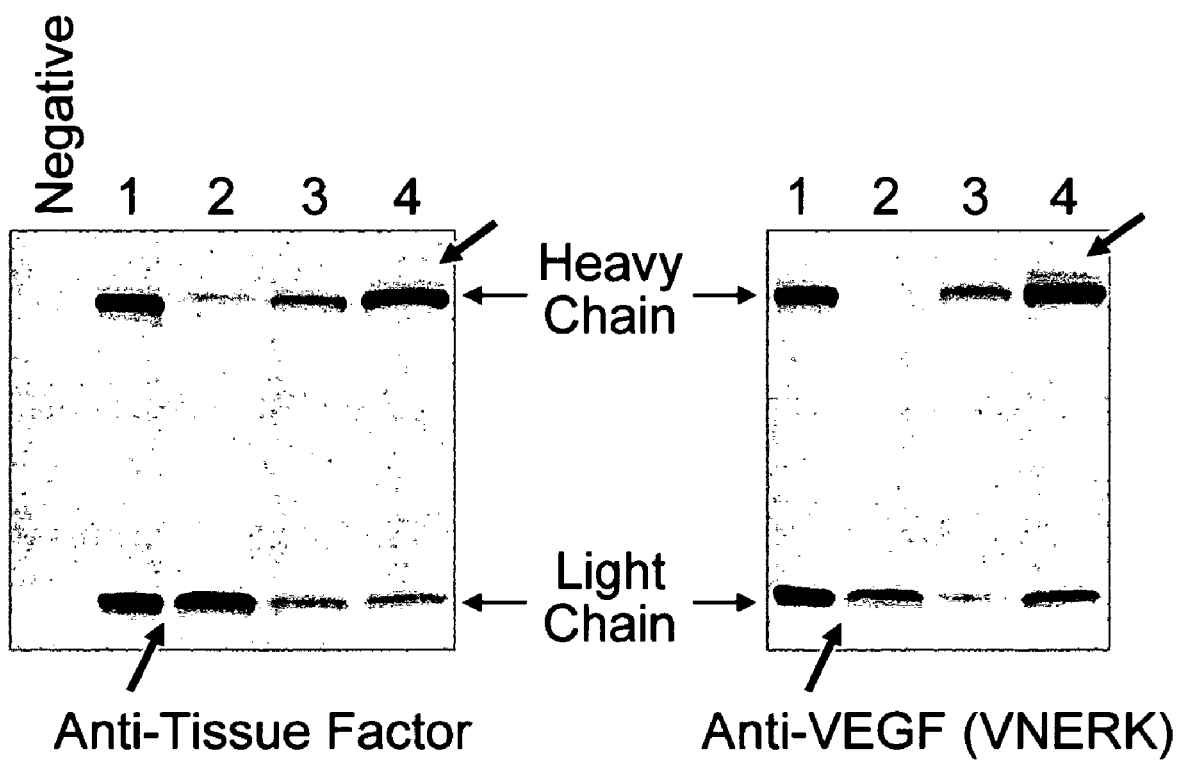
FIG. 1 shows the solubility differences between heavy and light chains produced in *E. coli*. Two different antibodies, anti-tissue factor antibody (A) and anti-VEGF antibody (B), were produced in *E. coli* and whole cell lysates were analyzed by SDS-PAGE under reducing conditions. Different fractions from the whole cell lysates were analyzed and compared to the total whole cell lysates. The location of heavy and light chains are shown. The arrows show that more heavy chains are found in the SDS/DTT soluble fraction and that light chains are mostly found in the soluble fraction. The first lane is the negative control; lane 1 is the whole cell lysate; lane 2 is the soluble fraction; lane 3 is the SDS soluble fraction; and lane 4 is the SDS/DTT soluble fraction.

| SEQ ID NO: | Name | Sequence | Page |
|---|---|---|---|
| 1 | FR1 Subgroup I | QVQLVQSGAEVKKPGASVKVSCKAS | 68, 70 |
| 2 | FR1 Subgroup II | QVQLQESGPGLVKPSQTLSLTCTVS | 68, 70 |
| 3 | FR1 Subgroup III | EVQLVESGGGLVQPGGSLRLSCAAS | 68 |
| 4 | Heavy and light chains of VNERK in pxVG11VNERK | polynucleotide sequence | FIG. 15 |
| 5 | Heavy and light chains of VNERK in pxVG11VNERK | amino acid sequence | FIG. 15 |
| 6 | Heavy and light chains of YO317 in pxVG2AP11 | polynucleotide sequence | FIG. 16 |

-continued

Table of Sequences

Figure 20A:
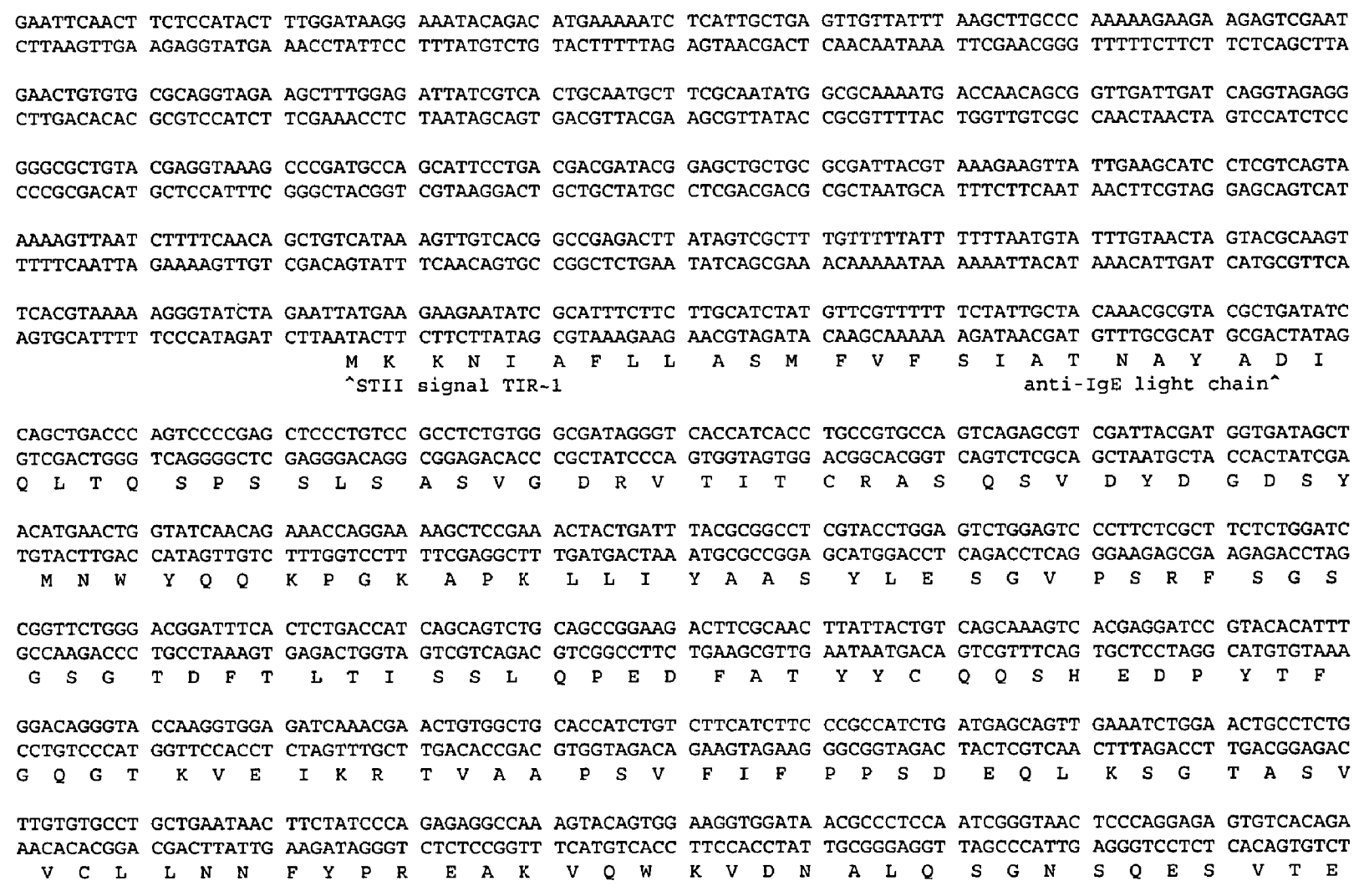
Figure 21A:
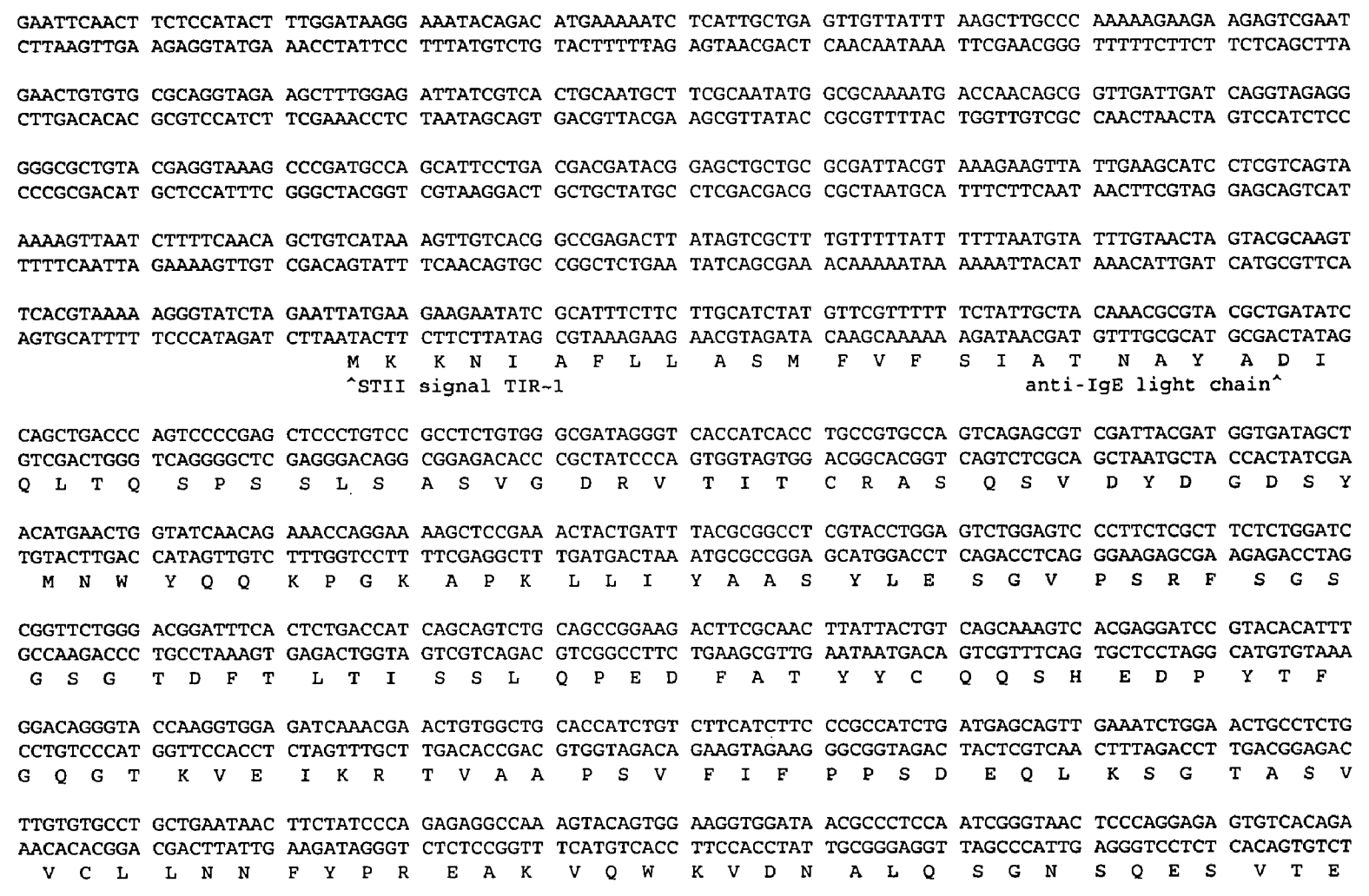

| SEQ ID NO: | Name | Sequence | Page |
|---|---|---|---|
| 7 | Heavy and light chains of YO317 in pxVG2AP11 | amino acid sequence | FIG. 16 |
| 8 | Heavy and light chains of VNERK with heavy chain FRI SGI in pVKFR1-2 | polynucleotide sequence | FIG. 17 |
| 9 | Heavy and light chains of VNERK with heavy chain FRI SGII in pVKFR1-2 | amino acid sequence | FIG. 17 |
| 10 | Heavy and light chains of VNERK with heavy chain FRI SGII in pVKSGII | polynucleotide sequence | FIG. 18 |
| 11 | Heavy and light chains of VNERK with heavy chain FRI SGII in pVKSGII | amino acid sequence | FIG. 18 |
| 12 | Heavy and light chains of YO317 with heavy chain FRI SGI in pYOFR1-2 | polynucleotide sequence | FIG. 19 |
| 13 | Heavy and light chains of YO317 with heavy chain FRI SGI in pYOFR1-2 | amino acid sequence | FIG. 19 |
| 14 | VNERK heavy chain HVR1 residues 26-35 | GYTFTNYGIN | 36, 79, 81 |
| 15 | Human heavy chain consensus sequence from Subgroup I | GYTFTSYAIS | 36, 79, 81, 82 |
| 16 | Human heavy chain consensus sequence from Subgroup II | GGSVSSYWSWN | 36, 79, 81, 82 |
| 17 | Human heavy chain consensus sequence from Subgroup III | GFTFSSYAMS | 36, 79, 81, 82 |
| 18 | YO317 heavy chain HVR1 residues 26-35 | GYDFTHYGMN | 80, 81 |
| 19 | E25 heavy chain HVR1 residues 26-35 | GYSITSGYSWN | 82 |
| 20 | Heavy and light chains of anti-IgE antibody E25 in pE25-11 | polynucleotide sequence | FIG. 20 |
| 21 | Heavy and light chains of anti-IgE antibody E25 in pE25-11 | amino acid sequence | FIG. 20 |
| 22 | Heavy and light chains of anti-IgE antibody E25 with heavy chain FR1 SGII in pE25-SGII | polynucleotide sequence | FIG. 21 |
| 23 | Heavy and light chains of anti-IgE antibody E25 with heavy chain FR1 SGII in pE25-SGII | amino acid sequence | FIG. 21 |

-continued

Table of Sequences

Figure 23C:
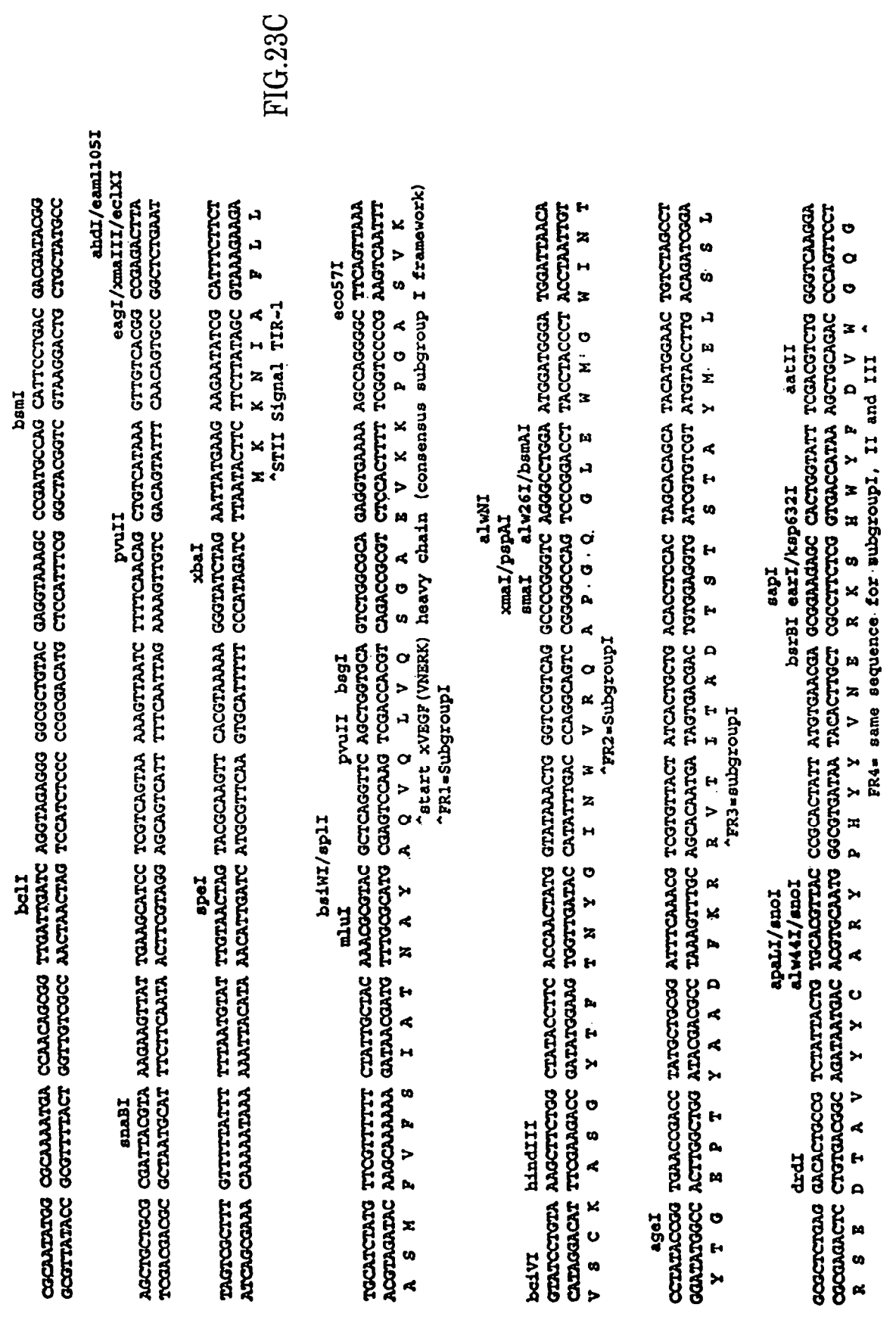
Figure 23D:
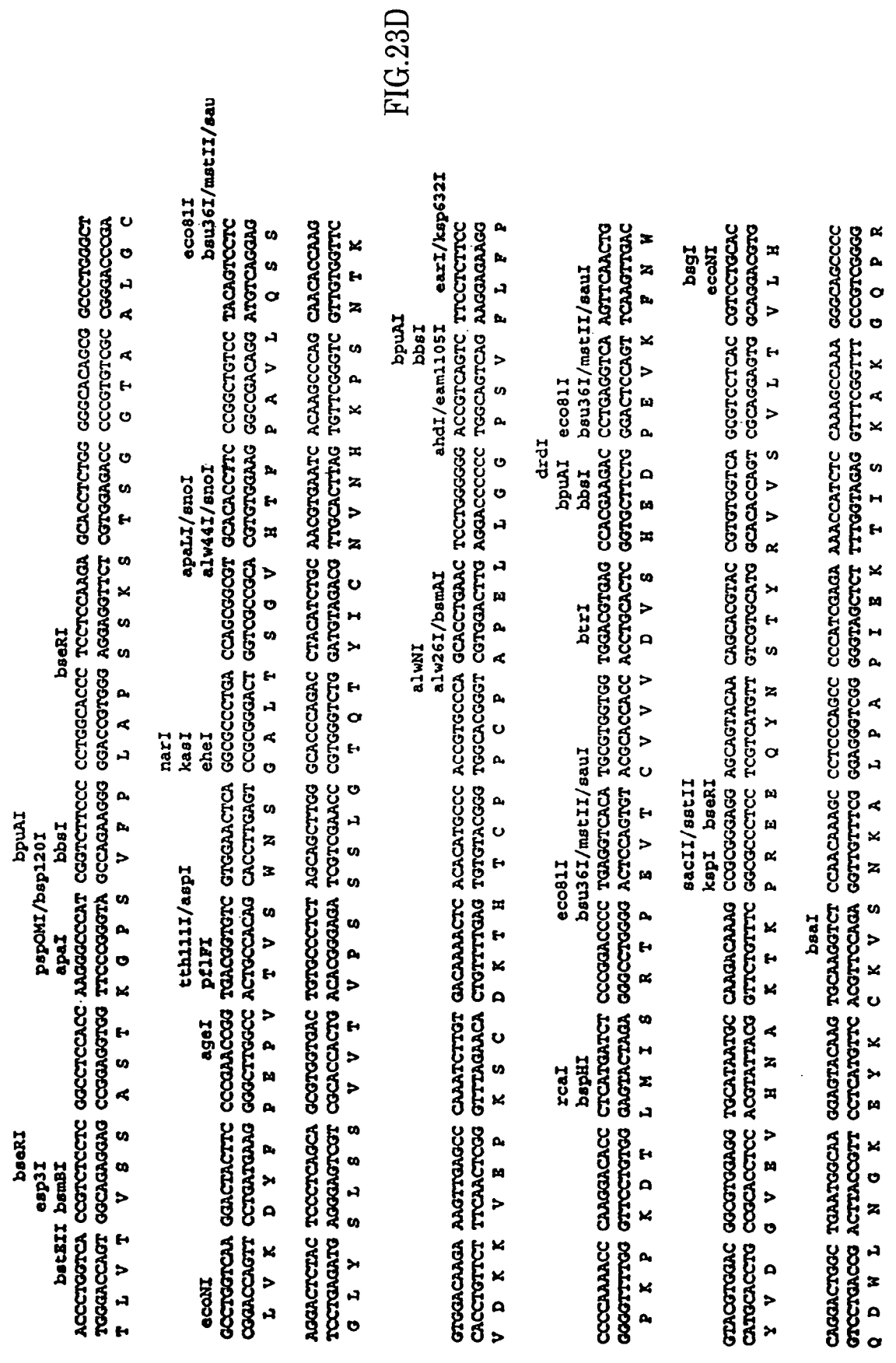

| SEQ ID NO: | Name | Sequence | Page |
|---|---|---|---|
| 24 | Heavy and light chains of anti-VEGF first generation wild type in pVG50 | polynucleotide sequence | FIG. 22 |
| 25 | Heavy and light chains of anti-VEGF first generation wild type in pVG50 | amino acid sequence | FIG. 22 |
| 26 | Heavy and light chains of VNERK in pVKSGI with FR1, 2, 3, and 4 SGI consensus sequence | polynucleotide sequence | FIG. 23 |
| 27 | Heavy and light chains of VNERK in pVKSGI with FR1, 2, 3, and 4 SGI consensus sequence | amino acid sequence | FIG. 23 |
| 28 | heavy chain FR2 Subgroup III consensus sequence | WVRQAPGKGLEWVS | 80 |
| 29 | heavy chain FR2 anti-VEGF VNERK sequence | WVRQAPGKGLEWVG | 80 |
| 30 | heavy chain FR3 Subgroup III consensus sequence | RFTISRDNSKNTLYLQMNSLRAEDTAVYYCAR | 80 |
| 31 | heavy chain FR3 anti-VEGF VNERK sequence | RFTFSLDTSKSTAYLQMNSLRAEDTAVYYCAK | 80 |
| 32 | heavy chain FR4 Subgroup III consensus sequence | WGQGTLVTVSS | 80 |

DETAILED DESCRIPTION

The numbering system of all of the antibodies described herein is according to Kabat et al. (1991) *Sequence of proteins of Immunological Interest,* 4th Ed. National Institute of Health, Bethesda, Md.

A. Definitions

The terms "antibody" and "immunoglobulin" are used interchangeably in the broadest sense and include monoclonal antibodies (full-length or intact monoclonal antibodies), polyclonal antibodies, humanized, multivalent antibodies, and multispecific antibodies (e.g., bispecific antibodies so long as they exhibit the desired biological activity). A naturally occurring antibody comprises four polypeptide chains, two identical heavy (H) chains and two identical light (L) chains inter-connected by disulfide bonds. Each heavy chain is comprised of a heavy chain variable region domain ($V_H$) and a heavy chain constant region. The heavy chain constant region is comprised of three domains, CH1, CH2 and CH3. Each light chain is comprised of a light chain variable region domain ($V_L$) and a light chain constant region domain. The light chain constant region is comprised of one domain, $C_L$. The $V_H$ and $V_L$ domains can be further subdivided into hyper-variability regions (HVR), interspersed with regions that are more conserved, termed framework regions (FR). Each $V_H$ and $V_L$ is composed of three HVRs and four FRs, arranged from amino-terminus to carboxy-terminus in the following order: FR1, HVR1, FR2, HVR2, FR3, HVR3, FR4.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG-1, IgG-2, IgA-1, IgA-2, and etc. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al., *Cellular and Mol. Immunology,* 4th ed. (2000). An antibody may be part of a larger fusion molecule, formed by covalent or non-covalent association of the antibody with one or more other proteins or peptides.

The light chains of antibodies from any vertebrate species can be assigned to one of two clearly distinct types, called kappa (κ) and lambda (λ), based on the amino acid sequences of their constant domains.

The terms "full-length antibody," "intact antibody" and "whole antibody" are used herein interchangeably, to refer to an antibody in its substantially intact form including at least 2 heavy and 2 light chains, not antibody fragments as defined below. The terms particularly refer to an antibody with heavy chains that contain Fc region. A full-length antibody can be a native sequence antibody or a recombinant antibody. A full-length antibody can be human, humanized and/or affinity matured.

The term "parent antibody", "parent antigen binding fragment" or "unmodified variable domain" are used interchangeably and as used herein refer to an antibody or antigen binding fragment that provides variable domain sequences that are the source material for a method of producing a humanized antibody or for modification in accord with the methods of the invention. Parent antibody or antigen binding fragment variable domain sequences are known or can readily be ascertained using methods known in the art. A parent antibody includes but is not limited to a humanized antibody, human antibody, monoclonal antibody, chimeric antibodies, polyclonal antibodies, multivalent antibodies and multispecific antibodies. Human consensus subgroup sequences can also serve as a source of antibody variable domain sequences. Antigen binding fragments can include Fab fragments, Fab' fragments, Fd' fragment, Fv fragment, Fd fragment, F(ab')$_2$ fragment, dAb fragment, hingeless antibodies, single chain antibodies, diabodies, single arm antigen binding molecules comprising a light chain, a heavy chain and a N-terminally truncated heavy chain constant region sufficient to form a Fc region capable of increasing the half life of the single arm antigen binding molecule, and linear antibodies.

The phrase "assembled antibody products or assembled antibody" as used herein refers to an antibody or antibody fragment that comprises at least one antibody variable domain, for example a light and a heavy chain variable domain, that forms an antigen binding site. In some cases, the association may involve one or more interchain disulfide bonds. For example, a completely assembled full-length antibody refers to an antibody including 2 heavy and 2 light chains and is completely disulfide bonded so as to form the structure of a naturally occurring antibody.

"Antibody fragments" comprise only a portion of an intact antibody, generally including an antigen binding site of the intact antibody and thus retaining the ability to bind antigen. Examples of antibody fragments encompassed by the present definition include: (i) the Fab fragment, having VL, CL, VH and CH1 domains having one interchain disulfide bond between the heavy and light chain; (ii) the Fab' fragment, which is a Fab fragment having one or more cysteine residues at the C-terminus of the CH1 domain; (iii) the Fd fragment having VH and CH1 domains; (iv) the Fd' fragment having VH and CH1 domains and one or more cysteine residues at the C-terminus of the CH1 domain; (v) the Fv fragment having the VL and VH domains of a single arm of an antibody; (vi) the dAb fragment which consists of a VH domain; (vii) hingeless antibodies including at least VL, VH, CL, CH1 domains and lacking hinge region; (viii) F(ab')$_2$ fragments, a bivalent fragment including two Fab' fragments linked by a disulfide bridge at the hinge region; (ix) single chain antibody molecules (e.g. single chain Fv; scFv); (x) "diabodies" with two antigen binding sites, comprising a heavy chain variable domain (VH) connected to a light chain variable domain (VL) in the same polypeptide chain; (xi) single arm antigen binding molecules comprising a light chain, a heavy chain and a N-terminally truncated heavy chain constant region sufficient to form a Fc region capable of increasing the half life of the single arm antigen binding domain; (xii) "linear antibodies" comprising a pair of tandem Fd segments (VH-CH1-VH-CH1) which, together with complementary light chain polypeptides, form a pair of antigen binding regions.

A "biologically active" or "functional" immunoglobulin is one capable of exerting one or more of its natural activities in structural, regulatory, biochemical or biophysical events. For example, a biologically active antibody may have the ability to specifically bind an antigen and the binding may in turn elicit or alter a cellular or molecular event such as signaling transduction or enzymatic activity. A biologically active antibody may also block ligand activation of a receptor or act as an agonist antibody. The capability of a full-length antibody to exert one or more of its natural activities depends on several factors, including proper folding and assembly of the polypeptide chains. As used herein, the biologically active immunoglobulins generated by the disclosed methods are typically, but not necessarily, heterotetramers having two identical L chains and two identical H chains that are linked by multiple disulfide bonds and properly folded and assembled.

The term "monoclonal antibody" as used herein refers to an antibody obtained from a population of substantially homogeneous antibodies, i.e., the individual antibodies comprising the population are essentially identical except for variants that may arise during production of the antibody.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region (HVR) of the recipient are replaced by residues from a hypervariable region (HVR) of a non-human species (donor antibody) such as mouse, rat, rabbit or nonhuman primate having the desired specificity, affinity, and capacity. In some instances, framework region (FR) residues of the human immunoglobulin are replaced by corresponding non-human residues to improve antigen binding affinity. Furthermore, humanized antibodies may comprise residues that are not found in the recipient antibody or the donor antibody. These modifications may be made to improve antibody affinity or functional activity. In general, the humanized antibody will comprise substantially all of at least one, and typically two, variable domains, in which all or substantially all of the hypervariable regions correspond to those of a non-human immunoglobulin and all or substantially all of the FRs are those of a human immunoglobulin sequence. Humanized anitbodies can also be produced as antigen binding fragments as described herein. The humanized antibody optionally will also comprise at least a portion of an immunoglobulin constant region (Fc), typically that of or derived from a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992). See also the following review articles and references cited therein: Vaswani and Hamilton, *Ann. Allergy, Asthma & Immunol.* 1: 105-115 (1998); Harris, *Biochem. Soc. Transactions* 23:1035-1038 (1995); Hurle and Gross, *Curr. Op. Biotech* 5:428-433 (1994).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen binding residues.

An "affinity matured" antibody is one with one or more alterations in one or more hypervariable regions which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al., *Bio/Technology* 10:779-783 (1992) describes affinity maturation by VH and VL domain shuffling. Random mutagenesis of CDR and/or framework residues is described by: Barbas et al., *Proc. Nat. Acad. Sci. USA* 91:3809-3813 (1994); Scier et al., *Gene* 169:147-155 (1995); Yelton et al., *J. Immunol.* 155:1994-2004 (1995); Jackson et al., *J. Immunol.* 154(7):3310-9 (1995); and Hawkins et al., *J. Mol. Biol.* 226:889-896 (1992).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVR1, HVR2 and HVR3) both in the light chain (LC) and the heavy chain (HC) variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions. The β-sheet structure formed by the FRs are also connected to one another by an intravariable domain disulfide bond. The hypervariable regions in each chain are held together in close proximity by the FRs and, with the hypervariable regions from the other chain, contribute to the formation of the antigen binding site of antibodies (see Kabat et al., *Sequences of proteins of Immunological Interest*, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity, and long half-life through size and FcRn binding.

The term "hypervariable region" (hereinafter "HVR") when used herein refers to the amino acid residues of an antibody variable domain the presence of which are necessary for antigen binding. Each variable domain typically has three HVR regions identified as HVR1, HVR2 and HVR3. Each hypervariable region comprises amino acid residues from a "complementarity determining region" (hereinafter "CDR") (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). In some instances, a hypervariable region can include amino acids from both a CDR region and a hypervariable loop. For example, the hypervariable region I (HVR1) of the heavy chain can include amino acids 26 to 35.

"Framework regions" (hereinafter FR) are those variable domain residues other than the hypervariable region residues. Each variable domain typically has four FRs identified as FR1, FR2, FR3 and FR4. If the hypervariable regions comprise amino acid residues from CDRs, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the hypervariable regions comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the hypervariable region comprises amino acids from both a CDR and hypervariable loop, the FR residues will be adjusted accordingly. For example, when HC HVR1 includes amino acids H26-H35, the heavy chain FR1 residues are at positions 1-25 and the FR2 residues are at positions 36-49.

The term "human variable domain subgroup consensus sequence" refers to an artificial amino acid sequence for a variable region that is generally not obtained from any single naturally occurring immunoglobulin. Sequences of naturally occurring immunoglobulins have been compiled and analyzed, for example, by Kabat et al. supra or at immuno-bme-nwu-edu. The variable domain sequences have been placed in subgroups based on similarity of the sequences. For example, human heavy chain variable domain sequences identified by Kabat can be categorized into three subgroups identified as subgroup I, subgroup II and subgroup III. The consensus sequence is an artificial sequence that is derived from a comparison of the amino acid sequences of known human immunoglobulin variable region sequences in a subgroup. Using this comparison, an amino acid variable region sequence is derived to form a consensus, or average, of the sequences of the natural immunoglobulins in the subgroup. A consensus amino acid sequence is a sequence that at each position has an amino acid found most frequently in known immunoglobulins in the subgroup. Useful consensus sequences include variable domain consensus sequences derived from the data provided in Kabat et al., 1991, *Sequences of proteins of Immunological Interest*, 5th Ed. Public Health Service, National Institutes of Health, Bethesda, Md. and variants thereof.

The term "corresponding" or "corresponds" refers to an amino acid position or amino acid sequence that is found at the same position or positions in a sequence when the sequence is aligned with a reference sequence. Typically, the amino acid sequences are aligned using the same numbering system in each sequence.

A sequence has the "most sequence identity" if it has an amino acid sequence that has the greatest degree of sequence identity to a reference sequence when the two sequences are aligned. The percent identity between two sequences can be determined by aligning the two sequences, accounting for gaps as necessary to achieve the best alignment and determining the number of residues that are the same in both sequences divided by the number of amino acids in the reference sequence. A number of computer programs can also be utilized for the purposes of aligning sequences and determining the % identity. For example, a heavy chain HVR1 amino acid sequence from an antibody or antigen binding fragment is compared to the corresponding HVR1 sequence of a heavy chain subgroup consensus sequence and the number of amino acids that are the same is divided by the number of amino acids in the HVR1 subgroup consensus sequence resulting in the % identity. The comparison is repeated with other heavy chain consensus sequences and the heavy chain subgroup consensus sequence which has the most % sequence identity is selected.

The phrase "proximal to a cys residue that forms an intrachain disulfide bond" refers to an amino acid position in a three-dimensional structure that is located near a cys residue that forms an intrachain variable domain disulfide bond or an amino acid position adjacent to a cys residue that forms an intrachain disulfide bond. Each variable domain of an antibody or antigen binding fragment typically has a single intrachain disulfide bond formed between 2 cys residues. In many antibodies the position of these cys residues is conserved. The cys residues are usually found at positions L23 and L88 in the light chain and at position H22 and H92 in the heavy chain.

Amino acid positions adjacent to the cys residues are the two amino acid positions on either side of the cys residue in a linear sequence. For example, in the heavy chain variable domain where the cys residue is at position 22, adjacent residues are at positions 20 and 21 and positions 23 and 24 in the linear sequence.

An amino acid position in a three dimensional structure that is near to a cys residue is a position where a side chain (or in the case of Gly, an alpha carbon) of the amino acid in that position is about 5 angstroms or less from the cys residue or is a position where the amino acid in that position has lost about 10 square angstroms or more of solvent accessible surface area by contacting the cys residue. Amino acid positions proximal to a cys residues can be determined by analysis of the crystal structure of the antibody or a three dimensional molecular model of the antibody using computer programs such as MIDAS (UCSF) and solvent accessible surface areas can be calculated using programs such as SOLV (G. S. Smith (1985) "A computer program for the calculation of the molecular volume and surface area of proteins", Merck, Sharpe and Dohme Res. Laboratories, QCPE).

The term "improved yield" refers to an increase in the amount of assembled antibody product with modified framework regions or variable domains when compared to an unmodified or control antibody product that is prepared under similar conditions in similar cell types. The yield of antibodies or antigen binding fragment modified in accord with the methods of the invention is increased at least about 2 fold or more, more preferably about 2 to 4 fold, more preferably about 2 to 8 fold, and most preferably 2 to 16 fold when compared to the yield of an unmodified or control antibody. Relative yields of antibody products can be determined using standard methods including scanning densitometry of SDS-PAGE gels and/or immunoblots and the AME5-RP assay.

The term "improved folding efficiency" refers to an improved ability of an antibody or antigen binding fragment to completely fold and assemble when produced in a cell culture. For example, a full-length IgG antibody is completely assembled and folded when it forms a molecule comprised of 2 heavy and 2 light chains connected by 4 interchain disulfide bonds. An antibody has improved folding efficiency when the amount of completely assembled antibody product is increased while the expression level of the heavy and light chains remains about the same compared to a reference or control antibody that has not been modified as determined by methods such as SDS-PAGE, immunoblot analysis, and scanning densitometry as described herein.

"Affinity binding" refers to the strength of the sum total of noncovalent interactions between a single binding site of a molecule (e.g., an antibody) and its binding partner (e.g., an antigen or FcRn receptor). The affinity of a molecule X for its partner Y is represented by the dissociation constant (Kd), which can generally be determined by using methods known in the art.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

The term "cistron," as used herein, is intended to refer to a genetic element broadly equivalent to a translational unit comprising the nucleotide sequence coding for a polypeptide chain and adjacent control regions. "Adjacent control regions" include, for example, a translational initiation region and a termination region.

A "separate cistron" expression vector according to the present invention refers to a single vector comprising at least two separate promoter-cistron pairs, wherein each cistron is under the control of its own promoter. Upon expression of a separate cistron expression vector, both transcription and translation processes of different genes are separate and independent.

The term "host cell" (or "recombinant host cell"), as used herein, is intended to refer to a cell that has been genetically altered, or is capable of being genetically altered by introduction of an exogenous polynucleotide molecule, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

A "disorder" is any condition that would benefit from treatment with the antibody. This includes chronic and acute disorders or diseases including those pathological conditions which predispose the mammal to the disorder in question. Non-limiting examples of disorders to be treated herein include malignant and benign tumors, non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

Modes for Carrying Out the Invention

The present invention concerns methods for improving the process of humanization and improving the yield of recombinantly produced antibodies or antigen binding fragments in cell culture, especially bacterial cell culture. Bacterial systems have been widely used for expressing antibody fragments, but there have been few attempts to express and recover functional completely assembled full-length antibodies in high yield. Because of the complex structure and large size of completely assembled full-length antibodies, it is often difficult to achieve proper folding and assembly of the expressed heavy and light chains, especially in bacterial cells. The invention is based on the discovery that the sequence of antibody variable domains can be designed or modified to contribute to correct folding and assembly of antibodies or antibody fragments, and thereby increase yield. The invention involves identifying not only which residues should be substituted but also identifying which substitutions to make at those residues in a more predictable manner to result in improved yield of the antibodies or antigen binding fragments.

In particular, it has now been discovered that folding, assembly, and yield of antibodies or antigen binding fragments is improved by substituting at least one amino acid residue of a framework region of a variable domain with an amino acid residue found at the corresponding position in the framework region of the human variable domain subgroup consensus sequence with the most sequence identity with the HVR1 and/or HVR2 amino acid sequence of the variable domain. In one embodiment of the invention, the FR1 sequence of the heavy chain variable domain is substituted with FR1 amino acid sequence of the human heavy chain variable domain subgroup consensus sequence with the most sequence identity to the HVR1 sequence of the antibody. In another aspect, at least one amino acid position proximal to a cys residue that forms an intrachain disulfide bond is substituted with an amino acid at the corresponding position in the human variable domain subgroup consensus sequence with the most identity to the HVR1 and/or HVR2 amino acid sequence of the antibody. While the processes of the invention for improving yield of antibodies in cell culture have been illustrated for production of full-length completely assembled antibodies, it should be understood that the approach described herein is applicable to the production of antigen binding fragments.

This approach is also useful for designing and producing recombinantly produced antibodies, such as humanized antibodies or antigen binding fragments, to include features that enhance yield of antibody when produced in cell culture. For example, when the desired HVR1 and/or HVR2 amino acid sequence of the recombinant antibody is identified, the human variable domain subgroup consensus sequence with the most identity to that HVR1 and/or HVR2 amino acid sequence can be selected and at least one of the FRs of that subgroup selected for the FR sequence of the recombinant antibody or antigen binding fragment. In another aspect, the variable domain of the humanized antibody or antigen binding fragment can be formed or modified so that at least one amino acid position proximal to a cys residue that forms an intrachain disulfide bond has a substitution with an amino acid at the corresponding position in the human variable domain subgroup consensus sequence with the most identity to the HVR1 and/or HVR2 amino acid sequence of the antibody. The methods for improving the process of humanization may provide for a humanized antibody or antigen binding fragment that can be produced in high yield in cell culture in less time.

Parent Antibody Variable Domains

The present invention is applicable to modification of antibodies including monoclonal antibodies (full-length or intact monoclonal antibodies), polyclonal antibodies, humanized, multivalent antibodies, and multispecific antibodies (e.g., bispecific antibodies so long as they exhibit the desired biological activity). The methods of the invention can also be employed for improving the yield of antigen binding fragments of antibodies including Fab, Fab', Fd, Fd', Fv, dAb, F(ab')$_2$, scFv, scFv$_2$, single chain antibodies, hingeless antibodies, diabodies, a single arm antigen binding molecule comprising one light chain, one heavy chain and a -terminally truncated heavy chain constant region sufficient to form a Fc region capable of increasing the half life of the single arm antigen binding molecule, and linear antibodies.

The source or parent antibody variable domains useful in the methods of the invention include those from naturally occurring and/or synthetic antibodies including monoclonal antibodies, humanized antibodies, chimeric antibodies, antibody variable domains produced by phage display, and human antibodies. Human antibodies may be obtained from transgenic animals having the human immune system such as produced by Abgenix (See, e.g., U.S. Pat. Nos. 5,591,669, 5,589,369, 5,545,807, and 6,075,181).

In one embodiment, the source or parent antibody variable domains for the HVRs is a non-human monoclonal antibody and the source or parent antibody variable domain for the FR sequences is a human antibody or human subgroup consensus sequences. The FR sequences are preferably consensus framework region sequences from a human subgroup of antibody variable domain sequences. The HVR1 and/or HVR2 of the non-human monoclonal antibody are compared to the corresponding HVR1 and/or HVR2 sequences of the human subgroup consensus sequences, and the human consensus subgroup with the most sequence identity is selected to provide at least one of the framework region sequences in the humanized antibody or antigen binding fragment.

The antibodies or antigen binding fragments modified in accord with the methods of the invention have antigen binding specificity. Preferably, the antibodies of the invention are specific to antigens that are biologically important polypeptides. More preferably, the antibodies of the invention are useful for therapy or diagnosis of diseases or disorders in a mammal. Full-length antibodies made according to the present invention are particularly useful as therapeutic antibodies such as blocking antibodies, agonist antibodies or antibody conjugates. Non-limiting examples of therapeutic antibodies include anti-VEGF, anti-IgE, anti-CD 11, anti-CD18, anti-CD4O, anti-tissue factor (TF), anti-HER2, and anti-TrkC antibodies. Antibodies directed against non-polypeptide antigens (such as tumor-associated glycolipid antigens) are also contemplated.

Where the antigen is a polypeptide, it may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain;

proinsulin; follicle stimulating hormone; calcitonin; luteinizing hormone; glucagon; clotting factors such as factor VIIIC, factor IX, tissue factor (TP), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNE), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGE); transforming growth factor (TGF) such as TGP-alpha and TGF-beta, including TGF-β1, TGF-β2, TGF-β3, TGF-β4, or TGF-β5; insulin-like growth factor-I and -II (IGF-I and IGF-II); des(1-3)—IGF-I (brain IGF-I), insulin-like growth factor binding proteins; CD proteins such as CD3, CD4, CD8, CD19, CD2O and CD4O; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Preferred antigens for antibodies encompassed by the present invention include CD proteins such as CD3, CD4, CD8, CD19, CD2O, CD34, and CD46; members of the ErbB receptor family such as the EGF receptor, HER2, HER3 or HER4 receptor; cell adhesion molecules such as LFA-1, Mac1, p150.95, VLA-4, ICAM-1, VCAM, α4/β7 integrin, and αv/β3 integrin including either α or β subunits thereof (e.g. anti-CD11a, anti-CD 18 or anti-CD11b antibodies); growth factors such as VEGF; tissue factor (TF); TGF-β alpha interferon (α-IFN); an interleukin, such as IL-8; IgE; blood group antigens Apo2, death receptor; flk2/flt3 receptor; obesity (OB) receptor; mpl receptor; CTLA4; protein C etc. The most preferred targets herein are VEGF, IgE, TF, CD19, CD2O, CD4O, TGF-β, CD11a, CD18, Apo2 and C24.

Soluble antigens or fragments thereof, optionally conjugated to other molecules, can be used as immunogens for generating antibodies. For transmembrane molecules, such as receptors, fragments of these molecules (e.g. the extracellular domain of a receptor) can be used as the immunogen. Alternatively, cells expressing the transmembrane molecule can be used as the immunogen. Such cells can be derived from a natural source (e.g. cancer cell lines) or maybe cells which have been transformed by recombinant techniques to express the transmembrane molecule. Other antigens and forms thereof useful for preparing antibodies will be apparent to those in the art.

The antibodies used as starting material in the methods of the present invention maybe monospecific, bispecific, trispecific or of greater multispecificity. Multispecific antibodies may be specific to different epitopes of a single molecule or maybe specific to epitopes on different molecules. Methods for designing and making multispecific antibodies are known in the art. See, e.g., Millstein Ct at. (1983) Nature 305:537-539; Kostelny et al. (1992) J. Immunol. 148:1547-1553; WO 93/17715.

Humanized Antibodies or Antigen Binding Fragments

The present invention is applicable to preparation of or modification of humanized antibodies or antigen binding fragment. Various methods for humanizing non-human antibodies are known in the art. Preferably, a humanized antibody or antigen binding fragment has one or more amino acid residues introduced into it from a source which is non-human. These non-human amino acid residues are often referred to as "donor" residues, which are typically taken from an "donor" variable domain. Humanization can be essentially performed following the method of Winter and co-workers (Jones et al. (1986) Nature 321:522-525; Riechmann et al. (1988) Nature 332:323-327; Verhoeyen et al (1988) Science 239:1534-1536).

Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

Previous methods for preparing humanized antibodies have involved selecting human variable domains, both light and heavy, to be used in making the humanized antibodies. According to the so-called "best-fit" method, the entire sequence of the variable domain of rodent antibody is screened against the entire library of known human variable-domain sequences. The human sequence which is closest to that of the rodent antibody is then accepted as the human framework for the humanized antibody (Sims et al. (1993) J. Immunol. 151:2296; Chothia et al. (1987) J. Mol. Biol. 196:901). Another method uses a particular framework derived from the consensus sequence of all human antibodies of a particular subgroup of light or heavy chains. Carter et al., (1992), Proc. Natl. Acad. Sci. USA 89: 4285. In some cases, the framework region consensus sequences used are subgroup III for the heavy chain and subgroup I of the kappa light chain. These subgroups were the most commonly occurring subgroups based on the 1991 compilation of sequences of Kabat et al. cited supra.

The methods of the invention provide for improving the process of humanization by identifying at least one human consensus subgroup FR sequence that can be combined with HVRs from a non-human monoclonal antibody to form a humanized antibody or antigen binding fragment that has improved characteristics for production in cell culture. In some embodiments, the method comprises expressing a variable domain comprising at least one FR sequence from a selected human subgroup variable domain consensus sequence, and a HVR1 and/or HVR2 sequence of a non-human antibody in a host cell, wherein the selected human subgroup consensus sequence is the human subgroup consensus sequence that has a HVR1 and/or HVR2 sequence that has the most sequence identity to the HVR1 and/or HVR2 of the non-human antibody; and recovering the antibody variable domain from the host cell. The antibody variable domain can be a part of an antigen binding fragment, heavy chain, light chain, or full length completely assembled antibody.

In other embodiments, the HVR1 and/or HVR2 of the non-human monoclonal antibody are compared to the corresponding HVR1 and/or HVR2 sequences of the human subgroup consensus sequences, and the human consensus subgroup with the most sequence identity to the HVR1 and/or HVR2 of the non-human monoclonal antibody is selected to provide at least one of the framework region sequences in the humanized antibody or antigen binding fragment. The variable domain can be a heavy or light chain or both. A single selected FR or more than one FR selected from the group consisting of FR1, FR2, FR3, FR4 and mixtures thereof can be used to prepare the recombinant antibody. In one embodiment, the recombinant antibody includes the selected FR1 of the human heavy chain subgroup consensus sequence that has the most seqeunce identity with HVR1 and/or HVR2 of the non-human antibody. Identifying and selecting a human consensus subgroup to use for the source of at least one FR sequence may shorten the time required to form a humanized antibody or antigen binding fragment that can be produced in high yield in cell culture. The host cells can be prokaryotic or eukaryotic.

In some embodiments, a method for preparing a humanized antibody or antigen binding fragment comprises expressing a variable domain in a host cell, wherein the variable domain has a substitution of at least one amino acid position proximal to a cys residue that participates in an intrachain variable domain disulfide bond with a different amino acid, wherein the different amino acid is the amino acid found at corresponding position of a human subgroup variable domain consensus sequence that has a HVR1 and/or HVR2 amino acid sequence with the most sequence identity with a corresponding HVR1 and/or HVR2 amino acid sequence of the variable domain; and recovering the antibody variable domain from the host cell. The antibody variable domain can be a part of an antigen binding fragment, heavy chain, light chain, or full length completely assembled antibody.

In one embodiment, the method comprises comparing a HVR1 and/or HVR2 amino acid sequence of a variable domain of a non-human antibody to a corresponding HVR1 and/or HVR2 amino acid sequence of each human subgroup variable domain consensus sequences and selecting a human subgroup variable domain consensus sequence that has the most sequence identity with the HVR1 and/or HVR2 sequence of the variable domain; identifying at least one framework region to combine with the HVR1 and/HVR2 of the non-human antibody to form a variable domain of a humanized antibody or antigen binding fragment; further modifying the humanized antibody or antigen binding fragment by identifying at least one amino acid position in the variable domain of the humanized antibody or antigen binding fragment that is proximal to a cys residue that forms an intrachain variable domain disulfide bond in the variable domain; and placing at said at least one identified position in the variable domain the amino acid found at the corresponding position in the selected subgroup consensus sequence to form a modified variable domain of the humanized antibody or antigen binding fragment.

Methods for Improving the Yield of Antibodies: Modifying FRs

A method of the invention provides for modifying the framework regions of the variable domains of a parent antibody or antigen binding fragment to improve yield and/or designing a variable domain for improved yield when produced in cell culture. The parent antibody variable domain sequences for the method may be obtained from antibodies produced by various means. A naturally occurring antibody or synthetic antibody variable domain sequences can provide the framework to be modified. The method of the invention can also be employed during the process of humanization to select at least one framework region for use in the humanized antibody or antigen binding fragment.

In some embodiments, a method comprises expressing a variable domain of the antibody or antigen binding fragment comprising at least one modified FR in a host cell, wherein the modified FR has a substitution of at least one amino acid position in at least one FR with a different amino acid, wherein the different amino acid is the amino acid found at the corresponding FR position of a human subgroup variable domain consensus sequence that has a HVR1 and/or HVR2 amino acid sequence with the most sequence identity with a corresponding HVR1 and/or HVR2 sequence of the variable domain, wherein the antibody or antigen binding fragment with the modified FR has improved yield in cell culture compared to an unmodified parent antibody or antigen binding fragment; and recovering the antibody or antigen binding fragment variable domain comprising the modified framework from the host cell. The antibody variable domain can be a part of an antigen binding fragment, heavy chain, light chain, or full length completely assembled antibody.

In some embodiments, a method comprises expressing a variable domain of the antibody or antigen binding fragment comprising at least one modified FR in a host cell, wherein the modified FR is obtained by substituting at least one amino acid in a FR of a parent variable domain of the antibody or antigen binding fragment with a different amino acid; wherein the different amino acid is an amino acid found at the corresponding FR position of a human subgroup variable domain consensus sequence that has a HVR1 and/or HVR2 amino acid sequence with the most sequence identity with a corresponding HVR1 and/or HVR2 amino acid sequence of the parent variable domain to form a modified FR. The antibody or antigen binding fragment with the modified FR has improved yield in cell cultures compared to an antibody or antigen binding fragment comprising the parent variable domain. The antibody or antigen binding fragment variable domain comprising the modified framework is recovered from the host cell. The antibody variable domain can be a part of an antigen binding fragment, heavy chain, light chain, or full length completely assembled antibody.

In some embodiments of the invention, a method comprises, expressing a variable domain of the antibody or antigen binding fragment comprising at least one modified FR of a heavy chain in a host cell, wherein the modified FR has a substitution of at least one amino acid position in at least one FR with a different amino acid, wherein the different amino acid is the amino acid found at the corresponding FR position of a human subgroup heavy chain variable domain consensus sequence that has a HVR1 and/or HVR2 amino acid sequence with the most sequence identity with a corresponding HVR1 and/or HVR2 sequence of the variable domain, wherein the antibody or antigen binding fragment with the modified FR of the heavy chain has improved yield in cell culture compared to an unmodified parent antibody or antigen binding fragment; and recovering the antibody or antigen binding fragment variable domain comprising the modified framework from the host cell. The antibody variable domain can be a part of an antigen binding fragment, heavy chain, light chain, or full length completely assembled antibody.

In one embodiment of the invention, the method comprises a) comparing a HVR1 and/or HVR2 amino acid sequence of a variable domain or parent antibody or antigen binding fragment to a corresponding HVR1 and/or HVR2 amino acid sequence of each of human variable domain subgroup consensus amino acid sequences and selecting the subgroup consensus sequence that has the most sequence identity with the HVR1 and/or HVR2 amino acid sequence of the variable domain; b) identifying at least one amino acid in a FR in the variable domain that is different from an amino acid of the corresponding position of the selected subgroup consensus sequence; and c) substituting the at least one amino acid so identified with the corresponding amino acid residue of the selected subgroup consensus sequence to form a variable domain with modified framework region. The antibody or antigen binding fragment with the modified framework region has improved yield when produced in cell culture compared to the parent antibody or antigen binding fragment from which it was derived.

In some embodiments, at least two or more of the residues in a FR of the variable domain are substituted with the corresponding amino acid residues of the selected subgroup consensus sequence, and preferably, all of the residues that are different in the FR are substituted with the corresponding amino acids from the selected subgroup consensus sequence. In one embodiment, all of the residues that are different in FR1 are substituted with the corresponding amino acids from the selected subgroup consensus sequences The parent antibody or antigen binding fragment provides variable domain sequences as source materials for the methods of the invention. Variable domain sequences may be known or readily ascertained using known methods. A parent antibody or antigen binding fragment is modified in accord with the methods of the invention to improve yield when produced in cell culture. Parent antibodies can include humanized antibody, a chimeric antibody, a monoclonal antibody, a human antibody, a multispecific antibody, diabodies, or an antibody generated by phage display. Antigen binding fragments can include Fab fragments, F(ab')$_2$ fragments, scFv fragments, scFv2 fragments, a single arm antibody comprising one light chain, one heavy chain and a N-terminally truncated heavy chain constant region sufficient to form a Fc region capable of increasing the half life of the single arm antigen binding molecule, or single chain antibodies.

A HVR1 and/or HVR2 amino acid sequence of a variable domain of parent antibody or antigen binding fragment is identified and compared to the corresponding HVR1 and/or HVR2 amino acid sequence of each human variable domain subgroup consensus sequences. Preferably, the HVR1 sequences are compared. A HVR1 and/or HVR2 amino acid sequence can be obtained from a heavy or light chain variable domain or both. The HVR1 and/or HVR2 includes amino acids from a CDR and/or in a hypervariable loop or both. For example, in the case of some humanized antibodies, the HC-HVR1 includes amino acids of both the CDR and hypervariable loop, i.e. amino acids 26-35.

Once the amino acid sequence of a HVR1 and/or HVR2 of a variable domain is identified, it is aligned with the amino acid sequence at the corresponding positions in each of the human variable domain subgroup consensus sequences. A consensus sequence for each variable domain subgroup is derived by selecting the most frequently occurring amino acid at each position in the known sequences of variable domains. The sequences of human variable domains from naturally occurring antibodies have been and continue to be compiled online and/or in published form. A useful compilation of sequences of naturally occurring immoglobulins is that prepared by Kabat; Kabat et al., *Sequences of proteins of Immunological Interest*, 5th Ed. Public Health Service, National Institute of Health, Bethesda, Md. (1991) and published online at immuno-bme-nwu-edu. Subgroups of the variable domains of naturally occurring antibodies have been identified based on overall sequence similarity. For example, Kabat has identified 3 subgroups for the human heavy chain variable domain: Subgroup I, Subgroup II and Subgroup III. Kabat et al. supra. The consensus sequence for a subgroup of variable domains may change as more sequences of naturally occurring antibodies are added to the subgroup.

After aligning the HVR1 and/or HVR2 sequences, the subgroup consensus sequence with the most sequence identity to the HVR1 and/or HVR2 amino acid sequence of the variable domain that is to be modified is selected. Once a subgroup consensus sequence is selected, a FR sequence of the variable domain is compared to the corresponding FR sequence in the selected subgroup consensus sequence. The amino acid positions in the FR where the two sequences differ are identified and at least one amino acid position in the FR that differs is substituted with the amino acid at that position in the selected human subgroup consensus sequence. In some embodiments, at least about 10%, 30%, 50%, 70%, 80%, 90% of the amino acid positions that differ are subjected to substitution as described.

In one embodiment, a FR sequence of a variable domain is obtained from a heavy chain, a light chain or both. One or more FRs selected from the group consisting of FR1, FR2, FR3, FR4 and mixtures thereof can be substituted at at least one amino acid residue that differs from the selected subgroup consensus sequence. A FR can be modified at one or more than one amino acid residues. In some embodiments, at least two amino acid positions in at least one FR are substituted with amino acids in the corresponding positions of the selected subgroup sequence. In some embodiments, the FR is a heavy chain FR1 and one of the identified amino acid positions is position 6 or position 23 or both, and the other position is selected from the group consisting of amino acid positions 1, 11, 13, 18, 19, and mixtures thereof. In some embodiments, all of the amino acid positions at positions 1, 6, 11, 13, 18, 19, and 23 of the heavy chain FR1 are substituted.

A FR of the variable domain of a parent antibody or antigen binding fragment can be modified such that it has any one of at least 50% to 100% sequence identity to the corresponding FR sequence of the selected subgroup consensus sequence, preferably at least 50%, more preferably at least 55%, more preferably at least 60%, more preferably at least 65%, more preferably at least 70%, more preferably at least 75%, more preferably at least 80%, more preferably at least 85%, more preferably at least 90%, and most preferably at least 95%, identical in sequence to the corresponding FR sequence of the selected subgroup consensus sequence.

The HVR1 of a heavy or light chain can be compared to the corresponding HVR1 sequences of the human heavy or light chain subgroup consensus sequences. In one embodiment, the heavy chain HVR1 of anti-VEGF humanized antibody VNERK (amino acids 26 to 35) is compared to the corresponding HVR1 sequences of the human heavy chain subgroup consensus sequences:

| Sequence | HVR Alignment | | % Identity |
|---|---|---|---|
| Subgroup I HVRH1: | GYTFTSYAIS | (SEQ ID NO: 15) | 70% |
| VNERK HVR1: | GYTFTNYGIN | (SEQ ID NO: 14) | 7/10 |

-continued

| Sequence | HVR Alignment | | % Identity |
|---|---|---|---|
| Subgroup II HVRH1: | GGSVSSYWSWN | (SEQ ID NO: 16) | 18% |
| VNERK HVR1: | GYTFTNYGIN. | (SEQ ID NO: 14) | 2/11 |
| Subgroup III HVRH1: | GFTFSSYAMS | (SEQ ID NO: 17) | 40% |
| VNERK HVR1: | GYTFTNYGIN | (SEQ ID NO: 14) | 4/10 |

The human consensus subgroup having the most sequence identity with HVR1 is the subgroup I sequence and at least one of the FR sequences of the consensus subgroup sequence I is compared to the corresponding FR sequence of the of the anti-VEGF antibody. Those positions that differ between the two sequences are selected for substitutions.

In other embodiments, The HVR2 of a heavy or light chain can be compared to the corresponding HVR2 sequences of the human heavy or light chain subgroup consensus sequences. In one embodiment, the Kabat defined heavy chain HVR2 of anti-VEGF humanized antibody VNERK (amino acids 50 to 65) is compared to the corresponding HVR2 sequences of the human heavy chain subgroup consensus sequences. The human consensus subgroup having the most sequence identity with HVR2 is the subgroup I sequence and at least one of the FR sequences of the consensus subgroup sequence I is compared to the corresponding FR sequence of the of the anti-VEGF antibody. Those positions that differ between the two sequences are selected for substitutions.

In other embodiments, the HVR1 and the HVR2 of a heavy or light chain can be compared to the corresponding HVR1 and HVR2 sequences of the human heavy or light chain subgroup consensus sequences. If the human consensus subgroup having the most sequence identity with HVR1 differs from that of the HVR2 sequence, then the human consensus subgroup having the most sequence identity with HVR1 sequence is selected. For example, in one embodiment, the heavy chain HVR1 of anti-VEGF humanized antibody VNERK (amino acids 26 to 35) is compared to the corresponding HVR1 sequences of the human heavy chain subgroup consensus sequences and the Kabat defined heavy chain HVR2 of anti-VEGF humanized antibody VNERK (amino acids 50 to 65) is compared to the corresponding HVR2 sequences of the human heavy chain subgroup consensus sequences. The human consensus subgroup having the most sequence identity with HVR1 and HVR2 is the subgroup I sequence and at least one of the FR sequences of the consensus subgroup sequence I is compared to the corresponding FR sequence of the of the anti-VEGF antibody. Those positions that differ between the two sequences are selected for substitutions.

In an anti-VEGF antibody (described herein) comprising amino acid subgroup III consensus sequence in the heavy chain FR1, substitution of the FR1 subgroup III consensus sequence with the corresponding amino acid residues of the selected human consensus subgroup I in the heavy chain FR1 resulted in improved antibody yield. Conversion of the heavy chain subgroup III FR1 residues of this antibody to the subgroup I residues required 12 amino acid substitutions in the FR1 sequence. The modified FR sequence with all 12 substitutions has 100% sequence identity to the selected human subgroup consensus sequence. A single amino acid substitution at a consensus sequence III residue with a consensus sequence subgroup I residue results in a modified FR sequence that has about 56% sequence identity with the selected subgroup consensus sequence.

When the antibody to be modified in accord with the methods of the invention is a humanized antibody or antigen binding fragment, some changes to the framework and HVRs for improving binding affinity may have been made during the process of humanization. For example, the humanized anti-VEGF VNERK antibody was prepared with heavy chain consensus framework region sequences from subgroup III. In the process of improving antibody binding affinity, seven changes were made in the framework region sequences. When the changes at these positions were made during the process of humanization, the amino acids substituted at each of these positions was that of the murine antibody at the corresponding position. Four of the changes also happen to correspond to a change from a subgroup consensus subgroup III residue to a subgroup I residue and one represents a conservative substitution for the subgroup I sequence. Because the humanized antibody or antigen binding fragment may have some of the FR region substitutions at the positions identified in accord with the methods of the invention, the improvement of the yield may be less than that would be expected if the changes to the subgroup III sequence had not already been made to the humanized antibody. Producing the anti-VEGF VNERK antibody with heavy chain FR regions from the human consensus subgroup I instead of subgroup III initially using the methods of the invention could have shortened the time to producing an antibody that can be produced in high yield in cell culture.

In another embodiment, at least one amino acid, and preferably all, of the amino acids in positions in the FR1 of the heavy chain variable domain that differ from the selected subgroup consensus sequence are substituted with subgroup consensus amino acids at those positions. For example, a humanized antibody prepared with framework regions from heavy chain variable domain subgroup III consensus sequence can be modified as follows. The FR1 of the heavy chain variable domain can be replaced either with the FR1 sequence of the subgroup I or subgroup II consensus sequences depending on which subgroup sequence has the most sequence identity with the HVR1 and/or HVR2 sequence of the heavy chain variable domain. The human heavy chain FR1 subgroup consensus sequence can be selected from the group consisting of SEQ. ID NO: 1, SEQ ID NO:2 and SEQ ID NO:3. As illustrated in the examples, the FR1 sequence of an anti-VEGF antibody comprising the heavy chain subgroup III consensus FR1 sequence can be replaced with the heavy chain subgroup I consensus FR1 by making a total of 12 amino acid substitutions at those amino acid residues that differ between the two sequences.

The antibodies or antigen binding fragments with at least one modified framework region amino acid formed in accord with the process of the invention are characterized by improved yield of assembled antibody products when produced in cell culture under similar conditions and cell types as the unmodified antibodies or antigen binding fragments. The host cells can be prokaryotic or eukaryotic. In some embodiments, the antibodies or antigen binding fragments with modified framework regions are produced in high yield without detrimental effects on expression levels or on antigen binding affinity. In some cases, further modifications to the modified antibody may be necessary, for example, to enhance antigen binding affinity. For example, when the methods of the invention are applied to producing a humanized antibody or antigen binding fragment, other changes to antibody sequence may be made to improve antigen binding affinity. If improvement in antigen binding affinity of antibodies or antigen binding fragments with modified framework regions is necessary, it can be achieved by altering residues as needed and in accord with methods well-known in the art (i.e., Presta et al., supra) and as described herein.

The relative yield can be determined using standard methods such as by separating out the antibody or antigen binding fragment produced in cell culture by SDS-PAGE, transferring the protein to an immunoblot, and analyzing the amount of completely assembled antibody products by scanning densitometry. The yield of the completely assembled antibody or antigen binding fragment is improved at least about 2 fold or more, more preferably about 2 to 4 fold, more preferably about 2 to 8 fold, and most preferably about 2 to 16 fold when compared to the yield of unmodified antibody or antigen binding fragment when produced under similar cell culture conditions.

In addition, the method for improved yield of antibodies can be applied to producing a humanized antibody or antigen binding fragment for improved folding and/or yield. The method can be applied to the humanization process and may result in decreasing the time it takes to prepare a humanized antibody with the desired characteristics. Once a HVR1 and/or HVR2 amino acid sequence of a variable domain is selected, the HVR1 and/or HVR2 sequence can be aligned and compared to the corresponding sequence of each of the human subgroup consensus sequences for that variable domain and the subgroup with the most identity to HVR1 and/or HVR2 sequence is selected. The selected subgroup sequence is then used to provide at least one FR sequence for the antibody or antigen binding fragment that is being produced.

The invention also includes antibody variable domains, antigen binding fragments, heavy chains, lights chains, and/or full length completely assembled antibodies produced or modified in accord with the methods of the invention.

Methods for Improving Antibody Yield: Modifying Residues Proximal to a Cys Residue That Forms an Intrachain Disulfide Bond.

Another aspect of the invention includes a method for preparing a humanized antibody or antigen binding fragment or for improving the yield of antibodies or antigen binding fragments when produced in cell culture by modifying at least one amino acid residue in a variable domain proximal to a cys residue that forms an intrachain variable domain disulfide bond. The at least one amino acid position is modified by placing in that position a different amino acid, wherein the different amino acid is found at the corresponding position in a human variable domain subgroup consensus sequence that has the most sequence identity with a HVR1 and/or HVR2 amino acid sequence of the variable domain. Modifications can be made to either the heavy chain or light chain variable domain. The antibody variable domain so modified can be a part of an antigen binding fragment, heavy chain, light chain, or full length completely assembled antibody. In one embodiment, at least two positions are modified: either in a single variable domain or one substitution in each of the heavy and light chain variable domains.

In some embodiments, the method comprises expressing a modified variable domain of the antibody or antigen binding fragment in a host cell, wherein the modified variable domain has a substitution of at least one amino acid position proximal to a cys residue that participates in an intrachain variable domain disulfide bond with a different amino acid, wherein the different amino acid is the amino acid found at corresponding position of a human subgroup variable domain consensus sequence that has a HVR1 and/or HVR2 amino acid sequence with the most sequence identity with a corresponding HVR1 and/or HVR2 amino acid sequence of the variable domain, wherein the antibody or antigen binding fragment comprising the modified variable domain has improved yield in cell culture compared to the antibody or antigen binding fragment; and recovering the antibody or antigen binding fragment comprising the modified variable domain from the host cell.

A variable domain is modified at one or more amino acid positions that are proximal to a cys residue that forms an intrachain variable domain disulfide bond. Typically, each variable domain has a single intrachain disulfide bond between 2 cys residues. The position of cys residues that form the intrachain disulfide bond in a variable domain are usually at conserved positions e.g. at positions L23 and L88 in the light chain and at positions H22 and H92 in the heavy chain. Amino acid positions proximal to a cys residue are those positions that are near to the cys residue in a three-dimensional structure of the antibody or adjacent to the cys residue in a linear sequence. A position adjacent to the cys residue includes the two amino acid positions on either side of the cys residue in a linear sequence. A position is near to a cys residue in a three-dimensional structure if the side chain of the amino acid (or the α carbon for Gly) in that position is about 5 angstroms or less from the cys residue or is a position where the amino acid in that position has lost about 10 square angstroms or more of solvent accessible surface area by contacting the cys residue.

One way to identify amino acid positions proximal to cys residues in a three-dimensional structure involves analysis of the crystal structure of the antibody or antigen binding fragment using a computer program such as MIDAS (available from University of California San Francisco). To determine amino acid positions proximal to cys residues based on a loss of surface area, computer programs such as SOLV may be employed. If a crystal structure of the antibody or antigen binding fragment is not available, a three-dimensional structure based on the primary sequence may be modeled. Computer programs are available which illustrate probable three-dimensional conformational structures of antibody sequences.

For antibodies that have the framework regions from the same human subgroup consensus sequence, amino acid positions proximal to the cys residues may be conserved. For example, for antibodies that have FRs in the heavy chain with the sequence of the human heavy chain variable domain subgroup III consensus sequence, the amino acid positions identified as proximal to the cys residues in the three dimensional structure of the heavy chain include position 4, position 6, position 34, position 36, position 78, and position 104 (numbering according to Kabat et al., supra). For antibodies that have FRs in the light chain with the sequence of human light chain variable domain Kappa subgroup I consensus sequence, the amino acid positions identified as proximal to cys residues in the three dimensional structure of the light chain include position 4, position 6, position 33, position 35, and position 71.

Proximal residues adjacent to a cys residue can include residues in positions adjacent to the cys residues in the linear sequence. The position of cys residues that form the intrachain disulfide bond in a variable domain are usually at conserved positions e.g. at positions L23 and L88 in the light chain and at positions H22 and H92 in the heavy chain. In the heavy chain variable domain, amino acid positions adjacent to the cys residues include amino acid positions 20, 21, 23, 24, 90, 91, 93, and 94. Proximal residues adjacent to a cys residue in the light chain variable domain include residues at amino acid positions 21, 22, 24, 25, 86, 87, 89 and 90.

Once at least one amino acid position proximal to the cys residue is identified, an amino acid from the corresponding position in the human variable domain subgroup consensus sequence with the most sequence identity to the HVR1 and/or HVR2 amino acid sequence of the variable domain is placed at that position if the amino acid at that position is different from the amino acid in the variable domain. As described previously, the human variable domain subgroup consensus sequence with the most identity is selected after the HVR1 and/or HVR2 sequence of the variable domain of the antibody or antigen binding fragment is aligned and compared with the corresponding sequence of each of subgroup consensus sequences. An amino acid is placed at a position proximal to the cys residue, typically by substituting the amino acid residue at that position with corresponding amino acid from the selected subgroup consensus sequence.

In some embodiments, at least two positions proximal to a cys residue are modified. The two positions can be modified in a single variable domain or two positions can be modified by making a single substitution in a light chain variable domain and a single substitution in a heavy chain variable domain. In some embodiments, a heavy chain variable domain has a substitution at amino acid position 4, 6, 34, 78, or mixtures thereof. In other embodiments, a light chain variable domain has a substitution at amino acid positions 4, 71, or mixtures thereof. In some embodiments, a heavy chain has substitutions at postion 6 and position 34, and a light chain has a substitution at position 4 and at position 71. In some embodiments, all of the amino acid positions proximal to a cys residue in a heavy or light chain are substituted.

The antibodies or antigen binding fragments with at least one modification to at least one amino acid proximal to a cys residue formed in accord with process of the invention are characterized by improved yield of assembled antibody or antigen binding fragment when produced in cell culture. Preferably, the antibodies or antigen binding fragments have improved yield with minimal, if any, detrimental effect on expression levels, the antigen binding affinity, biological activity and/or physicochemical properties. If improvement in antigen binding affinity of antibodies with modified framework regions is needed it can be achieved by altering HVR residues as needed and in accord with methods known in the art, for example as described by Presta et al, supra. The relative yield can be determined using standard methods such as by separating out the antibody product produced in cell culture by SDS-PAGE, transferring the protein to an immunoblot, and analyzing the amount of assembled antibody products by scanning densitometry. The yield of assembled antibody products is improved at least about 2 fold or more, more preferably, about 2 to 4 fold, about 2 to 8 fold and most preferably about 2 to 16 fold when compared to the yield of unmodified antibody or antigen binding fragment when produced under similar cell culture conditions.

In addition, the method for improving the yield of antibodies can be applied to producing an antibody or antigen binding fragment, for example, a humanized antibody or antigen binding fragment, for improved folding and yield. Once a HVR1 and/or HVR2 region sequence of a variable domain is selected, the HVR1 and/or HVR2 sequence can be aligned and compared to the corresponding sequence of each of the human subgroup consensus sequences and the subgroup with the most identity to HVR1 and/or HVR2 sequence selected. The selected subgroup sequence is then used to identify an amino acid(s) to place in at least one amino acid position, preferably all of the positions, proximal to the cys residues that form an intrachain disulfide bond for the antibody or antigen binding fragment in the humanized antibody or antigen binding fragment.

The invention also includes antibody variable domains, antigen binding fragments, heavy chains, lights chains, and/or full length completely assembled antibodies produced or modified in accord with the methods of the invention.

Methods for Preparing Antibodies or Antigen Binding Fragments with Modified Framework Region Residues When the methods of the invention are applied to antibodies or antigen binding fragments whose sequences are known or readily ascertainable using known methods, targeted substitutions are made in at least one FR residue and/or in at least one amino acid position proximal to cys residues that form an intrachain disulfide bond. The antibodies with amino acid substitutions in the variable domain can be prepared synthetically or by using recombinant methods.

For recombinant methods, nucleic acid sequences encoding variable domains of heavy and light chains are prepared using standard methods. The sequences of the variable domains of many naturally occurring antibodies and the human subgroup consensus sequences are known and sequences of humanized or antigen binding fragments can be readily determined by standard methods. Nucleic acid molecules encoding variable domains with at least one modification in the framework region and/or with substitutions at one or more positions proximal to cys residues are prepared by a variety of methods known in the art. These methods include, but are not limited to, isolation from a natural source (in the case of naturally occurring amino acid sequence variants), synthesis, or preparation by oligonucleotide-mediated mutagenesis, site-directed mutagenesis, PCR mutagenesis, and cassette mutagenesis of a parent variable domain of an antibody or antigen binding fragment.

Using recombinant methods, a polynucleotide molecule encoding the heavy and light chain variable domain of the antibody is modified using standard methods. For example, the polynucleotide molecule encoding the heavy and/or light chain variable domain can be modified in a single step using a double stranded oligonucleotide encoding one or more amino acid substitutions according to the method described by Carter et al., *PNAS* 89:4285 (1992) or as described in U.S. Pat. No. 5,747,662.

The variable domains of the invention have one or more amino acid substitutions in FR residues and/or in positions proximal to cys residues of the variable domain. A FR of the variable domain of a parent antibody or antigen binding fragment can be modified such that it has any one of 50% to 100% sequence identity to the corresponding FR sequence of the selected subgroup consensus sequence, preferably at least 50%, more preferably at least 55%, more preferably at least 60%, more preferably at least 65%, more preferably at least 70%, more preferably at least 75%, more preferably at least 80%, more preferably at least 85%, more preferably at least 90%, and most preferably at least 95%, identical in sequence to the corresponding FR sequence of the selected subgroup consensus sequence.

A variable domain of a parent antibody or antigen binding fragment can be modified so that it has anyone of 50% to 100% sequence identity to the corresponding variable domain of the parent antibody, preferably at least 50%, more preferably at least 55%, more preferably at least 60%, more preferably at least 65%, more preferably at least 70%, more preferably at least 75%, more preferably at least 80%, more preferably at least 85%, more preferably at least 90%, and most preferably at least 95%, identical in sequence to the corresponding variable domain sequence of the parent antibody or antigen binding fragment.

When an entire framework region is substituted at all of the residues that differ from the selected human consensus subgroup, more than one amino acid substitution may be made in the framework region to form a modified framework region that can be used to construct a variable domain or replace the framework region in a variable domain of a parent antibody or antigen binding fragment that has the HVR1 and/or HVR2 amino acid sequence. When more than one FR selected from the group consisting of FR1, FR2, FR3 and FR4 regions are modified to correspond to the sequence for the selected human consensus sequence, multiple amino acid substitutions may be made to form modified framework regions that can be used to replace framework regions in antibodies or antigen binding fragments with the selected HVR1 and/or HVR2 sequence or to construct a new variable domain.

Once variable domains are modified or prepared in accord with the methods of the invention, they can be combined with the appropriate constant domains to form a full length heavy or light chain using methods known to those of skill in the art. DNA constructs encoding the heavy and light chains can be coexpressed in host cells for production of completely assembled full length antibodies. The modifications can be in either the heavy or light chain variable domains or both.

Additional Modifications

In another aspect of the invention, antibodies or antigen binding fragments with additional amino acid sequence modification(s) are contemplated. For example, it may be desirable to improve the binding affinity and/or other biological properties of the antibody besides improved yield. These modifications may be made at amino acid positions other than at amino acid positions proximal to a cys residue that participates in an intrachain variable domain disulfide bond or at amino acid positions in one or more of the framework regions that have been identified and modified in accord with the process of the invention.

Another type of amino acid sequence modification is amino acid substitution at residues other than the selected FR residues or other than at amino acid positions proximal to cys residues that participate in an intrachain variable domain disulfide bond. The sites of greatest interest for substitutional mutagenesis include the hypervariable regions, but FR alterations are also contemplated, especially those that improve binding affinity. When the methods of the invention are used to produce a humanized antibody or antigen binding fragment, it may be desirable to make further modification to the antibody sequence after at least one FR has been selected in accord with the methods of the invention, for example, to enhance affinity. When the methods of the invention are applied to humanized antibodies, the human consensus framework sequences may have been modified to improve antigen binding affinity in the process of humanization. Some of those modifications may occur at amino acid positions other than the selected FR residues such as at FR positions that have amino acids that do not differ between the selected subgroup consensus sequence and the parent variable domain FR sequence.

Conservative substitutions are shown in Table 1 under the heading of "preferred substitutions". If such substitutions result in a change in biological activity, then more substantial changes, denominated "exemplary substitutions" as shown in Table 1, or as further described below in reference to amino acid classes, may be introduced and the products screened, for example for improved binding affinity.

TABLE 1

| Original Residue | Exemplary Substitutions | Exemplary Substitutions |
|---|---|---|
| Ala (A) | val; leu; ile | val |
| Arg (R) | lye; gln; asn | lys |
| Asn (N) | gln; his; asp; lys; arg | gln |
| Asp (D) | glu; asn | glu |
| Cys (C) | ser; ala | ser |
| Gln (Q) | asn; glu | asn |
| Gly (G) | ala | ala |
| His (H) | asn; gln; lys; arg | arg |
| Ile | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr; cys | cys |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge of hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody or not involved in forming the intrachain variable region disulfide bond also may be substituted, generally with serine, to improve the oxidative stability of the molecule and prevent aberrant crosslinking.

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated, especially antigen binding affinity. A convenient way for generating such substitutional variants involves affinity maturation using phage display. Briefly, several hypervariable region sites (e.g. 6-7 sites) are mutated to generate all possible amino substitutions at each site. The antibodies thus generated are displayed from filamentous phage particles as fusions to a gene product of M13 (e.g. gene III) packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

It also may be desirable to introduce one or more amino acid modifications in an Fc region of the antibody of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

These modifications to the amino acid sequence of the antibody or antigen binding fragment are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics of improved yield when produced in cell culture and antigen binding specificity. The amino acid alterations may be introduced in the subject antibody amino acid sequence at the time that sequence is made.

Antibody or Antigen Binding Fragment Conjugates

Another aspect of the invention contemplates that antibodies or antigen binding fragments with a modified framework region are conjugated to another molecule. The other molecules can include a detectable label, a purification tag, another polypeptide (for e.g., a cytotoxic polypeptide) or a cytotoxic compound.

Amino acid sequence conjugates include amino- and/or carboxyl-terminal fusions ranging in length from one residue to polypeptides containing a hundred or more residues. Examples of terminal fusions or conjugates include an antibody with an N-terminal methionyl residue of the antibody fused to a cytotoxic polypeptide or compound. Other fusions of the antibody molecule include the fusion of the N- or C-terminus of the antibody to an enzyme (e.g. for ADEPT) or a polypeptide which increases the serum half-life of the antibody.

Vector Construction

Polynucleotide sequences encoding the immunoglobulin light and heavy chains of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the light and heavy chains are inserted into a recombinant vector capable of replicating and expressing heterologous polynucleotides in host cells. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237, and the "Examples" section herein below.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as *E. coli* LE392.

An expression vector for prokaryotic host cells comprises a promoter-cistron pair or multiple pairs. The promoter is an untranslated regulatory sequence located upstream (5') to a cistron that modulates the cistron's expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature. Although both constitutive and inducible promoters can be used in the present invention, inducible promoters under tight regulation are preferred in the prokaryotic expression vectors disclosed herein. A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. However, heterologous promoters are preferred, as they generally permit greater transcription and higher yields of expressed target gene as compared to the native target polypeptide promoter.

Promoters suitable for use with prokaryotic hosts include the PhoA promoter, the β-galactosidase and lactose promoter systems, a tryptophan (trp) promoter system, T7 promoter, and hybrid promoters such as the tac, tacII or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) *Cell* 20: 269) using linkers or adaptors to supply any required restriction sites. More preferred promoter for use in this invention is the PhoA promoter.

For recombinant production of the antibody, the nucleic acid encoding it may be isolated and inserted into a replicable vector for further cloning (amplification of the DNA) or for expression in cells, for example eukaryotic cells. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following:

a signal sequence, an origin of replication, one or more marker genes, an enhancer element, a promoter, and a transcription termination sequence, e.g., as described in U.S. Pat. No. 5,534,615 issued Jul. 9, 1996 and specifically incorporated herein by reference.

In one aspect of the present invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, or heat-stable enterotoxin II (STIII) leaders, LamB, PhoE, PelB, OmpA and MBP. In a preferred embodiment of the invention, the signal sequences used in both cistrons of the expression system are STII signal sequences or variants thereof.

In another aspect, the production of the antibodies or antigen binding fragments according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB strains) provide cytoplasm conditions that are favorable for disulfide bond formation, thereby permitting proper folding and assembly of expressed protein subunits. Probe and Pluckthun, *Gene,* 159:203 (1995).

The use of an expression system in which the quantitative ratio of expressed light and heavy chains can be modulated in order to maximize the yield of secreted and completely assembled antibodies or antigen binding fragments is preferred. Such modulation is accomplished by simultaneously modulating translational strengths for light and heavy chains. One technique for modulating translational strength is disclosed in Simmons et al. U.S. Pat. No. 5,840,523.

Preferably, a set of vectors is generated with a range of TIR strengths for each cistron therein. This limited set provides a comparison of expression levels of each chain as well as the yield of assembled products under various TIR strength combinations. TIR strengths can be determined by quantifying the expression level of a reporter gene as described in detail in Simmons et al. U.S. Pat. No. 5,840,523. For the purpose of this invention, the translational strength combination for a particular pair of TIRs within a vector is represented by (N-light, M-heavy), wherein N is the relative TIR strength of light chain and M is the relative TIR strength of heavy chain. For example, (3-light, 7-heavy) means the vector provides a relative TIR strength of about 3 for light chain expression and a relative TIR strength of about 7 for heavy chain expression. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), *Bacilli* (e.g., *B. subtilis*), *Enterobacteria*, *Pseudomonas* species (e.g., *P. aeruginosa*), *Salmonella typhimuruim, Serratia marcescens, Klebsiella, Proteus, Shigella, Rhizobia, Vitreoscilla*, or *Paracoccus*. Preferably, gram-negative cells are used. More preferably, *E. coli* cells are used as hosts for the invention. Preferred *E. coli* strain are strain W 3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W 3110 kan$^R$ ΔfhuA (Δ tonA) ptr3 lacIq lacL8 ompTΔ(nmpc-fepE) deg P (U.S. Pat. No. 5,639, 635). Of course other strains and derivatives thereof, such as *E. coli* 294 (ATCC 31,446), *E. coli* B, *E. coli* 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., *Proteins,* 8:309-314 (1990). It is, of course, necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, pUC or pKN41O are used to supply the replicon. Preferably the host cell should secrete minimal amounts of proteolytic enzymes, and additional protease inhibitors may desirably be incorporated in the cell culture.

Other suitable host cells are described below. In addition to prokaryotes, eukaryotic microbes such as filamentous fungi or yeast are suitable cloning or expression hosts for vectors encoding a modified polypeptide. *Saccharomyces cerevisiae* is a commonly used lower eukaryotic host microorganism. Others include *Schizosaccharomyces pombe* (Beach and Nurse, *Nature,* 290: 140 [1981]; EP 139,383 published 2 May 1985); *Kluyveromyces* hosts (U.S. Pat. No. 4,943,529; Fleer et al., *Bio/Technology,* 9:968-975 (1991)) such as, e.g., *K. lactis* (MW98-8C, CBS683, CBS4574; Louvencourt et al., *J. Bacteriol.,* 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology,* 8:135 (1990)), *K. thermotolerans,* and *K. marxianus; yarrowia* (EP 402, 226); *Pichia pastoris* (EP 183,070; Sreekrishna et al., *J. Basic Microbiol.,* 28:265-278 [1988]); *Candida; Trichoderma reesia* (EP 244,234); *Neurospora crassa* (Case et al., *Proc. Natl. Acad. Sci. USA,* 76:5259-5263 [1979]); *Schwanniomyces* such as *Schwanniomyces occidentalis* (EP 394,538 published 31 Oct. 1990); and filamentous fungi such as, e.g., *Neurospora, Penicillium, Tolypocladium* (WO 91/00357 published 10 Jan. 1991), and *Aspergillus* hosts such as *A. nidulans* (Ballance et al., *Biochem. Biophys. Res. Commun.,* 112: 284-289 [1983]; Tilbum et al., *Gene,* 26:205-221 [1983]; Yelton et al., *Proc. Natl. Acad. Sci. USA,* 81: 1470-1474 [1984]) and *A. niger* (Kelly and Hynes, *EMBO J.,* 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces, Torulopsis,* and *Rhodotorula*. A list of specific species that are exemplary of this class of yeasts may be found in C. Anthony, *The Biochemistry of Methylotrophs,* 269 (1982).

Suitable host cells for the expression of modified antibodies are derived from multicellular organisms. Examples of invertebrate cells include insect cells such as *Drosophila* S2 and *Spodoptera* Sf9, as well as plants and plant cells.

Examples of useful mammalian host cell lines include Chinese hamster ovary (CHO) and COS cells. More specific examples include monkey kidney CV1 line transformed by SV40 (COS-7, ATCC CRL 1651); Chinese hamster ovary cells/-DHFR(CHO, Urlaub and Chasin, *Proc. Natl. Acad. Sci. USA,* 77:4216 (1980)); mouse sertoli cells (TM4, Mather, Biol. Reprod., 23:243-251 (1980)); and mouse mammary tumor (MMT 060562, ATCC CCL51).

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria-Bertani (LB) broth plus necessary nutrient supplements. In preferred embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally, the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, the transcription of the light and heavy chain are each under the control of a Pho promoter. Accordingly, the transformed host cells are cultured in a phosphate-limiting medium for induction. Preferably, the phosphate-limiting medium is the C.R.A.P medium, as described in detail below in Examples 1 and 2. A variety of other inducers may be used, according to the vector construct employed, as is known in the art.

Eukaryotic host cells are cultured under conditions suitable for expression of the antibody products of the invention. The host cells used to produce the antibody or antigen binding fragments of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in one or more of Ham et al., 1979, *Meth. Enz.* 58:44, Barnes et al., 1980, *Anal. Biochem.* 102: 255, U.S. Pat. No. 4,767,704, U.S. Pat. No. 4,657,866, U.S. Pat. No. 4,927,762, U.S. Pat. No. 4,560,655, or U.S. Pat. No. 5,122,469, WO 90/103430, WO 87/00195, and U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES™), nucleotides (such as adenosine and thymidine), antibiotics (such as GENTAMYCIN™), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

The expressed light and heavy chain polypeptides of the present invention are generally but not necessarily secreted into and recovered from the periplasm of the prokaryotic host cells or from the medium of eukaryotic cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and immunoblot assay.

In one aspect of the invention, the antibody production is conducted in large quantity by a fermentation process. Various large-scale fed-batch fermentation procedures are available for production of recombinant proteins. Large-scale fermentations have at least 10 liters of capacity, preferably about 100 to 100,000 liters of capacity. These fermentors use agitator impellers to distribute oxygen and nutrients, especially glucose (the preferred carbon/energy source). Small-scale fermentation refers generally to fermentation in a fermentor that is no more than approximately 9 liters in volumetric capacity, and can range from about 1 liter to about 9 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time maybe used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and/or OsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J. Biol. Chem.* 274:19601-19605; Georgiou et al., U.S. Pat. No. 6,083,715; Georgiou et al., U.S. Pat. No. 6,027,888; Botbmano and Pluckthun (2000) *J. Biol. Chem.* 275:17100-17105;

Ramm and Pluckthun (2000) J. Biol. Chem. 275:17106-17113; Arie et al. (2001) Mol. Microbiol. 39:199-210.

To minimize proteolysis of expressed heterologous proteins (especially those that are proteolytically sensitive), certain prokaryotic host strains deficient for proteolytic enzymes can be used for the present invention. For example, host cell strains maybe modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly at al. (1998), supra; Georgiou et al., U.S. Pat. No. 5,264,365; Georgiou et al., U.S. Pat. No. 5,508,192; Hara et al., *Microbiol Drug Resistance*, 2:63-72 (1996).

In one embodiment, *E. coli* strains deficient for proteolytic enzymes are used as host cells in the expression system of the invention. Some of these strains are further described in the Examples section below.

The methods of the invention also include methods expressing polynucleotides encoding the variable domain produced or modified in accord with the methods of the invention. In one embodiment, the method comprises expressing a polynulceotide encoding a variable domain with at least one modified FR in a host cell. In another embodiment, the method comprises expressing a modified variable domain, wherein the modified varaible domain has a substitution of at least one amino acid proximal to a cys residue that participates in an intrachain variable domain disulfide bond. The polynucleotides in the methods can further comprise an expression vector encoding both the modified variable domain and constant domains to express a full length heavy and/or light chain. Host cells can coexpress a polynucleotide encoding a light chain and polynucleotide encoding a heavy chain, one or both formed in accord with the methods of the invention, so that full length completely assembled antibodies are produced by the host cell.

Antibody Purification

In one embodiment, the antibody or antigen binding fragment produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing. SDS-PAGE, ammonium sulfate precipitation, and gel filtration using, for example, Sephadex G-75.

In one aspect, Protein A immobilized on a solid phase is used for immunoaffinity purification of the full-length antibody products of the invention. Protein A is a 41 kD cell wall protein from *Staphylococcus aureas* which binds with a high affinity to the Fc region of antibodies. Lindmark et al., *J. Immunol. Meth.* 62:1-13 (1983). The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the full-length antibody to Protein A. The solid phase is then washed to remove contaminants non-specifically bound to the solid phase. Finally the full-length antibody is recovered from the solid phase by elution.

Activity Assays

Antibody and/or antigen binding fragments modified according to methods of the present invention can be characterized for its physical/chemical properties and biological functions by various assays known in the art. Methods for protein quantification are well known in the art. For example, samples of the expressed proteins can be compared for their quantitative intensities on a Coomassie-stained SDS-PAGE. Alternatively, the specific band(s) of interest (e.g., the full-length band) can be detected by, for example, immunoblot gel analysis and quantitative intensities detected by scanning densitometer.

Isolated antibody or antigen binding fragments can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the antibody or antigen binding fragment produced herein is analyzed for its biological activity. Preferably, the antibody of the present invention is tested for its antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An exemplary antigen binding assay is provided below in the Examples section. In some embodiments, the antibody or antigen binding fragment thereof modified according to the methods of the invention has an affinity of the antibody not significantly different from or even better than the parent antibody from which it is derived. If improvement in antigen binding affinity of antibodies or antigen binding fragments with modified framework regions is necessary, it can be achieved by altering residues as needed (discussed supra).

In one embodiment, the present invention contemplates a full-length antibody that is aglycosylated. The unique features of the antibody (i.e., having an intact Fc region, yet lacking effector functions) make it a desired candidate for many applications in which the half life of the antibody in vivo is important yet the effector functions (i.e., complement and ADCC) are unnecessary or deleterious. In certain embodiments, the Fc activities of the produced full-length antibody are measured to ensure that only the desirable properties are maintained.

Pharmaceutical Formulations

Therapeutic formulations of the antibody or antigen binding fragment modified according to the methods of the invention are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervasion techniques or by lutes-facial polymerization, for example, hydroxymethylcellulose or gelatin-microcapsule and poly-(methylmethaeylate) microcapsule, respectively, in colloidal drug delivery systems (for example, liposomes, albumin microspheres, microemulsions, nano-particles and nanocapsules) or in macroemusions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the full-length antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

The methods of the invention are useful to produce humanized antibodies and to improve the yield of antibodies or antigen binding fragments when produced in cell culture. In particular, many antibodies useful therapeutically are produced on a large scale. The methods of the inventions are useful to improve the yield of antibodies produced in both small and large-scale cell culture. The methods can be applied to antibodies or antigen binding fragments produced in prokaryotic or eukaryotic cells. The antibody products produced by the methods of the inventions have many uses some of which are described below.

An antibody or antigen binding fragment modified in accord with the present invention may be used, for example, to purify, detect, and target a specific polypeptide it recognizes, including both in vitro and in vivo diagnostic and therapeutic methods.

In one aspect, an antibody or antigen binding fragment of the invention can be used in immunoassays for qualitatively and quantitatively measuring specific antigens in biological samples. Conventional methods for detecting antigen-antibody binding includes, for example, an enzyme linked immunosorbent assay (ELISA), an radioimmunoassay (RIA) or tissue immuonhistochemistry. Many methods may use a label bound to the antibody for detection purposes. The label used with the antibody is any detectable functionality that does not interfere with its binding to antibody. Numerous labels are known, including the radioisotopes $^{32}P$, $^{32}S$, $^{14}C$, $^{125}I$, $^{3}H$ and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, .beta.-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, lactoperoxidase, biotin/avidin, spin labels, bacteriophage labels, stable free radicals, imaging radionuclides (such as Technecium) and the like.

Conventional methods are available to bind these labels covalently to the antibody polypeptides. For instance, coupling agents such as dialdehydes, carbodilmides, dimaleimides, bis-imidates, bis-diazotized beozidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter at al. *Nature* 144: 945 (1962); David et al. *Biochemistry* 13:1014-1021 (1974); Pain et al. *J. Immunol. Methods* 40:219-230 (1981); and Nygren *Histochem. and Cytochem* 30:407-412 (1982). Preferred labels herein are enzymes such as horseradish peroxidase and alkaline phosphatase. The conjugation of such label, including the enzymes, to the antibody polypeptide is a standard manipulative procedure for one of ordinary skill in immunoassay techniques. See, for example, O'Sullivan at al., "Methods for the Preparation of Enzyme-antibody Conjugates for Use in Enzyme Iummunoassay," in Methods in Enzymology, ed. J. J. Langone and H. Van Vunakis, Vol. 73 (Academic Press, New York, N.Y., 1981), pp. 147-166. Such bonding methods are suitable for use with the antibody polypeptides of this invention.

Alternative to labeling the antibody, antigen can be assayed in biological fluids by a competition immunoassay utilizing a competing antigen standard labeled with a detectable substance and an unlabeled antibody. In this assay, the biological sample, the labeled antigen standards and the antibody are combined and the amount of labeled antigen standard bound to the unlabeled antibody is determined. The amount of tested antigen in the biological sample is inversely proportional to the amount of labeled antigen standard bound to the antibody.

In one aspect, a full-length antibody of the invention is particularly useful to detect and profile expressions of specific surface antigens in vitro or in vivo. The surface antigen can be specific to a particular cell or tissue type, therefore serving as a marker of the cell or tissue type. Preferably, the surface antigen marker is differentially expressed at various differentiation stages of particular cell or tissue types. The full-length antibody directed against such surface antigen can thus be used for the screening of cell or tissue populations expressing the marker. For example, the antibody of the invention can be used for the screening and isolation of stem cells such as embryonic stem cells, hematopoietic stem cells and mesenchymal stem cells. The antibody of the invention can also be used so detect tumor cells expressing tumor-associated surface antigens such HER2, HER3 or HER4 receptors.

In one aspect, an antibody of the invention can be used in a method for inhibiting an antigen in a subject suffering from a disorder in which the antigen activity is detrimental, comprising administering to the subject an antibody of the invention such that the antigen activity in the subject is inhibited. Preferably the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Blocking antibodies of the invention that are therapeutically useful include, for example but not limited to, anti-VEGF, anti-IgE, anti-CD 11 and anti-tissue factor antibodies. The antibodies of the invention can be used to diagnose, treat, inhibit or prevent diseases, disorders or conditions associated with abnormal expression and or activity of one or more antigen molecules, including but not limited to malignant and benign tumors; non-leukemias and lymphoid malignancies; neuronal, gust, astrocytal, hypothalamic and other glandular, macrophagal, epitheial, stromal and blastocoelic disorders; and inflammatory, angiogenic and immunologic disorders.

In certain embodiments, an immunoconjugate comprising the antibody conjugated with a cytotoxic agent is administered to the patient. Preferably, the immunoconjugate and/or antigen to which it is bound is/are internalized by the cell, resulting in increased therapeutic efficacy of the immunoconjugate in killing the target cell to which it binds. In a preferred embodiment, the cytotoxic agent targets or interferes with nucleic acid in the target cell. Examples of such cytotoxic agents include any of the chemotherapeutic agents noted herein (such as a maytansinoid or a calicheainicin), a radioactive isotope, or a ribonuclease or a DNA endonuclease.

Antibodies of the present invention can be used either alone or in combination with other compositions in a therapy. For instance, the antibody may be co-administered with another antibody, chemotherapeutic agent(s) (including cocktails of chemotherapeutic agents), other cytotoxic agent(s), anti-angiogenic agent(s), cytokines, and/or growth inhibitory agent(s). Where the full-length antibody inhibits tumor growth, it maybe particularly desirable to combine the full-length antibody with one or more other therapeutic agent(s) which also inhibits tumor growth. For instance, anti-VEGF antibodies blocking VEGF activities may be combined with anti-ErbB antibodies (e.g. HERCEPTIN® anti-HER2 antibody) in a treatment of metastatic breast cancer. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the full-length antibody can occur prior to, and/or following, administration of the adjunct therapy or therapies.

The antibody or antigen binding fragment (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the full-length antibody is suitably administered by pulse infusion, particularly with declining doses of the antibody. Preferably the dosing is given by injections, most preferably intravenous or subcutaneous injections.

The antibody or antigen binding fragment composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of the antibody (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-1Omg/ls-g) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The preferred dosage of the antibody will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses maybe administered. An exemplary dosing regimen comprises administering an initial loading dose of about 4 mg/kg, followed by a weekly maintenance dose of about 2 mg/kg of the antibody. However, other dosage regimens maybe useful. The progress of this therapy is easily monitored by conventional techniques and assays.

The following examples are intended merely to illustrate the practice of the present invention and are not provided by way of limitation.

EXAMPLES

Example 1

Heavy Chain Aggregation During Expression and Folding of Antibodies

Antibodies produced in cell culture can accumulate intracellularly, in the periplasm or in the extracellular medium. Antibody production typically involves expression of the light and heavy chains in the cytoplasm, secretion into the periplasmic space, folding of the light and heavy chains, and assembly of the folded light and heavy chains to form an antibody molecule. Multiple covalent and non-covalent interactions occur between and within the heavy and light chains during these folding and assembly processes. Antibody yield can be greatly affected by the efficiency and fidelity of these processes. Following synthesis of the heavy and light chains, protein aggregation or proteolysis can occur thereby reducing the yield of the antibody. Solubility experiments were carried out in order to assess the efficiency of steps in the antibody production pathway in bacterial cells for the purpose of improving antibody yield.

Materials and Methods

A. Expression and Solubilization of Anti-TF and Anti-VEGF Antibodies.

In order to evaluate several parameters of antibody production, including expression, folding, assembly, and yield of antibody molecules, expression vectors encoding anti-Tissue Factor (anti-TF) monoclonal antibody and anti-VEGF monoclonal antibody, VNERK, were transformed into bacterial cells. Since conditions under which a protein is soluble may provide insight into the basis of folding problems, cell cultures of transformants were subject to various procedures to examine the solubility of heavy and light chains.

1. Transformation and Expression

Expression constructs were transformed into strain 33D3 (W3110 kan$^R$ ΔfhuA (ΔtonA) ptr3 lacIq lacL8 ompTΔ (nmpc-fepE) deg P). Transformants were inoculated into 5 ml Luria-Bertani medium plus carbenicillin (50 ug/ml) and grown overnight at 30° C. Each culture was then diluted (1:100) into C.R.A.P. phosphate-limiting media (3.57 g (NH4)2SO4, 0.71 g NaCitrate-2H2O, 1.07 g KCl, 5.36 g Yeast Extract (certified), 5.36 g HycaseSF-Sheffield, pH adjusted with KOH to 7.3, qs to 872 ml with SQ H2O and autoclaved; cooled to 55° C. and supplemented with 110 ml 1M MOPS pH 7.3, 11 ml 50% glucose, 7 ml 1 M MgSO4) plus carbenicillin (50 ug/ml) and grown for about 24 hours at 30° C. on a culture wheel.

2. Solubilization

For each culture, two 1 O.D.$_{600}$ pellets were centrifuged in a microfuge for 5 minutes. The cell pellets were then placed at −20° C. until preparation. Upon removal from −20° C., one pellet from each culture was used for the solubilization study and the other pellet was used for the preparation of whole cell lysate. See Example 2, Section B.

The solubilization experiment consisted of a multi-step process involving lysis of the cells and preparation of each cell fraction. Cell lysis was the first step in the process. The 1 O.D. pellets were resuspended in 225 ul of 50 mM NaCl, 5 mM EDTA, 50 mM Tris-HCl (pH 8)+1 mg/ml lysozyme+25 ul of 100 mM IAA (Iodoacetic Acid, Sigma I-2512; to prevent disulfide shuffling). The cells were then lysed by sonicating for 2×2 minutes at 50% pulse (Sonics & Materials, Inc., Danbury, Conn.). The samples were kept in an ice water bath during sonication to dissipate the heat generated during the process. Following sonication, the samples were centrifuged in a microfuge for 5 minutes. At this point, the supernatant and pellet constitute the soluble and insoluble fractions, respectively.

3. Preparation of the Soluble Fraction

For gel analysis, about 500 ul of acetone was added to 125 ul of each soluble fraction (about half of the volume generated) to precipitate the protein. The samples were left at room temperature for about 15 minutes followed by centrifugation for 5 minutes in a microfuge. The protein precipitates were then each resuspended in 25 μl of dH$_2$O+25 μl of 2X Sample Buffer. The samples were then heated for about 3-5 minutes at about 90° C., vortexed well and allowed to cool to room temperature. A final 5 minute centrifugation was then done and the supernatants were transferred to clean tubes.

4. Preparation of the Insoluble Fraction

The cell pellets, or insoluble fractions, generated following sonication of the cells, were each resuspended in 100 μl of TE (10 mM Tris pH 7.6, 1 mM EDTA)+20 μl 10% SDS and vortexed well. The samples were then heated at 90° C. for about 3 minutes and vortexed hard again. After cooling to room temperature, about 500 μl of acetone was added to the samples to precipitate the protein and they were left at room temperature for about 15 minutes followed by centrifugation in a microfuge for 5 minutes. The pellets were then resuspended in 50 μl of dH$_2$O+50 μl of 2X sample buffer. The samples were then heated for about 3-5 minutes at about 90° C., vortexed well and allowed to cool to room temperature. A final 5 minute centrifugation was then done and the supernatants, designated SDS Soluble, were transferred to clean tubes.

The pellets from the final centrifugation of the SDS Soluble Fraction were further processed. These pellets were each resuspended in 40 μl dH$_2$O+10 μl 1M DTT+50 μl 2X sample buffer. The samples were then heated for about 3-5 minutes at about 90° C., vortexed well, allowed to cool to room temperature and centrifuged for 5 minutes in a microfuge. The supernatants, designated SDS/DTT soluble, were transferred to clean tubes.

B. Immunoblot Analysis

Following preparation, 5 μl of each sample (soluble, SDS soluble and SDS/DTT soluble) was mixed with 1 μl of 1M DTT and loaded onto a 10 well, 1.0 mm NOVEX manufactured 12% Tris-Glycine SDS-PAGE and electrophoresed at about 120 volts for 1.5-2 hours. The resulting gels were then used for immunoblots.

The SDS-PAGE gels were electroblotted onto a nitrocellulose membrane (NOVEX). The membrane was then blocked using a solution of 1X NET (150 mM NaCl, 5 mM EDTA, 50 mM Tris pH 7.4, 0.05% Triton® X-100)+0.5% gelatin for approximately 30 min.-1 hour rocking at room temperature. Following the blocking step, the membrane was placed in a solution of 1 X NET+0.5% gelatin+anti-Fab antibody (peroxidase-conjugated goat IgG fraction to human IgG Fab; CAPPEL #55223). The anti-Fab antibody dilution ranged from 1:50,000 to 1:1,000,000 depending on the lot of antibody. The membrane was left in the antibody solution overnight at room temperature with rocking. The next morning, the membrane was washed a minimum of 3×10 minutes in 1X NET+0.5% gelatin and then 1×15 minutes in TBS (20 mM Tris pH 7.5, 500 mM NaCl). The protein bands bound by the anti-Fab antibody were visualized by using Amersham Pharmacia Biotech ECL detection and exposing the membrane to x-ray film.

C. Results of Immunoblot Analysis

FIG. 1A shows the results of immunoblot analysis of different fractions from cells expressing the anti-TF antibody. FIG. 1B shows the results of immunoblot analysis of different fractions from cells expressing the anti-VEGF (VNERK) antibody. The location of heavy chain and light chains are designated with arrows. In both FIGS. 1A and 1B, lane 1 is whole cell lysate, lane 2 is the sonication-soluble fraction, lane 3 is the SDS-soluble fraction, and lane 4 is the SDS/DTT soluble fraction.

The whole cell lysates from cells expressing anti-TF and the anti-VEGF (VNERK) antibody, shown in lane 1 of both FIGS. 1A and 1B, serve as a reference for the approximate amount of total heavy and light chain to follow through the experiment. As seen in lane 2 in both FIGS. 1A and 1B, the results show that significantly more light chain was present in the sonication-soluble fraction than heavy chain. This result suggests that a large percentage of the expressed light chain is correctly folded. On the other hand, heavy chain is observed primarily in the SDS soluble and SDS/DTT soluble fractions. The protein in the SDS soluble fraction implies aggregation through hydrophobic interactions, while protein found in the SDS/DTT soluble fraction implies that mispaired disulfide bonds either contribute to, or are largely responsible for, the aggregation process. A significant amount of heavy chain was observed in the fraction that was SDS/DTT soluble. This result indicates that following translation, much of the heavy chain forms protein aggregates that are primarily soluble in denaturing and reducing conditions. Following heavy chain synthesis, a significant amount of the heavy chain misfolds and aggregates, leaving free intracellular light chain and thereby reducing antibody yield.

Example 2

Preparation of Anti-VEGF Antibodies with Improved Yield

The yield of antibodies or antigen binding fragments from cells can be influenced by the in vivo folding and/or assembly of the antibody. In order to increase antibody or antigen binding fragment yield, the sequence of the antibody or fragment was modified and the effect on folding and yield on the antibody was examined. As described in Example 1, aggregation of heavy chains may contribute to a decrease in antibody folding, assembly and yield. Targeted modification of the heavy chain variable region FR1 of anti-VEGF antibodies was performed. Antibody variants with different human variable domain subgroup consensus sequences in the FR1 were prepared and the yield of completely assembled antibody products was examined.

Materials and Methods

A. Preparation of Expression Vectors Encoding Modified Anti-VEGF Antibodies

To evaluate the effect of different heavy chain FR1 human subgroup consensus sequences on the expression, folding, assembly, and yield of anti-VEGF antibodies, vectors encoding the light and heavy chains for two different anti-VEGF antibodies, VNERK and Y0317, were constructed. Both of these antibodies were originally constructed with framework regions in the heavy chain from human variable domain subgroup III consensus sequence. The FR1 subgroup III residues of the antibodies were substituted with either the FR1 subgroup I or subgroup II residues at those positions where the sequence differed.

The human variable domain subgroup sequences can be found in the Kabat database available at a number of locations on the internet, and have been described in Kabat et al., *Sequences of proteins of immunological interest*, Ed.5. Public Health Service, National Institutes of Health, Bethesda, Md., 1991. A consensus variable domain sequence for each subgroup was constructed by selecting the most frequently occurring amino acid for each position in the variable domain. The FR1 sequences corresponding to amino acids 1-25 for each subgroup are:

| Subgroup I | QVQLVQSGAEVKKPGASVKVSCKAS | (SEQ ID NO: 1) |
| Subgroup II | QVQLQESGPGLVKPSQTLSLTCTVS | (SEQ ID NO: 2) |
| Subgroup III | EVQLVESGGGLVQPGGSLRLSCAAS | (SEQ ID NO: 3) |

The anti-VEGF antibody VNERK is a higher affinity variant of the humanized anti-VEGF antibody described in Presta et al, *Cancer Res.*, 57, 4593 (1997).

Anti-VEGF antibody Y0317 is described in pending U.S. Patent Application Publication No. US2002/0032315, application. Ser. No. 09/056,160 filed Apr. 6, 1998 and Chen et al, (1999) *J. Mol. Biol,* 293:865-881. Briefly, Y0317 is a humanized antibody isolated using phage display methods starting with a template antibody with HVRs from murine anti-VEGF monoclonal antibody A.4.6.1; human consensus kappa subgroup I light chain framework and constant sequences; and human consensus subgroup III heavy chain framework and constant sequences. The antibody sequence also has substitutions at H101Y and S105T.

Figure 2:
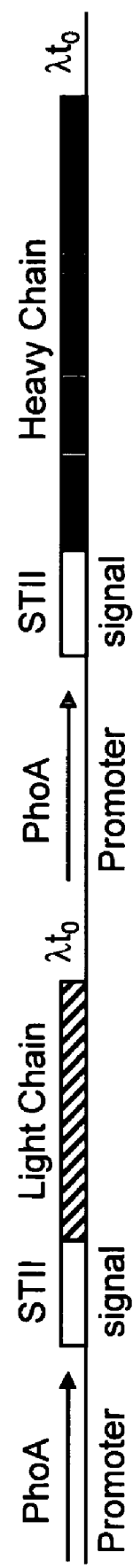
FIG. 2 schematically illustrates the construction of a separate cistron vector for expression of a full-length antibody.

The construction of a separate cistron vector is illustrated in FIG. 2 and has been described in Simmons et al., *J. Immunol. Methods* 263:133-147 (2002) and in WO 02/061090 published Aug. 8, 2002. Vectors with separate cistrons were designed to provide independent transcription and translation of the light and heavy chain genes of an antibody. For all vector constructions, expression cassettes encoding anti-VEGF antibody VNERK and Y0317 heavy and light chain sequences were cloned into the *E. coli* plasmid pBR322 at the EcoRI site. Sutcliffe, *Cold Spring Harbor Symp. Quant. Biol.* 43:77-90 (1978).

The expression cassette in each designed vector contains at least the following basic components: (1) phoA promoter for the control of transcription; (2) $\lambda t_0$ terminator to end transcription; (3) the Shine-Dalgarno sequence from the *E. coli* trp or the heat stable enterotoxin II (STII) gene, or a combination of both, to facilitate translation. The basic components of bacterial expression cassettes are known in the art and have been described in, for example, Kikuchi et al., *Nucleic Acids Res.* 9(21):5671-5678 (1981) (for phoA promoter); Scholtissek and Grosse, *Nucleic Acids Res.* 15:3185 (1987) (for $\lambda t_0$ terminator); Yanofsky et al., *Nucleic Acids Res.* 9:6647-6668 (1981) (for trp); Picken et al., *Infect. Immun.* 42:269-275 (1983) for STII); and Chang et al., *Gene* 55:189-196 (1987) (for combination use of trp and STII Shine-Dalgarno sequence). Additionally, the STII signal sequence or silent codon variants thereof precedes the coding sequence for both light and heavy chains in all constructs described and directs the secretion of the protein into the periplasm. Picken et al., *Infect. Immun.* 42:269-275 (1983); Simmons and Yansura, *Nature Biotechnology* 14:629-634 (1996). In this design, the cistron unit for each chain is under the control of its own PhoA promoter and is followed by a $\lambda t_0$ terminator. Construction of suitable vectors containing one or more of the above listed components employs standard ligation techniques and or other molecular cloning techniques known in the art. Isolated plasmids or DNA fragments are cleaved, tailored, and re-ligated in the form desired to generate the plasmids required.

Separate cistron vectors encoding the heavy and light chains from anti-VEGF antibodies VNERK and Y0317 were constructed as described in U.S. Pat. No. 5,747,662.

The vector designated pxVG11VNERK is a separate cistron vector encoding the VNERK heavy and light chain sequences. The nucleotide (SEQ ID NO: 4) and amino acid sequences (SEQ ID NO: 5) for the heavy and light chain of VNERK are shown in FIG. 15. The vector designated pxVG2AP11 is a separate cistron vector encoding the heavy and light chain sequences from Y0317. The nucleotide (SEQ ID NO: 6) and amino acid sequence (SEQ ID NO: 7) for the heavy and light chains of Y0317 are shown in FIG. 16.

Additional expression vectors were constructed to determine the effects of replacement of heavy chain consensus FR1 subgroup III amino acid residues with the heavy chain consensus subgroup I or subgroup II amino acid residues.

In order to change the heavy chain FR1 subgroup III sequence to that of the subgroup I sequence, 12 amino acid substitutions in FR1 sequence were required in the anti-VEGF VNERK heavy chain variable domain. Replacement of the heavy chain FR1 subgroup III consensus sequence in pxVGII VNERK with heavy chain FR1 subgroup I consensus sequence QVQLVQSGAEVKKPGASVKVSCKAS (SEQ ID NO: 1) was performed in a single step by replacing nucleotide sequence encoding the heavy chain FR1 subgroup III sequence with a double stranded oligonucleotide encoding the FR1 subgroup I sequence. The resulting plasmid, pVKFR1-2, encodes heavy and light chain variable domain amino acid sequences (SEQ ID NO: 9) shown in FIG. 17. The nucleotide sequence for pVKFR1-2 (SEQ ID NO: 8) is also shown in FIG. 17.

In order to change the heavy chain FR1 subgroup III sequence to that of the subgroup II sequence, 11 amino acid substitutions in FR1 sequence are required. Replacement of the heavy chain FR1 subgroup III in pxVG11VNERK with heavy chain FR1 subgroup II consensus sequence QVQLQESGPGLVKPSQTLSLTCTVS (SEQ ID NO: 2) was performed in a similar manner. The resulting plasmid pVKSGII, encodes heavy and light chain variable domain amino acid sequences (SEQ ID NO: 11) shown in FIG. 18. The nucleotide sequence encoding the heavy and light chains (SEQ ID NO: 10) is also shown in FIG. 18.

Replacement of the heavy chain FR1 subgroup II in pxVG2API 1 (Y0317 anti-VEGF antibody) with heavy chain FR1 subgroup I sequence QVQLVQSGAEVKKPGAS-VKVSCKAS (SEQ ID NO: 1) was performed in a similar manner. The resulting plasmid, pY0FR1-2 includes the polynucleotide sequence (SEQ ID NO: 12), encoding heavy and light chain variable domain amino acid sequences (SEQ ID NO: 13) shown in FIG. 19.

B. Expression, Folding and Yield of Humanized Anti-VEGF Antibody Variants

Expression vectors as described in Section A were transformed into bacteria to determine the expression, folding, assembly and yield of the anti-VEGF antibodies having the indicated changes in the heavy chain FR1 sequence.

1. Shake Flask Inductions

Plasmids prepared as described in Section A were transformed into strain 33D3 (W3110 $kan^R$ ΔfhuA (ΔtonA) ptr3 lacIq lacL8 ompTΔ (nmpc-fepE) deg P). Transformants were inoculated into 5 ml Luria-Bertani medium plus carbenicillin (50 ug/ml) and grown overnight at 30° C. Each culture was then diluted (1:100) into C.R.A.P. phosphate-limiting media (3.57 g $(NH_4)_2SO_4$, 0.71 g NaCitrate-$2H_2O$, 1.07 g KCl, 5.36 g Yeast Extract (certified), 5.36 g HycaseSF-Sheffield, pH adjusted with KOH to 7.3, qs to 872 ml with SQ $H_2O$ and autoclaved; cooled to 55° C. and supplemented with 110 ml 1M MOPS pH 7.3, 11 ml 50% glucose, 7 ml 1 M $MgSO_4$) plus carbenicillin (50 μg/ml) and grown for about 24 hours at 30° C. on a culture wheel.

2. Preparation of Samples for SDS-PAGE

Non-reduced whole cell lysates from induced cultures were prepared as follows: (1) 1 $OD_{600}$-ml pellets were centrifuged in a microfuge tube; (2) each pellet was resuspended in 90 μl TE (10 mM Tris pH 7.6, 1 mM EDTA); (3) 10 μl of 100 mM iodoacetic acid (Sigma I-2512) was added to each sample to block any free cysteines and prevent disulfide shuffling; (4) 20 μl of 10% SDS was added to each sample. The samples were vortexed, heated to about 90° C. for about 3 minutes and then vortexed again. After the samples had cooled to room temperature, about 750-1000 μl acetone was added to precipitate the protein. The samples were vortexed and left at room temperature for about 15 minutes. Following centrifugation for 5 minutes in a microcentrifuge, the supernatant of each sample was aspirated off and each protein pellet was resuspended in 50 μl $dH_2O$+50 μl 2X NOVEX sample buffer. The samples were then heated for about 3-5 minutes at about 90° C., vortexed well and allowed to cool to room temperature. A final 5 minute centrifugation was then done and the supernatants were transferred to clean tubes.

Reduced samples were prepared by following steps similar to the steps described above for non-reduced samples, except that 10 μl of 1M DTT was added to the cell resuspension solution in Step (2) and the addition of IAA was omitted in Step (3). Reducing agent was also added to a concentration of 100 mM when the protein precipitate was resuspended in 2X NOVEX sample buffer+$dH_2O$.

3. Immunoblot Analysis

Following preparation, 5-10 μl of each sample was loaded onto a 10 well, 1.0 mm NOVEX manufactured 12% Tris-Glycine SDS-PAGE and electrophoresed at about 120 volts for 1.5-2 hours. The resulting gels were then used for immunoblots.

The SDS-PAGE gels were electroblotted onto a nitrocellulose membrane (NOVEX). The membrane was then blocked using a solution of 1X NET (150 mM NaCl, 5 mM EDTA, 50 mM Tris pH 7.4, 0.05% Triton® X-100)+0.5% gelatin for approximately 30 min.-1 hour rocking at room temperature. Following the blocking step, the membrane was placed in a solution of 1X NET+0.5% gelatin+anti-Fab antibody (peroxidase-conjugated goat IgG fraction to human IgG Fab; CAPPEL #55223). The anti-Fab antibody dilution ranged from 1:50,000 to 1:1,000,000 depending on the lot of antibody. The membrane was left in the antibody solution overnight at room temperature with rocking. The next morning, the membrane was washed a minimum of 3×10 minutes in 1X NET+0.5% gelatin and then 1×15 minutes in TBS (20 mM Tris pH 7.5, 500 mM NaCl). The protein bands bound by the anti-Fab antibody were visualized by using Amersham Pharmacia Biotech ECL detection and exposing the membrane to X-Ray film.

The relative amounts of the completely assembled product in bands detected on the immunoblot were measured using scanning denistometry. The net intensity (in pixels) of each full-length completely assembled antibody band (i.e. the top band on the immunoblots) was determined using the following tools: Kodak Digital Science Image Station 440CF, Software: Kodak Digital Science ID Image Analysis Software (v. 3.0.2), System: Microsoft Windows® 95. The net intensity of each of the full-length completely assembled antibody bands for the variant antibodies with framework changes were then divided by the net intensity of the unmodified antibody to provide a value for the yield. The unmodified or control antibody was assigned a value of 1.

4. Large-Scale Fermentation Conditions

The organisms used for large scale fermentations included 61 D6 W3110 kan$^R$ ΔfhuA (ΔtonA) ptr3 lacIq lacL8 ompT Δ(nmpc-fepE) deg P as described in WO 02/061090.

For each 10-liter fermentation, 0.5 mL of frozen stock culture (containing 10-15% DMSO) was thawed and used to inoculate a 2 L shake flask containing 500 ml of LB medium supplemented with either 0.5 ml of tetracycline solution (5 mg/ml) or 10 mL of ampicillin solution (2 mg/mL) and 2.5 ml 1M sodium phosphate solution. This seed culture was grown for approximately 16 hours at 30° C. with shaking and was then used to inoculate the 10-liter fermentor.

The fermentor initially contained approximately 7.0 liters of medium containing 1.1 g of glucose, 100 ml of 1M magnesium sulfate, 10 ml of a trace element solution (100 ml hydrochloric acid, 27 g ferric chloride hexahydrate, 8 g zinc sulfate heptahydrate, 7 g cobalt chloride hexahydrate, 7 g sodium molybdate dihydrate, 8 g cupric sulfate pentahydrate, 2 g boric acid, 5 g manganese sulfate monohydrate, in a final volume of 1 liter), either 20 ml of a tetracycline solution (5 mg/ml in ethanol) or 250 mL of an ampicillin solution (2 mg/mL), 1 bag of HCD salts, (37.5 g ammonium sulfate, 19.5 g potassium phosphate dibasic, 9.75 g sodium phosphate monobasic dihydrate, 7.5 g sodium citrate dihydrate, 11.3 g potassium phosphate monobasic), 200 g of NZ Amine A (a protein hydrolysate), and 100 grams of Yeast Extract. Fermentations were performed at 30° C. with 20 slpm of air flow and were controlled at a pH of 7.0±0.2 (although occasional excursions beyond this range occurred in some cases). The back pressure of the fermentor was maintained at 1 bar gauge and the agitation rate was set to 650 rpm. The back pressure of the fermentor and agitation rate can also be varied to manipulate the oxygen transfer rate in the fermentor, and, consequently, control the cellular respiration rate.

Following inoculation of the fermentor with the cell-containing medium from the shake flask, the culture was grown in the fermentor to high cell densities using a computer-based algorithm to feed a concentrated glucose solution to the fermentor. Ammonium hydroxide (58% solution) and sulfuric acid (24% solution) were also fed to the fermentor as needed to control pH. Additions of L-61 (an antifoam—others can be used) were also used in some cases to control foaming. When the culture reached a cell density of approximately 40 $OD_{550}$, an additional 100 ml of 1M magnesium sulfate was added to the fermentor. Additionally, a concentrated salt feed (12.5 g ammonium sulfate, 32.5 g potassium phosphate dibasic, 16.25 g sodium phosphate monobasic dihydrate, 2.5 g sodium citrate dihydrate, 18.75 g potassium phosphate monobasic, 10 ml of 2.7% ferric chloride and 10 ml of trace elements in a final volume of 1250 ml) was added to the fermentor and started at a rate of 2.5 ml/min when the culture reached approximately 20 $OD_{550}$ and continued until approximately 1250 ml were added to the fermentation. Fermentations were typically continued for 70-80 hours. During the fermentation, once the dissolved oxygen set point for the fermentation was reached, the concentrated glucose solution was fed based on the dissolved oxygen probe signal in order to control the dissolved oxygen concentration at the set point. Consequently, in this control scheme, manipulations of fermentor operating parameters such as the agitation rate or back pressure which affect the oxygen transfer capacity in the fermentation correspondingly also manipulated the oxygen uptake rate or metabolic rate of the cells. A mass spectrometer was used to monitor the composition of the off-gas from the fermentations and enable the calculation of the oxygen uptake and carbon dioxide evolution rates in the fermentations.

5. AME5-RP Assay

Samples of the soluble fractions were submitted for analysis by an AME5-RP assay. This assay is a dual column HPLC assay where the first column is an affinity column that captures light chain and the second column is a reversed-phase column. An Integral Workstation was configured in the dual column mode. The solvent reservoirs were: Solvent 1A, affinity loading buffer; Solvent 1B, reversed-phase aqueous buffer and affinity elution buffer, 0.1% TFA in water; Solvent 2A, water; Solvent 2B, reversed-phase organic elution buffer, 0.09% TFA/80% acetonitrile. The first column was the affinity column (30×2.1 mm) containing an immobilized anti-light-chain (kappa) Fab antibody (AME5) immobilized on controlled pore glass. All procedures involving the affinity column were performed at ambient temperature. The second column was the reversed-phase column containing the polymer based POROS R220 packing material (30×2.1 mm). The reversed-phase column temperature was maintained at 60° C.

The affinity column was equilibrated in 30% loading buffer (5 ml) and a 50 μl sample was loaded at a flow rate of 0.1 ml/min. The flow-through was directed to waste. After the sample was loaded the affinity column was washed with 30% loading buffer (2 ml), followed by 100% loading buffer (5 ml) to reduce non-specifically bound components. A final wash with water prepared the affinity column for elution (3 ml). The affinity column was now connected to the reversed-phase column (by valve switching) and eluted with elution buffer (2 ml) at a flow rate of 2 ml/min to transfer the affinity captured components to the reversed phase column. During this transfer step the Integral UV detector is located after the affinity column and before the reversed-phase column and hence monitors the elution of the affinity column (which becomes the load to the reversed-phase column). In addition to this detector, a second detector was added after the reversed-phase column to monitor its flow-through to confirm that all the components eluted from the affinity column were in fact captured by the reversed-phase column.

Re-equilibration of the affinity column was subsequently performed with loading buffer (4 ml) after removing its connection to the reversed-phase column.

The loaded reversed-phase column was washed with aqueous 0.1% TFA (2 ml). The flow rate was set to 1 ml/min and a rapid gradient (1 min) was run to 35% solvent 2B (0.1% TFA/80% acetonitrile) followed by a shallow gradient to 50% solvent 2B over 14 min. Elution is completed by a gradient to 90% solvent 2B over 4 min. The reversed phase column was then returned to initial conditions over 1 min. and re-equilibrated for 3 min at 2 ml/min. The column eluate was monitored at 280 and 214 nm. Quantitation was performed by comparison of the integrated peak areas with those of standards of known concentrations.

6. Antibody Binding Affinity Assays

BIAcore™ Binding Analysis

The VEGF-binding affinities of full length antibodies produced in bacterial cells were calculated from association and disassociation rate constants measured using a BIAcore™-2000 surface plasmon resonance system (BIAcore, Inc., Piscataway, N.J.) as described in Chen et al, (1999) *J. Mol. Biol.* 293:865-881). A biosensor chip was activated for covalent coupling of VEGF using N-ethyl-N'-(3-dimethylaminopropyl)-carbo-dimide hydrochloride (EDC) and N-hydroxysuccinimid (NHS) according to the supplier's (BIAcore, Inc., Piscataway, N.J.) instructions. VEGF (109) or VEGF (165) was buffer-exchanged into 20 mM sodium acetate, pH 4.8 and diluted to approximately 50 µl/minute to achieve approximately 700-1400 response units (RU) of coupled protein. A solution of 1 M ethanolamine was injected as a blocking agent.

For kinetics measurements, twofold serial dilutions of full length antibodies were injected in PBS/Tween® buffer (0.05% Tween®-20 in phosphate-buffered saline) at 25° C. or 37° C. at a flow rate of 10 µl/minute. Equilibrium dissociation constants, $K_d$ values from SPR measurements were calculated as $k_{off}/k_{on}$.

C. Results

FIG. 3 shows the results of a representative immunoblot of lysates from induced cells transformed with pxVG11VNERK (SGIII/lane 1), pVKFR1-2 (SGI/lane 2), and pVKSGII(SGII/lane 3); lane 4 is a negative control (cells transformed with the plasmid, pBR322). Samples were prepared under reduced or non-reduced conditions. In FIG. 3A, lysates prepared under reduced conditions are shown. Locations of the heavy and light chains are shown. In FIG. 3B, nonreduced lysates were separated on a polyacrylamide gel. The drawings to the right of the figure refer to the various antibody structures, including the completely assembled full-length product, various species lacking one or more disulfide bonds including a heavy-light band, monomeric heavy chain, light chain dimer and monomeric light chain, and the relative migration of these structures on the non-reducing gel. The band at the top of the non-reducing gel typically represents the full-length completely disulfide bonded antibody product.

When the cell lysates were prepared under reducing conditions and separated, the results show (FIG. 3A) that there were no significant differences in the amounts of heavy or light chains produced in the cells when the three antibodies were compared. When the same cell lysates were prepared under non-reducing conditions and separated, the results show that the unmodified antibody with heavy chain FR1 subgroup III produced a number of products including the full-length completely assembled product. (FIG. 3B, lane 1). Replacement of the heavy chain FR1 subgroup III sequence with heavy chain FR subgroup I sequence increased the yield of the assembled antibody products including the completely assembled full-length product. (FIG. 3B, lane 2) Replacement of heavy chain FR1 subgroup III sequence with the subgroup II sequence resulted in production of little or no folded and assembled products. (FIG. 3B, lane 3).

The yield of anti-VEGF(VNERK) antibody with the FR1 subgroup I sequence was about 2 fold greater than the anti-VEGF(VNERK) antibody with subgroup III FR1 sequences based on densitometer scans of the completely assembled bands as shown in Table 2 below. The value of n is the number of different gels that were scanned.

TABLE 2

| Plasmid | Yield |
|---|---|
| xVEGF (VNERK) | |
| pxVG11VNERK (FR1 = SGIII) | 1 |
| pVKFR1-2 (FR1 = SGI) | 2.2 +/− 0.2 (n = 9) |
| pVKSGII (FR1 = SGII) | Band not detected (n = 2) |
| xVEGF (Y0317) | |
| pxVG2AP11 (FR1 = SGIII) | 1 |
| pY0FR1-2 (FR1 = SGI) | 8.2 +/− 1.9 (n = 2) |

These results show that replacement of heavy chain FR1 subgroup III sequences with heavy chain FR1 subgroup I sequences in anti-VEGF antibody VNERK increases the yield of completely assembled antibody products. The results from the samples separated under reducing conditions indicate approximately equivalent amount of heavy and light chains were produced in these cells. The increase in full-length completely assembled antibody products demonstrated by the non-reduced samples (FIG. 3B, lane 2) combined with essentially unchanged overall expression level of heavy and light chains demonstrated by the reduced samples (FIG. 3A, lane 2) suggests that the substitution of heavy chain FR1 residues resulted in an increase in folding and/or assembly efficiency which may account for the observed increase in yield.

To determine if the FR1 subgroup substitutions had any effect on the binding affinity for VEGF antigen, an affinity assay was performed using the expressed antibodies obtained from bacterial cells. VNERK antibodies having the original FR1 subgroup III sequence (pxVG11VNERK) and the subgroup I sequence substitution (pVKFR1-2) showed no significant difference in binding affinity for the VEGF antigen. The anti-VEGF antibody with subgroup III had a binding affinity of 0.12 nM and the anti-VEGF with subgroup I had a binding affinity of 0.19 nM (data not shown).

Figure 4A:
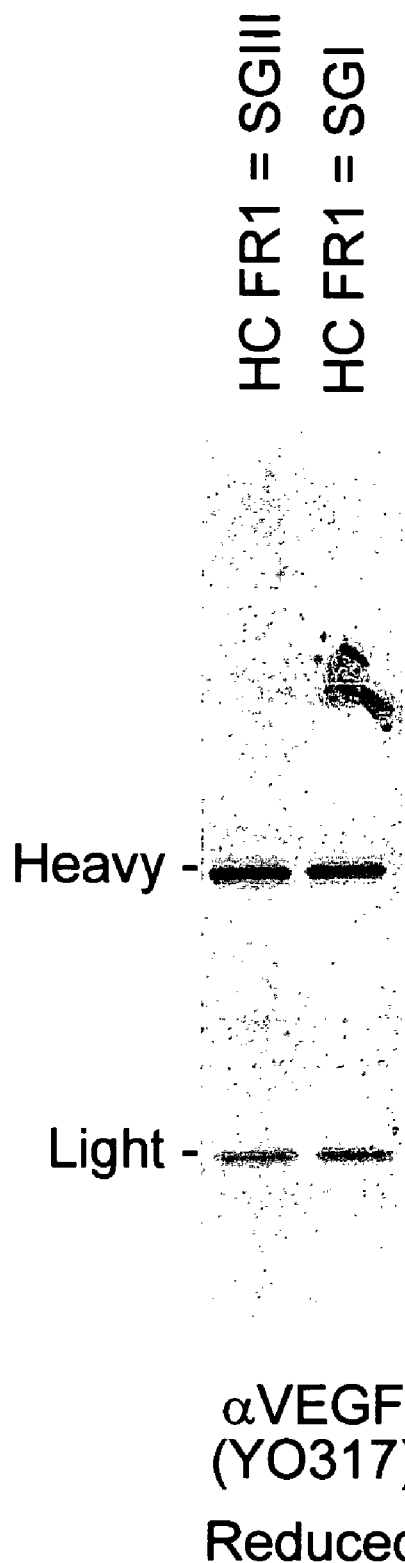
FIG. 4 shows that substitution of HC FR1 subgroup III amino acid residues with subgroup I amino acid residues in anti-VEGF Y0317 antibody improves assembled antibody yield in E. coli. The yield of heavy and light chains is shown in panel A and the yield of assembled antibody products is shown in panel B. Whole cell lysates were prepared under reducing (A) and non-reducing (B) conditions and were analyzed by SDS PAGE immunoblot. Lane 1 is Y0317 antibody with HC FR1 subgroup III (HCFR1=SGIII); and Lane 2 is Y0317 antibody with HC FR1 subgroup I (HCFR1=SGI). In panel A, positions of the heavy and light chains are identified. In panel B, the figures to the right of the gel show position of completely assembled (at the top) and partially assembled antibody products.
Figure 4B:
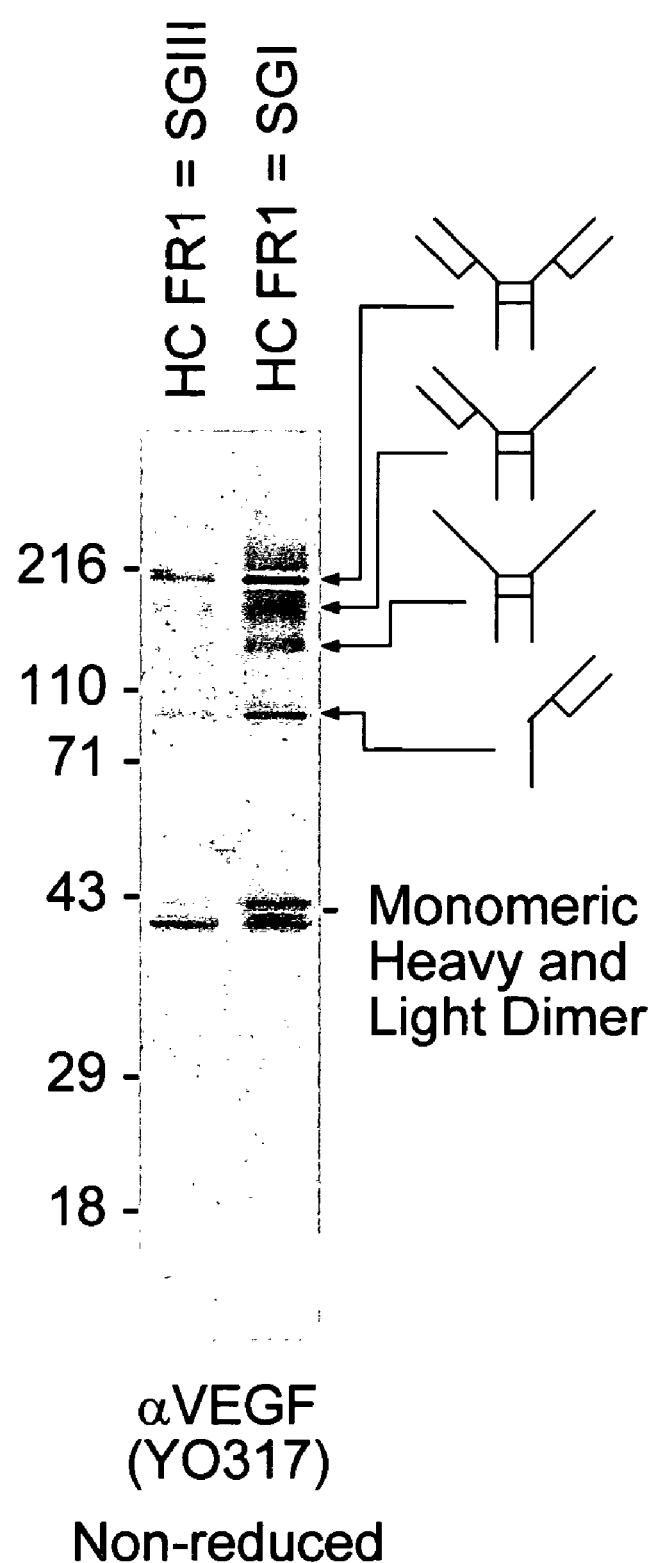

FIG. 4 shows the results of immunoblot analysis of lysates from induced cells transformed with pxVG2AP11 (Y0317 antibody) (original FR1—SGIII/lane 1) or pY0FR1-2 (new FR1—SGI/lane 2). The reduced samples, shown in FIG. 4A, demonstrate that approximately equivalent levels of heavy and light chain are expressed from both constructs. Non-reduced lysates were also separated on a polyacrylamide gel as shown in FIG. 4B. The results in FIG. 4B demonstrate that replacement of the heavy chain FR1 subgroup III sequence with the FR1 subgroup I sequence increases the yield of the folded Y0317 antibody. As shown in Table 2, the yield of the completely disulfide bonded product was increased about 8 fold over the antibody with the subgroup III sequence. As stated previously for anti-VEGF VNERK, this increased yield is likely due to improved heavy chain folding and/or assembly efficiency.

The results show that replacement of the heavy chain FR1 subgroup III consensus sequence with the subgroup I consensus sequence in two different anti-VEGF antibodies, VNERK and Y0317, improved the yield of assembled antibody. The substitutions did not significantly alter the amount of heavy and light chains expressed and did not significantly change the antigen binding affinity of the anti-VEGF VNERK antibody. Additionally, in contrast to the subgroup I replacement, the replacement of the FR1 subgroup III consensus sequence with the subgroup II consensus sequence significantly reduced the yield of assembled antibody.

Figure 14A:
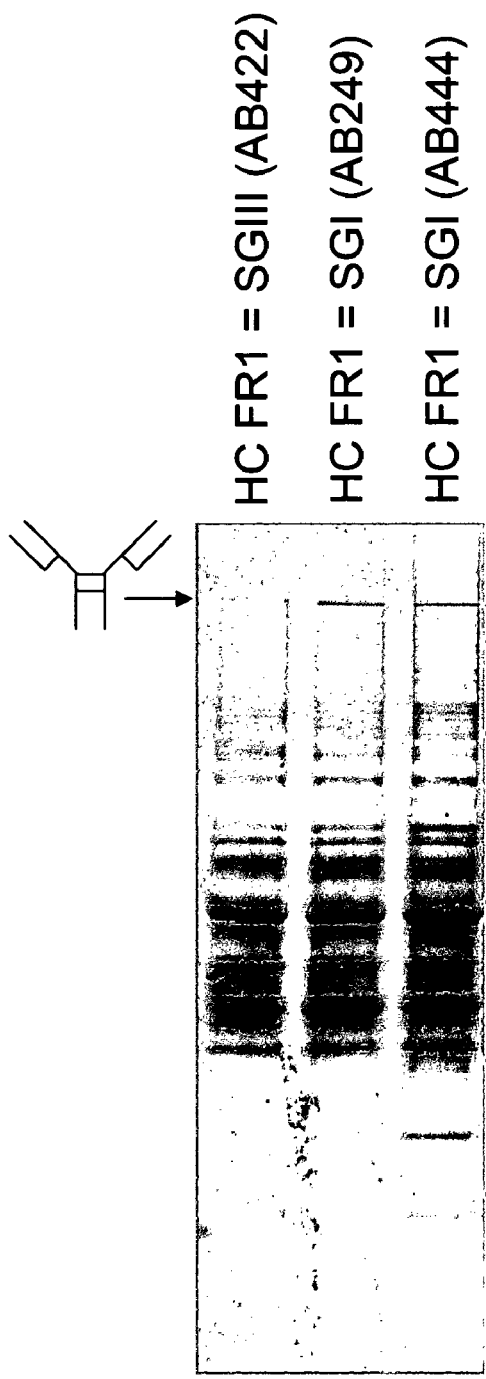
FIG. 14 shows the yield of assembled antibody products of anti-VEGF VNERK antibodies prepared by large scale fermentation. The samples were prepared under non-reducing conditions and run on a SDS PAGE gel. The gels were stained with Coomassie Blue (A) or detectably labeled anti-Fab antibody (B). The anti-VEGF antibody with HC FR1 sequences from consensus subgroup I was prepared by large-scale fermentation on two separate occasions (one batch was labeled AB249; the other batch was labeled AB444). Lane 1 is anti-VEGF VNERK antibody with HC FR1 subgroup III (AB422); lane 2 is anti-VEGF VNERK with HC FR1 subgroup I batch AB249; and lane 3 is anti-VEGF VNERK with HC FR1 subgroup I batch AB444.
Figure 14B:
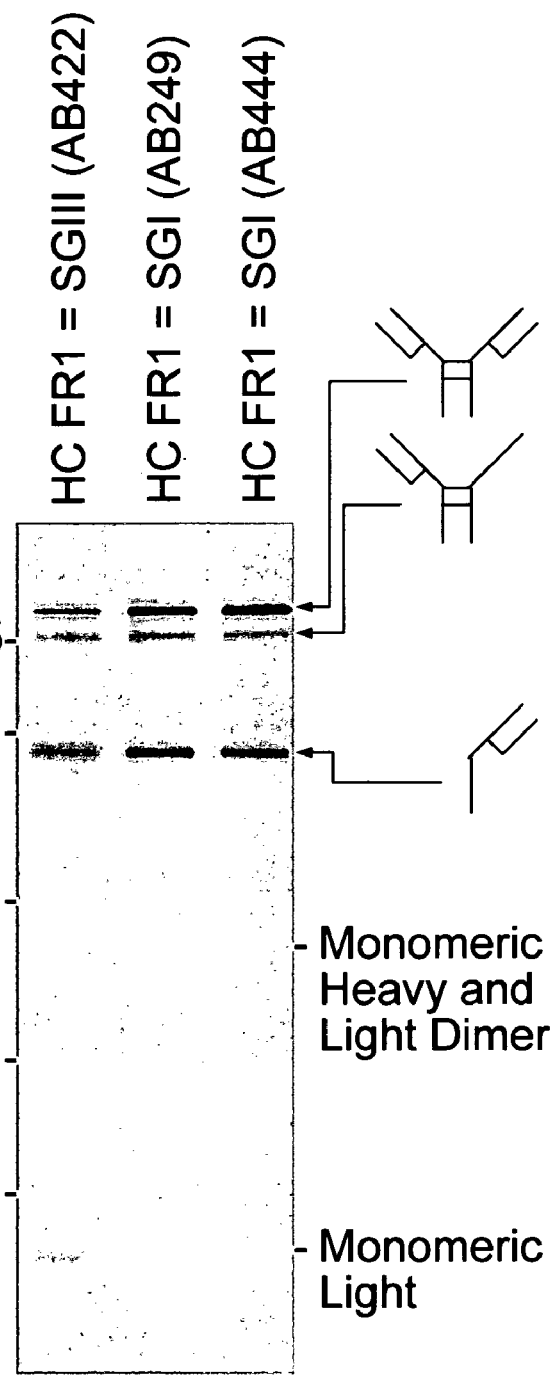

Similar results are seen when the antibodies were produced in cells by large scale fermentation methods. Bacterial cells transformed with plasmids encoding anti-VEGF antibody VNERK (pxVG11VNERK; Fermentation run #AB422) and anti-VEGF antibody VNERK antibody modified to have heavy chain FR1 subgroup I consensus sequence (pVKFR1-2; Fermentation runs #AB249 and # AB444) were grown under large scale fermentation conditions. The results are shown in FIG. 14. In FIG. 14A, the non-reduced soluble fraction samples from bacterial paste were run on a SDS-PAGE and stained with Coomassie Blue. In FIG. 14B, the SDS-PAGE immunoblot of the non-reduced lysates stained with detectably labeled anti-Fab antibody is shown. The results show that there was an increase in yield in the anti-VEGF VNERK antibody with heavy chain FR1 subgroup I consensus sequence when produced on a large scale. The soluble fractions were also submitted for AME5RP assay. No peak was detectable for the soluble fraction sample from cells transformed with plasmid pxVG11VNERK (AB422). The extracts of cells transformed with pVKFR1-2 yielded about 47 (AB249) or 49 (AB444) mg/L of antibody.

These results confirm the finding seen with smaller scale production runs and show that an increase in antibody yield is seen when the heavy chain FR1 amino acid results are modified from the subgroup III consensus sequence to the subgroup I consensus sequence in anti-VEGF antibodies.

D. Selection of a Heavy Chain FR1 Sequence for Anti-VEGF Antibody VNERK Based on HVR Consensus Subgroup I-III Comparisons The anti-VEGF antibody VNERK is a humanized antibody with HVR region sequences from a mouse monoclonal antibody and heavy chain framework regions from consensus sequence subgroup III. As discussed above, substitution of the heavy chain FR1 subgroup III sequences with subgroup I sequence surprisingly resulted in a significant increase in assembled antibody yield when the antibodies were produced in E. coli.

When the HVR1 sequence of the antibody VNERK was compared to each of the consensus sequence HVR1 regions of the heavy chain subgroups, it was discovered that the HVR1 region of VNERK had the most sequence identity with HVR1 region of the subgroup I heavy chain consensus sequence. VNERK has a heavy chain HVR1 including amino acid residues 26-35 having the following sequence: GYTFT-NYGIN. (SEQ ID NO: 14) This sequence was compared to the corresponding residues 26-35 of each of human heavy chain consensus sequences from subgroups I-III. The percentage identity was determined by calculating the number of amino acids that were identical at the same position between the VNERK sequence and each subgroup consensus sequence. The identity is based on the total number of identical amino acids divided by the number of amino acids in the relative HVR1 subgroup consensus sequence. Table 3 shows alignment of these HVR1 sequences and the percentage identity between the pairs.

TABLE 4

| Sequence | Heavy Chain Alignment |
|---|---|
| FR1 | |
| SGIII | EVQLVESGGGLVQPGGSLRLSCAAS |
| VNERK | EVQLVESGGGLVQPGGSLRLSCAAS |
| | |
| FR2 | |
| SGIII | WVRQAPGKGLEWV<u>S</u> |
| VNERK | WVRQAPGKGLEWV<u>G</u> |
| SGI | G |
| | |
| FR3 | __71__78 |

TABLE 4-continued

| Sequence | Heavy Chain Alignment |
|---|---|
| SGIII | RFT<u>I</u>S<u>RD</u>NS<u>K</u><u>NTL</u>YLQMNSLRAEDTAVYYCA<u>R</u> |
| VNERK | RFT<u>F</u>S<u>LD</u>TS<u>K</u><u>STA</u>YLQMNSLRAEDTAVYYCA<u>K</u> |
| SGI |    I  A T   S A                    R |
| | |
| FR4 | |
| SGIII | WGQGTLVTVSS |
| VNERK | WGQGTLVTVSS |

The heavy chain HVR1 of anti-VEGF (VNERK) GYTFT-NYGIN (SEQ ID NO: 14) shows the most sequence identity with the HVR1 consensus sequence of Subgroup I and the least sequence identity with the HVR1 consensus sequence of Subgroup II. As described above, substitution of the heavy chain FR1 subgroup III of anti-VEGF (VNERK) with FR1 of subgroup I enhanced yield while substitution of FR1 with Subgroup II reduced yield. This result suggests a correlation between the FR1 sequence selected and the yield of assembled antibody and folding efficiency.

As part of the humanization process, several substitutions were made to the consensus subgroup III sequences in FR2 and FR3. The substitutions at these positions were from the corresponding position in the murine antibody. Four of the seven substitutions also happen to involve a change from a SGIII consensus residue to a SGI consensus residue. Table 4 shows the four FRs of VNERK following humanization.

TABLE 3

| Sequence | HVR Alignment | | % Identity |
|---|---|---|---|
| Subgroup I HVRH1: | GYTFTSYAIS | (SEQ ID NO: 15) | 70% |
| VNERK HVR1: | GYTFTNYGIN | (SEQ ID NO: 14) | 7/10 |
| Subgroup II HVRH1: | GGSVSSYWSWN | (SEQ ID NO: 15) | 18% |
| VNERK HVR1: | GYTFTNYGIN | (SEQ ID NO: 14) | 2/11 |
| Subgroup III HVRH1: | GFTFSSYAMS | (SEQ ID NO: 17) | 40% |
| VNERK HVR1: | GYTFTNYGIN | (SEQ ID NO: 14) | 4/10 |

Some of the changes made during humanization to improve antibody affinity were made at positions that did not differ in amino acid sequence between the subgroup I and subgroup III sequence, such as at position 94 (Kabat numbering). This suggests that some additional modifications at positions other than those that differ between the selected subgroup consensus sequence and the antibody variable domain sequence may be made in order improve binding affinity in the humanized antibody or antigen binding fragment.

When applying this method to humanized antibodies or antigen binding fragments, some of the FR region substitutions at the positions identified in accord with the methods of the invention may have already been made to improve antigen binding affinity, the improvement of the yield may be less than that would be expected if the changes to the subgroup III sequence had not already been made to the humanized antibody. Designing the anti-VEGF VNERK antibody with heavy chain FR regions from the human consensus subgroup I instead of subgroup III may have shortened the time to producing a humanized antibody or antigen binding fragment that can be produced in high yield in cell culture.

The HVR1 sequence of the heavy chain variable domain antibody Y0317 was also compared to consensus sequence HVR1 regions of each of the heavy chain subgroups. The HVR1 region of Y0317 had the most sequence identity with HVR1 region of the subgroup I. Y0317 includes a heavy chain HVR1 including amino acid residues 26-35 having the following sequence: GYDFTHYGMN. (SEQ ID NO: 18) This sequence was compared to the corresponding residues 26-35 of each of human heavy chain consensus sequences from subgroups I-III. The percentage identity was determined by calculating the number of amino acids that were identical at the same position between the Y0317 HVR1 sequence and each subgroup consensus sequence. The identity is based on the total number of identical amino acids divided by the number of amino acids in the relative HVR1 subgroup consensus sequence. Table 5 shows alignment of these HVR1 sequences and the percentage identity between the pairs.

TABLE 5

| Sequence | HVR Alignment | | % Identity |
|---|---|---|---|
| Subgroup I HVRH1: | GYTFTSYAIS | (SEQ ID NO: 15) | 50% |
| Y0317 HVR1: | GYDFTHYGMN | (SEQ ID NO: 18) | 5/10 |
| Subgroup II HVRH1: | GGSVSSYWSWN | (SEQ ID NO: 16) | 18% |
| Y0317 HVR1: | GYDFTHYGMN | (SEQ ID NO: 18) | 2/11 |
| Subgroup III HVRH1: | GFTFSSYAMS | (SEQ ID NO: 17) | 40% |
| Y0317 HVR1: | GYDFTHYGMN | (SEQ ID NO: 18) | 4/10 |

These results suggest that FR1 sequences that provide improved antibody assembly and yield can be identified by comparing the HVR1 region sequence of the antibody with corresponding consensus sequence subgroup sequences and identifying the subgroup with the most sequence identity to the HVR1 sequence of the antibody.

Example 3

Selection of a Heavy Chain FR1 Sequence for Antibodies Based on Comparison of HVR1 Antibody Sequences to HVR1 Consensus Subgroup I-III Sequences Substitution of heavy chain FR1 consensus sequence subgroup III with consensus sequence subgroup I in anti-VEGF antibodies increased assembled antibody yield, presumably due to improved folding efficiency. Framework region sequences that provide for improved yield for other antibodies or antigen binding fragments can be identified based upon identifying the consensus sequence subgroup that has the most sequence identity in the HVR1 region of the variable domain when the HVR1 region of the antibody or fragment is compared to the corresponding HVR1 sequences of each of the subgroup consensus sequences. The method of identifying a heavy chain FR1 sequence for increasing the yield of antibodies based on HVR1 consensus subgroup I-III comparisons was tested for an anti-IgE antibody, E25.

A. Identification of a Heavy Chain FR1 Sequence for Humanized Anti-IgE Antibody E25 Based on HVR Consensus Subgroup I-III Comparisons The anti-IgE antibody E25 is described in Shields R. L., et al., 1995 (Int Arch Allergy Immunol; 107:308) and U.S. Pat. No. 6,172,213. The sequence of this antibody is provided in U.S. Pat. No. 6,172,213. Antibody E25 is a humanized antibody specific for IgE and was prepared with HVR sequences from mouse anti-human IgE monoclonal antibody MaE11 and framework sequences from human consensus subgroup I for the kappa light chain and human consensus subgroup III sequences for the heavy chain. As part of the humanization process, at least one residue in the FR1 of heavy chain was changed. This modification, A24V, changes a subgroup III residue, Alanine, to the murine residue, Valine, at this position. The murine residue at this position also corresponds to the residue in human variable domain subgroup II consensus sequence.

E25 includes a heavy chain variable region HVR1 including amino acid residues 26 to 35 having the following sequence: GYSITSGYSWN. (SEQ ID NO: 19) This E25 heavy chain HVR1 sequence was compared to the each of the heavy chain HVR1 subgroup consensus sequences I-III as shown below.

The alignment was performed by pairing the E25 HVR1 sequence with the corresponding sequence in each subgroup I-III consensus sequence. The percentage identity was determined by calculating the number of amino acids that were identical at the same position between the E25 sequence and each subgroup consensus sequence. The identity is based on the total number of identical amino acids divided by the number of amino acids in the relative HVR1 subgroup consensus sequence. Table 6 shows alignment of these HVR1 sequences and the percentage identity between the pairs.

TABLE 6

| Sequence | HVR Alignment | | % Identity |
|---|---|---|---|
| Subgroup I HVRH1: | GYTFTSYAIS | (SEQ ID NO: 15) | 40% |
| E25 HVR1: | GYSITSGYSWN | (SEQ ID NO: 19) | (4/10) |
| Subgroup II HVRH1: | GGSVSSYWSWN | (SEQ ID NO: 16) | 55% |
| E25 HVR1: | GYSITSGYSWN | (SEQ ID NO: 19) | 6/11 |
| Subgroup III HVRH1: | GFTFSSYAMS | (SEQ ID NO: 17) | 20% |
| E25 HVR1: | GYSITSGYSWN | (SEQ ID NO: 19) | (2/10) |

Heavy chain variable region HVR1 consensus sequence subgroup II showed the most sequence identity with the heavy chain variable region HVR1 of the E25 antibody.

Based on this comparison, the heavy chain variable region FR1 consensus sequence II was chosen to be imported into the E25 antibody sequence in order to determine whether identification of a FR1 sequence according to this method would improve folding and yield of the expressed antibody.

B. Preparation of Expression Vectors Encoding Humanized Anti-IgE Antibody E25 Having Human Subgroup II Framework Sequences The heavy chain FR1 subgroup III sequence in the E25 antibody was substituted with a consensus sequence subgroup II to determine the effect of the substitution on the expression, folding and yield of the anti-IgE antibody E25.

Sequences of the heavy and light variable domains of E25 were subcloned into PRK plasmids as described in U.S. Pat. No. 6,172,213 B1 for generation of full-length humanized anti-IgE molecules. The sequences for the heavy and light chains for the anti-IgE humanized antibody were subcloned into separate cistron vector as described in Example 2. The resulting plasmid, pE25-1±1, has a polynucleotide sequence (SEQ ID NO: 20) encoding heavy and light chain variable domain amino acid sequences (SEQ ID NO: 21), shown in FIG. 20. The heavy chain FR1 sequences of E25 are according to subgroup III, except for change A24V made as part of humanization.

Replacement of the heavy chain FR1 subgroup III sequence with the subgroup II sequence, was performed as described previously. In order to change the FR1 subgroup III consensus to the subgroup II consensus sequence, 10 amino acid substitutions were required. The resulting plasmid, pE25-SGII, encodes heavy and light chain variable domain amino acid sequences shown in FIG. 21.

C. Expression, Folding and Yield of Humanized Anti-IgE Antibodies Having FR1 Consensus Subgroup Substitution Expression constructs as described in Section B were transformed into bacteria to determine expression, folding and yield of the E25 antibodies as described in Example 2. Non-reducing and reducing SDS-PAGE and immunoblot analysis of the resulting bacterial lysates was performed as described in Example 2, except that the samples were generated from fermentation cell paste, not from a shake flask induction. However, the cell lysates were obtained and processed as described previously for shake flask samples.

D. Results

Figure 5A:
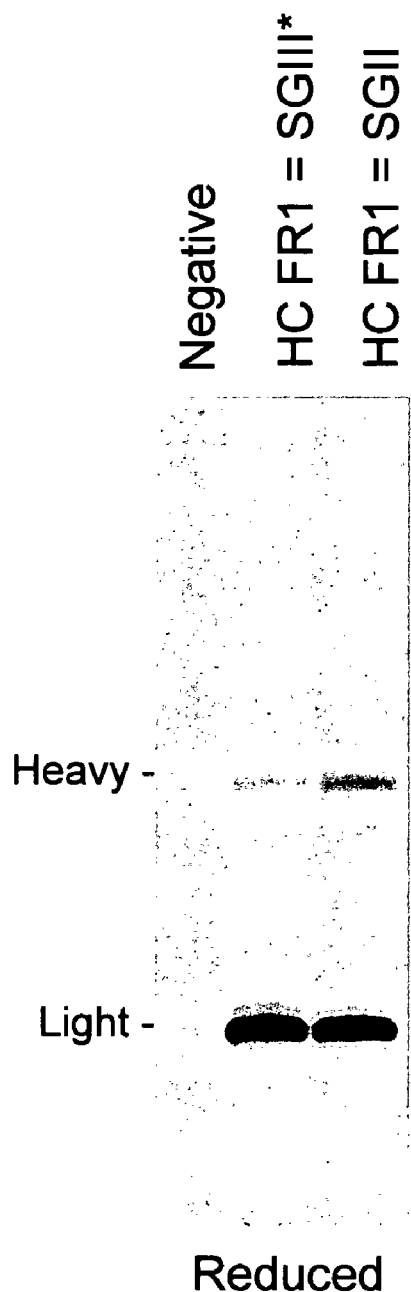
FIG. 5 shows that substitution of HC FR1 subgroup II amino acid residues with FR1 subgroup II amino acid residues in anti-IgE E25 antibody improves assembled antibody yield. The yield of heavy and light chains is shown in panel A and the yield of assembled antibody products is shown in panel B. Whole cell lysates were prepared under reducing (A) and non-reducing (B) conditions and were analyzed by SDS PAGE immunoblot. Lane 1 is negative control; Lane 2 is "wild type" antibody with HC FR1 subgroup III sequence (HCFR1=SGIII*); and Lane 3 is antibody with HC FR1 subgroup III sequence replaced with the subgroup II sequence (HCFR1=SGII). In panel A, positions of heavy and light chains are indicated. In panel B, the figures to the right of the gel show completely assembled (at the top) and partially assembled antibody products. The asterisk indicates that wild type antibody E25 includes a change at position 24 from an alanine to a valine at that position. Valine at position 24 corresponds to the amino acid at that position in the murine sequence and in the human consensus subgroup II sequence.
Figure 5B:
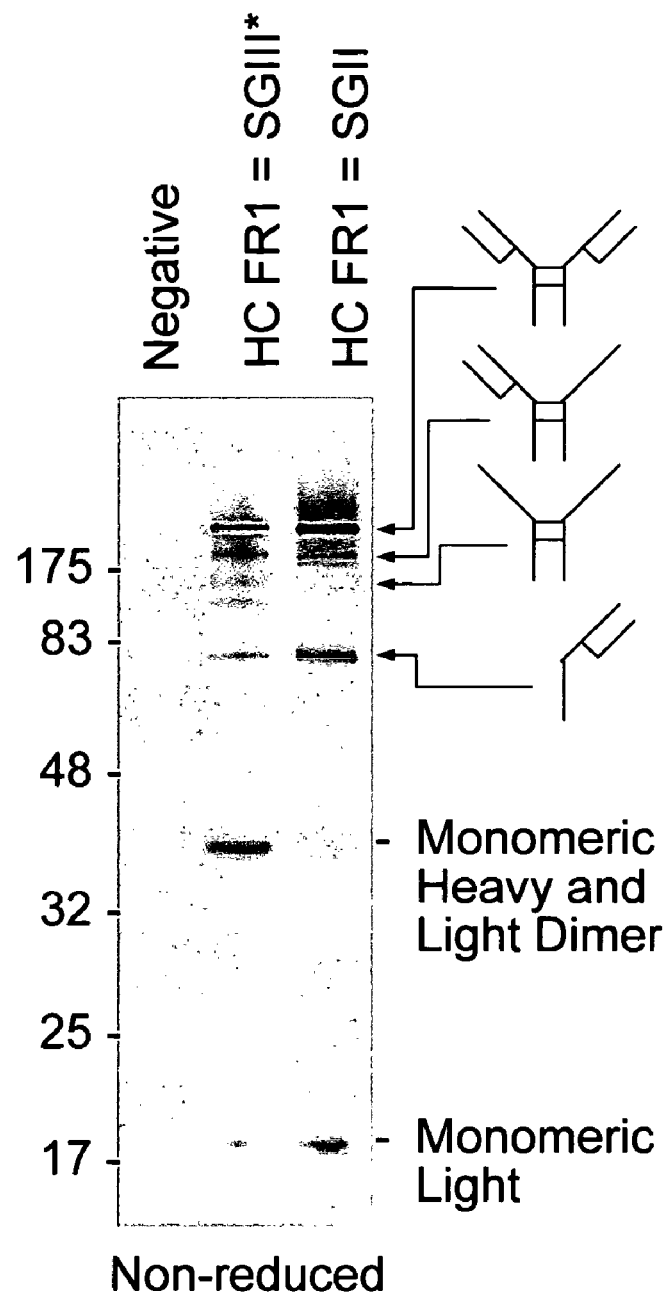
Figure 9A:
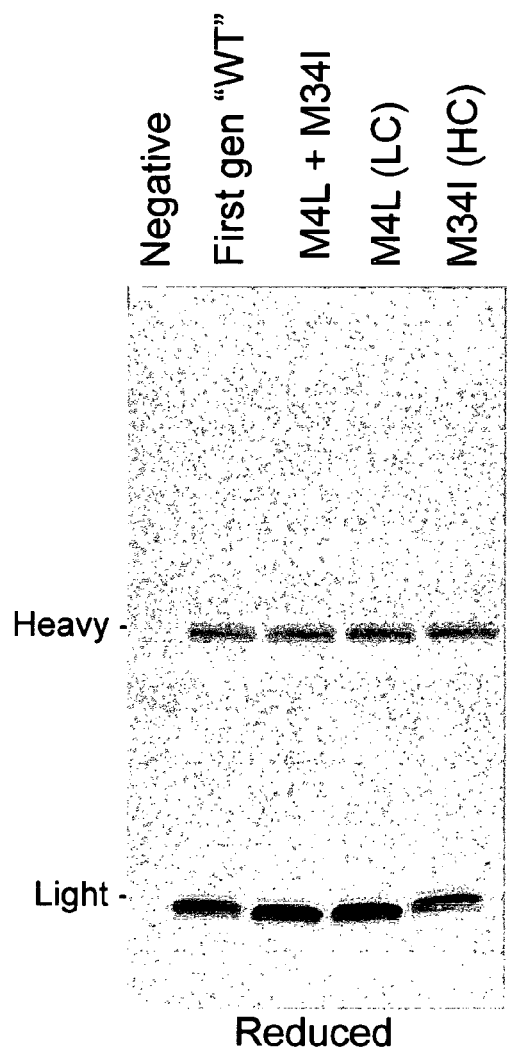
FIG. 9 shows the yield of heavy and light chains (A) and assembled antibody products (B) for anti-VEGF antibodies with a modified variable domain. The antibodies have double or single amino acid substitutions in positions proximal to cys residues that form an intrachain disulfide bond. Whole cell lysates were prepared under reducing (A) and non-reducing (B) conditions and were analyzed by SDS PAGE immunoblot. Lane 1 is negative control; lane 2 is anti-VEGF first generation wt; lane 3 is an antibody with a substitution M4L in the light chain and a substitution M34I in the heavy chain; lane 4 is an antibody with a M4L substitution in the light chain; and lane 5 is an antibody with a M34I substitution in the heavy chain.
Figure 9B:
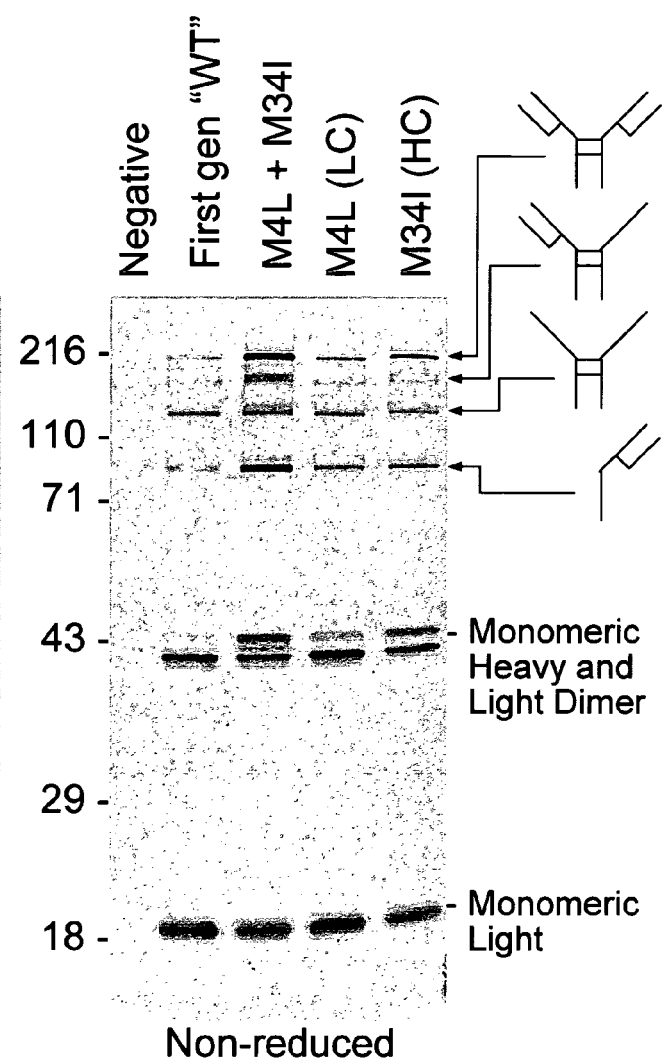

FIG. 5 shows the results of immunoblot analysis of lysates from induced cells transformed with pE25-11 (E25HCFR1/SGII; lane 2), and pE25-SGII (E25HCFR1/SGH; lane 3). FIG. 5A shows an immunoblot analysis of the whole cell lysates prepared under reducing conditions and separated on a polyacrylamide gel, demonstrating that approximately equal amounts of heavy and light chains are produced from induced cells expressing pE25-11 (E25HCFR1/SGIII; lane 2), and pE25-SGII (E25FR1/SGII; lane 3). FIG. 5B demonstrates that substitution of the heavy chain FR1 Subgroup III consensus sequence (+A24V) with the subgroup II consensus sequence results in increased yield of assembled anti-IgE E25 antibody. This increased yield may be due to improved heavy chain folding efficiency since, regardless of which FR1 is used, the production of the individual heavy and light chains does not significantly change.

The relative yield of the completely disulfide bonded antibody products was determined by scanning densitometry of the gels as described in Example 2. The results shown in Table 7 below indicate that replacement of the FR1 subgroup III residues with Subgroup II residues increased antibody yield in a fermentation sample about 2 fold. In all likelihood, the improvement would have been greater if pE25-11 did not have the A24V change (done as part of the humanization process; Ala is the SGIII consensus residue and V is the SGII consensus residue at position 24). This change probably improves the folding and yield of the starting construct, pE25-11.

TABLE 7 anti-IgE (E25)

| Plasmid | Yield |
|---|---|
| pE25-11 (FR1 = SGIII) | 1 |
| pE25-SGII (FR1 = SGII) | 1.2 (n = 1) |
| pE25-SGII (fermentation sample) | 1.8 (n = 1) |

These results support the view that heavy chain FR1 sequences that provide for increased antibody folding, assembly and yield can be predicted by comparing the HVR1 region sequence of the antibody with the corresponding sequences in the human variable domain subgroup consensus sequences and identifying the subgroup with the most sequence identity to the HVR1 sequence of the antibody.

Example 4

Heavy Chain HVR1, HVR2 and HVR3 Comparisons to Human Subgroup Heavy Chain Variable Domain Consensus Sequences To examine whether other HVR sequences could be used to select the human subgroup variable domain consensus sequence, a number of different antibodies were analyzed for sequence identity in HVR sequences with the corresponding sequences in the human subgroup variable domain consensus sequences. The heavy chain HVR1 (amino acids 26-35), HVR2 (kabat defined, amino acids 50-65) and HVR3 (kabat defined, amino acids 95-102)amino acid sequences of an antibody were aligned with each of the corresponding sequences of each of the human subgroup heavy chain variable domain consensus sequence and the % identity calculated as described previously. The results for each antibody are shown in Table 8 below.

TABLE 8

SEQUENCE SIMILARITY CHART

| | HVR1 | HVR2 | HVR3 |
|---|---|---|---|
| xVEGF (VNERK) Heavy Chain | | | |
| Consensus Subgroup I | 70% | 44% | 28% |
| Consensus Subgroup II | 18% | 28% | 19% |
| Consensus Subgroup III | 40% | 26% | 25% |
| xIgE (E25) Heavy Chain | | | |
| Consensus Subgroup I | 40% | 33% | 6% |
| Consensus Subgroup II | 55% | 50% | 25% |
| Consensus Subgroup III | 20% | 47% | 25% |
| xTF Heavy Chain | | | |
| Consensus Subgroup I | 20% | 44% | 22% |
| Consensus Subgroup II | 18% | 28% | 19% |
| Consensus Subgroup III | 40% | 26% | 25% |
| xCD40 Heavy Chain | | | |
| Consensus Subgroup I | 60% | 44% | 11% |
| Consensus Subgroup II | 27% | 28% | 6% |
| Consensus Subgroup III | 30% | 26% | 13% |

The comparison shows that in 3 out of 4 cases, a comparison of the HVR1 and/or HVR2 sequences of an antibody varaible domain resulted in the selection of the same human subgroup variable domain consensus sequence. In cases where the HVR1 and HVR2 differ in the identification of the human consensus subgroup with the most sequence identity, the consensus sequence with the most sequence identity to the HVR1 is preferably selected. In contrast, the HVR3 amino acid sequences tend to be very diverse in both sequence and in length when antibodies are compared to one another or to consensus sequences and therefore, were not useful in the selection of the human subroup variable domain consensus sequence.

Example 5

Expression and Assembly of Anti-VEGF VNERK Antibodies with Single Amino Acid Substitution in FR1

A. Preparation of Humanized Anti-VEGF Antibody Expression Vectors Having Single Amino Acid Substitutions in FR1

Substitution of the FR1 heavy chain subgroup III residues with the FR subgroup I residues in anti-VEGF antibodies increased the yield of assembled antibody. Anti-VEGF antibodies were constructed with single amino acid substitutions at each of the FR1 subgroup III residues which were different than subgroup I residues at that position. The FR1 subgroup III residues were compared to FR subgroup I residues and where the amino acid differed at a position, the FR1 subgroup III residue was changed to the amino acid at the corresponding position in the subgroup I sequence. The antibodies with single amino acid substitutions were examined for folding efficiency and yield.

B. Preparation of Single Substitution Antibodies in Subgroup III Backbone.

The heavy chain FR1 subgroup III consensus sequence (SEQ ID NO: 3) was compared to heavy chain FR1 subgroup I consensus sequence (SEQ ID NO: 1) as shown below:

```
Subgroup III  1 2 3 4 5 6 7 8 9 10 11 12 13 14 15 16 17 18 19 20 21 22 23 24 25
Sequence      E V Q L V E S G G  L  V  Q  P  G  G  S  L  R  L  S  C  A  A  S
              |     | |   | |  |  |           |     |  |  |        |
Subgroup I    Q     Q A   E V  K  K           A     V  K  V        K
Sequence
```

Single amino acid substitutions at each of residues 1, 6, 9, 10, 11, 12, 13, 16, 18, 19, 20 and 23 in the heavy chain FR1 were made one at a time to determine the effect of substitution of the subgroup I amino acid at each position. The antibodies are identified by the position and type of substitution made. For example, a substitution at the first residue of the glutamic acid residue in the subgroup III sequence for glutamine residue in the subgroup I sequence is designated E1Q. Other antibodies with substitutions are identified in a similar manner.

The vector designated pVKE6Q is a separate cistron vector prepared by modifying plasmid pxVG11NERK. Single amino acid substitutions were made by oligonucleotide mutagenesis as described previously. The heavy chain FR1 of VNERK was modified so that the glutamate at amino acid position 6 was converted to glutamine. Other single amino acid substitutions were made in a similar manner.

C. Expression, Folding and Yield of Humanized Anti-VEGF FR1 with Single Amino Acid Substitutions Anti-VEGF expression constructs were transformed into bacteria as described in Example 2 to determine expression, folding, and yield of the anti-VEGF VNERK antibodies having the indicated single amino acid substitutions in the heavy chain FR1 sequence. Lysates prepared under non-reducing and reducing conditions were separated by SDS-PAGE and immunoblot analysis of the resulting bacterial lysates was performed as described in Example 2.

D. Results

FIG. 6 shows the results of immunoblot analysis of lysates from cells expressing the antibodies with the single amino acid substitutions in FR1 of the anti-VEGF antibody as described above. In each blot, the antibodies were compared to the wild type VNERK having the subgroup III FR1 sequence (lane 1) and the VNERK antibody having the subgroup I FR1 replacement (lane 8).

The results in FIGS. 6A and 6B show that when separated under reducing conditions, the antibodies with single substitutions produced approximately equivalent amounts of heavy and light chains when compared to one another. The analysis of the anti-VEGF VNERK antibody lysates prepared under non-reducing conditions (FIGS. 6C and D) show that single amino acid substitutions at E6Q and A23K increased the yield of assembled anti-VEGF antibody about 2 fold; E1Q, L11V, Q13K, L18V and R19K resulted in slight improvement or were neutral; and G9A, G10E, V12K, G16A and L20V resulted in a decrease in the yield of assembled anti-VEGF antibody. (FIGS. 6C and 6D).

The relative yield of the single amino acid substitution antibodies relative to the unmodified VNERK antibody are shown in Table 9 below.

TABLE 9

| Plasmid | Yield |
|---|---|
| pxVG11VNERK | 1 |
| E1Q | 1.4 +/− 0.1 (n = 4) |

TABLE 9-continued

| Plasmid | Yield |
|---|---|
| E6Q | 1.9 +/− 0.2 (n = 5) |
| G9A | band not detected (n = 2) |
| G10E | 0.3 +/− 0.1 (n = 2) |
| L11V | 1.5 +/− 0.0 (n = 3) |
| V12K | 0.1 +/− 0.0 (n = 2) |
| Q13K | 1.1 (n = 1) |
| G16A | 0.7 (n = 1) |
| L18V | 1.1 (n = 1) |
| R19K | 1.4 (n = 1) |
| L20V | 0.2 (n = 1) |
| A23K | 2.1 +/− 0.2 (n = 2) |
| pVKFR1-2 | 2.2 +/− 0.2 (n = 9) |

A second series of samples was prepared under non-reducing conditions to compare yield of assembled products for the antibodies with single amino acid substitutions E1Q, E6Q, L11V and A23K with one another and the VNERK with unmodified subgroup I or subgroup III FR1 sequences. (FIG. 7B).

The results show that the improved yield was primarily seen when changes were made at position 6 and position 23. Since each of these antibodies produced about equal amounts of heavy and light chains, the improved yield due to change at E6Q and A23K suggest that certain residues within the FR1 may have a greater influence on folding efficiency than others.

Example 6

Preparation of Expression Vectors Encoding Humanized Anti-VEGF Antibodies with Substitutions at Residues Proximal to Variable Region Disulfide Bonded Cys Residues An important structural feature of antibody variable domains is the intrachain variable domain disulfide bond connecting both of the B sheets formed in the antibody variable domain. Removal of the disulfide bond residues, especially in the variable heavy chain, results in a decrease in assembled products and an increase in aggregates (Ramon et al., *J. Mol. Biol,* 290:535 (1999)). Typically, each variable domain has a single disulfide bond between a pair of cys residues found at conserved positions. Experiments were undertaken to determine whether any residue proximal to the disulfide bonded cys residues could also impact the folding and assembly of antibody molecules and whether one could predict which substitutions at those residues would improve antibody yield.

A. Identification of Amino Acid Positions Proximal to Disulfide Bonded Cys Residues Positions in the antibody variable domain proximal to the disulfide bonded cys residues in the 3-dimensional structure of the antibody were identified by inspection of the crystal structure of humanized anti-VEGF variant Fab-12 (accession no. IBJ1; Nucler et al., *Structure* 6:1153 (1998)) using the graphics program MIDAS (available from University of California, San Francisco). An amino acid position in a three-dimensional structure was considered proximal to a cys residue that forms an intrachain disulfide bond when the side chain of the amino acid in that position (or for Gly, its alpha carbon) is about 5 angstroms or less from the cys residue or its side chain.

The amino acid positions proximal to the disulfide bonded cys residue for the anti-VEGF antibody variable domains were identified as follows:

In the light chain, the amino acid positions were 4, 6, 33, 35, and 71.

In the heavy chain, the amino acid positions were 4, 6, 34, 36, 78, and 104.

The anti-VEGF antibody, anti-TF antibody, anti-CD-18 antibody, and the 4D5 antibody all have framework regions from heavy chain consensus subgroup III. A crystal structure of each antibody was also analyzed using the program SOLV (G. S. Smith 1985, "A computer program for the calculation of molecular volume and surface area of proteins", Merch, Sharpe and Dohme, Res. Laboratories, QCPE). Amino acid positions with a loss of about 10 square angstroms or greater of solvent accessible surface area by contacting the cys residue were selected. The same amino acid positions identified above were identified as positions proximal to disulfide bonded cys residues in each of the variable domains.

B. Construction of Anti-VEGF Antibodies with Substitutions at Positions Proximal to Disulfide Bonded Cys Residues Anti-VEGF antibodies were constructed with single or double mutations at one or more of the amino acid positions identified as proximal to disulfide bonded cys residues in the 3-dimensional structure. The anti-VEGF antibody used to construct the modified antibodies is an anti-VEGF antibody identified as first generation wild type. The nucleotide (SEQ ID NO: 24) and amino acid sequence (SEQ ID NO: 25) of the heavy and light chain of anti-VEGF first generation wild type are shown in FIG. 22. The starting construct is designated pVG50. The antibodies constructed are identified below.

| | |
|---|---|
| M4L | single substitution in the light chain |
| F71Y | single substitution in the light chain |
| M34I | single substitution in the heavy chain |
| E6Q; M34I | double substitution in the heavy chain |
| A78L | single substitution in the heavy chain |

Amino acid residues at positions L33 and W35 in the light chain and L4, W36, and G104 in the heavy chain were not substituted because the amino acid residues in these positions are highly conserved across all subgroup consensus sequences and have the same amino acid at that position. Results from Example 5 show that the E6Q mutation greatly increased the yield of assembled product and was not tested as single mutation in this example.

The amino acid at position 78 in the first generation "wt" anti-VEGF antibody was changed from the consensus subgroup III residue leucine to the murine residue alanine at that position as a part of humanization of the antibody and to improve affinity of the antibody. Presta et al., *Cancer Res.,* 57:45934599 (1997). Thus, the first generation wt antibody has an alanine at position 78 which corresponds to the amino acid found at that position in the subgroup I consensus sequence. The variant antibody A78L shown above has a substitution changing the subgroup I amino acid, Ala, of the first generation wt parent antibody back to the subgroup II amino acid, leucine at position 78.

Once the amino acid positions proximal to the cys residues were identified, single or double amino acid substitutions were made. The amino acid that was selected for substitution at each position was the amino acid found at the corresponding position in subgroup I sequence, except for position 78. The first generation wt anti-VEGF antibody heavy chain has a HVR1 sequence that has more sequence identity to consensus subgroup I HVR1 sequence than the subgroup III sequence. Thus, the amino acid substituted was the amino acid found at that position in the subgroup I sequence.

The anti-VEGF antibody Y0317 was also substituted at residue M34 in the heavy chain and F71 in the light chain. The M34 residue (subgroup III) was substituted with isoleucine (subgroup I). The F71 residue (subgroup III) was substituted with tyrosine.

Anti-VEGF antibody VNERK antibodies were constructed with the subgroup I amino acid at position 78 (A78), with the subgroup II amino acid at position 78 (F78), and the subgroup III amino acid at position 78 (L78).

The antibodies modified as described above were prepared by using the vectors described previously; anti-VEGF (VNERK) (FIG. 15, SEQ ID NO: 5; and anti-VEGF Y0317 (FIG. 16, SEQ ID NO: 6). The first generation wt anti-VEGF nucleotide and amino acid sequence is provided in FIG. 22.

C. Expression, Folding and Yield of Humanized Anti-VEGF with Substitutions at Positions Proximal to Disulfide Bonded Cys Residues Expression constructs were transformed into bacteria to determine expression, folding and yield of the anti-VEGF antibodies as described in Example 2. Non-reducing and reducing lysates were separated by SDS-PAGE and immunoblot analysis of the resulting bacterial lysates was performed as described in Example 2.

D. Results of Immunoblot Analysis

FIG. 8 shows the results of the immunoblot analysis of lysates from induced cells transformed with first generation wt VEGF antibody and the antibodies with amino acid substitutions at the following positions: M4L (light chain); F71Y (light chain); M34I (heavy chain); E6Q/M34I (heavy chain). The results in FIG. 8A demonstrate that approximately equal amounts of the heavy and light chains are produced when each antibody is compared to one another. In FIG. 8B, the results show that the E6Q/M34I variant had greatly increased yield (about 16 fold) of completely disulfide bonded antibody product compared to the first generation wt control. The antibodies with mutations at positions 4 (about 2 fold) and 71 in the light chain (about 2.4 fold) and 34 (about 4.4 fold) in the heavy chain had an improvement in yield over the first generation wild type control. The results from the densitometry scans are shown below in Table 10.

TABLE 10

| Plasmid | Yield |
| --- | --- |
| pVG50 (Ist gen wt) | 1 |
| pVG50M4L (LC M4L) | 1.9 +/- 0.2 (n = 2) |
| pVG50F71Y (LC F71Y) | 2.4 (n = 1) |
| pVG50M34I (HC M34I) | 4.4 +/- 0.1 (n = 2) |
| pVG50AA (M4L + M34I) | 10.4 +/- 1.0 (n = 3) |
| pVG50E6Q (HC E6Q + M34I) | 16.0 (n = 1) |

Figure 10A:
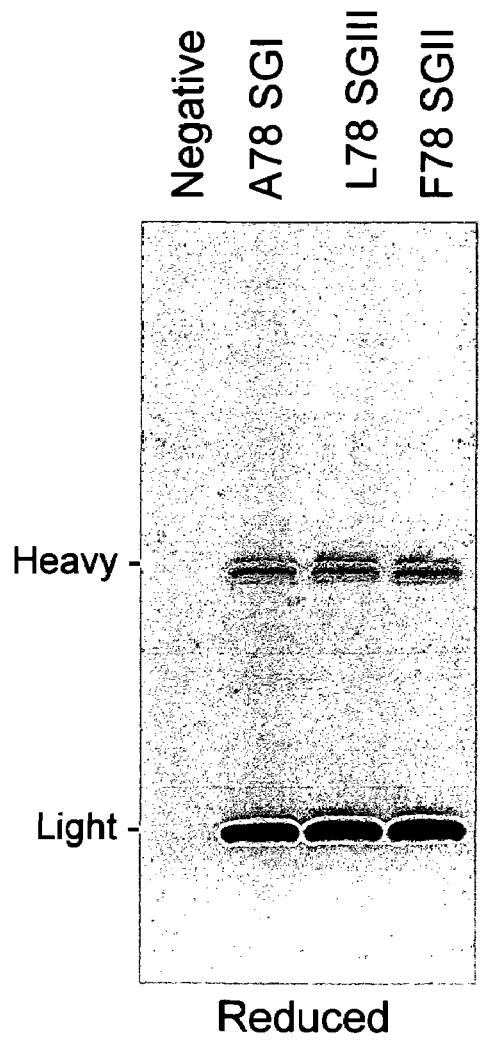
FIG. 10 shows the yield of heavy and light chains (A) and assembled antibody products (B) of anti-VEGF VNERK antibodies with a modified variable domain. The antibodies have single amino acid substitutions at position 78 in the heavy chain replacing the subgroup III (L78) residue with either the subgroup I (A78) or the subgroup II residue (F78). Whole cell lysates were prepared under reducing (A) and non-reducing (B) conditions and were analyzed by SDS PAGE immunoblot. Lane 1 is a negative control; lane 2 is anti-VEGF antibody with a HC subgroup I residue at position 78 (A78-SGI); lane 3 is anti-VEGF antibody with a HC subgroup III residue at position 78, (L78-SGIII); and lane 4 is an antibody with a HC subgroup II residue at position 78 (F78-SGII).
Figure 10B:
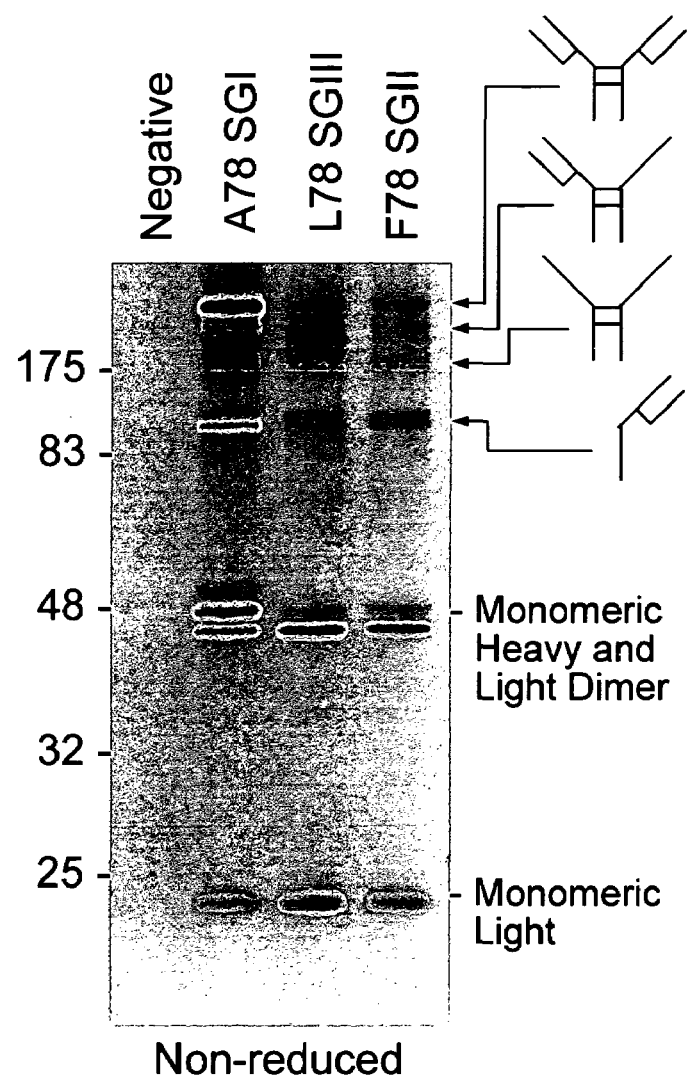
Figure 11A:
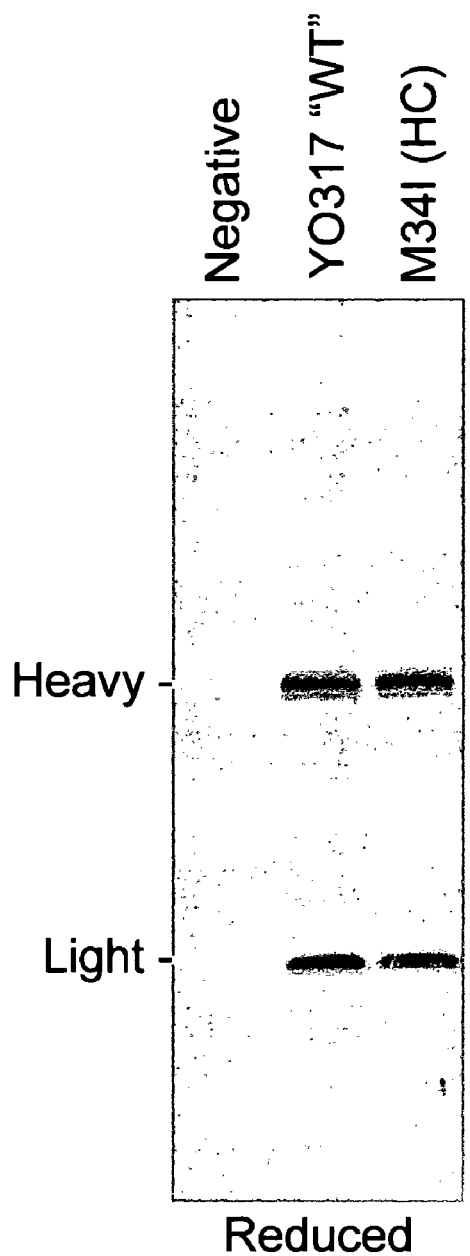
FIG. 11 shows the yield of heavy and light chains (A) and assembled antibody products (B) of anti-VEGF antibody Y0317 with a single amino acid substitution at position 34 in the heavy chain. Whole cell lysates were prepared under reducing (A) and non-reducing (B) conditions and were analyzed by SDS PAGE immunoblot. Lane 1 is a negative control; lane 2 is anti-VEGF YO317 with HC FR1 subgroup III; and lane 3 is YO317 antibody with M34I substitution in heavy chain.
Figure 11B:
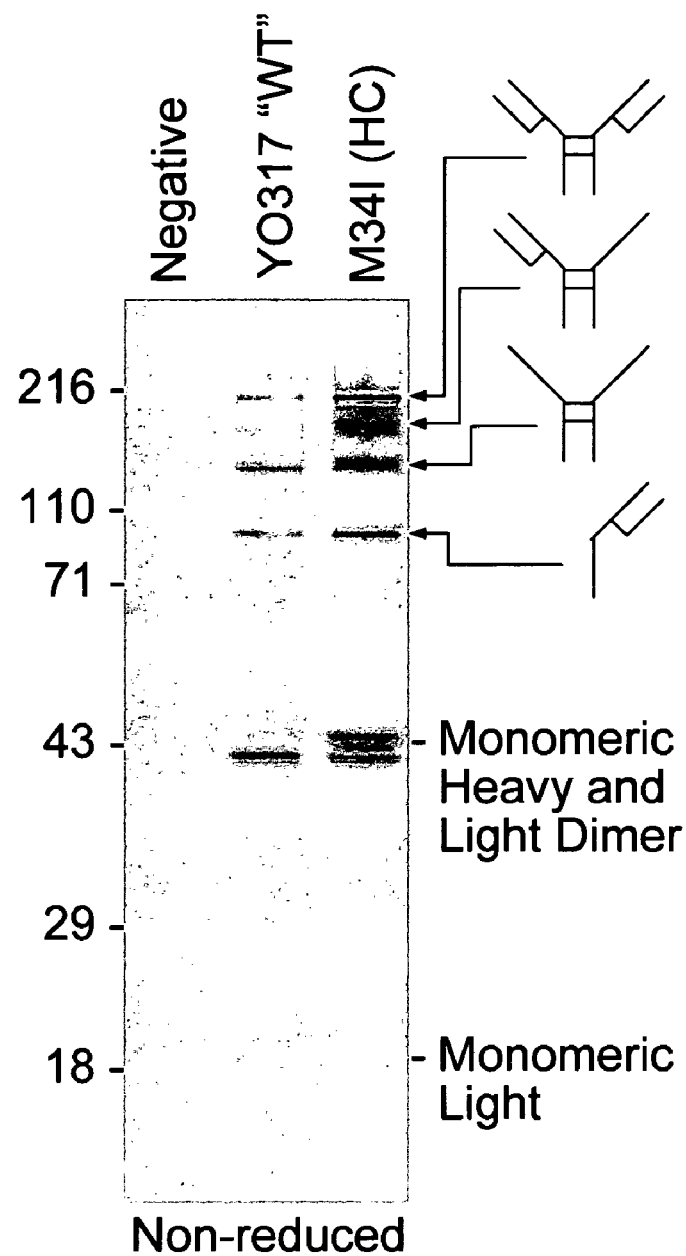
Figure 12A:
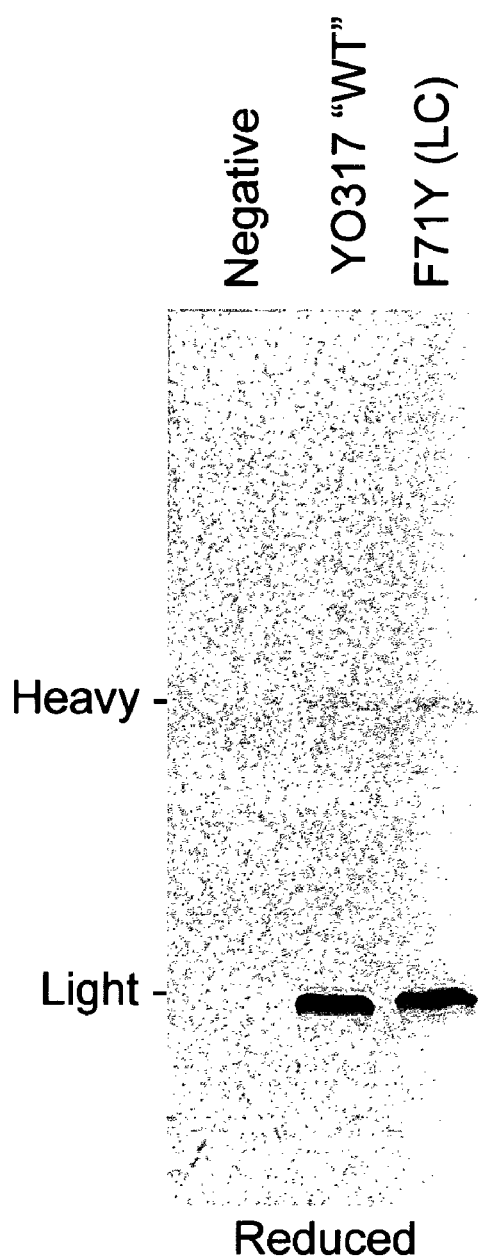
FIG. 12 shows the yield of heavy and light chains (A) and assembled antibody products (B) of anti-VEGF antibody YO317 antibody with an amino acid substitution F71Y in the light chain. Whole cell lysates were prepared under reducing (A) and non-reducing (B) conditions and were analyzed by SDS PAGE immunoblot. Lane 1 is a negative control; lane 2 is anti-VEGF antibody YO317; lane 3 is an antibody with F71Y substitution in the light chain.
Figure 12B:
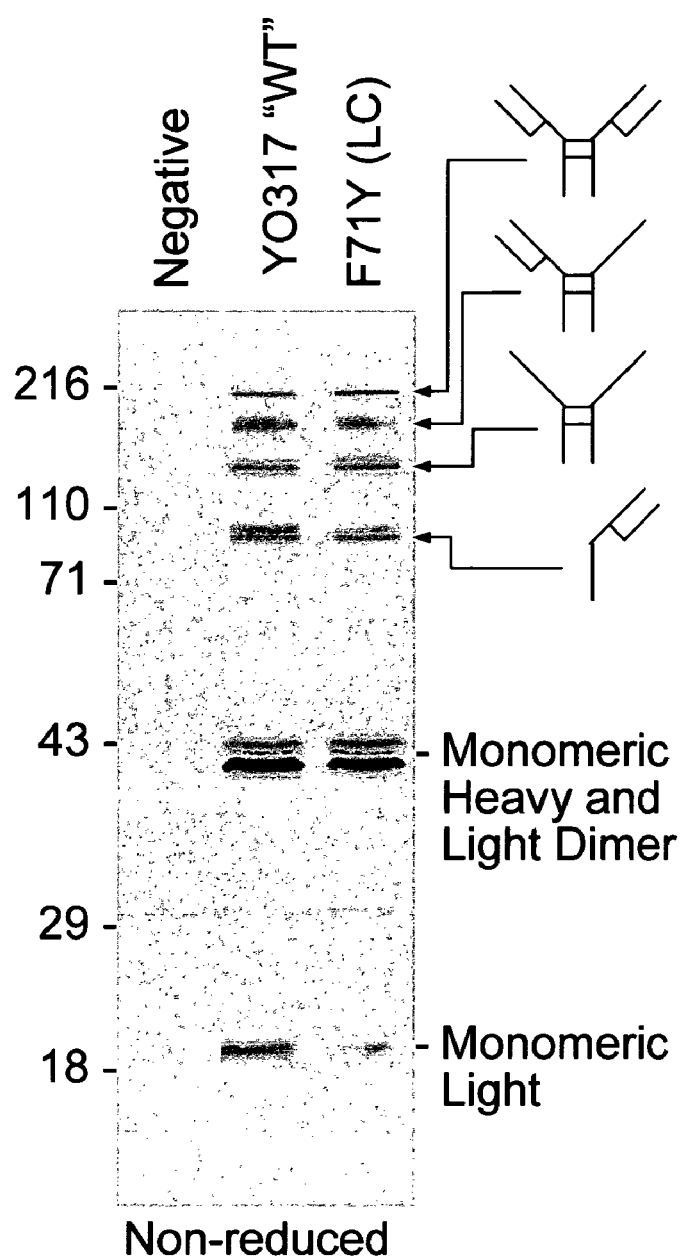

When the residue at position 78 was changed from subgroup I residue back to the subgroup III residue, the antibody yield was reduced. Anti-VEGF VNERK antibodies with subgroup I amino acid A78 at position 78; subgroup II amino acid F78 at position 78; and subgroup III amino acid L78 were also tested for antibody yield. The results are shown in FIG. 10. The anti-VEGF VNERK antibody having the subgroup I A78 residue displayed significantly higher assembled antibody yield (about 36 fold) compared to the antibody with the subgroup III (A78L) substitution at that position. The results of the scanning densitometry are shown in Table 11.

TABLE 11

| Plasmid | Yield |
|---|---|
| A78L-SGIII | 1 |
| A78-SGI | 36.0 (n = 1) |
| A78F-SGII | 2.7 (n = 1) |

Thus, substitutions of amino acids in positions proximal to disulfide bonded cys residues with subgroup I amino acids improves antibody yield. Substitution back to subgroup III residues or subgroup II residue at position 78 reduced assembled antibody yield.

Another double mutant was constructed with a single amino acid substitution in each of the light chain and the heavy chain: M4L (light chain) and M34I (heavy chain). The yield of assembled antibody products was compared to the wt first generation anti-VEGF antibody and the M4L and M34I single substitution antibodies. Each antibody produced approximately equivalent heavy and light chains as seen in FIG. 9A. The results in FIG. 9B show that anti-VEGF with both substitutions had increase in assembled antibody yield about 10.4 fold over first generation wild type. (See Table 10). The anti-VEGF antibody with both substitutions also had an increased yield as compared with the antibodies with a single amino acid substitution at position 4 and position 34.

The effect of single substitutions in the light and heavy chain in antibody Y0317 was examined. Single amino acid substitution antibodies were constructed and tested for antibody yield. The antibodies had the following substitutions: M34I (heavy chain) and F71Y in the light chain. The results are shown in FIGS. 11 and 12. In FIG. 11, the M34I change in the heavy chain increased antibody yield over the YO317 antibody about 5 fold. The F71Y change in the light chain also increased antibody yield about 2.4 fold compared to Y0317, but not to the same extent as the M34I change. (FIG. 12) The results of the scanning densitometry are shown in Table 12.

TABLE 12

| Plasmid | Yield |
|---|---|
| pxVG2AP11 | 1 |
| pY0M34I (HC M34I) | 5.0 (n = 1) |
| pY0F71Y (LC F71Y) | 2.4 (n = 1) |

In summary, we analyzed a number of different anti-VEGF antibodies and variants of the antibodies with one or more substitutions at amino acids in positions proximal to disulfide bonded cys residues. The results show that substitution of all of the amino acids in positions proximal to disulfide bonded cys residues with amino acids found at corresponding positions in the subgroup I consensus sequence in the heavy chain increased antibody yield, likely through improved folding efficiency. These results suggest that prediction of the heavy chain subgroup FR based on HVR1 and/or HVR2 comparison may also predict which substitutions to make at positions proximal to the disulfide bonded cys residues to improve antibody folding and/or assembly and, therefore, yield.

Example 7

Expression and Yield of Anti-VEGF VNERK Antibodies with FR2 and FR3 Substitutions The anti-VEGF VNERK antibody was modified by additional changes to the framework regions of the heavy chain. The parent or wild-type anti-VEGF VNERK antibody was originally constructed with human heavy chain consensus sequences subgroup III for all of the framework regions in the heavy chain variable domain. The earlier studies demonstrated that replacement of the FR1 sequence of the heavy chain to the FR1 subgroup I consensus sequence improved antibody yield. The subgroup I consensus sequence was selected as the consensus sequence subgroup with the greatest sequence identity in the HVR1 region to the HVR1 region of the anti-VEGF VNERK antibody. The next step addressed the question of whether substitution of additional heavy chain FRs with the subgroup I consensus sequence could further increase antibody yield.

A. Preparation of Expression Vectors Encoding Anti-VEGF Antibody with Modified FRs Plasmid pVKFR1-2 prepared as described in Example 2 was used to make additional anti-VEGF VNERK antibodies with modified framework regions. Plasmid pVKSGI.1.2 was prepared by modifying the sequence of plasmid pVKFR1-2 so that the FR2 amino acid sequence was changed from the subgroup III consensus sequence to the subgroup I consensus sequence using the method described in U.S. Pat. No. 5,747,662. The change in the FR2 heavy chain sequence was in the region of amino acids 36-49. A total of 2 amino acid substitutions were necessary to change the FR2 subgroup III consensus sequence to that of the subgroup I consensus sequence. The plasmid pVKSGI. 1.2 encodes an anti-VEGF antibody with both the heavy chain FR1 and FR2 region residues having the sequence of human consensus sequence subgroup I.

Plasmid pVKSGI was prepared by further modifying plasmid pVKSGI. 1.2. Plasmid pVKSGI encodes an anti-VEGF heavy chain variable domain with FR1, FR2, and FR3 regions corresponding to that of the human consensus subgroup I sequence. The polynucleotide sequence (SEQ ID NO:26) and amino acid sequence (SEQ ID NO:27) of anti-VEGF antibody with all FR sequence of human consensus sequence subgroup I in plasmid pVKSGI is shown in FIG. 23. The amino acid sequence of FR4 is identical for all three heavy chain consensus subgroup sequences. The FR3 region of the anti-VEGF antibody includes amino acids 66 to 94 in the heavy chain variable domain. A total of 11 amino acid substitutions were necessary to change the FR3 region sequence of the parent antibody, pxVG11VNERK, from the consensus sequence subgroup III sequence, including changes made to this region as a part of the humanization process, to that of the subgroup I sequence.

B. Expression, Folding and Yield of Modified Anti-VEGF Antibodies

Expression vectors described in Section A were transformed into bacteria to determine expression, folding and yield as described in Example 2.

C. Immunoblot Analysis

Soluble fractions of each sample were prepared as follows: (1) a 5 O.D.$_{600}$ pellet of each sample was resuspended in 225 µl of 50 mM NaCl+5 mM EDTA+50 mM Tris pH 8+1 mg/ml lysozyme; (2) 25 µl of 100 mM IAA (Iodoacetic acid; Sigma I-2512) was then added; (3) the cell suspensions were vortexed and lysed by sonicating for 2×2 minutes at 50% pulse (Sonics & Materials, Inc., Danbury, Conn.) (the samples were kept in an ice water bath during sonication to dissipate the heat generated during the process); (4) the samples were centrifuged for 5 minutes in a microfuge; (5) 100 µl of each supernatant (soluble fraction) was then acetone precipitated by adding approximately 500 µl of acetone to each sample and leaving the samples at RT approximately 15 minutes; (6) each precipitate was resuspended in 50 µl of dH20+50 µl of 2X sample buffer; (7) the samples were heated at about 90° C. for 3-5 minutes, vortexed well, allowed to cool to RT; and, (8) the samples were centrifuged again for 5 minutes and the supernatants were transferred to clean eppendorf tubes.

The soluble fractions were then loaded (5-10 µl in each well) onto a 10 well, 1.0 mm NOVEX manufactured 12% Tris-Glycine SDS-PAGE and electrophoresed at about 120 volts for 1.5-2 hours. The resulting gels were either stained with Coomassie Blue or used for an immunoblot.

For the immunoblot, the gel was transferred and treated as previously described in Example 2 except a different detecting antibody was used. The antibody used for detection in this experiment was an anti-Fc antibody (Bethyl Laboratories, Inc.; Goat anti-Human IgG-Fc Fragment HRP conjugated #A80-104P) diluted 1:500,000. Relative yields were calculated using scanning densitometry as previously described.

D. Results

Figure 13A:
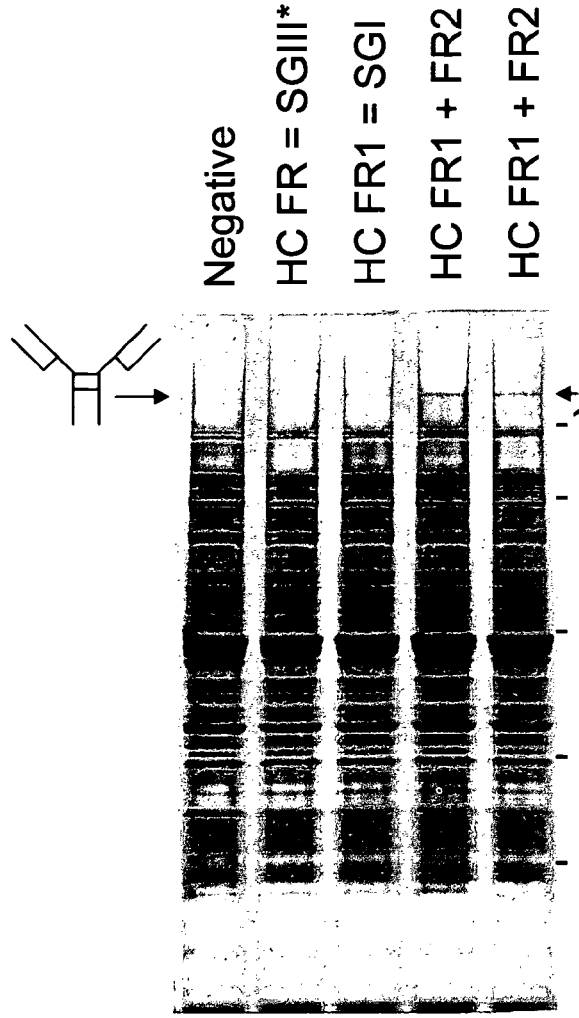
FIG. 13 shows the yield of assembled antibody products of anti-VEGF VNERK antibodies with modified framework regions. The samples were prepared under non-reducing conditions and run on a SDS PAGE gel. The gels were stained with Coomassie Blue (A) or detectably labeled anti-Fc antibody (B). Lane 1 is a negative control; Lane 2 is the anti-VEGF antibody VNERK with HC subgroup III framework residues, except for those changed as a part of humanization (HCFR=SGIII); lane 3 is anti-VEGF VNERK with HC FR1 residues from heavy chain subgroup I consensus sequence; lane 4 is anti-VEGF VNERK with HC FR1 and FR2 region residues from heavy chain subgroup I; and lane 5 is anti-VEGF VNERK antibody with HC FR1, FR2 and FR3 residues of heavy chain consensus sequence subgroup I.
Figure 13B:
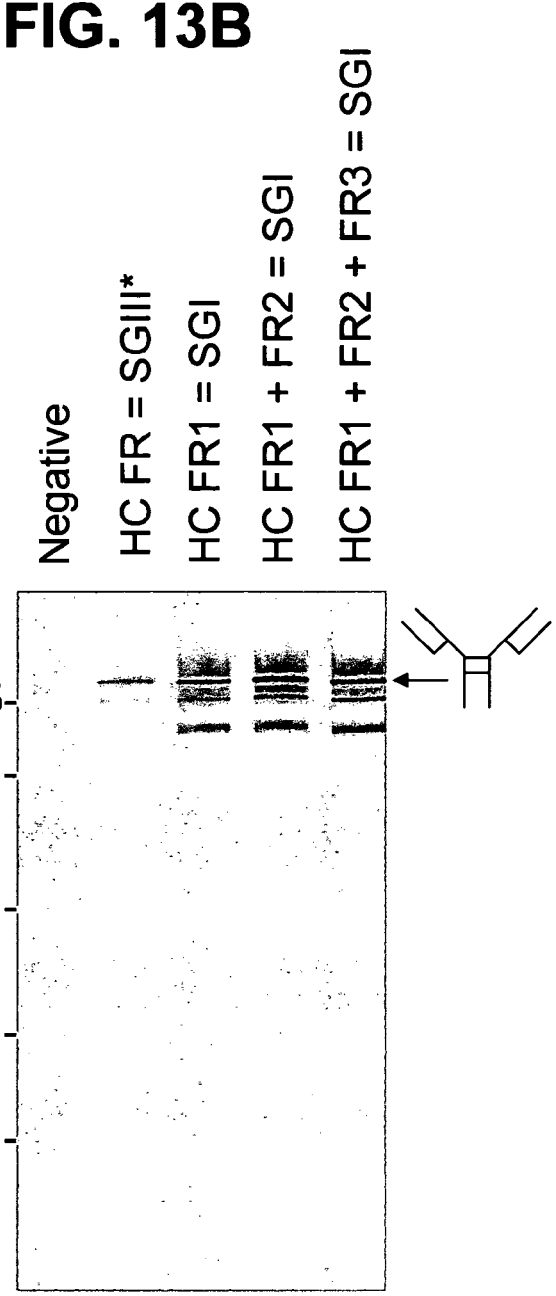

The effect of substitution of additional FR residues on antibody yield was examined. An antibody was constructed with both FR1 and FR2 region residue changes from human consensus subgroup III residues to the human consensus subgroup I residues. An antibody was also constructed with FR1, FR2, and FR3 changed to human consensus subgroup I. The results of the antibody yield are shown in FIG. 13. FIG. 13A shows a gel stained with Coomassie Blue and FIG. 13B shows the immunoblot results using an anti-Fc antibody. The results show that changing the FR sequences from the subgroup III consensus sequence to the subgroup I consensus sequence increased antibody yield. Scanning densitometry results are shown in Table 13.

TABLE 13

| Plasmid | Yield Coomassie Gel | antiFc Blot |
|---|---|---|
| pxVG11VNERK (SGIII, except for humanization changes) | Band not detected | 1 |
| pVKFR1-2 (FR1 = SGI) | 1* | 2.8 |
| pVKSGI.1.2 (FR1 + FR2 = SGI) | 1.9 | 3.2 |
| pVKSGI (FR1 + FR2 + FR3 = SGI) | 2.6 | 3.6 |

*Since the band for pxVG11VNERK was not detectable by Coomassie Blue staining, data was normalized to pVKFR1-2.

These results suggest that making changes in more than one framework region provides a greater increase in antibody yield over the increase demonstrated by changing only one framework region. Substitution of all three framework region residues with the selected subgroup consensus sequence resulted in about a 3.5 fold increase in antibody yield compared to the parent antibody anti-VEGF VNERK. This increase in antibody yield is most likely due to increased folding efficiency of the heavy chain. Since anti-VEGF VNERK is a humanized antibody, some of the FR region substitutions at the positions identified in accord with the methods of the invention were already made to improve antigen binding affinity. As a result, the improvement in yield seen with the subgroup I constructs may have been greater than about 3.5 fold if the changes to the starting subgroup III sequence had not already been made. The increase in yield may have been greater if the changes were made prior to humanization, i.e. starting with the chimeric xVEGF instead of the humanized xVEGF thereby going from a purely SGIII consensus sequence to a SGI consensus sequence in all four FRs. Additionally, starting with the chimeric antibody and making the substitutions to SGI, rather than SGIII, may have also significantly shortened the time required for humanization.

Example 8

Expression and Secretion of Anti-VEGF Antibodies from CHO Cells

In prokaryotic cell cultures, FR1 substitution of the subgroup III heavy chain with subgroup I heavy chain sequences in anti-VEGF antibodies increased assembled antibody yield. The anti-VEGF antibodies first generation wild-type with HC M34I, VNERK, and YO317 were tested to compare the effect of the same FR1 substitution on antibody secretion in mammalian cells. Specifically, the heavy chain FR1 sequence from Subgroup III was substituted with the heavy chain FR1 sequence from Subgroup I. Secretion levels of fully assembled antibody from a mammalian Chinese hamster ovary (CHO) cell line were measured by ELISA and by densitometry of immunoblots.

A. Preparation of Expression Vectors Encoding Anti-VEGF Antibodies with Modified FRs The heavy chain constructs were subcloned from the prokaryotic expression vectors, as described in Examples 2 and 6 into mammalian production vector SV40.PD. The vector contains a Simian Virus 40 (SV40) promoter and a puromycin and dihyrdrofolate reductase (DHFR) fusion gene for selection. In addition, the mammalian signal sequences used for antibody production were cloned into the vector. For this experiment, there were six different heavy chain constructs— $1^{st}$ Generation xVEGF SGI with HC M34I, $1^{st}$ Generation xVEGF SGIII with HC M34I, YO317 xVEGF SGI, YO317 xVEGF SGIII, and VNERK xVEGF SGI, and VNERK xVEGF SGIII.

In parallel, the light chain constructs from the prokaryotic expression vectors were subcloned into a pRK expression vector containing a Cytomegalovirus (CMV) promoter. The two light chain constructs were the M4 xVEGF light chain (normally coexpressed with the first generation wild-type xVEGF heavy chain) and the L4 xVEGF light chain (normally coexpressed with the Y0317 and VNERK xVEGF heavy chain). The light chain expression vectors also contained the aforementioned mammalian signal sequences used for antibody production.

B. Expression, Folding, and Secretion of Modified Anti-VEGF Antibodies

1. Transfection

The heavy chain constructs were co-transfected with either the M4 or L4 light chain constructs. Plasmids were transiently transfected into DP12 cells. DP12 cells have been described in U.S. Pat. No. 6,673,580, which is hereby incorporated by reference

2. ELISA

ELISA methods for quantitating full length antibody are known to those of skill in the art and have been published in U.S. Patent Application Publication 20030190317.

3. Immunoblot

Immuno blot analysis was performed according to methods well known in the art.

C. Results

The previously disclosed examples demonstrated that constructs with SGI FR1 consensus sequences had improved antibody yields over constructs with SGIII in the prokaryotic system. The yield of VNERK xVEGF with a SGI FR1 consensus sequence was 2.2±0.2-fold higher than VNERK constructs containing a SGIII FR1 consensus sequence. The yield of YO317 xVEGF with a SGI FR1 consensus sequence was 8.2±1.9-fold higher than YO317 constructs with a SGIII FR1 consensus sequence. Similarly, the 1st generation wild-type xVEGF had higher yields when SGI substitutions were made in the heavy chain at positions proximal to disulfide bonded cysteine residues. Whether the higher yields could be replicated in the mammalian cell culture system was tested.

The amounts of fully assembled antibodies secreted were measured by ELISA four days post-transfection. In the CHO cells, two of the three constructs with SGI FR1 consensus sequences had increased yield and secretion of assembled antibodies. The VNERK construct containing SGI sequence had approximately a 3.6 fold increase in secretion above the VNERK construct containing SGIII sequence. Similarly, the YO317 construct containing SGI sequence had approximately a 2.2 fold increase in secretion above the YO317 construct containing SGIII sequence. However, the 1st generation wild-type construct with M34I had approximately a 3.8-fold decrease in secretion when the SGI FR1 consensus sequence was substituted for the SGIII FR1 sequence. Coexpression of the M4 or L4 light chain did not affect the secretion levels of a particular construct. Immunoblot analysis of the CHO cell culture media and cell lysates confirmed the ELISA results. (data not shown)

TABLE 14

| Antibody Construct | Relative Secretion |
|---|---|
| VNERK SG1:VNERK SG3 | 3.6:1.0 |
| YO317 SG1:YO317 SG3 | 2.2:1.0 |
| 1st Gen SG1:1st Gen SG3 | 1.0:3.8 |

It is expected that some variation in results may occur when experiments are repeated. When the experiment was repeated, some differences were seen in the results but the trend was the same. The VNERK construct containing SGI sequence and the YO317 construct containing SGI sequence had increased yield and anti-VEGF 1st generation containing the SGI sequences had decreased yield.

The above results demonstrate that some antibodies modified with SGI sequences in accord with the methods of the invention are secreted from mammalian cells in greater quantities than antibodies containing SGIII sequences. Constructs modified in accord with the methods of the invention yield greater quantities of completely assembled antibodies in both the prokaryotic and mammalian cell cultures.

Although the foregoing refers to particular embodiments, it will be understood that the present invention is not so limited. It will occur to those of ordinary skill in the art that various modifications may be made to the disclosed embodiments without changing from the overall concept of the invention. All such modifications are intended to be within the scope of the invention. All references cited throughout the specification are hereby expressly incorporated by reference.

I claim:

1. A method for producing a recombinant antibody or antigen binding fragment thereof with improved yield from a host cell, comprising:
   (i) providing a nucleic acid encoding a non-human antibody or antigen binding fragment thereof made by a method comprising:
      (a) aligning a hypervariable region (HVR1) and/or a hypervariable region 2 (HVR2) of a heavy chain variable domain of a non-human antibody or antigen binding fragment thereof to corresponding HVR1 and/or HVR2 sequences of human subgroup variable domain consensus sequences;
      (b) selecting a human subgroup heavy chain variable domain consensus sequence that has a HVR1 and/or HVR2 amino acid sequence with the most sequence identity with the non-human HVR1 sequence and/or the non-human HVR2 sequence;
      (c) identifying at least one amino acid position in at least one framework region (FR) of the selected human subgroup variable domain consensus sequence that has a different amino acid residue than that of a corresponding position in a FR of the variable domain of the non-human antibody or antigen binding fragment thereof; and
      (d) substituting at least one amino acid in the FR of the non-human variable domain of the antibody or the antigen binding fragment thereof identified in step (i)(c) with the corresponding amino acid from the selected subgroup consensus sequence in step (b) to form a substituted FR in the non-human variable domain of the antibody or antigen binding fragment thereof; and
   (ii) expressing the non-human antibody or antigen binding fragment thereof of having at least one substitution in the FR in the host cell, wherein the non-human antibody or antigen binding fragment thereof having the at least one substitution in the FR has improved yield in a cell or a cell culture as compared to the corresponding unsubstituted antibody or antigen binding fragment thereof.

2. The method according to claim 1, wherein the non-human antibody or antigen binding fragment thereof to be substituted is selected from the group consisting of a humanized antibody, a chimeric antibody, a monoclonal antibody, a multispecific antibody, a diabody, or an antibody generated by phage display.

3. The method according to claim 2, wherein the non-human antigen binding fragment thereof is a Fab fragment, F(ab')$_2$ fragment, scFV fragment, sc(Fv)$_2$ fragment, a single arm antibody or single chain antibody.

4. The method according to claim 1, wherein the non-human antibody is an anti-vascular endothelial growth factor (VEGF) antibody.

5. The method according to claim 4, wherein the non-human antibody is a humanized antibody.

6. The method of claim 1, wherein the nuclei acid encoding the recombinant non-human antibody or antigen binding fragment thereof having at least one substitution in the FR is contained in an expression vector.

7. The method according to claim 1, wherein the host cell is a prokaryotic host cell.

8. The method according to claim 1, wherein the host cell is a mammalian cell.

9. The method according to claim 1, further comprising isolating the expressed non-human heavy chain variable domain having a substituted FR from the cell or cell culture.

10. The method according to claim 9, wherein the non-human variable domain is a heavy chain variable domain and the HVR1 amino acid sequence of the heavy chain variable domain of said antibody or antigen binding fragment thereof is GYTFTNYGIN (SEQ ID NO: 14) or GYDFTHYGMN (SEQ ID NO:18).

11. The method according to claim 1, wherein the non-human framework region to be substituted is selected from the group consisting of a FR1, a FR2, a FR3, a FR4 and a mixture thereof.

12. The method according to claim 11, wherein the human subgroup variable domain consensus sequence comprises a variable domain FR1 sequence that is selected from the group consisting of SEQ ID NO:1, SEQ ID NO:2 and SEQ ID NO:3.

13. The method according to claim 1, wherein the yield of the non-human antibody or antigen binding fragment thereof comprising the substituted FR is improved at least 2 fold compared to the corresponding unsubstituted antibody or antigen binding fragment thereof.

14. The method according to claim 13, wherein the yield of the non-human antibody or antigen binding fragment thereof comprising the substituted FR is improved at least 2 fold to 16 fold compared to the corresponding unsubstituted antibody or antigen binding fragment thereof.

15. The method of claim 1, wherein in step (d) two, three, four, five, six or seven amino acid positions in the non-human FR are substituted.

16. The method of claim 1, wherein the non-human antibody or antigen binding fragment thereof is an anti-vascular endothelial growth factor (VEGF) antibody or antigen binding fragment thereof comprising a heavy chain variable domain FR1 sequence of SEQ ID NO:3, wherein and one of the amino acid positions is position 6 or position 23 or both, and the other position is selected from the group consisting of position 1, 11, 13, 18, 19, and a mixture thereof, are substituted with the corresponding amino acid residues found in the heavy chain FR1 consensus sequence of SLO ID NO: 1.

17. The method of claim 16, wherein amino acid positions 6 and 23 are substituted.

18. The method of claim 16, wherein the amino acid positions at positions 1, 6, 11, 13, 18, 19, and 23 of the heavy chain FR1 are substituted.

19. The method of claim 1, wherein at least two of the different amino acid positions in the non-human FR are substituted.

20. The method of claim 19, wherein the substituted FR is FR1, FR2, or FR3.

21. The method of claim 1, wherein all of the amino acid positions that have a different amino acid as compared to the human consensus sequence in all framework regions (FRs) of the non-human variable region are substitute.

22. A method for preparing a humanized antibody or an antigen binding fragment thereof having an improved folding efficiency and yield when expressed in a host cell, comprising:
(a) preparing a humanized antibody or antigen binding fragment thereof comprising a variable domain comprising at least one substituted framework region (FR) sequence, wherein the variable domain is made by a method comprising:
(i) aligning a hypervariable region (HVR1) and/or a hypervariable region 2 (HVR2) of a heavy chain variable domain of a non-human antibody or antigen binding fragment thereof to corresponding HVR1 and/or HVR2 sequences of human subgroup variable domain consensus sequences;
(ii) selecting a human subgroup variable domain consensus sequence that has a HVR1 and/or HVR2 amino acid sequence with the most sequence identity with the non-human HVR1 sequence and/or the non-human HVR2 sequence;
(iii) identifying at least one amino acid position in at least one framework region (FR) of the human subgroup variable domain consensus sequence selected in step (ii) that has a different amino acid residue than that of a corresponding position in a FR of the variable domain or antigen binding fragment thereof of the non-human antibody; and p2 (iv) substituting at least one amino acid in the FR of the non-human variable domain or antigen binding fragment thereof identified in step (a)(iii) with the corresponding amino acid from the selected subgroup consensus sequence in step (a)(ii) to form a substituted FR non-human variable domain or antigen binding fragment thereof of the antibody,
wherein the substitution results in an antibody or antigen binding fragment thereof having an improved folding efficiency and yield when expressed in the host cell, and
(b) expressing said humanized antibody or antigen binding fragment thereof having at least one amino acid substitution in the FR in the host cell wherein the substitution results in an antibody or antigen binding fragment thereof having an improved folding efficiency and yield.

23. The method according to claim 22 wherein the non-human variable domain is a heavy chain variable domain and the HVR1 amino acid sequence of a heavy chain variable domain of the non-human antibody or antigen binding fragment thereof is GYTFTNYGIN (SEQ ID NO: 14) or GYDFTHYGMN (SEQ ID NO:18).

24. The method according to claim 22, wherein the FR is selected from the group consisting of a FR1, a FR2, a FR3, a FR4 and a mixture thereof.

25. The method according to claim 24, wherein the human subgroup variable domain consensus sequence comprises a heavy chain variable domain FR1 sequence that is selected from the group consisting of SEQ. ID NO: 1, SEQ ID NO:2andSEQ ID NO: 3.

26. The method of claim 22, wherein all of the different amino acid positions in the non-human FR identified in (a) (iii) are substituted.

27. The method of claim 22, wherein the host cell comprises an expression vector comprising the nuclei acid sequence that encodes the non-human antibody or antigen binding fragment thereof having substitution in the FR.

28. The method of claim 22, wherein the variable domain of the non-human antibody or antigen binding fragment thereof comprising the HVR1 and HVR2 and the selected FR substitution further comprises immunoglobulin constant domain to form a full-length heavy chain.

29. The method according claim 22, wherein the host cell is a prokaryotic host cell.

30. The method according to claim 22, wherein the host cell is a mammalian cell.

31. A method for improving the yield of an assembled non-human monoclonal antibody or antigen binding fragment thereof in a host cell, comprising:
   (a) aligning a hypervariable region 1 (HVR1) and/or a hypervariable 2 (HVR2) sequence of a heavy chain variable domain of the non-human monoclonal antibody to conesponding HVR1 and/or HVR2 sequences of human subgroup heavy chain variable domain consensus sequences,
   (b) selecting a human subgroup heavy chain variable domain consensus sequence that has the HVR1 and/or HVR2 amino acid sequence with the most sequence identity with the HVR1 and/or the HVR2 sequence of the heavy chain variable domain of the non human monoclonal antibody,
   (c) substituting at least one amino acid in at least one framework region (FR) of the non-human monoclonal antibody heavy chain variable domain for an amino acid residue found at a corresponding position from the selected human subgroup heavy chain variable domain consensus sequence to form at least one substituted FR, wherein the non-human monoclonal antibody or antigen binding fragment thereof with the substituted FR has improved folding efficiency and yield, in cell culture compared to the folding efficiency and yield of a corresponding unsubstituted antibody or antigen binding fragment thereof; and
   (d) expressing the non-human monoclonal antibody or antigen binding fragment thereof comprising the substituted FR in the host cell.

32. A method for improving the yield of a recombinant antibody or antigen binding fragment thereof expressed in a host cell, comprising:
   (a) selecting a human subgroup heavy chain variable domain consensus sequence by aligning a hypervariable region 1 (HVR1) and/or a hypervariable 2 (HVR2) sequence of a variable domain heavy chain variable domain of a non-human antibody or antigen binding fragment thereof to corresponding HVR1 and/or HVR2 sequences of human subgroup heavy chain variable domain consensus sequences, and selecting the human subgroup variable domain consensus sequence that has the HVR1 and/or HVR2 amino acid sequence with the most sequence identity with the HVR1 and/or HVR2 sequence of the variable domain of the non-human antibody or antigen binding fragment thereof,
   (b) substituting at least one amino acid residue the at least one framework region (FR) of the variable domain of the non-human antibody or antigen binding fragment thereof for the corresponding amino acid from the selected human subgroup variable domain consensus sequence to form a modified FR,
   wherein the recombinant antibody or antigen binding fragment thereof with the modified FR has improved folding efficiency and yield in cell culture compared to the folding efficiency and yield of a corresponding unmodified antibody or antigen binding fragment thereof; and
   (c) expressing the recombinant antibody or antigen binding fragment thereof with the modified FR in the host cell and recovering the recombinant antibody or antigen binding fragment thereof with the modified FR from the host cell.

33. The method according to claim 32, wherein the variable domain is a heavy chain variable domain and the HVR1 amino acid sequence of a heavy chain variable domain of the non-human antibody or antigen binding fragment thereof is GYTFTNYGIN (SEQ ID NO: 14) or GYDFTHYGMN (SEQ ID NO: 18).

34. The method of claim 33, wherein at least two amino acid positions that have a different amino acid in at least one FR are substituted with amino acids in the corresponding position from the selected human subgroup consensus sequence.

35. The method of claim 34, wherein the antibody or antibody binding fragment thereof is an anti-vascular endothelial growth factor (VEGF) antibody or an antigen binding fragment thereof comprising a heavy chain variable domain FR1 comprising the amino acid sequence of SEQ ID NO:3 and amino acid positions 1, 6 11, 13, 18, 19 and 23 of SEQ ID NO:3 are substituted with the corresponding amino acid found in SEQ ID NO: 1.

36. The method of claim 35, wherein amino acid positions 6 and 23 of the heavy chain FR1 of SEQ ID NO:3 are substituted with the corresponding amino acid found in SEQ ID NO: 1.

37. The method according to claim 31, wherein the host cell is a prokaryotic host cell.

38. The method according to claim 31, wherein the host cell is a mammalian cell.

39. The method according to claim 32, wherein the step (b) comprises substituting at least one amino acid residue in all of the FRs of the variable domain of the non-human antibody or antigen binding fragment thereof with the corresponding amino acid residues from the selected human subgroup heavy chain variable domain consensus sequence.

40. The method according to claim 31, wherein the framework region (FR) is selected from the group consisting of FR1, FR2, FR3, FR4 and a mixture thereof.

41. A method for improving the yield of antibody or antigen binding fragment thereof in a host cell or cell culture, comprising:
   a) expressing a nucleic acid encoding a variable domain of a non-human antibody or antigen binding fragment thereof comprising at least one substituted framework region (FR) in the host cell, wherein the substituted FR has: a substitution of at least one amino acids in the at least one FR with a different amino acid,
   wherein the amino acid residue or residues to be substituted is determined by aligning a hypervariable region 1 (HVR1) and/or hypervariable region HVR2 sequence of a heavy chain variable domain of the non-human antibody or antigen binding fragment thereof to corresponding HVR1 and/or HVR2 sequence of human subgroup variable domain consensus sequences, and selecting the amino acid found at the corresponding FR position of the human subgroup variable domain consensus sequence that has a HVR1 and/or HVR2 amino acid sequence with the most sequence identity with the HVR1 and/or HVR2 sequence of the non-human variable domain of the recombinant antibody or antigen binding fragment thereof, and b) recovering the antibody or antigen binding fragment thereof comprising the non-human variable domain comprising the said antibody or antigen binding fragment thereof having amino acid substitution in the FR has improved folding efficiency and yield in the cell or cell culture as compared to the folding efficiency and yield of an unsubstituted antibody or antigen binding fragment thereof.

42. The method according to claim 41, wherein: (a) the nucleic acid is contained in an expression vector, (b) the nucleic acid is operably linked to a promoter, (c) the method of (a) or (b), wherein the nucleic acid further comprises a heat stable enterotoxin sequence that can direct secretion to the periplasm, or (d) the method of any of (a) to (c), wherein the nucleic acid further comprises a terminator sequence.

43. The method according to claim 41, wherein the host cell is a prokaryotic host cell.

44. The method according to claim 41, wherein the host cell is a eukaryotic host cell.

45. A method for improving the yield of a non-human antibody, or antigen binding fragments thereof, in a host cell or cell culture comprising:

(a) comparing a hypervariable region 1 (HVR1) and/or hypervariable region 2 (HVR2) amino acid sequence of a heavy chain variable domain of the non-human antibody or antigen binding fragment thereof to a corresponding HVR1 and/or HVR2 amino acid sequence of each human heavy chain variable domain consensus sequence and selecting the human subgroup heavy chain variable domain consensus sequence that has the most sequence identity with the HVR1 and/or HVR2 sequence of the heavy chain variable domain of the non-human antibody or antigen binding fragment thereof;

(b) identifying at least one amino acid position in at least one framework region (FR) in the heavy chain variable domain of the non-human antibody or antigen binding fragment thereof, wherein the FR is selected from the group consisting of a FR1, a FR2, a FR3, a FR4 and a mixture thereof, wherein the amino acid position has a different amino acid than the amino acid at a corresponding position of the selected human subgroup heavy chain variable domain consensus sequence; and (c) substituting said amino acid identified in step (b), with the corresponding amino acid from the selected human heavy chain subgroup variable domain consensus sequence, to form a variable domain with a substituted FR; and (d) expressing the non-human antibody or antigen binding fragment thereof comprising the heavy chain variable domain with the substituted FR in the host cell or cell culture, and (e) recovering the antibody or antigen binding fragment thereof from the host cell or cell culture, wherein the non-human antibody or antigen binding fragment thereof with the substituted FR has improved yield in the host cell or cell culture compared to the folding efficiency and yield of a corresponding unsubstituted non-human antibody or antigen binding fragment thereof.

46. The method according to claim 45, wherein the non-human antibody is selected from the group consisting of a humanized antibody, a chimeric antibody, a monoclonal antibody, a multispecific antibody, a diabody, or an antibody generated by phage display.

47. The method according to claim 46, wherein the non-human antigen binding fragment thereof is a Fab fragment, F(ab')$_2$ fragment, scFV fragment, or sc(Fv)$_2$ fragment, single arm antibody, or single chain antibody.

48. The method according to claim 45, wherein the non-human antibody is an anti-VEGF antibody.

49. The method according to claim 48, wherein the non-human antibody is a humanized antibody.

50. The method of claim 45, wherein the variable domain of the non-human antibody or antigen binding fragment thereof further comprises immunoglobulin constant region domain to form a full-length heavy chain.

51. The method of claim 45, wherein the host cell comprises an expression vector comprising the nucleic acid sequence that encodes the antibody or antigen binding fragment thereof with the substitute FR.

52. The method of claim 51 further comprising recovering the full-length heavy chain or light chain from the cell or cell culture.

53. The method according to claim 52, wherein the host cell is a prokaryotic host cell.

54. The method according to claim 52, wherein the host cell is a mammalian cell.

55. The method according to claim 45, wherein the variable domain is a heavy chain variable domain and the HVR1 amino acid sequence is GYTFTNYGIN (SEQ ID NO: 14) or GYDFTHYGMN (SEQ ID NO:18).

56. The method according to claim 45, wherein the framework region is selected from the group consisting of FR1, FR2, FR3, and a mixture thereof.

57. The method according to claim 56, wherein the human subgroup FR consensus sequence is a heavy chain FR1 sequence that is selected from the group consisting of SEQ ID NO: 1, SEQ ID NO: 2 and SEQ ID NO: 3.

58. The method according to claim 45, wherein the yield of the antibody or antigen binding fragment thereof with the substituted FR is improved at least 2 fold compared to the corresponding unsubstituted antibody or antigen binding fragment thereof.

59. The method according to claim 58, wherein the yield of the antibody or antigen binding fragment thereof with the substituted FR is improved at least 2 fold to 16 fold compared to the corresponding unsubstituted antibody or antigen binding fragment thereof.

60. The method of claim 45, wherein at least two of the identified amino acid positions in at least one FR of the non-human antibody or antigen binding fragment thereof are: substituted with amino acids in the corresponding position of the selected human subgroup consensus sequence.

61. The method of claim 60, wherein the non-human antibody or antigen binding fragment thereof is an anti-vascular endothelial growth factor (VEGF) antibody or antigen binding fragment thereof that comprises a heavy chain variable domain FR1 comprising the amino acid sequence of SEQ ID NO:3, and the amino acid is position 6 or position 23 or both, and the other position is selected from the group consisting of position 1, 11, 13, 18, 19, and a mixture thereof of SEQ ID NO:3 are substituted with the corresponding amino acids from SEQ ID NO:1.

62. The method of claim 61 wherein amino acid positions 6 and 23 are substituted with the conesponding amino acids from SEQ ID NO: 1.

63. The method of claim 61, wherein amino acid position 1, 6, 11, 13, 18, 19 and 23 of the heavy chain FR1 are substituted with the corresponding amino acids from SEQ ID NO: 1.

64. The method of claim 45, wherein at least three of the identified amino acid positions in a FR are substituted with the amino acid in the corresponding position in the selected human subgroup consensus sequence.

65. The method of claim 64, wherein the FR is a FR1, a FR2, or a FR3.

66. The method of claim 45, wherein at least four of the identified amino acid positions in all FR are substituted with the amino acid in the corresponding position in the selected subgroup consensus sequence.

67. The method of claim 45 further comprising:

(a) comparing a hypervariable region 1 (HVR1) and/or hypervariable region 2 (HVR2) amino acid sequence of a light chain variable domain of a non-human antibody or antigen binding fragment thereof to a corresponding HVR1 and/or HVR2 amino acid sequence of a human subgroup light chain variable domain consensus sequence and selecting the human subgroup light chain variable domain consensus sequence that has the most sequence identity with the HVR1 and/or HVR2 sequence of the non-human light chain variable domain;

(b) identifying at least one amino acid position in at least one FR in the non-human light chain variable domain wherein the FR is selected from the group consisting of a FR1, a FR2, a FR3, a FR4 and a mixture thereof, wherein the amino acid position has a different amino acid than the amino acid at a corresponding position of the selected human subgroup light chain variable domain consensus sequence; and (c) (i) substituting at least one amino acid in the FR of the light chain variable domain of the non-human antibody or the antigen binding fragment thereof identified in step (b) with the corresponding amino acid from the selected subgroup consensus sequence to form a substituted FR in the light chain variable domain non-human antibody or antigen binding fragment thereof.

68. The method of claim 1, wherein the host cell is a prokaryotic cell or a eukaryotic cell.

69. The method of claim 68, wherein the host cell is a filamentous fungi or yeast cell, an insect cell, a mammalian cell or a bacterial cell.

70. The method of claim 69, wherein the host cell is an *Archaebacteria* or a *Eubacteria*, or a Gram-negative or a Gram-positive bacteria.

* * * * *

UNITED STATES PATENT AND TRADEMARK OFFICE
CERTIFICATE OF CORRECTION

| | | |
|---|---|---|
| PATENT NO. | : 7,575,893 B2 | Page 1 of 1 |
| APPLICATION NO. | : 10/764428 | |
| DATED | : August 18, 2009 | |
| INVENTOR(S) | : Simmons | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 150 days Delete the phrase "by 150 days" and insert -- by 135 days --

Signed and Sealed this

Fifteenth Day of June, 2010

David J. Kappos
*Director of the United States Patent and Trademark Office*

SEQUENCE LISTING

<160> NUMBER OF SEQ ID NOS: 33

<210> SEQ ID NO 1
<211> LENGTH: 25
<212> TYPE: PRT
<213> ORGANISM: Artificial Sequence
<220> FEATURE:
<223> OTHER INFORMATION: FR1 SGI

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 2
<211> LENGTH: 25
<212> TYPE: PRT
<213> ORGANISM: Artificial Sequence
<220> FEATURE:
<223> OTHER INFORMATION: FR1 SGII

<400> SEQUENCE: 2

-continued

```
Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 3
<211> LENGTH: 25
<212> TYPE: PRT
<213> ORGANISM: Artificial Sequence
<220> FEATURE:
<223> OTHER INFORMATION: FR1 SGIII

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 4
<211> LENGTH: 3300
<212> TYPE: DNA
<213> ORGANISM: Artificial Sequence
<220> FEATURE:
<223> OTHER INFORMATION: pxVG11VNERK

<400> SEQUENCE: 4
gaattcaact tctccatact ttggataagg aaatacagac atgaaaaatc tcattgctga      60
gttgttattt aagcttgccc aaaaagaaga agagtcgaat gaactgtgtg cgcaggtaga     120
agctttggag attatcgtca ctgcaatgct tcgcaatatg gcgcaaaatg accaacagcg     180
gttgattgat caggtagagg gggcgctgta cgaggtaaag cccgatgcca gcattcctga     240
cgacgatacg gagctgctgc gcgattacgt aaagaagtta ttgaagcatc ctcgtcagta     300
aaaagttaat cttttcaaca gctgtcataa agttgtcacg gccgagactt atagtcgctt     360 tgttttttatt ttttaatgta tttgtaacta gtacgcaagt tcacgtaaaa agggtatcta    420
gaattatgaa gagaatatc gcatttcttc ttgcatctat gttcgttttt tctattgcta      480
caaacgcgta cgctgatatc cagttgaccc agtccccgag ctccctgtcc gcctctgtgg     540
gcgatagggt caccatcacc tgcagcgcaa gtcaggatat tagcaactat ttaaactggt     600
atcaacagaa accaggaaaa gctccgaaag tactgattta cttcacctcc tctctccact     660
ctggagtccc ttctcgcttc tctggatccg gttctgggac ggatttcact ctgaccatca     720
gcagtctgca gccagaagac ttcgcaactt attactgtca acagtatagc accgtgccgt     780
ggacgtttgg acagggtacc aaggtggaga tcaaacgaac tgtggctgca ccatctgtct     840
tcatcttccc gccatctgat gagcagttga atctgaac tgcttctgtt gtgtgcctgc      900
tgaataactt ctatcccaga gaggccaaag tacagtggaa ggtggataac gccctccaat     960
cgggtaactc ccaggagagt gtcacagagc aggacagcaa ggacagcacc tacagcctca    1020
gcagcaccct gacgctgagc aaagcagact acgagaaaca caaagtctac gcctgcgaag    1080
tcacccatca gggcctgagc tcgcccgtca caaagagctt caacagggga gagtgttaat    1140
taaatcctct acgccggacg catcgtggcg agctcggtac ccgggatct aggcctaacg    1200 ctcggttgcc gccgggcgtt ttttattgtt gccgacgcgc atctcgaatg aactgtgtgc    1260
gcaggtagaa gctttggaga ttatcgtcac tgcaatgctt cgcaatatgg cgcaaaatga    1320
ccaacagcgg ttgattgatc aggtagaggg ggcgctgtac gaggtaaagc ccgatgccag    1380
cattcctgac gacgatacgg agctgctgcg cgattacgta aagaagttat tgaagcatcc    1440
```

-continued

```
tcgtcagtaa aaagttaatc ttttcaacag ctgtcataaa gttgtcacgg ccgagactta    1500
tagtcgcttt gtttttattt tttaatgtat ttgtaactag tacgcaagtt cacgtaaaaa    1560
gggtatctag aattatgaag aagaatatcg catttcttct tgcatctatg ttcgtttttt    1620
ctattgctac aaacgcgtac gctgaggttc agctggtgga gtctggcggt ggcctggtgc    1680
agccaggggg ctcactccgt ttgtcctgtg cagcttctgg ctataccttc accaactatg    1740
gtataaactg ggtccgtcag gccccgggta agggcctgga atgggttgga tggattaaca    1800
cctataccgg tgaaccgacc tatgctgcgg atttcaaacg tcgtttcact ttttctttag    1860
acacctccaa aagcacagca tacctgcaga tgaacagcct gcgcgctgag gacactgccg    1920
tctattactg tgcaaagtac cgcactatt atgtgaacga gcggaagagc cactggtatt     1980
tcgacgtctg gggtcaagga accctggtca ccgtctcctc ggcctccacc aagggcccat    2040
cggtcttccc cctggcaccc tcctccaaga gcacctctgg gggcacagcg gccctgggct    2100
gcctggtcaa ggactacttc cccgaaccgg tgacggtgtc gtggaactca ggcgccctga    2160
ccagcggcgt gcacaccttc ccggctgtcc tacagtcctc aggactctac tccctcagca    2220
gcgtggtgac tgtgccctct agcagcttgg gcacccagac ctacatctgc aacgtgaatc    2280
acaagcccag caacaccaag gtggacaaga agttgagcc caaatcttgt gacaaaactc      2340
acacatgccc accgtgccca gcacctgaac tcctgggggg accgtcagtc ttcctcttcc    2400
ccccaaaacc caaggacacc ctcatgatct cccggacccc tgaggtcaca tgcgtggtgg    2460
tggacgtgag ccacgaagac cctgaggtca agttcaactg gtacgtggac ggcgtggagg    2520
tgcataatgc caagacaaag ccgcgggagg agcagtacaa cagcacgtac cgtgtggtca    2580
gcgtcctcac cgtcctgcac caggactggc tgaatggcaa ggagtacaag tgcaaggtct    2640
ccaacaaagc cctcccagcc cccatcgaga aaaccatctc caaagccaaa gggcagcccc    2700
gagaaccaca ggtgtacacc ctgcccccat cccgggaaga gatgaccaag aaccaggtca    2760
gcctgacctg cctggtcaaa ggcttctatc ccagcgacat cgccgtggag tgggagagca    2820
atgggcagcc ggagaacaac tacaagacca cgcctcccgt gctggactcc gacggctcct    2880
tcttcctcta cagcaagctc accgtggaca agagcaggtg gcagcagggg aacgtcttct    2940
catgctccgt gatgcatgag gctctgcaca accactacac gcagaagagc ctctccctgt    3000
ctccgggtaa ataagcatgc gacggcccta gagtccctaa cgctcggttg ccgccgggcg    3060
ttttttattg ttaactcatg tttgacagct tatcatcgat aagctttaat gcggtagttt    3120
atcacagtta aattgctaac gcagtcaggc accgtgtatg aaatctaaca atgcgctcat    3180
cgtcatcctc ggcaccgtca ccctggatgc tgtaggcata ggcttggtta tgccggtact    3240
gccgggcctc ttgcgggata tcgtccattc cgacagcatc gccagtcact atggcgtgct    3300
```

<210> SEQ ID NO 5
<211> LENGTH: 670
<212> TYPE: PRT
<213> ORGANISM: Artificial Sequence
<220> FEATURE:
<223> OTHER INFORMATION: The first 214 amino acids are the light chain
      followed by the heavy chain beginning at position 215 (E).

<400> SEQUENCE: 5

```
Asp Ile Gln Leu Thr Gln Ser Pro Ser Ser Leu Ser Ala Ser Val Gly
1               5                  10                  15

Asp Arg Val Thr Ile Thr Cys Ser Ala Ser Gln Asp Ile Ser Asn Tyr
            20                  25                  30
```

```
Leu Asn Trp Tyr Gln Gln Lys Pro Gly Lys Ala Pro Lys Val Leu Ile
            35                  40                  45
Tyr Phe Thr Ser Ser Leu His Ser Gly Val Pro Ser Arg Phe Ser Gly
         50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Tyr Ser Thr Val Pro Trp
                 85                  90                  95
Thr Phe Gly Gln Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Glu Val Gln Leu Val Glu Ser Gly Gly Gly
    210                 215                 220
Leu Val Gln Pro Gly Gly Ser Leu Arg Leu Ser Cys Ala Ala Ser Gly
225                 230                 235                 240
Tyr Thr Phe Thr Asn Tyr Gly Ile Asn Trp Val Arg Gln Ala Pro Gly
                245                 250                 255
Lys Gly Leu Glu Trp Val Gly Trp Ile Asn Thr Tyr Thr Gly Glu Pro
            260                 265                 270
Thr Tyr Ala Ala Asp Phe Lys Arg Arg Phe Thr Phe Ser Leu Asp Thr
        275                 280                 285
Ser Lys Ser Thr Ala Tyr Leu Gln Met Asn Ser Leu Arg Ala Glu Asp
    290                 295                 300
Thr Ala Val Tyr Tyr Cys Ala Lys Tyr Pro His Tyr Tyr Val Asn Glu
305                 310                 315                 320
Arg Lys Ser His Trp Tyr Phe Asp Val Trp Gly Gln Gly Thr Leu Val
                325                 330                 335
Thr Val Ser Ser Ala Ser Thr Lys Gly Pro Ser Val Phe Pro Leu Ala
            340                 345                 350
Pro Ser Ser Lys Ser Thr Ser Gly Gly Thr Ala Ala Leu Gly Cys Leu
        355                 360                 365
Val Lys Asp Tyr Phe Pro Glu Pro Val Thr Val Ser Trp Asn Ser Gly
    370                 375                 380
Ala Leu Thr Ser Gly Val His Thr Phe Pro Ala Val Leu Gln Ser Ser
385                 390                 395                 400
Gly Leu Tyr Ser Leu Ser Ser Val Val Thr Val Pro Ser Ser Ser Leu
                405                 410                 415
Gly Thr Gln Thr Tyr Ile Cys Asn Val Asn His Lys Pro Ser Asn Thr
            420                 425                 430
Lys Val Asp Lys Lys Val Glu Pro Lys Ser Cys Asp Lys Thr His Thr
        435                 440                 445
```

```
Cys Pro Pro Cys Pro Ala Pro Glu Leu Leu Gly Gly Pro Ser Val Phe
    450                 455                 460
Leu Phe Pro Pro Lys Pro Lys Asp Thr Leu Met Ile Ser Arg Thr Pro
465                 470                 475                 480
Glu Val Thr Cys Val Val Val Asp Val Ser His Glu Asp Pro Glu Val
                485                 490                 495
Lys Phe Asn Trp Tyr Val Asp Gly Val Glu Val His Asn Ala Lys Thr
                500                 505                 510
Lys Pro Arg Glu Glu Gln Tyr Asn Ser Thr Tyr Arg Val Val Ser Val
            515                 520                 525
Leu Thr Val Leu His Gln Asp Trp Leu Asn Gly Lys Glu Tyr Lys Cys
    530                 535                 540
Lys Val Ser Asn Lys Ala Leu Pro Ala Pro Ile Glu Lys Thr Ile Ser
545                 550                 555                 560
Lys Ala Lys Gly Gln Pro Arg Glu Pro Gln Val Tyr Thr Leu Pro Pro
                565                 570                 575
Ser Arg Glu Glu Met Thr Lys Asn Gln Val Ser Leu Thr Cys Leu Val
                580                 585                 590
Lys Gly Phe Tyr Pro Ser Asp Ile Ala Val Glu Trp Glu Ser Asn Gly
            595                 600                 605
Gln Pro Glu Asn Asn Tyr Lys Thr Thr Pro Pro Val Leu Asp Ser Asp
    610                 615                 620
Gly Ser Phe Phe Leu Tyr Ser Lys Leu Thr Val Asp Lys Ser Arg Trp
625                 630                 635                 640
Gln Gln Gly Asn Val Phe Ser Cys Ser Val Met His Glu Ala Leu His
                645                 650                 655
Asn His Tyr Thr Gln Lys Ser Leu Ser Leu Ser Pro Gly Lys
            660                 665                 670

<210> SEQ ID NO 6
<211> LENGTH: 3300
<212> TYPE: DNA
<213> ORGANISM: Artificial Sequence
<220> FEATURE:
<223> OTHER INFORMATION: pxVG2AP11

<400> SEQUENCE: 6
gaattcaact tctccatact ttggataagg aaatacagac atgaaaaatc tcattgctga      60
gttgttattt aagcttgccc aaaaagaaga agagtcgaat gaactgtgtg cgcaggtaga     120
agctttggag attatcgtca ctgcaatgct tcgcaatatg gcgcaaaatg accaacagcg     180
gttgattgat caggtagagg gggcgctgta cgaggtaaag cccgatgcca gcattcctga     240
cgacgatacg gagctgctgc gcgattacgt aaagaagtta ttgaagcatc ctcgtcagta     300
aaaagttaat cttttcaaca gctgtcataa agttgtcacg gccgagactt atagtcgctt     360
tgtttttatt tttaatgta tttgtaacta gtacgcaagt tcacgtaaaa agggtatcta     420
gaattatgaa gaagaatatc gcatttcttc ttgcatctat gttcgttttt tctattgcta     480
caaacgcgta cgctgatatc cagttgaccc agtccccgag ctccctgtcc gcctctgtgg     540
gcgatagggt caccatcacc tgcagcgcaa gtcaggatat tagcaactat ttaaactggt     600
atcaacagaa accaggaaaa gctccgaaag tactgattta cttcacctcc tctctccact     660
ctggagtccc ttctcgcttc tctggatccg ttctgggac ggatttcact ctgaccatca     720
gcagtctgca gccagaagac ttcgcaactt attactgtca acagtatagc accgtgccgt     780
ggacgtttgg acagggtacc aaggtggaga tcaaacgaac tgtggctgca ccatctgtct     840
```

```
tcatcttccc gccatctgat gagcagttga aatctggaac tgcttctgtt gtgtgcctgc    900
tgaataactt ctatcccaga gaggccaaag tacagtggaa ggtggataac gccctccaat    960
cgggtaactc ccaggagagt gtcacagagc aggacagcaa ggacagcacc tacagcctca   1020
gcagcaccct gacgctgagc aaagcagact acgagaaaca caaagtctac gcctgcgaag   1080
tcacccatca gggcctgagc tcgcccgtca caaagagctt caacagggga gagtgttaat   1140
taaatcctct acgccggacg catcgtggcg agctcggtac ccggggatct aggcctaacg   1200
ctcggttgcc gccgggcgtt ttttattgtt gccgacgcgc atctcgaatg aactgtgtgc   1260
gcaggtagaa gctttggaga ttatcgtcac tgcaatgctt cgcaatatgg cgcaaaatga   1320
ccaacagcgg ttgattgatc aggtagaggg ggcgctgtac gaggtaaagc ccgatgccag   1380
cattcctgac gacgatacgg agctgctgcg cgattacgta aagaagttat tgaagcatcc   1440
tcgtcagtaa aaagttaatc ttttcaacag ctgtcataaa gttgtcacgg ccagacttga   1500
tagtcgcttt gttttatttt tttaatgtat ttgtaactag tacgcaagtt cacgtaaaaa   1560
gggtatctag aattatgaag aagaatatcg catttcttct tgcatctatg ttcgtttttt   1620
ctattgctac aaacgcgtac gctgaggttc agctggtgga gtctggcggt ggcctggtgc   1680
agccaggggg ctcactccgt ttgtcctgtg cagcttctgg ctacgacttc acgcactacg   1740
gtatgaactg ggtccgtcag gccccgggta agggcctgga atgggttgga tggattaaca   1800
cctataccgg tgaaccgacc tatgctgcgc atttcaaacg tcgtttcact ttttctttag   1860
acacctccaa aagcacagca tacctgcaga tgaacagcct gcgcgctgag gacactgccg   1920
tctattactg tgcaaagtac ccgtactatt atgggacgag ccactggtat ttcgacgtct   1980
ggggtcaagg aaccctggtc accgtctcct cggcctccac caagggccca tcggtcttcc   2040
ccctggcacc ctcctccaag agcacctctg ggggcacagc ggccctgggc tgcctggtca   2100
aggactactt ccccgaaccg gtgacggtgt cgtggaactc aggcgccctg accagcggcg   2160
tgcacacctt cccggctgtc ctacagtcct caggactcta ctccctcagc agcgtggtga   2220
ctgtgccctc tagcagcttg ggcacccaga cctacatctg caacgtgaat cacaagccca   2280
gcaacaccaa ggtggacaag aaagttgagc ccaaatcttg tgacaaaact cacacatgcc   2340
caccgtgccc agcacctgaa ctcctggggg gaccgtcagt cttcctcttc cccccaaaac   2400
ccaaggacac cctcatgatc tcccggaccc ctgaggtcac atgcgtggtg gtggacgtga   2460
gccacgaaga ccctgaggtc aagttcaact ggtacgtgga cggcgtggag gtgcataatg   2520
ccaagacaaa gccgcgggag gagcagtaca acagcacgta ccgtgtggtc agcgtcctca   2580
ccgtcctgca ccaggactgg ctgaatggca aggagtacaa gtgcaaggtc tccaacaaag   2640
ccctcccagc ccccatcgag aaaaccatct ccaaagccaa agggcagccc cgagaaccac   2700
aggtgtacac cctgccccca tcccgggaag agatgaccaa gaaccaggtc agcctgacct   2760
gcctggtcaa aggcttctat cccagcgaca tcgccgtgga gtgggagagc aatgggcagc   2820
cggagaacaa ctacaagacc acgcctcccg tgctggactc cgacggctcc ttcttcctct   2880
acagcaagct caccgtggac aagagcaggt ggcagcaggg gaacgtcttc tcatgctccg   2940
tgatgcatga ggctctgcac aaccactaca cgcagaagag cctctccctg tctccgggta   3000
aataagcatg cgacggccct agagtcccta acgctcggtt gccgccgggc gttttttatt   3060
gttaactcat gtttgacagc ttatcatcga taagctttaa tgcggtagtt tatcacagtt   3120
aaattgctaa cgcagtcagg caccgtgtat gaaatctaac aatgcgctca tcgtcatcct   3180
```

```
cggcaccgtc acctggatg ctgtaggcat aggcttggtt atgccggtac tgccgggcct   3240
cttgcgggat atcgtccatt ccgacagcat cgccagtcac tatggcgtgc tgctagcgct   3300
```

<210> SEQ ID NO 7
<211> LENGTH: 667
<212> TYPE: PRT
<213> ORGANISM: Artificial Sequence
<220> FEATURE:
<223> OTHER INFORMATION: Light chain begins at residue 1 (D); Heavy
      chain begins at residue 215 (E)

<400> SEQUENCE: 7

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Glu Val Gln Leu Val Glu Ser Gly Gly Gly
    210                 215                 220

Leu Val Gln Pro Gly Gly Ser Leu Arg Leu Ser Cys Ala Ala Ser Gly
225                 230                 235                 240

Tyr Asp Phe Thr His Tyr Gly Met Asn Trp Val Arg Gln Ala Pro Gly
                245                 250                 255

Lys Gly Leu Glu Trp Val Gly Trp Ile Asn Thr Tyr Thr Gly Glu Pro
            260                 265                 270

Thr Tyr Ala Ala Asp Phe Lys Arg Arg Phe Thr Phe Ser Leu Asp Thr
        275                 280                 285

Ser Lys Ser Thr Ala Tyr Leu Gln Met Asn Ser Leu Arg Ala Glu Asp
    290                 295                 300

Thr Ala Val Tyr Tyr Cys Ala Lys Tyr Pro Tyr Tyr Gly Thr Ser
305                 310                 315                 320

His Trp Tyr Phe Asp Val Trp Gly Gln Gly Thr Leu Val Thr Val Ser
                325                 330                 335

Ser Ala Ser Thr Lys Gly Pro Ser Val Phe Pro Leu Ala Pro Ser Ser
```

```
                340             345              350
Lys Ser Thr Ser Gly Gly Thr Ala Ala Leu Gly Cys Leu Val Lys Asp
            355                 360                 365
Tyr Phe Pro Glu Pro Val Thr Val Ser Trp Asn Ser Gly Ala Leu Thr
        370                 375                 380
Ser Gly Val His Thr Phe Pro Ala Val Leu Gln Ser Ser Gly Leu Tyr
385                 390                 395                 400
Ser Leu Ser Ser Val Val Thr Val Pro Ser Ser Ser Leu Gly Thr Gln
                405                 410                 415
Thr Tyr Ile Cys Asn Val Asn His Lys Pro Ser Asn Thr Lys Val Asp
            420                 425                 430
Lys Lys Val Glu Pro Lys Ser Cys Asp Lys Thr His Thr Cys Pro Pro
        435                 440                 445
Cys Pro Ala Pro Glu Leu Leu Gly Gly Pro Ser Val Phe Leu Phe Pro
    450                 455                 460
Pro Lys Pro Lys Asp Thr Leu Met Ile Ser Arg Thr Pro Glu Val Thr
465                 470                 475                 480
Cys Val Val Val Asp Val Ser His Glu Asp Pro Glu Val Lys Phe Asn
                485                 490                 495
Trp Tyr Val Asp Gly Val Glu Val His Asn Ala Lys Thr Lys Pro Arg
            500                 505                 510
Glu Glu Gln Tyr Asn Ser Thr Tyr Arg Val Val Ser Val Leu Thr Val
        515                 520                 525
Leu His Gln Asp Trp Leu Asn Gly Lys Glu Tyr Lys Cys Lys Val Ser
    530                 535                 540
Asn Lys Ala Leu Pro Ala Pro Ile Glu Lys Thr Ile Ser Lys Ala Lys
545                 550                 555                 560
Gly Gln Pro Arg Glu Pro Gln Val Tyr Thr Leu Pro Pro Ser Arg Glu
                565                 570                 575
Glu Met Thr Lys Asn Gln Val Ser Leu Thr Cys Leu Val Lys Gly Phe
            580                 585                 590
Tyr Pro Ser Asp Ile Ala Val Glu Trp Glu Ser Asn Gly Gln Pro Glu
        595                 600                 605
Asn Asn Tyr Lys Thr Thr Pro Pro Val Leu Asp Ser Asp Gly Ser Phe
    610                 615                 620
Phe Leu Tyr Ser Lys Leu Thr Val Asp Lys Ser Arg Trp Gln Gln Gly
625                 630                 635                 640
Asn Val Phe Ser Cys Ser Val Met His Glu Ala Leu His Asn His Tyr
                645                 650                 655
Thr Gln Lys Ser Leu Ser Leu Ser Pro Gly Lys
            660                 665

<210> SEQ ID NO 8
<211> LENGTH: 3300
<212> TYPE: DNA
<213> ORGANISM: Artificial Sequence
<220> FEATURE:
<223> OTHER INFORMATION: pVKFR1-2

<400> SEQUENCE: 8
gaattcaact ctccatact  ttggataagg aaatacagac atgaaaaatc tcattgctga      60
gttgttattt aagcttgccc aaaaagaaga agagtcgaat gaactgtgtg cgcaggtaga     120
agctttggag attatcgtca ctgcaatgct tcgcaatatg gcgcaaaatg accaacagcg     180
gttgattgat caggtagagg gggcgctgta cgaggtaaag cccgatgcca gcattcctga     240
```

-continued

```
cgacgatacg gagctgctgc gcgattacgt aaagaagtta ttgaagcatc ctcgtcagta        300
aaaagttaat cttttcaaca gctgtcataa agttgtcacg gccgagactt atagtcgctt        360
tgtttttatt ttttaatgta tttgtaacta gtacgcaagt tcacgtaaaa agggtatcta        420
gaattatgaa gaagaatatc gcatttcttc ttgcatctat gttcgttttt ctattgcta         480
caaacgcgta cgctgatatc cagttgaccc agtccccgag ctccctgtcc gcctctgtgg        540
gcgatagggt caccatcacc tgcagcgcaa gtcaggatat tagcaactat ttaaactggt        600
atcaacagaa accaggaaaa gctccgaaag tactgattta cttcacctcc tctctccact        660
ctggagtccc ttctcgcttc tctggatccg gttctgggac ggatttcact ctgaccatca        720
gcagtctgca gccagaagac ttcgcaactt attactgtca acagtatagc accgtgccgt        780
ggacgtttgg acagggtacc aaggtggaga tcaaacgaac tgtggctgca ccatctgtct        840
tcatcttccc gccatctgat gagcagttga atctggaac tgcttctgtt gtgtgcctgc         900
tgaataactt ctatcccaga gaggccaaag tacagtggaa ggtggataac gccctccaat        960
cgggtaactc ccaggagagt gtcacagagc aggacagcaa ggacagcacc tacagcctca       1020
gcagcaccct gacgctgagc aaagcagact acgagaaaca caaagtctac gcctgcgaag       1080
tcacccatca gggcctgagc tcgcccgtca caaagagctt caacagggga gagtgttaat       1140
taaatcctct acgccggacg catcgtggcg agctcggtac ccggggatct aggcctaacg       1200
ctcggttgcc gccgggcgtt ttttattgtt gccgacgcgc atctcgaatg aactgtgtgc       1260
gcaggtagaa gctttggaga ttatcgtcac tgcaatgctt cgcaatatgg cgcaaaatga       1320
ccaacagcgg ttgattgatc aggtagaggg ggcgctgtac gaggtaaagc ccgatgccag       1380
cattcctgac gacgatacgg agctgctgcg cgattacgta aagaagttat tgaagcatcc       1440
tcgtcagtaa aaagttaatc ttttcaacag ctgtcataaa gttgtcacgg ccgagactta       1500
tagtcgcttt gttttatttt ttaatgtat tgtaactag tacgcaagtt cacgtaaaaa         1560
gggtatctag aattatgaag aagaatatcg catttcttct tgcatctatg ttcgtttttt       1620
ctattgctac aaacgcgtac gctcaggttc agctggtgca gtctggcgca gaggtgaaaa       1680
agccaggggc ttcagttaaa gtatcctgta agcttctgg ctataccttc accaactatg        1740
gtataaactg ggtccgtcag gccccgggta agggcctgga atgggttgga tggattaaca       1800
cctataccgg tgaaccgacc tatgctgcgg atttcaaacg tcgtttcact ttttctttag       1860
acacctccaa aagcacagca tacctgcaga tgaacagcct gcgcgctgag gacactgccg       1920
tctattactg tgcaaagtac ccgcactatt atgtgaacga gcggaagagc cactggtatt       1980
tcgacgtctg gggtcaagga accctggtca ccgtctcctc ggcctccacc aagggcccat       2040
cggtcttccc cctggcaccc tcctccaaga gcacctctgg gggcacagcg gccctgggct       2100
gcctggtcaa ggactacttc cccgaaccgg tgacggtgtc gtggaactca ggcgccctga       2160
ccagcggcgt gcacaccttc ccggctgtcc tacagtcctc aggactctac tccctcagca       2220
gcgtggtgac tgtgccctct agcagcttgg gcacccagac ctacatctgc aacgtgaatc       2280
acaagcccag caacaccaag gtggacaaga agttgagcc caaatcttgt gacaaaactc        2340
acacatgccc accgtgccca gcacctgaac tcctgggggg accgtcagtc ttcctcttcc       2400
ccccaaaacc caaggacacc ctcatgatct cccggacccc tgaggtcaca tgcgtggtgg       2460
tggacgtgag ccacgaagac cctgaggtca agttcaactg gtacgtggac ggcgtggagg       2520
tgcataatgc caagacaaag ccgcgggagg agcagtacaa cagcacgtac cgtgtggtca       2580
```

-continued

```
gcgtcctcac cgtcctgcac caggactggc tgaatggcaa ggagtacaag tgcaaggtct    2640
ccaacaaagc cctcccagcc cccatcgaga aaaccatctc caaagccaaa gggcagcccc    2700
gagaaccaca ggtgtacacc ctgcccccat cccgggaaga gatgaccaag aaccaggtca    2760
gcctgacctg cctggtcaaa ggcttctatc ccagcgacat cgccgtggag tgggagagca    2820
atgggcagcc ggagaacaac tacaagacca cgcctcccgt gctggactcc gacggctcct    2880
tcttcctcta cagcaagctc accgtggaca agagcaggtg gcagcagggg aacgtcttct    2940
catgctccgt gatgcatgag gctctgcaca accactacac gcagaagagc ctctccctgt    3000
ctccgggtaa ataagcatgc gacggcccta gagtccctaa cgctcggttg ccgccgggcg    3060
ttttttattg ttaactcatg tttgacagct tatcatcgat aagctttaat gcggtagttt    3120
atcacagtta aattgctaac gcagtcaggc accgtgtatg aaatctaaca atgcgctcat    3180
cgtcatcctc ggcaccgtca ccctggatgc tgtaggcata ggcttggtta tgccggtact    3240
gccgggcctc ttgcgggata tcgtccattc cgacagcatc gccagtcact atggcgtgct    3300
```

<210> SEQ ID NO 9
<211> LENGTH: 670
<212> TYPE: PRT
<213> ORGANISM: Artificial Sequence
<220> FEATURE:
<223> OTHER INFORMATION: Light chain starts at residue 1 (D); Heavy chain starts at residue 215 (Q)

<400> SEQUENCE: 9

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Val Gln Ser Gly Ala Glu
    210                 215                 220

Val Lys Lys Pro Gly Ala Ser Val Lys Val Ser Cys Lys Ala Ser Gly
225                 230                 235                 240
```

-continued

```
Tyr Thr Phe Thr Asn Tyr Gly Ile Asn Trp Val Arg Gln Ala Pro Gly
                245                 250                 255

Lys Gly Leu Glu Trp Val Gly Trp Ile Asn Thr Tyr Thr Gly Glu Pro
            260                 265                 270

Thr Tyr Ala Ala Asp Phe Lys Arg Arg Phe Thr Phe Ser Leu Asp Thr
        275                 280                 285

Ser Lys Ser Thr Ala Tyr Leu Gln Met Asn Ser Leu Arg Ala Glu Asp
    290                 295                 300

Thr Ala Val Tyr Tyr Cys Ala Lys Tyr Pro His Tyr Val Asn Glu
305                 310                 315                 320

Arg Lys Ser His Trp Tyr Phe Asp Val Trp Gly Gln Gly Thr Leu Val
                325                 330                 335

Thr Val Ser Ser Ala Ser Thr Lys Gly Pro Ser Val Phe Pro Leu Ala
            340                 345                 350

Pro Ser Ser Lys Ser Thr Ser Gly Gly Thr Ala Ala Leu Gly Cys Leu
        355                 360                 365

Val Lys Asp Tyr Phe Pro Glu Pro Val Thr Val Ser Trp Asn Ser Gly
    370                 375                 380

Ala Leu Thr Ser Gly Val His Thr Phe Pro Ala Val Leu Gln Ser Ser
385                 390                 395                 400

Gly Leu Tyr Ser Leu Ser Ser Val Val Thr Val Pro Ser Ser Ser Leu
                405                 410                 415

Gly Thr Gln Thr Tyr Ile Cys Asn Val Asn His Lys Pro Ser Asn Thr
            420                 425                 430

Lys Val Asp Lys Lys Val Glu Pro Lys Ser Cys Asp Lys Thr His Thr
        435                 440                 445

Cys Pro Pro Cys Pro Ala Pro Glu Leu Leu Gly Gly Pro Ser Val Phe
    450                 455                 460

Leu Phe Pro Pro Lys Pro Lys Asp Thr Leu Met Ile Ser Arg Thr Pro
465                 470                 475                 480

Glu Val Thr Cys Val Val Val Asp Val Ser His Glu Asp Pro Glu Val
                485                 490                 495

Lys Phe Asn Trp Tyr Val Asp Gly Val Glu Val His Asn Ala Lys Thr
            500                 505                 510

Lys Pro Arg Glu Glu Gln Tyr Asn Ser Thr Tyr Arg Val Val Ser Val
        515                 520                 525

Leu Thr Val Leu His Gln Asp Trp Leu Asn Gly Lys Glu Tyr Lys Cys
    530                 535                 540

Lys Val Ser Asn Lys Ala Leu Pro Ala Pro Ile Glu Lys Thr Ile Ser
545                 550                 555                 560

Lys Ala Lys Gly Gln Pro Arg Glu Pro Gln Val Tyr Thr Leu Pro Pro
                565                 570                 575

Ser Arg Glu Glu Met Thr Lys Asn Gln Val Ser Leu Thr Cys Leu Val
            580                 585                 590

Lys Gly Phe Tyr Pro Ser Asp Ile Ala Val Glu Trp Glu Ser Asn Gly
        595                 600                 605

Gln Pro Glu Asn Asn Tyr Lys Thr Thr Pro Pro Val Leu Asp Ser Asp
    610                 615                 620

Gly Ser Phe Phe Leu Tyr Ser Lys Leu Thr Val Asp Lys Ser Arg Trp
625                 630                 635                 640

Gln Gln Gly Asn Val Phe Ser Cys Ser Val Met His Glu Ala Leu His
                645                 650                 655
```

```
          Asn His Tyr Thr Gln Lys Ser Leu Ser Leu Ser Pro Gly Lys
                      660                 665                 670

<210> SEQ ID NO 10
<211> LENGTH: 3300
<212> TYPE: DNA
<213> ORGANISM: Artificial Sequence
<220> FEATURE:
<223> OTHER INFORMATION: pVKSGII

<400> SEQUENCE: 10
gaattcaact  tctccatact  ttggataagg  aaatacagac  atgaaaaatc  tcattgctga     60
gttgttattt  aagcttgccc  aaaaagaaga  agagtcgaat  gaactgtgtg  cgcaggtaga    120
agctttggag  attatcgtca  ctgcaatgct  tcgcaatatg  gcgcaaaatg  accaacagcg    180
gttgattgat  caggtagagg  gggcgctgta  cgaggtaaag  cccgatgcca  gcattcctga    240
cgacgatacg  gagctgctgc  gcgattacgt  aaagaagtta  ttgaagcatc  ctcgtcagta    300
aaaagttaat  cttttcaaca  gctgtcataa  agttgtcacg  gccgagactt  atagtcgctt    360 tgttttatt   ttttaatgta  tttgtaacta  gtacgcaagt  tcacgtaaaa  agggtatcta    420
gaattatgaa  gaagaatatc  gcatttcttc  ttgcatctat  gttcgttttt  tctattgcta    480
caaacgcgta  cgctgatatc  cagttgaccc  agtccccgag  ctccctgtcc  gcctctgtgg    540
gcgatagggt  caccatcacc  tgcagcgcaa  gtcaggatat  tagcaactat  ttaaactggt    600
atcaacagaa  accaggaaaa  gctccgaaag  tactgattta  cttcacctcc  tctctccact    660
ctggagtccc  ttctcgcttc  tctggatccg  gttctgggac  ggatttcact  ctgaccatca    720
gcagtctgca  gccagaagac  ttcgcaactt  attactgtca  acagtatagc  accgtgccgt    780
ggacgtttgg  acagggtacc  aaggtggaga  tcaaacgaac  tgtggctgca  ccatctgtct    840
tcatcttccc  gccatctgat  gagcagttga  aatctggaac  tgcttctgtt  gtgtgcctgc    900
tgaataactt  ctatcccaga  gaggccaaag  tacagtggaa  ggtggataac  gccctccaat    960
cgggtaactc  ccaggagagt  gtcacagagc  aggacagcaa  ggacagcacc  tacagcctca   1020
gcagcaccct  gacgctgagc  aaagcagact  acgagaaaca  caaagtctac  gcctgcgaag   1080
tcacccatca  gggcctgagc  tcgcccgtca  caaagagctt  caacagggga  gagtgttaat   1140
taaatcctct  acgccggacg  catcgtggcg  agctcggtac  ccggggatct  aggcctaacg   1200
ctcggttgcc  gccgggcgtt  ttttattgtt  gccgacgcgc  atctcgaatg  aactgtgtgc   1260
gcaggtagaa  gctttggaga  ttatcgtcac  tgcaatgctt  cgcaatatgg  cgcaaaatga   1320
ccaacagcgg  ttgattgatc  aggtagaggg  ggcgctgtac  gaggtaaagc  ccgatgccag   1380
cattcctgac  gacgatacgg  agctgctgcg  cgattacgta  aagaagttat  tgaagcatcc   1440
tcgtcagtaa  aaagttaatc  ttttcaacag  ctgtcataaa  gttgtcacgg  ccgagactta   1500
tagtcgcttt  gttttattt   tttaatgtat  ttgtaactag  tacgcaagtt  cacgtaaaaa   1560
gggtatctag  aattatgaag  aagaatatcg  catttcttct  tgcatctatg  ttcgtttttt   1620
ctattgctac  aaacgcgtac  gctcaggttc  agctgcaaga  gtctggcccg  ggcctggtga   1680
aaccatctca  gactctctcc  ttgacttgta  ctgtttctgg  ctataccttc  accaactatg   1740
gtataaactg  ggtccgtcag  gccccgggta  agggcctgga  atgggttgga  tggattaaca   1800
cctataccgg  tgaaccgacc  tatgctgcgg  atttcaaacg  tcgtttcact  ttttctttag   1860
acacctccaa  aagcacagca  tacctgcaga  tgaacagcct  gcgcgctgag  gacactgccg   1920
tctattactg  tgcaaagtac  ccgcactatt  atgtgaacga  gcggaagagc  cactggtatt   1980
```

-continued

```
tcgacgtctg gggtcaagga accctggtca ccgtctcctc ggcctccacc aagggcccat   2040
cggtcttccc cctggcaccc tcctccaaga gcacctctgg gggcacagcg ccctgggct    2100 gcctggtcaa ggactacttc cccgaaccgg tgacggtgtc gtggaactca ggcgccctga   2160
ccagcggcgt gcacaccttc ccggctgtcc tacagtcctc aggactctac tccctcagca   2220
gcgtggtgac tgtgccctct agcagcttgg gcacccagac ctacatctgc aacgtgaatc   2280
acaagcccag caacaccaag gtggacaaga agttgagcc caaatcttgt gacaaaactc    2340
acacatgccc accgtgccca gcacctgaac tcctggggg accgtcagtc ttcctcttcc    2400
ccccaaaacc caaggacacc ctcatgatct cccggacccc tgaggtcaca tgcgtggtgg   2460
tggacgtgag ccacgaagac cctgaggtca agttcaactg gtacgtggac ggcgtggagg   2520
tgcataatgc caagacaaag ccgcgggagg agcagtacaa cagcacgtac cgtgtggtca   2580
gcgtcctcac cgtcctgcac caggactggc tgaatggcaa ggagtacaag tgcaaggtct   2640
ccaacaaagc cctcccagcc cccatcgaga aaaccatctc caaagccaaa gggcagcccc   2700
gagaaccaca ggtgtacacc ctgcccccat cccgggaaga gatgaccaag aaccaggtca   2760
gcctgacctg cctggtcaaa ggcttctatc ccagcgacat cgccgtggag tgggagagca   2820
atgggcagcc ggagaacaac tacaagacca cgcctcccgt gctggactcc gacggctcct   2880
tcttcctcta cagcaagctc accgtggaca agagcaggtg gcagcagggg aacgtcttct   2940
catgctccgt gatgcatgag gctctgcaca accactacac gcagaagagc ctctccctgt   3000
ctccgggtaa ataagcatgc gacggcccta gagtccctaa cgctcggttg ccgccgggcg   3060
ttttttattg ttaactcatg tttgacagct tatcatcgat aagctttaat gcggtagttt   3120
atcacagtta aattgctaac gcagtcaggc accgtgtatg aaatctaaca atgcgctcat   3180
cgtcatcctc ggcaccgtca ccctggatgc tgtaggcata ggcttggtta tgccggtact   3240
gccgggcctc ttgcgggata tcgtccattc cgacagcatc gccagtcact atggcgtgct   3300
```

<210> SEQ ID NO 11
<211> LENGTH: 670
<212> TYPE: PRT
<213> ORGANISM: Artificial Sequence
<220> FEATURE:
<223> OTHER INFORMATION: Light chain starts at residue 1 (D); Heavy
      chain starts at residue 215 (Q)

<400> SEQUENCE: 11

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gln Val Gln Leu Gln Glu Ser Gly Pro Gly
210                 215                 220

Leu Val Lys Pro Ser Gln Thr Leu Ser Leu Thr Cys Thr Val Ser Gly
225                 230                 235                 240

Tyr Thr Phe Thr Asn Tyr Gly Ile Asn Trp Val Arg Gln Ala Pro Gly
                245                 250                 255

Lys Gly Leu Glu Trp Val Gly Trp Ile Asn Thr Tyr Thr Gly Glu Pro
            260                 265                 270

Thr Tyr Ala Ala Asp Phe Lys Arg Arg Phe Thr Phe Ser Leu Asp Thr
        275                 280                 285

Ser Lys Ser Thr Ala Tyr Leu Gln Met Asn Ser Leu Arg Ala Glu Asp
290                 295                 300

Thr Ala Val Tyr Tyr Cys Ala Lys Tyr Pro His Tyr Tyr Val Asn Glu
305                 310                 315                 320

Arg Lys Ser His Trp Tyr Phe Asp Val Trp Gly Gln Gly Thr Leu Val
                325                 330                 335

Thr Val Ser Ser Ala Ser Thr Lys Gly Pro Ser Val Phe Pro Leu Ala
            340                 345                 350

Pro Ser Ser Lys Ser Thr Ser Gly Gly Thr Ala Ala Leu Gly Cys Leu
        355                 360                 365

Val Lys Asp Tyr Phe Pro Glu Pro Val Thr Val Ser Trp Asn Ser Gly
370                 375                 380

Ala Leu Thr Ser Gly Val His Thr Phe Pro Ala Val Leu Gln Ser Ser
385                 390                 395                 400

Gly Leu Tyr Ser Leu Ser Ser Val Val Thr Val Pro Ser Ser Ser Leu
                405                 410                 415

Gly Thr Gln Thr Tyr Ile Cys Asn Val Asn His Lys Pro Ser Asn Thr
            420                 425                 430

Lys Val Asp Lys Lys Val Glu Pro Lys Ser Cys Asp Lys Thr His Thr
        435                 440                 445

Cys Pro Pro Cys Pro Ala Pro Glu Leu Leu Gly Gly Pro Ser Val Phe
450                 455                 460

Leu Phe Pro Pro Lys Pro Lys Asp Thr Leu Met Ile Ser Arg Thr Pro
465                 470                 475                 480

Glu Val Thr Cys Val Val Val Asp Val Ser His Glu Asp Pro Glu Val
                485                 490                 495

Lys Phe Asn Trp Tyr Val Asp Gly Val Glu Val His Asn Ala Lys Thr
            500                 505                 510

Lys Pro Arg Glu Glu Gln Tyr Asn Ser Thr Tyr Arg Val Val Ser Val
        515                 520                 525

Leu Thr Val Leu His Gln Asp Trp Leu Asn Gly Lys Glu Tyr Lys Cys
530                 535                 540

Lys Val Ser Asn Lys Ala Leu Pro Ala Pro Ile Glu Lys Thr Ile Ser
```

-continued

```
              545                 550                 555                 560
Lys Ala Lys Gly Gln Pro Arg Glu Pro Gln Val Tyr Thr Leu Pro Pro
                565                 570                 575
Ser Arg Glu Glu Met Thr Lys Asn Gln Val Ser Leu Thr Cys Leu Val
                580                 585                 590
Lys Gly Phe Tyr Pro Ser Asp Ile Ala Val Glu Trp Glu Ser Asn Gly
                595                 600                 605
Gln Pro Glu Asn Asn Tyr Lys Thr Thr Pro Pro Val Leu Asp Ser Asp
            610                 615                 620
Gly Ser Phe Phe Leu Tyr Ser Lys Leu Thr Val Asp Lys Ser Arg Trp
625                 630                 635                 640
Gln Gln Gly Asn Val Phe Ser Cys Ser Val Met His Glu Ala Leu His
                645                 650                 655
Asn His Tyr Thr Gln Lys Ser Leu Ser Leu Ser Pro Gly Lys
                660                 665                 670
```

<210> SEQ ID NO 12
<211> LENGTH: 3300
<212> TYPE: DNA
<213> ORGANISM: Artificial Sequence
<220> FEATURE:
<223> OTHER INFORMATION: pYOFR1-2

<400> SEQUENCE: 12

```
gaattcaact tctccatact ttggataagg aaatacagac atgaaaaatc tcattgctga     60
gttgttattt aagcttgccc aaaaagaaga agagtcgaat gaactgtgtg cgcaggtaga    120
agctttggag attatcgtca ctgcaatgct tcgcaatatg gcgcaaaatg accaacagcg    180
gttgattgat caggtagagg gggcgctgta cgaggtaaag cccgatgcca gcattcctga    240
cgacgatacg gagctgctgc gcgattacgt aaagaagtta tgaagcatc ctcgtcagta    300
aaaagttaat cttttcaaca gctgtcataa agttgtcacg gccgagactt atagtcgctt    360
tgtttttatt ttttaatgta tttgtaacta gtacgcaagt tcacgtaaaa agggtatcta    420
gaattatgaa gaagaatatc gcatttcttc ttgcatctat gttcgttttt tctattgcta    480
caaacgcgta cgctgatatc cagttgaccc agtccccgag ctccctgtcc gcctctgtgg    540
gcgatagggt caccatcacc tgcagcgcaa gtcaggatat tagcaactat ttaaactggt    600
atcaacagaa accaggaaaa gctccgaaag tactgattta cttcacctcc tctctccact    660
ctggagtccc ttctcgcttc tctggatccg gttctgggac ggatttcact ctgaccatca    720
gcagtctgca gccagaagac ttcgcaactt attactgtca acagtatagc accgtgccgt    780
ggacgtttgg acagggtacc aaggtggaga tcaaacgaac tgtggctgca ccatctgtct    840
tcatcttccc gccatctgat gagcagttga aatctggaac tgcttctgtt gtgtgcctgc    900
tgaataactt ctatcccaga gaggccaaag tacagtggaa ggtggataac gccctccaat    960
cgggtaactc ccaggagagt gtcacagagc aggacagcaa ggacagcacc tacagcctca   1020
gcagcaccct gacgctgagc aaagcagact acgagaaaca caaagtctac gcctgcgaag   1080
tcacccatca gggcctgagc tcgcccgtca caaagagctt caacagggga gagtgttaat   1140
taaatcctct acgccggacg catcgtggcg agctcggtac ccggggatct aggcctaacg   1200
ctcggttgcc gccgggcgtt ttttattgtt gccgacgcgc atctcgaatg aactgtgtgc   1260
gcaggtagaa gctttggaga ttatcgtcac tgcaatgctt cgcaatatgg cgcaaaatga   1320
ccaacagcgg ttgattgatc aggtagaggg ggcgctgtac gaggtaaagc ccgatgccag   1380
```

| | |
|---|---|
| cattcctgac dacgatacgg agctgctgcg cgattacgta aagaagttat tgaagcatcc | 1440 |
| tcgtcagtaa aaagttaatc ttttcaacag ctgtcataaa gttgtcacgg ccgagactta | 1500 |
| tagtcgcttt gttttttattt tttaatgtat ttgtaactag tacgcaagtt cacgtaaaaa | 1560 |
| gggtatctag aattatgaag aagaatatcg catttcttct tgcatctatg ttcgtttttt | 1620 |
| ctattgctac aaacgcgtac gctcaggttc agctggtgca gtctggcgca gaggtgaaaa | 1680 |
| agccagggc ttcagttaaa gtatcctgta agcttctgg ctacgacttc acgcactacg | 1740 |
| gtatgaactg ggtccgtcag gccccgggta agggcctgga atgggttgga tggattaaca | 1800 |
| cctataccgg tgaaccgacc tatgctgcgg atttcaaacg tcgtttcact ttttctttag | 1860 |
| acacctccaa aagcacagca tacctgcaga tgaacagcct gcgcgctgag gacactgccg | 1920 |
| tctattactg tgcaaagtac ccgtactatt atgggacgag ccactggtat ttcgacgtct | 1980 |
| ggggtcaagg aaccctggtc accgtctcct cggcctccac caagggccca tcggtcttcc | 2040 |
| ccctggcacc ctcctccaag agcacctctg ggggcacagc ggccctgggc tgcctggtca | 2100 |
| aggactactt ccccgaaccg gtgacggtgt cgtggaactc aggcgccctg accagcggcg | 2160 |
| tgcacacctt cccggctgtc ctacagtcct caggactcta ctccctcagc agcgtggtga | 2220 |
| ctgtgccctc tagcagcttg ggcacccaga cctacatctg caacgtgaat cacaagccca | 2280 |
| gcaacaccaa ggtggacaag aaagttgagc ccaaatcttg tgacaaaact cacacatgcc | 2340 |
| caccgtgccc agcacctgaa ctcctggggg gaccgtcagt cttcctcttc cccccaaaac | 2400 |
| ccaaggacac cctcatgatc tcccggaccc ctgaggtcac atgcgtggtg gtggacgtga | 2460 |
| gccacgaaga ccctgaggtc aagttcaact ggtacgtgga cggcgtggag gtgcataatg | 2520 |
| ccaagacaaa gccgcgggag gagcagtaca acagcacgta ccgtgtggtc agcgtcctca | 2580 |
| ccgtcctgca ccaggactgg ctgaatggca aggagtacaa gtgcaaggtc tccaacaaag | 2640 |
| ccctcccagc ccccatcgag aaaaccatct ccaaagccaa agggcagccc cgagaaccac | 2700 |
| aggtgtacac cctgccccca tcccgggaag agatgaccaa gaaccaggtc agcctgacct | 2760 |
| gcctggtcaa aggcttctat cccagcgaca tcgccgtgga gtgggagagc aatgggcagc | 2820 |
| cggagaacaa ctacaagacc acgcctcccg tgctggactc cgacggctcc ttcttcctct | 2880 |
| acagcaagct caccgtggac aagagcaggt ggcagcaggg gaacgtcttc tcatgctccg | 2940 |
| tgatgcatga ggctctgcac aaccactaca cgcagaagag cctctccctg tctccgggta | 3000 |
| aataagcatg cgacggccct agagtcccta acgctcggtt gccgccgggc gttttttatt | 3060 |
| gttaactcat gtttgacagc ttatcatcga taagctttaa tgcggtagtt tatcacagtt | 3120 |
| aaattgctaa cgcagtcagg caccgtgtat gaaatctaac aatgcgctca tcgtcatcct | 3180 |
| cggcaccgtc accctggatg ctgtaggcat aggcttggtt atgccggtac tgccgggcct | 3240 |
| cttgcgggat atcgtccatt ccgacagcat cgccagtcac tatggcgtgc tgctagcgct | 3300 |

<210> SEQ ID NO 13
<211> LENGTH: 667
<212> TYPE: PRT
<213> ORGANISM: Artificial Sequence
<220> FEATURE:
<223> OTHER INFORMATION: Light chain starts at residue 1 (D); Heavy
      chain starts at residue 215 (Q)

<400> SEQUENCE: 13

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr

-continued

```
                20                  25                  30
Leu Asn Trp Tyr Gln Gln Lys Pro Gly Lys Ala Pro Lys Val Leu Ile
                35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
                130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys Gln Val Gln Leu Val Gln Ser Gly Ala Glu
                210                 215                 220

Val Lys Lys Pro Gly Ala Ser Val Lys Val Ser Cys Lys Ala Ser Gly
225                 230                 235                 240

Tyr Asp Phe Thr His Tyr Gly Met Asn Trp Val Arg Gln Ala Pro Gly
                245                 250                 255

Lys Gly Leu Glu Trp Val Gly Trp Ile Asn Thr Tyr Thr Gly Glu Pro
                260                 265                 270

Thr Tyr Ala Ala Asp Phe Lys Arg Arg Phe Thr Phe Ser Leu Asp Thr
                275                 280                 285

Ser Lys Ser Thr Ala Tyr Leu Gln Met Asn Ser Leu Arg Ala Glu Asp
                290                 295                 300

Thr Ala Val Tyr Tyr Cys Ala Lys Tyr Pro Tyr Tyr Gly Thr Ser
305                 310                 315                 320

His Trp Tyr Phe Asp Val Trp Gly Gln Gly Thr Leu Val Thr Val Ser
                325                 330                 335

Ser Ala Ser Thr Lys Gly Pro Ser Val Phe Pro Leu Ala Pro Ser Ser
                340                 345                 350

Lys Ser Thr Ser Gly Gly Thr Ala Ala Leu Gly Cys Leu Val Lys Asp
                355                 360                 365

Tyr Phe Pro Glu Pro Val Thr Val Ser Trp Asn Ser Gly Ala Leu Thr
                370                 375                 380

Ser Gly Val His Thr Phe Pro Ala Val Leu Gln Ser Ser Gly Leu Tyr
385                 390                 395                 400

Ser Leu Ser Ser Val Val Thr Val Pro Ser Ser Ser Leu Gly Thr Gln
                405                 410                 415

Thr Tyr Ile Cys Asn Val Asn His Lys Pro Ser Asn Thr Lys Val Asp
                420                 425                 430

Lys Lys Val Glu Pro Lys Ser Cys Asp Lys Thr His Thr Cys Pro Pro
                435                 440                 445
```

```
Cys Pro Ala Pro Glu Leu Leu Gly Gly Pro Ser Val Phe Leu Phe Pro
    450                 455                 460

Pro Lys Pro Lys Asp Thr Leu Met Ile Ser Arg Thr Pro Glu Val Thr
465                 470                 475                 480

Cys Val Val Val Asp Val Ser His Glu Asp Pro Glu Val Lys Phe Asn
                485                 490                 495

Trp Tyr Val Asp Gly Val Glu Val His Asn Ala Lys Thr Lys Pro Arg
            500                 505                 510

Glu Glu Gln Tyr Asn Ser Thr Tyr Arg Val Val Ser Val Leu Thr Val
        515                 520                 525

Leu His Gln Asp Trp Leu Asn Gly Lys Glu Tyr Lys Cys Lys Val Ser
    530                 535                 540

Asn Lys Ala Leu Pro Ala Pro Ile Glu Lys Thr Ile Ser Lys Ala Lys
545                 550                 555                 560

Gly Gln Pro Arg Glu Pro Gln Val Tyr Thr Leu Pro Pro Ser Arg Glu
                565                 570                 575

Glu Met Thr Lys Asn Gln Val Ser Leu Thr Cys Leu Val Lys Gly Phe
            580                 585                 590

Tyr Pro Ser Asp Ile Ala Val Glu Trp Glu Ser Asn Gly Gln Pro Glu
        595                 600                 605

Asn Asn Tyr Lys Thr Thr Pro Pro Val Leu Asp Ser Asp Gly Ser Phe
    610                 615                 620

Phe Leu Tyr Ser Lys Leu Thr Val Asp Lys Ser Arg Trp Gln Gln Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Pro Gly Lys
            660                 665

<210> SEQ ID NO 14
<211> LENGTH: 10
<212> TYPE: PRT
<213> ORGANISM: Artificial Sequence
<220> FEATURE:
<223> OTHER INFORMATION: HVR1 residues 26-35

<400> SEQUENCE: 14

Gly Tyr Thr Phe Thr Asn Tyr Gly Ile Asn
1               5                   10

<210> SEQ ID NO 15
<211> LENGTH: 10
<212> TYPE: PRT
<213> ORGANISM: Artificial Sequence
<220> FEATURE:
<223> OTHER INFORMATION: SGI consensus sequence

<400> SEQUENCE: 15

Gly Tyr Thr Phe Thr Ser Tyr Ala Ile Ser
1               5                   10

<210> SEQ ID NO 16
<211> LENGTH: 11
<212> TYPE: PRT
<213> ORGANISM: Artificial Sequence
<220> FEATURE:
<223> OTHER INFORMATION: SGII consensus sequence

<400> SEQUENCE: 16
```

Gly Gly Ser Val Ser Ser Tyr Trp Ser Trp Asn
1               5                   10

<210> SEQ ID NO 17
<211> LENGTH: 10
<212> TYPE: PRT
<213> ORGANISM: Artificial Sequence
<220> FEATURE:
<223> OTHER INFORMATION: SGIII consensus sequence

<400> SEQUENCE: 17

Gly Phe Thr Phe Ser Ser Tyr Ala Met Ser
1               5                   10

<210> SEQ ID NO 18
<211> LENGTH: 10
<212> TYPE: PRT
<213> ORGANISM: Artificial Sequence
<220> FEATURE:
<223> OTHER INFORMATION: YO317 VH HVR1 residues 26-35

<400> SEQUENCE: 18

Gly Tyr Asp Phe Thr His Tyr Gly Met Asn
1               5                   10

<210> SEQ ID NO 19
<211> LENGTH: 11
<212> TYPE: PRT
<213> ORGANISM: Artificial Sequence
<220> FEATURE:
<223> OTHER INFORMATION: E25 VH HVR1 residues 26-35

<400> SEQUENCE: 19

Gly Tyr Ser Ile Thr Ser Gly Tyr Ser Trp Asn
1               5                   10

<210> SEQ ID NO 20
<211> LENGTH: 3300
<212> TYPE: DNA
<213> ORGANISM: Artificial Sequence
<220> FEATURE:
<223> OTHER INFORMATION: E25 in pE25-11

<400> SEQUENCE: 20
gaattcaact tctccatact ttggataagg aaatacagac atgaaaaatc tcattgctga      60
gttgttattt aagcttgccc aaaaagaaga agagtcgaat gaactgtgtg cgcaggtaga     120
agctttggag attatcgtca ctgcaatgct tcgcaatatg gcgcaaaatg accaacagcg     180
gttgattgat caggtagagg gggcgctgta cgaggtaaag cccgatgcca gcattcctga     240
cgacgatacg gagctgctgc gcgattacgt aaagaagtta ttgaagcatc ctcgtcagta     300
aaaagttaat cttttcaaca gctgtcataa agttgtcacg gccgagactt atagtcgctt     360 tgttttatt ttaatgta tttgtaacta gtacgcaagt tcacgtaaaa agggtatcta     420
gaattatgaa gaagaatatc gcatttcttc ttgcatctat gttcgttttt tctattgcta     480
caaacgcgta cgctgatatc cagctgaccc agtccccgag ctcccgtcc gcctctgtgg     540 gcgatagggt caccatcacc tgccgtgcca gtcagagcgt cgattacgat ggtgatagct     600
acatgaactg gtatcaacag aaaccaggaa agctccgaa actactgatt tacgcggcct     660
cgtacctgga gtctggagtc ccttctcgct tctctggatc cggttctggg acggatttca     720
ctctgaccat cagcagtctg cagccggaag acttcgcaac ttattactgt cagcaaagtc     780
acgaggatcc gtacacattt ggacagggta ccaaggtgga gatcaaacga actgtggctg     840

```
caccatctgt cttcatcttc ccgccatctg atgagcagtt gaaatctgga actgcctctg      900
ttgtgtgcct gctgaataac ttctatccca gagaggccaa agtacagtgg aaggtggata      960
acgccctcca atcgggtaac tcccaggaga gtgtcacaga gcaggacagc aaggacagca     1020
cctacagcct cagcagcacc ctgacgctga gcaaagcaga ctacgagaaa cacaaagtct     1080
acgcctgcga agtcacccat cagggcctga gctcgcccgt cacaaagagc ttcaacaggg     1140
gagagtgtta attaaatcct ctacgccgga cgcatcgtgg cgagctcggt acccggggat     1200
ctaggcctaa cgctcggttg ccgccggggcg ttttttattg ttgccgacgc gcatctcgaa     1260
tgaactgtgt gcgcaggtag aagctttgga gattatcgtc actgcaatgc ttcgcaatat     1320
ggcgcaaaat gaccaacagc ggttgattga tcaggtagag ggggcgctgt acgaggtaaa     1380
gcccgatgcc agcattcctg acgacgatac ggagctgctg cgcgattacg taaagaagtt     1440
attgaagcat cctcgtcagt aaaaagttaa tcttttcaac agctgtcata aagttgtcac     1500
ggccgagact tatagtcgct ttgttttat tttttaatgt atttgtaact agtacgcaag     1560
ttcacgtaaa aagggtatct agaattatga agaagaatat cgcatttctt cttgcatcta     1620
tgttcgtttt ttctattgct acaaacgcgt acgctgaggt tcagctggtg gagtctggcg     1680
gtggcctggt gcagccaggg ggctcactcc gtttgtcctg tgcagtttct ggctactcca     1740
tcacctccgg atatagctgg aactggatcc gtcaggcccc gggtaagggc ctggaatggg     1800
ttgcatcgat tacgtatgac ggatcgacta actataaccc tagcgtcaag gccgtatca     1860
ctataagtcg cgacgactcc aaaaacacat tctacctgca gatgaacagc ctgcgtgctg     1920
aggacactgc cgtctattat tgtgctcgag gcagccacta tttcggtcac tggcacttcg     1980
ccgtgtgggg tcaaggaacc ctggtcaccg tctcctcggc ctccaccaag ggcccatcgg     2040
tcttcccccct ggcaccctcc tccaagagca cctctggggg cacagcggcc ctgggctgcc     2100
tggtcaagga ctacttcccc gaaccggtga cggtgtcgtg gaactcaggc gccctgacca     2160
gcggcgtgca caccttcccg gctgtcctac agtcctcagg actctactcc ctcagcagcg     2220
tggtgactgt gccctctagc agcttgggca cccagaccta catctgcaac gtgaatcaca     2280
agcccagcaa caccaaggtg gacaagaaag ttgagcccaa atcttgtgac aaaactcaca     2340
catgcccacc gtgcccagca cctgaactcc tggggggacc gtcagtcttc ctcttccccc     2400
caaaacccaa ggacaccctc atgatctccc ggacccctga ggtcacatgc gtggtggtgg     2460
acgtgagcca cgaagaccct gaggtcaagt tcaactggta cgtggacggc gtggaggtgc     2520
ataatgccaa gacaaagccg cgggaggagc agtacaacag cacgtaccgt gtggtcagcg     2580
tcctcaccgt cctgcaccag gactggctga atggcaagga gtacaagtgc aaggtctcca     2640
acaaagccct cccagccccc atcgagaaaa ccatctccaa agccaagggg cagccccgag     2700
aaccacaggt gtacaccctg cccccatccc gggaagagat gaccaagaac caggtcagcc     2760
tgacctgcct ggtcaaaggc ttctatccca gcgacatcgc cgtggagtgg gagagcaatg     2820
ggcagccgga gaacaactac aagaccacgc ctcccgtgct ggactccgac ggctccttct     2880
tcctctacag caagctcacc gtggacaaga gcaggtggca gcaggggaac gtcttctcat     2940
gctccgtgat gcatgaggct ctgcacaacc actacacgca gaagagcctc tccctgtctc     3000
cgggtaaata agcatgcgac ggccctagag tccctaacgc tcggttgccg ccgggcgttt     3060
tttattgtta actcatgttt gacagcttat catcgataag ctttaatgcg gtagtttatc     3120
acagttaaat tgctaacgca gtcaggcacc gtgtatgaaa tctaacaatg cgctcatcgt     3180
```

-continued

```
catcctcggc accgtcaccc tgga tgctgt aggcatag gc ttggttatgc cggtactgcc    3240
gggcctcttg cgggatatcg tccattccga cagcatcgcc agtcactatg gcgtgctgct    3300
```

<210> SEQ ID NO 21
<211> LENGTH: 669
<212> TYPE: PRT
<213> ORGANISM: Artificial Sequence
<220> FEATURE:
<223> OTHER INFORMATION: Light chain starts at residue 1 (D); Heavy
      chain starts at residue 220 (E)

<400> SEQUENCE: 21

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Glu Val Gln Leu Val Glu
    210                 215                 220

Ser Gly Gly Gly Leu Val Gln Pro Gly Gly Ser Leu Arg Leu Ser Cys
225                 230                 235                 240

Ala Val Ser Gly Tyr Ser Ile Thr Ser Gly Tyr Ser Trp Asn Trp Ile
                245                 250                 255

Arg Gln Ala Pro Gly Lys Gly Leu Glu Trp Val Ala Ser Ile Thr Tyr
            260                 265                 270

Asp Gly Ser Thr Asn Tyr Asn Pro Ser Val Lys Gly Arg Ile Thr Ile
        275                 280                 285

Ser Arg Asp Asp Ser Lys Asn Thr Phe Tyr Leu Gln Met Asn Ser Leu
    290                 295                 300

Arg Ala Glu Asp Thr Ala Val Tyr Tyr Cys Ala Arg Gly Ser His Tyr
305                 310                 315                 320

Phe Gly His Trp His Phe Ala Val Trp Gly Gln Gly Thr Leu Val Thr
                325                 330                 335

Val Ser Ser Ala Ser Thr Lys Gly Pro Ser Val Phe Pro Leu Ala Pro
```

```
                 340              345              350
Ser Ser Lys Ser Thr Ser Gly Gly Thr Ala Ala Leu Gly Cys Leu Val
            355              360              365

Lys Asp Tyr Phe Pro Glu Pro Val Thr Val Ser Trp Asn Ser Gly Ala
370              375              380

Leu Thr Ser Gly Val His Thr Phe Pro Ala Val Leu Gln Ser Ser Gly
385              390              395              400

Leu Tyr Ser Leu Ser Ser Val Val Thr Val Pro Ser Ser Ser Leu Gly
            405              410              415

Thr Gln Thr Tyr Ile Cys Asn Val Asn His Lys Pro Ser Asn Thr Lys
            420              425              430

Val Asp Lys Lys Val Glu Pro Lys Ser Cys Asp Lys Thr His Thr Cys
            435              440              445

Pro Pro Cys Pro Ala Pro Glu Leu Leu Gly Gly Pro Ser Val Phe Leu
            450              455              460

Phe Pro Pro Lys Pro Lys Asp Thr Leu Met Ile Ser Arg Thr Pro Glu
465              470              475              480

Val Thr Cys Val Val Val Asp Val Ser His Glu Asp Pro Glu Val Lys
            485              490              495

Phe Asn Trp Tyr Val Asp Gly Val Glu Val His Asn Ala Lys Thr Lys
            500              505              510

Pro Arg Glu Glu Gln Tyr Asn Ser Thr Tyr Arg Val Val Ser Val Leu
            515              520              525

Thr Val Leu His Gln Asp Trp Leu Asn Gly Lys Glu Tyr Lys Cys Lys
530              535              540

Val Ser Asn Lys Ala Leu Pro Ala Pro Ile Glu Lys Thr Ile Ser Lys
545              550              555              560

Ala Lys Gly Gln Pro Arg Glu Pro Gln Val Tyr Thr Leu Pro Pro Ser
            565              570              575

Arg Glu Glu Met Thr Lys Asn Gln Val Ser Leu Thr Cys Leu Val Lys
            580              585              590

Gly Phe Tyr Pro Ser Asp Ile Ala Val Glu Trp Glu Ser Asn Gly Gln
            595              600              605

Pro Glu Asn Asn Tyr Lys Thr Thr Pro Pro Val Leu Asp Ser Asp Gly
            610              615              620

Ser Phe Phe Leu Tyr Ser Lys Leu Thr Val Asp Lys Ser Arg Trp Gln
625              630              635              640

Gln Gly Asn Val Phe Ser Cys Ser Val Met His Glu Ala Leu His Asn
            645              650              655

His Tyr Thr Gln Lys Ser Leu Ser Leu Ser Pro Gly Lys
            660              665

<210> SEQ ID NO 22
<211> LENGTH: 3300
<212> TYPE: DNA
<213> ORGANISM: Artificial Sequence
<220> FEATURE:
<223> OTHER INFORMATION: E25 VH FR1 SGII in pE25-SGII

<400> SEQUENCE: 22
gaattcaact tctccatact ttggataagg aaatacagac atgaaaaatc tcattgctga        60
gttgttattt aagcttgccc aaaaagaaga agagtcgaat gaactgtgtg cgcaggtaga       120
agctttggag attatcgtca ctgcaatgct tcgcaaatat gcgcaaaatg accaacagcg       180
gttgattgat caggtagagg gggcgctgta cgaggtaaag cccgatgcca gcattcctga       240
```

-continued

```
cgacgatacg gagctgctgc gcgattacgt aaagaagtta ttgaagcatc ctcgtcagta    300
aaaagttaat cttttcaaca gctgtcataa agttgtcacg gccgagactt atagtcgctt    360 tgttttatt ttttaatgta tttgtaacta gtacgcaagt tcacgtaaaa agggtatcta    420
gaattatgaa gaagaatatc gcatttcttc ttgcatctat gttcgttttt tctattgcta    480
caaacgcgta cgctgatatc cagctgaccc agtccccgag ctccctgtcc gcctctgtgg    540
gcgatagggt caccatcacc tgccgtgcca gtcagagcgt cgattacgat ggtgatagct    600
acatgaactg gtatcaacag aaaccaggaa agctccgaa actactgatt tacgcggcct    660
cgtacctgga gtctggagtc ccttctcgct tctctggatc cggttctggg acggatttca    720
ctctgaccat cagcagtctg cagccggaag acttcgcaac ttattactgt cagcaaagtc    780
acgaggatcc gtacacattt ggacagggta ccaaggtgga gatcaaacga actgtggctg    840
caccatctgt cttcatcttc ccgccatctg atgagcagtt gaaatctgga actgcctctg    900
ttgtgtgcct gctgaataac ttctatccca gagaggccaa agtacagtgg aaggtggata    960
acgccctcca atcgggtaac tcccaggaga gtgtcacaga gcaggacagc aaggacagca   1020
cctacagcct cagcagcacc ctgacgctga gcaaagcaga ctacgagaaa cacaaagtct   1080
acgcctgcga agtcacccat cagggcctga gctcgcccgt cacaaagagc ttcaacaggg   1140
gagagtgtta attaaatcct ctacgccgga cgcatcgtgg cgagctcggt acccggggat   1200
ctaggcctaa cgctcggttg ccgccgggcg ttttttattg ttgccgacgc gcatctcgaa   1260
tgaactgtgt gcgcaggtag aagctttgga gattatcgtc actgcaatgc ttcgcaatat   1320
ggcgcaaaat gaccaacagc ggttgattga tcaggtagag gggcgctgt acgaggtaaa   1380 gcccgatgcc agcattcctg acgacgatac ggagctgctg cgcgattacg taaagaagtt   1440
attgaagcat cctcgtcagt aaaagttaa tcttttcaac agctgtcata agttgtcac    1500 ggccgagact tatagtcgct ttgttttat ttttaatgt atttgtaact agtacgcaag    1560
ttcacgtaaa aagggtatct agaattatga agaagaatat cgcatttctt cttgcatcta   1620
tgttcgtttt tctattgct acaaacgcgt acgctcaggt tcagctgcaa gagtctggcc   1680
cgggcctggt gaaaccatct cagactctct ccttgacttg tactgtttct ggctactcca   1740
tcacctccgg atatagctgg aactggatcc gtcaggcccc gggtaagggc ctggaatggg   1800
ttgcatcgat tacgtatgac ggatcgacta actataaccc tagcgtcaag gccgtatca    1860 ctataagtcg cgacgactcc aaaaacacat tctacctgca gatgaacagc ctgcgtgctg   1920
aggacactgc cgtctattat tgtgctcgag gcagccacta tttcggtcac tggcacttcg   1980
ccgtgtgggg tcaaggaacc ctggtcaccg tctcctcggc ctccaccaag ggcccatcgg   2040 tcttcccct ggcaccctcc tccaagagca cctctggggg cacagcggcc ctgggctgcc   2100
tggtcaagga ctacttcccc gaaccggtga cggtgtcgtg gaactcaggc gccctgacca   2160
gcggcgtgca caccttcccg gctgtcctac agtcctcagg actctactcc ctcagcagcg   2220
tggtgactgt gccctctagc agcttgggca cccagaccta catctgcaac gtgaatcaca   2280
agcccagcaa caccaaggtg gacaagaaag ttgagcccaa atcttgtgac aaaactcaca   2340
catgcccacc gtgcccagca cctgaactcc tggggggacc gtcagtcttc ctcttccccc   2400
caaaacccaa ggacaccctc atgatctccc ggacccctga ggtcacatgc gtggtggtgg   2460
acgtgagcca cgaagaccct gaggtcaagt tcaactggta cgtggacggc gtggaggtgc   2520
ataatgccaa gacaaagccg cgggaggagc agtacaacag cacgtaccgt gtggtcagcg   2580
```

```
tcctcaccgt cctgcaccag gactggctga atggcaagga gtacaagtgc aaggtctcca    2640
acaaagcccT cccagccccc atcgagaaaa ccatctccaa agccaaaggg cagccccgag    2700
aaccacaggt gtaccctg cccccatccc gggaagagat gaccaagaac caggtcagcc     2760
tgacctgcct ggtcaaaggc ttctatccca gcgacatcgc cgtggagtgg gagagcaatg    2820
ggcagccgga gaacaactac aagaccacgc ctcccgtgct ggactccgac ggctccttct    2880
tcctctacag caagctcacc gtggacaaga gcaggtggca gcaggggaac gtcttctcat    2940
gctccgtgat gcatgaggct ctgcacaacc actacacgca gaagagcctc tccctgtctc    3000
cgggtaaata agcatgcgac ggccctagag tccctaacgc tcggttgccg ccgggcgttt    3060
tttattgtta actcatgttt gacagcttat catcgataag ctttaatgcg gtagtttatc    3120
acagttaaat tgctaacgca gtcaggcacc gtgtatgaaa tctaacaatg cgctcatcgt    3180
catcctcggc accgtcaccc tggatgctgt aggcataggc ttggttatgc cggtactgcc    3240
gggcctcttg cgggatatcg tccattccga cagcatcgcc agtcactatg gcgtgctgct    3300
```

<210> SEQ ID NO 23
<211> LENGTH: 669
<212> TYPE: PRT
<213> ORGANISM: Artificial Sequence
<220> FEATURE:
<223> OTHER INFORMATION: Light chain starts at residue 1 (D); Heavy chain starts at residue 220 (Q)

<400> SEQUENCE: 23

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Ala Ser Tyr Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser His
                85                  90                  95

Glu Asp Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gln Val Gln Leu Gln Glu
    210                 215                 220

Ser Gly Pro Gly Leu Val Lys Pro Ser Gln Thr Leu Ser Leu Thr Cys
225                 230                 235                 240
```

-continued

```
Thr Val Ser Gly Tyr Ser Ile Thr Ser Gly Tyr Ser Trp Asn Trp Ile
                245                 250                 255
Arg Gln Ala Pro Gly Lys Gly Leu Glu Trp Val Ala Ser Ile Thr Tyr
            260                 265                 270
Asp Gly Ser Thr Asn Tyr Asn Pro Ser Val Lys Gly Arg Ile Thr Ile
        275                 280                 285
Ser Arg Asp Asp Ser Lys Asn Thr Phe Tyr Leu Gln Met Asn Ser Leu
    290                 295                 300
Arg Ala Glu Asp Thr Ala Val Tyr Tyr Cys Ala Arg Gly Ser His Tyr
305                 310                 315                 320
Phe Gly His Trp His Phe Ala Val Trp Gly Gln Gly Thr Leu Val Thr
                325                 330                 335
Val Ser Ser Ala Ser Thr Lys Gly Pro Ser Val Phe Pro Leu Ala Pro
            340                 345                 350
Ser Ser Lys Ser Thr Ser Gly Gly Thr Ala Ala Leu Gly Cys Leu Val
        355                 360                 365
Lys Asp Tyr Phe Pro Glu Pro Val Thr Val Ser Trp Asn Ser Gly Ala
    370                 375                 380
Leu Thr Ser Gly Val His Thr Phe Pro Ala Val Leu Gln Ser Ser Gly
385                 390                 395                 400
Leu Tyr Ser Leu Ser Ser Val Val Thr Val Pro Ser Ser Ser Leu Gly
                405                 410                 415
Thr Gln Thr Tyr Ile Cys Asn Val Asn His Lys Pro Ser Asn Thr Lys
            420                 425                 430
Val Asp Lys Lys Val Glu Pro Lys Ser Cys Asp Lys Thr His Thr Cys
        435                 440                 445
Pro Pro Cys Pro Ala Pro Glu Leu Leu Gly Gly Pro Ser Val Phe Leu
    450                 455                 460
Phe Pro Pro Lys Pro Lys Asp Thr Leu Met Ile Ser Arg Thr Pro Glu
465                 470                 475                 480
Val Thr Cys Val Val Val Asp Val Ser His Glu Asp Pro Glu Val Lys
                485                 490                 495
Phe Asn Trp Tyr Val Asp Gly Val Glu Val His Asn Ala Lys Thr Lys
            500                 505                 510
Pro Arg Glu Glu Gln Tyr Asn Ser Thr Tyr Arg Val Val Ser Val Leu
        515                 520                 525
Thr Val Leu His Gln Asp Trp Leu Asn Gly Lys Glu Tyr Lys Cys Lys
    530                 535                 540
Val Ser Asn Lys Ala Leu Pro Ala Pro Ile Glu Lys Thr Ile Ser Lys
545                 550                 555                 560
Ala Lys Gly Gln Pro Arg Glu Pro Gln Val Tyr Thr Leu Pro Pro Ser
                565                 570                 575
Arg Glu Glu Met Thr Lys Asn Gln Val Ser Leu Thr Cys Leu Val Lys
            580                 585                 590
Gly Phe Tyr Pro Ser Asp Ile Ala Val Glu Trp Glu Ser Asn Gly Gln
        595                 600                 605
Pro Glu Asn Asn Tyr Lys Thr Thr Pro Pro Val Leu Asp Ser Asp Gly
    610                 615                 620
Ser Phe Phe Leu Tyr Ser Lys Leu Thr Val Asp Lys Ser Arg Trp Gln
625                 630                 635                 640
Gln Gly Asn Val Phe Ser Cys Ser Val Met His Glu Ala Leu His Asn
                645                 650                 655
```

His Tyr Thr Gln Lys Ser Leu Ser Leu Ser Pro Gly Lys
        660                 665

<210> SEQ ID NO 24
<211> LENGTH: 3300
<212> TYPE: DNA
<213> ORGANISM: Artificial Sequence
<220> FEATURE:
<223> OTHER INFORMATION: pVG50

<400> SEQUENCE: 24

| | | | | | |
|---|---|---|---|---|---|
| gaattcaact | tctccatact | ttggataagg | aaatacagac | atgaaaaatc | tcattgctga | 60 |
| gttgttattt | aagcttgccc | aaaaagaaga | agagtcgaat | gaactgtgtg | cgcaggtaga | 120 |
| agctttggag | attatcgtca | ctgcaatgct | tcgcaatatg | gcgcaaaatg | accaacagcg | 180 |
| gttgattgat | caggtagagg | gggcgctgta | cgaggtaaag | cccgatgcca | gcattcctga | 240 |
| cgacgatacg | gagctgctgc | gcgattacgt | aaagaagtta | ttgaagcatc | ctcgtcagta | 300 |
| aaaagttaat | cttttcaaca | gctgtcataa | agttgtcacg | gccgagactt | atagtcgctt | 360 |
| tgttttatt | ttttaatgta | tttgtaacta | gtacgcaagt | tcacgtaaaa | agggtatcta | 420 |
| gaattatgaa | gaagaatatc | gcatttcttc | ttgcatctat | gttcgttttt | tctattgcta | 480 |
| caaacgcgta | cgctgatatc | cagatgaccc | agtccccgag | ctccctgtcc | gcctctgtgg | 540 |
| gcgatagggt | caccatcacc | tgcagcgcaa | gtcaggatat | tagcaactat | ttaaactggt | 600 |
| atcaacagaa | accaggaaaa | gctccgaaag | tactgattta | cttcacctcc | tctctccact | 660 |
| ctggagtccc | ttctcgcttc | tctggatccg | gttctgggac | ggatttcact | ctgaccatca | 720 |
| gcagtctgca | gccagaagac | ttcgcaactt | attactgtca | acagtatagc | accgtgccgt | 780 |
| ggacgtttgg | acagggtacc | aaggtggaga | tcaaacgaac | tgtggctgca | ccatctgtct | 840 |
| tcatcttccc | gccatctgat | gagcagttga | aatctggaac | tgcttctgtt | gtgtgcctgc | 900 |
| tgaataactt | ctatcccaga | gaggccaaag | tacagtggaa | ggtggataac | gccctccaat | 960 |
| cgggtaactc | ccaggagagt | gtcacagagc | aggacagcaa | ggacagcacc | tacagcctca | 1020 |
| gcagcaccct | gacgctgagc | aaagcagact | acgagaaaca | caaagtctac | gcctgcgaag | 1080 |
| tcacccatca | gggcctgagc | tcgcccgtca | caaagagctt | caacagggga | gagtgttaat | 1140 |
| taaatcctct | acgccggacg | catcgtggcg | agctcggtac | ccggggatct | aggcctaacg | 1200 |
| ctcggttgcc | gccgggcgtt | ttttattgtt | gccgacgcgc | atctcgaatg | aactgtgtgc | 1260 |
| gcaggtagaa | gctttggaga | ttatcgtcac | tgcaatgctt | cgcaatatgg | cgcaaaatga | 1320 |
| ccaacagcgg | ttgattgatc | aggtagaggg | ggcgctgtac | gaggtaaagc | ccgatgccag | 1380 |
| cattcctgac | gacgatacgg | agctgctgcg | cgattacgta | aagaagttat | tgaagcatcc | 1440 |
| tcgtcagtaa | aaagttaatc | ttttcaacag | ctgtcataaa | gttgtcacgg | ccgagactta | 1500 |
| tagtcgcttt | gttttatttt | tttaatgtat | ttgtaactag | tacgcaagtt | cacgtaaaaa | 1560 |
| gggtatctag | aattatgaag | aagaatatcg | catttcttct | tgcatctatg | ttcgtttttt | 1620 |
| ctattgctac | aaacgcgtac | gctgaggttc | agctggtgga | gtctggcggt | ggcctggtgc | 1680 |
| agccagggg | ctcactccgt | ttgtcctgtg | cagcttctgg | ctataccttc | accaactatg | 1740 |
| gtatgaactg | ggtccgtcag | gccccgggta | agggcctgga | atgggttgga | tggattaaca | 1800 |
| cctataccgg | tgaaccgacc | tatgctgcgg | atttcaaacg | tcgtttcact | ttcagcttag | 1860 |
| acacctccaa | gtcgacagca | tacctgcaga | tgaacagcct | gcgtgctgag | gacactgccg | 1920 |
| tctattactg | tgcaaagtac | ccccactatt | atggagcag | ccactggtat | ttcgacgtct | 1980 |

```
gggtcaagg  aaccctggtc  accgtctcct  cggcctccac  caagggccca  tcggtcttcc    2040
ccctggcacc  ctcctccaag  agcacctctg  ggggcacagc  ggccctgggc  tgcctggtca    2100
aggactactt  ccccgaaccg  gtgacggtgt  cgtggaactc  aggcgccctg  accagcggcg    2160
tgcacacctt  cccggctgtc  ctacagtcct  caggactcta  ctccctcagc  agcgtggtga    2220
ctgtgccctc  tagcagcttg  ggcacccaga  cctacatctg  caacgtgaat  cacaagccca    2280
gcaacaccaa  ggtggacaag  aaagttgagc  ccaaatcttg  tgacaaaact  cacacatgcc    2340
caccgtgccc  agcacctgaa  ctcctggggg  gaccgtcagt  cttcctcttc  cccccaaaac    2400
ccaaggacac  cctcatgatc  tcccggaccc  ctgaggtcac  atgcgtggtg  gtggacgtga    2460
gccacgaaga  ccctgaggtc  aagttcaact  ggtacgtgga  cggcgtggag  gtgcataatg    2520
ccaagacaaa  gccgcgggag  gagcagtaca  acagcacgta  ccgtgtggtc  agcgtcctca    2580
ccgtcctgca  ccaggactgg  ctgaatggca  aggagtacaa  gtgcaaggtc  tccaacaaag    2640
ccctcccagc  ccccatcgag  aaaaccatct  ccaaagccaa  aggcagcccc  gagaaccac     2700 aggtgtacac  cctgccccca  tcccgggaag  agatgaccaa  gaaccaggtc  agcctgacct    2760
gcctggtcaa  aggcttctat  cccagcgaca  tcgccgtgga  gtgggagagc  aatgggcagc    2820
cggagaacaa  ctacaagacc  acgcctcccg  tgctggactc  cgacggctcc  ttcttcctct    2880
acagcaagct  caccgtggac  aagagcaggt  ggcagcaggg  gaacgtcttc  tcatgctccg    2940
tgatgcatga  ggctctgcac  aaccactaca  cgcagaagag  cctctccctg  tctccgggta    3000
aataagcatg  cgacggccct  agagtcccta  acgtcggtt  gccgccgggc  gttttttatt    3060
gttaactcat  gtttgacagc  ttatcatcga  taagctttaa  tgcggtagtt  tatcacagtt    3120
aaattgctaa  cgcagtcagg  caccgtgtat  gaaatctaac  aatgcgctca  tcgtcatcct    3180
cggcaccgtc  accctggatg  ctgtaggcat  aggcttggtt  atgccggtac  tgccgggcct    3240
cttgcgggat  atcgtccatt  ccgacagcat  cgccagtcac  tatggcgtgc  tgctagcgct    3300
```

<210> SEQ ID NO 25
<211> LENGTH: 667
<212> TYPE: PRT
<213> ORGANISM: Artificial Sequence
<220> FEATURE:
<223> OTHER INFORMATION: Light chain starts at residue 1 (D); Heavy
      chain starts at residue 215 (E)

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125
```

-continued

```
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
        180                 185                 190
Ala Cys Glu Val Thr His Gln Gly Leu Ser Ser Pro Val Thr Lys Ser
        195                 200                 205
Phe Asn Arg Gly Glu Cys Glu Val Gln Leu Val Glu Ser Gly Gly Gly
        210                 215                 220
Leu Val Gln Pro Gly Gly Ser Leu Arg Leu Ser Cys Ala Ala Ser Gly
225                 230                 235                 240
Tyr Thr Phe Thr Asn Tyr Gly Met Asn Trp Val Arg Gln Ala Pro Gly
                245                 250                 255
Lys Gly Leu Glu Trp Val Gly Trp Ile Asn Thr Tyr Thr Gly Glu Pro
                260                 265                 270
Thr Tyr Ala Ala Asp Phe Lys Arg Arg Phe Thr Phe Ser Leu Asp Thr
        275                 280                 285
Ser Lys Ser Thr Ala Tyr Leu Gln Met Asn Ser Leu Arg Ala Glu Asp
290                 295                 300
Thr Ala Val Tyr Tyr Cys Ala Lys Tyr Pro His Tyr Tyr Gly Ser Ser
305                 310                 315                 320
His Trp Tyr Phe Asp Val Trp Gly Gln Gly Thr Leu Val Thr Val Ser
                325                 330                 335
Ser Ala Ser Thr Lys Gly Pro Ser Val Phe Pro Leu Ala Pro Ser Ser
        340                 345                 350
Lys Ser Thr Ser Gly Gly Thr Ala Ala Leu Gly Cys Leu Val Lys Asp
        355                 360                 365
Tyr Phe Pro Glu Pro Val Thr Val Ser Trp Asn Ser Gly Ala Leu Thr
        370                 375                 380
Ser Gly Val His Thr Phe Pro Ala Val Leu Gln Ser Ser Gly Leu Tyr
385                 390                 395                 400
Ser Leu Ser Ser Val Val Thr Val Pro Ser Ser Ser Leu Gly Thr Gln
                405                 410                 415
Thr Tyr Ile Cys Asn Val Asn His Lys Pro Ser Asn Thr Lys Val Asp
                420                 425                 430
Lys Lys Val Glu Pro Lys Ser Cys Asp Lys Thr His Thr Cys Pro Pro
        435                 440                 445
Cys Pro Ala Pro Glu Leu Leu Gly Gly Pro Ser Val Phe Leu Phe Pro
        450                 455                 460
Pro Lys Pro Lys Asp Thr Leu Met Ile Ser Arg Thr Pro Glu Val Thr
465                 470                 475                 480
Cys Val Val Val Asp Val Ser His Glu Asp Pro Glu Val Lys Phe Asn
                485                 490                 495
Trp Tyr Val Asp Gly Val Glu Val His Asn Ala Lys Thr Lys Pro Arg
                500                 505                 510
Glu Glu Gln Tyr Asn Ser Thr Tyr Arg Val Val Ser Val Leu Thr Val
        515                 520                 525
Leu His Gln Asp Trp Leu Asn Gly Lys Glu Tyr Lys Cys Lys Val Ser
        530                 535                 540
Asn Lys Ala Leu Pro Ala Pro Ile Glu Lys Thr Ile Ser Lys Ala Lys
```

```
                545                 550                 555                 560
Gly Gln Pro Arg Glu Pro Gln Val Tyr Thr Leu Pro Pro Ser Arg Glu
                    565                 570                 575
Glu Met Thr Lys Asn Gln Val Ser Leu Thr Cys Leu Val Lys Gly Phe
                580                 585                 590
Tyr Pro Ser Asp Ile Ala Val Glu Trp Glu Ser Asn Gly Gln Pro Glu
            595                 600                 605
Asn Asn Tyr Lys Thr Thr Pro Pro Val Leu Asp Ser Asp Gly Ser Phe
        610                 615                 620
Phe Leu Tyr Ser Lys Leu Thr Val Asp Lys Ser Arg Trp Gln Gln Gly
625                 630                 635                 640
Asn Val Phe Ser Cys Ser Val Met His Glu Ala Leu His Asn His Tyr
                645                 650                 655
Thr Gln Lys Ser Leu Ser Leu Ser Pro Gly Lys
            660                 665

<210> SEQ ID NO 26
<211> LENGTH: 3300
<212> TYPE: DNA
<213> ORGANISM: Artificial Sequence
<220> FEATURE:
<223> OTHER INFORMATION: pVKSGI with FR1-4 SGI consensus sequence

<400> SEQUENCE: 26
gaattcaact tctccatact ttggataagg aaatacagac atgaaaaatc tcattgctga      60
gttgttattt aagcttgccc aaaaagaaga agagtcgaat gaactgtgtg cgcaggtaga     120
agctttggag attatcgtca ctgcaatgct tcgcaatatg gcgcaaaatg accaacagcg     180
gttgattgat caggtagagg gggcgctgta cgaggtaaag cccgatgcca gcattcctga     240
cgacgatacg gagctgctgc gcgattacgt aaagaagtta tgaagcatc ctcgtcagta     300
aaaagttaat cttttcaaca gctgtcataa agttgtcacg gccgagactt atagtcgctt     360
tgtttttatt ttttaatgta tttgtaacta gtacgcaagt tcacgtaaaa agggtatcta     420
gaattatgaa aagaaatatc gcatttcttc ttgcatctat gttcgttttt tctattgcta     480
caaacgcgta cgctgatatc cagttgaccc agtccccgag ctccctgtcc gcctctgtgg     540
gcgatagggt caccatcacc tgcagcgcaa gtcaggatat tagcaactat ttaaactggt     600
atcaacagaa accaggaaaa gctccgaaag tactgattta cttcacctcc tctctccact     660
ctggagtccc ttctcgcttc tctggatccg gttctgggac ggatttcact ctgaccatca     720
gcagtctgca gccagaagac ttcgcaactt attactgtca acagtatagc accgtgccgt     780
ggacgtttgg acagggtacc aaggtggaga tcaaacgaac tgtggctgca ccatctgtct     840
tcatcttccc gccatctgat gagcagttga aatctggaac tgcttctgtt gtgtgcctgc     900
tgaataactt ctatcccaga gaggccaaag tacagtggaa ggtggataac gccctccaat     960
cgggtaactc ccaggagagt gtcacagagc aggacagcaa ggacagcacc tacagcctca    1020
gcagcaccct gacgctgagc aaagcagact acgagaaaca caaagtctac gcctgcgaag    1080
tcacccatca gggcctgagc tcgcccgtca caaagagctt caacagggga gagtgttaat    1140
taaatcctct acgccggacg catcgtggcg agctcggtac ccggggatct aggcctaacg    1200
ctcggttgcc gccgggcgtt ttttattgtt gccgacgcgc atctcgaatg aactgtgtgc    1260
gcaggtagaa gctttggaga ttatcgtcac tgcaatgctt cgcaatatgg cgcaaaatga    1320
ccaacagcgg ttgattgatc aggtagaggg ggcgctgtac gaggtaaagc ccgatgccag    1380
```

```
cattcctgac gacgatacgg agctgctgcg cgattacgta aagaagttat tgaagcatcc    1440
tcgtcagtaa aaagttaatc ttttcaacag ctgtcataaa gttgtcacgg ccgagactta    1500
tagtcgcttt gttttttattt tttaatgtat ttgtaactag tacgcaagtt cacgtaaaaa    1560
gggtatctag aattatgaag aagaatatcg catttcttct tgcatctatg ttcgtttttt    1620
ctattgctac aaacgcgtac gctcaggttc agctggtgca gtctggcgca gaggtgaaaa    1680
agccaggggc ttcagttaaa gtatcctgta agcttctgg ctataccttc accaactatg    1740
gtataaactg ggtccgtcag gccccgggtc agggcctgga atggatggga tggattaaca    1800
cctataccgg tgaaccgacc tatgctgcgg atttcaaacg tcgtgttact atcactgctg    1860
acacctccac tagcacagca tacatggaac tgtctagcct gcgctctgag gacactgccg    1920
tctattactg tgcacgttac ccgcactatt atgtgaacga gcggaagagc cactggtatt    1980
tcgacgtctg gggtcaagga accctggtca ccgtctcctc ggcctccacc aagggcccat    2040
cggtcttccc cctggcaccc tcctccaaga gcacctctgg gggcacagcg gccctgggct    2100
gcctggtcaa ggactacttc cccgaaccgg tgacggtgtc gtggaactca ggcgccctga    2160
ccagcggcgt gcacaccttc ccggctgtcc tacagtcctc aggactctac tccctcagca    2220
gcgtggtgac tgtgccctct agcagcttgg gcacccagac ctacatctgc aacgtgaatc    2280
acaagcccag caacaccaag gtggacaaga agttgagcc caaatcttgt gacaaaactc    2340
acacatgccc accgtgccca gcacctgaac tcctgggggg accgtcagtc ttcctcttcc    2400
ccccaaaacc caaggacacc ctcatgatct cccggacccc tgaggtcaca tgcgtggtgg    2460
tggacgtgag ccacgaagac cctgaggtca agttcaactg gtacgtggac ggcgtggagg    2520
tgcataatgc caagacaaag ccgcgggagg agcagtacaa cagcacgtac cgtgtggtca    2580
gcgtcctcac cgtcctgcac caggactggc tgaatggcaa ggagtacaag tgcaaggtct    2640
ccaacaaagc cctcccagcc cccatcgaga aaaccatctc caaagccaaa gggcagcccc    2700
gagaaccaca ggtgtacacc ctgcccccat cccgggaaga gatgaccaag aaccaggtca    2760
gcctgacctg cctggtcaaa ggcttctatc ccagcgacat cgccgtggag tgggagagca    2820
atgggcagcc ggagaacaac tacaagacca cgcctcccgt gctggactcc gacggctcct    2880
tcttcctcta cagcaagctc accgtggaca agagcaggtg gcagcagggg aacgtcttct    2940
catgctccgt gatgcatgag gctctgcaca accactacac gcagaagagc ctctccctgt    3000
ctccgggtaa ataagcatgc gacggcccta gagtccctaa cgctcggttg ccgccgggcg    3060
ttttttattg ttaactcatg tttgacagct tatcatcgat aagctttaat gcggtagttt    3120
atcacagtta aattgctaac gcagtcaggc accgtgtatg aaatctaaca atgcgctcat    3180
cgtcatcctc ggcaccgtca ccctggatgc tgtaggcata ggcttggtta tgccggtact    3240
gccgggcctc ttgcgggata tcgtccattc cgacagcatc gccagtcact atggcgtgct    3300
```

<210> SEQ ID NO 27
<211> LENGTH: 670
<212> TYPE: PRT
<213> ORGANISM: Artificial Sequence
<220> FEATURE:
<223> OTHER INFORMATION: Light chain starts at residue 1 (D); Heavy
      chain starts at residue 215 (Q)

<400> SEQUENCE: 27

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
```

-continued

```
                    20                  25                  30
Leu Asn Trp Tyr Gln Gln Lys Pro Gly Lys Ala Pro Lys Val Leu Ile
                35                  40                  45
Tyr Phe Thr Ser Ser Leu His Ser Gly Val Pro Ser Arg Phe Ser Gly
            50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Thr Val Pro Trp
                85                  90                  95
Thr Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
        130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Gln Val Gln Leu Val Gln Ser Gly Ala Glu
    210                 215                 220
Val Lys Lys Pro Gly Ala Ser Val Lys Val Ser Cys Lys Ala Ser Gly
225                 230                 235                 240
Tyr Thr Phe Thr Asn Tyr Gly Ile Asn Trp Val Arg Gln Ala Pro Gly
                245                 250                 255
Gln Gly Leu Glu Trp Met Gly Trp Ile Asn Thr Tyr Thr Gly Glu Pro
            260                 265                 270
Thr Tyr Ala Ala Asp Phe Lys Arg Arg Val Thr Ile Thr Ala Asp Thr
        275                 280                 285
Ser Thr Ser Thr Ala Tyr Met Glu Leu Ser Ser Leu Arg Ser Glu Asp
    290                 295                 300
Thr Ala Val Tyr Tyr Cys Ala Arg Tyr Pro His Tyr Tyr Val Asn Glu
305                 310                 315                 320
Arg Lys Ser His Trp Tyr Phe Asp Val Trp Gly Gln Gly Thr Leu Val
                325                 330                 335
Thr Val Ser Ser Ala Ser Thr Lys Gly Pro Ser Val Phe Pro Leu Ala
            340                 345                 350
Pro Ser Ser Lys Ser Thr Ser Gly Gly Thr Ala Ala Leu Gly Cys Leu
        355                 360                 365
Val Lys Asp Tyr Phe Pro Glu Pro Val Thr Val Ser Trp Asn Ser Gly
    370                 375                 380
Ala Leu Thr Ser Gly Val His Thr Phe Pro Ala Val Leu Gln Ser Ser
385                 390                 395                 400
Gly Leu Tyr Ser Leu Ser Ser Val Val Thr Val Pro Ser Ser Ser Leu
                405                 410                 415
Gly Thr Gln Thr Tyr Ile Cys Asn Val Asn His Lys Pro Ser Asn Thr
            420                 425                 430
Lys Val Asp Lys Lys Val Glu Pro Lys Ser Cys Asp Lys Thr His Thr
        435                 440                 445
```

```
Cys Pro Pro Cys Pro Ala Pro Glu Leu Leu Gly Gly Pro Ser Val Phe
    450                 455                 460

Leu Phe Pro Pro Lys Pro Lys Asp Thr Leu Met Ile Ser Arg Thr Pro
465                 470                 475                 480

Glu Val Thr Cys Val Val Asp Val Ser His Glu Asp Pro Glu Val
                485                 490                 495

Lys Phe Asn Trp Tyr Val Asp Gly Val Glu Val His Asn Ala Lys Thr
                500                 505                 510

Lys Pro Arg Glu Glu Gln Tyr Asn Ser Thr Tyr Arg Val Val Ser Val
                515                 520                 525

Leu Thr Val Leu His Gln Asp Trp Leu Asn Gly Lys Glu Tyr Lys Cys
    530                 535                 540

Lys Val Ser Asn Lys Ala Leu Pro Ala Pro Ile Glu Lys Thr Ile Ser
545                 550                 555                 560

Lys Ala Lys Gly Gln Pro Arg Glu Pro Gln Val Tyr Thr Leu Pro Pro
                565                 570                 575

Ser Arg Glu Glu Met Thr Lys Asn Gln Val Ser Leu Thr Cys Leu Val
                580                 585                 590

Lys Gly Phe Tyr Pro Ser Asp Ile Ala Val Glu Trp Glu Ser Asn Gly
    595                 600                 605

Gln Pro Glu Asn Asn Tyr Lys Thr Thr Pro Pro Val Leu Asp Ser Asp
    610                 615                 620

Gly Ser Phe Phe Leu Tyr Ser Lys Leu Thr Val Asp Lys Ser Arg Trp
625                 630                 635                 640

Gln Gln Gly Asn Val Phe Ser Cys Ser Val Met His Glu Ala Leu His
                645                 650                 655

Asn His Tyr Thr Gln Lys Ser Leu Ser Leu Ser Pro Gly Lys
                660                 665                 670

<210> SEQ ID NO 28
<211> LENGTH: 14
<212> TYPE: PRT
<213> ORGANISM: Artificial Sequence
<220> FEATURE:
<223> OTHER INFORMATION: VH FR2 SGIII

<400> SEQUENCE: 28

Trp Val Arg Gln Ala Pro Gly Lys Gly Leu Glu Trp Val Ser
1               5                   10

<210> SEQ ID NO 29
<211> LENGTH: 14
<212> TYPE: PRT
<213> ORGANISM: Artificial Sequence
<220> FEATURE:
<223> OTHER INFORMATION: VH FR2 VNERK

<400> SEQUENCE: 29

Trp Val Arg Gln Ala Pro Gly Lys Gly Leu Glu Trp Val Gly
1               5                   10

<210> SEQ ID NO 30
<211> LENGTH: 32
<212> TYPE: PRT
<213> ORGANISM: Artificial Sequence
<220> FEATURE:
<223> OTHER INFORMATION: VH FR3 SGIII

<400> SEQUENCE: 30
```

```
Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 31
<211> LENGTH: 32
<212> TYPE: PRT
<213> ORGANISM: Artificial Sequence
<220> FEATURE:
<223> OTHER INFORMATION: VH FR3 VNERK

<400> SEQUENCE: 31

Arg Phe Thr Phe Ser Leu Asp Thr Ser Lys Ser Thr Ala Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 32
<211> LENGTH: 11
<212> TYPE: PRT
<213> ORGANISM: Artificial Sequence
<220> FEATURE:
<223> OTHER INFORMATION: VH FR4 SGIII

<400> SEQUENCE: 32

Trp Gly Gln Gly Thr Leu Val Thr Val Ser Ser
1               5                   10

<210> SEQ ID NO 33
<211> LENGTH: 32
<212> TYPE: PRT
<213> ORGANISM: Artificial Sequence
<220> FEATURE:
<223> OTHER INFORMATION: VH FR3 SGI

<400> SEQUENCE: 33

Arg Phe Thr Ile Ser Ala Asp Thr Ser Lys Ser Thr Ala Tyr Leu Gln
1               5                   10                  15

Met Asn Ser Leu Arg Ala Glu Asp Thr Ala Val Tyr Tyr Cys Ala Arg
            20                  25                  30
```